United States Patent
Fischer et al.

(10) Patent No.: US 8,242,150 B2
(45) Date of Patent: Aug. 14, 2012

(54) TRIAZOLE DERIVATIVES FOR TREATING ALZHEIMER'S DISEASE AND RELATED CONDITIONS

(75) Inventors: Christian Fischer, Natick, MA (US); Ben Munoz, Brookline, MA (US); Susan Zultanski, Cambridge, MA (US); Joey Methot, Westwood, MA (US); Hua Zhou, Waitham, MA (US); W. Colby Brown, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 72 days.

(21) Appl. No.: 12/663,432

(22) PCT Filed: Jun. 9, 2008

(86) PCT No.: PCT/US2008/007205
§ 371 (c)(1),
(2), (4) Date: Dec. 7, 2009

(87) PCT Pub. No.: WO2008/156580
PCT Pub. Date: Dec. 24, 2008

(65) Prior Publication Data
US 2010/0222320 A1    Sep. 2, 2010

Related U.S. Application Data

(60) Provisional application No. 60/934,515, filed on Jun. 13, 2007.

(51) Int. Cl.
A61K 31/41 (2006.01)
C07D 249/00 (2006.01)
C07D 249/08 (2006.01)

(52) U.S. Cl. ............ 514/359; 548/255; 548/262.2; 548/400

(58) Field of Classification Search .......... 514/359, 514/383, 385, 415; 548/255, 262.2, 300.1, 548/452
See application file for complete search history.

(56) References Cited

U.S. PATENT DOCUMENTS

| | | |
|---|---|---|
| 2006/0004013 A1 | 1/2006 | Kimura et al. |
| 2006/0258658 A1 | 11/2006 | Bebbington et al. |
| 2006/0258695 A1 | 11/2006 | Waddell et al. |
| 2006/0270628 A1 | 11/2006 | Das et al. |
| 2007/0117798 A1 | 5/2007 | Kimura et al. |
| 2007/0219181 A1 | 9/2007 | Kimura et al. |
| 2008/0090834 A1* | 4/2008 | Hoover et al. ......... 514/253.06 |

FOREIGN PATENT DOCUMENTS

| | | |
|---|---|---|
| JP | 2000063363 A | 2/2000 |
| WO | 2006046575 A1 | 5/2006 |
| WO | 2007135969 A1 | 11/2007 |
| WO | 2007135970 A1 | 11/2007 |
| WO | 2008097538 A1 | 8/2008 |
| WO | 2008099210 A2 | 8/2008 |
| WO | 2008100412 A1 | 8/2008 |

OTHER PUBLICATIONS

Copending U.S. Appl. No. 12/526,074, filed Feb. 5, 2008, U.S. National Stage Entry of PCT/US08/001503, published as WO2008/097538.
Copending U.S. Appl. No. 12/526,706, filed Feb. 8, 2008, U.S. National Stage Entry of PCT/US08/001666, published as WO2008/100412.
Copending U.S. Appl. No. 12/526,687, filed Feb. 11, 2008, U.S. National Stage Entry of PCT/GB08/050085, published as WO2008/099210.

* cited by examiner

*Primary Examiner* — Susannah Chung
(74) *Attorney, Agent, or Firm* — Susan L. Hess; Raynard Yuro; Gerard M. Devlin

(57) ABSTRACT

Compounds of formula I: Selectively attenuate production of Aβ(1-42) and hence find use in treatment or prevention of diseases associated with deposition of Aβ in the brain, in particular Alzheimer's disease.

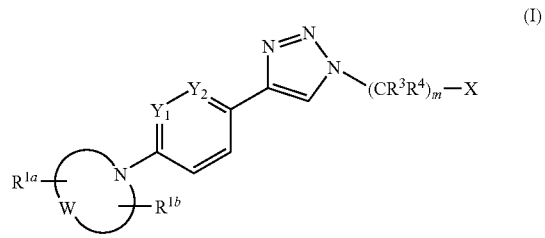

10 Claims, No Drawings

TRIAZOLE DERIVATIVES FOR TREATING ALZHEIMER'S DISEASE AND RELATED CONDITIONS

CROSS REFERENCE TO RELATED APPLICATIONS

This application is a U.S. National Phase application under 35 U.S.C. §371 of PCT Application No. PCT/US2008/007205, filed Jun. 9, 2008 which claims priority under 35 U.S.C. §119 from U.S. Provisional Application Ser. No. 60/934,515, filed Jun. 13, 2007.

This invention relates to compounds for use in therapeutic treatment of the human body. In particular, it provides triazole derivatives useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS*, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral hemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science*, 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature*, 423 (2003), 435-9). Other proposed methods of treatment include administering a compound which blocks the aggregation of Aβ, and administering an antibody which selectively binds to Aβ.

However, recent reports (Pearson and Peers, *J. Physiol.*, 575.1 (2006), 5-10) suggest that Aβ may exert important physiological effects independent of its role in AD, implying that blocking its production may lead to undesirable side effects. Furthermore, γ-secretase is known to act on several different substrates apart from APP (e.g. notch), and so inhibition thereof may also lead to unwanted side effects. There is therefore an interest in methods of treating AD that do not suppress completely the production of Aβ, and do not inhibit the action of γ-secretase.

One such proposed treatment involves modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience*, 22 (2002), 226-54). US 2002/0015941 teaches that agents which potentiate capacitative calcium entry activity can lower Aβ(1-42).

Further classes of compounds capable of selectively attenuating Aβ(1-42) production are disclosed in WO 2005/054193, WO 2005/013985, WO 2006/008558, WO 2005/108362, WO 2006/043064, WO 2007/054739, WO 2007/110667, WO 2007/116228 and WO 2007/125364.

US 2006/0004013 and WO 2006/046575 disclose cinnamide derivatives which inhibit production of Aβ. The compounds are said to reduce the production of both Aβ(1-40) and Aβ(1-42). Related cinnamide derivatives are disclosed in US 2007/0117798, US 2007/0219181, WO 2007/135969 and WO 2007/135970.

Further compounds which are claimed to modulate Aβ levels are disclosed in WO 2004/110350.

The compounds of the present invention selectively attenuate production of Aβ(1-42).

According to the invention there is provided a compound of formula I:

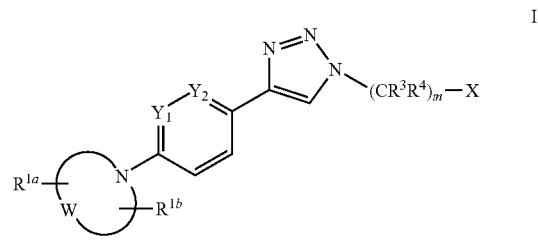

or a pharmaceutically acceptable salt or hydrate thereof;
wherein:

W completes an imidazole, triazole or pyrazole ring;

$R^{1a}$ and $R^{1b}$ independently represent H, $C_{1-6}$alkyl, or $CF_3$;

Y1 and Y2 each independently represents N or $CR^2$ provided Y1 and Y2 do not both represent N;

$R^2$ represents H, halogen, CN, $C_{1-6}$alkyl, $C_{1-6}$alkoxy or phenoxy, said alkyl, alkoxy and phenoxy optionally having up to 3 fluorine substituents or a cyclopropyl substituent;

each $R^3$ and each $R^4$ is independently H, $C_{1-6}$alkyl, F, $CO_2R^a$ or phenyl, where $R^a$ is H or $C_{1-4}$alkyl, with the proviso that not more than one $R^3$ or $R^4$ group may represent $CO_2R^a$ or phenyl;

or $R^3$ and $R^4$ attached to the same carbon atom may represent =O or may together complete a carbocycle of 3 to 6 atoms;

m is 0 or an integer in the range 1-6;

or —$(CR^3R^4)_m$— is a linker selected from:

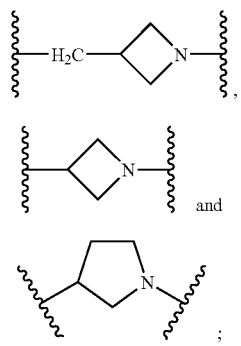

X is selected from H, $R^5$, $OR^6$, $OCOR^5$, $SR^5$, $NR^6R^7$, $NR^7COR^5$, $NR^7CO_2R^8$ and $Si(R^8)_3$;

$R^5$ is selected from:
(a) $C_{1-10}$alkyl, phenyl$C_{1-4}$alkyl, diphenylmethyl, $C_{3-10}$cycloalkyl or $C_{3-10}$cycloalkenyl, said $C_{3-10}$cycloalkyl or $C_{3-10}$cycloalkenyl optionally having up to 2 benzene rings fused thereto;
(b) phenyl which optionally forms part of a polycyclic system containing up to 3 additional rings, each of which independently comprises 5, 6 or 7 members and is independently carbocyclic or heterocyclic;
(c) 4-, 5-, 6- or 7-membered heterocyclic which optionally forms part of a polycyclic system containing up to 3 additional rings, each of which independently comprises 5, 6 or 7 members and is independently carbocyclic or heterocyclic;

where the term "polycyclic system" at each occurrence thereof refers to a system of fused rings, or a system of rings linked by covalent bonds, or any combination of fused and covalently-linked rings;

the group represented by $R^5$ optionally bearing up to 5 substituents independently selected from halogen, CN, $NO_2$, OH, oxo, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylsulfonyl, phenylsulfonyl, benzoyl, benzyl, naphthylmethyl, pyridylmethyl, $SO_2NR_2$, $CONR_2$, $NR_2$ and $R_2N$—$C_{1-4}$alkyl where each R is independently H or $C_{1-4}$alkyl or the two R groups together with the nitrogen to which they are attached complete a ring selected from azetidine, pyrrolidine, piperidine, piperazine and morpholine, and where the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$;

$R^6$ represents H or has the same definition as $R^5$;

$R^7$ represents H or $C_{1-6}$alkyl which optionally bears a substituent selected from halogen, CN, OH, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl; or $R^7$ represents $C_{3-6}$cycloalkyl, benzyl or phenyl, said $C_{3-6}$cycloalkyl, benzyl and phenyl optionally bearing up to 3 substituents selected from halogen, CN, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl;

or $R^6$ and $R^7$ attached to the same nitrogen atom may complete a heterocyclic ring of up to 6 members, optionally forming part of a fused ring system of up to 20 ring atoms, said ring or fused ring system optionally bearing up to 3 substituents selected from halogen, $C_{1-4}$alkyl, polyfluoro$C_{1-4}$alkyl, $C_{3-4}$cycloalkyl, phenyl, OH, $C_{1-4}$alkoxy, polyfluoro $C_{1-4}$ alkoxy, $C_{1-4}$alkylcarbonyl, $C_{1-4}$alkoxycarbonyl, $C_{1-4}$alkylsulfonyl, $CONR_2$ and $NR_2$ where each R is independently H or $C_{1-4}$alkyl or the two R groups together with the nitrogen to which they are attached complete a ring selected from azetidine, pyrrolidine, piperidine, piperazine and morpholine; and $R^8$ represents $C_{1-6}$alkyl, $C_{3-6}$cycloalkyl or phenyl;

with the proviso that if m is 0 or —$(CR^3R^4)_m$— is a linker represented by (i), (ii) or (iii) then X represents $R^5$ and $R^5$ is not N-heterocyclyl.

In a particular embodiment of the invention, there is provided a compound of formula IA:

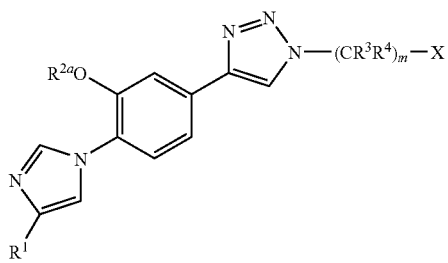

IA or a pharmaceutically acceptable salt or hydrate thereof; wherein:

$R^1$ represents H or $C_{1-6}$alkyl;

$R^{2a}$ represents $C_{1-6}$alkyl;

each $R^3$ and each $R^4$ is independently H, $C_{1-6}$alkyl, F or phenyl, with the proviso that not more than one $R^3$ or $R^4$ group may represent phenyl;

or $R^3$ and $R^4$ attached to the same carbon atom may represent =O or may together complete a carbocycle of 3 to 6 atoms;

X is selected from H, $R^5$, $OR^6$, $OCOR^5$, $SR^5$, $NR^6R^7$, $NR^7COR^5$, $NR^7CO_2R^8$ and $Si(R^8)_3$;

m is 0 or an integer in the range 1-6;

$R^5$ is selected from:
(a) $C_{1-10}$alkyl, phenyl$C_{1-4}$alkyl, or $C_{3-10}$cycloalkyl which optionally has up to 2 benzene rings fused thereto;
(b) phenyl which optionally forms part of a polycyclic system containing up to 3 additional rings, each of which is independently 5- or 6-membered and is independently carbocyclic or heterocyclic;
(c) 5- or 6-membered heterocyclic which optionally forms part of a polycyclic system containing up to 3 additional rings, each of which is independently 5- or 6-membered and is independently carbocyclic or heterocyclic;

(d) a lactam having the formula IB:

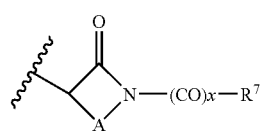

where x is 0 or 1 and A represents the atoms necessary to complete a 5-, 6- or 7-membered lactam ring which is optionally fused to a benzene ring;

and where the term "polycyclic system" at each occurrence thereof refers to a system of fused rings, or a system of rings linked by covalent bonds, or any combination of fused and covalently-linked rings;

the group represented by $R^5$ optionally bearing up to 4 substituents independently selected from halogen, CN, $NO_2$, OH, oxo, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl, $C_{1-4}$alkoxycarbonyl, $C_{1-4}$alkylthio, $C_{1-4}$alkylsulfonyl, $CONR_2$ and $NR_2$ where each R is independently H or $C_{1-4}$alkyl;

$R^6$ represents H or has the same definition as $R^5$;

$R^7$ represents H or $C_{1-6}$alkyl which optionally bears a substituent selected from halogen, CN, OH, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl; or $R^7$ represents $C_{3-6}$cycloalkyl, benzyl or phenyl, said $C_{3-6}$cycloalkyl, benzyl and phenyl optionally bearing up to 3 substituents selected from halogen, CN, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl;

or $R^6$ and $R^7$ attached to the same nitrogen atom may complete a heterocyclic ring of up to 6 members, optionally forming part of a fused ring system of up to 20 ring atoms, said ring or fused ring system optionally bearing up to 3 substituents selected from halogen, $C_{1-4}$alkyl, polyfluoro$C_{1-4}$alkyl, $C_{3-4}$cycloalkyl, phenyl, OH, $C_{1-4}$alkoxy, polyfluoro $C_{1-4}$ alkoxy, $C_{1-4}$alkylcarbonyl, $C_{1-4}$alkoxycarbonyl $C_{1-4}$alkylthio, $C_{1-4}$alkylsulfonyl, $CONR_2$ and $NR_2$ where each R is independently H or $C_{1-4}$alkyl; and $R^8$ represents $C_{1-6}$alkyl, $C_{3-6}$cycloalkyl or phenyl;

with the proviso that if m is 0 then X represents $R^5$ and $R^5$ is not N-heterocyclyl.

Where a variable occurs more than once in formula I, the identity taken by said variable at any particular occurrence is independent of the identity taken at any other occurrence.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expressions "polyfluoroalkyl" and "polyfluoroalkoxy" refer to alkyl and alkoxy groups respectively in which one or more of the hydrogen atoms is replaced by fluorine, and includes embodiments of such groups in which all the hydrogens are replaced by fluorine. Examples thus include $CH_2F$, $CHF_2$, $CF_3$, $CF_2CF_3$, $CH_2CF_3$ and $OCF_3$.

The expression "$C_{3-x}$cycloalkyl" where x is an integer greater than 3 refers to saturated cyclic hydrocarbon groups containing from 3 to x ring carbons. Where the value of x so permits, polycyclic systems containing fused rings and/or bridged bicyclic structures are included. Examples include cyclopropyl, cyclobutyl, cyclopentyl, cyclohexyl, decahydronaphthyl, bicyclo[2.2.2]octyl and adamantyl. "$C_{3-x}$cycloalkenyl" similarly refers to nonaromatic unsaturated cyclic hydrocarbon groups, such as cyclopentenyl and cyclohexenyl.

The term "heterocyclic" refers to ring systems in which at least one ring atom is selected from N, O and S. Unless indicated otherwise, the term includes both saturated and unsaturated systems, including aromatic systems. Heterocyclic groups may be bonded via a ring carbon or a ring nitrogen, unless otherwise indicated. "Heteroaryl" refers to a heterocyclic ring that is aromatic.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, benzenesulfonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of a carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the stereoisomeric forms encompassed by formula I, both optical and geometrical, fall within the scope of the invention, singly or as mixtures in any proportion.

In formula I, W completes an imidazole, triazole or pyrazole ring, said ring necessarily being connected to the rest of the molecule via one of its ring nitrogens. Most suitably W completes an imidazole or triazole ring, in particular 1H-imidazol-1-yl or 1H-imidazol-1,2,4-triazol-1-yl. $R^{1a}$ and $R^{1b}$ independently represent H, $C_{1-6}$alkyl or $CF_3$, in particular H, methyl or $CF_3$. In a particular embodiment at least one of $R^{1a}$ and $R^{1b}$ is other than H. Specific examples of groups completed by W, $R^{1a}$ and $R^{1b}$ include 4-methyl-1H-imidazol-1-yl, 2-methyl-1H-imidazol-1-yl, 2,4-dimethyl-1H-imidazol-1-yl, 4-trifluoromethyl-1H-imidazol-1-yl, 1H-imidazol-1-yl, 3-methyl-1H-1,2,4-triazol-1-yl and 4-methyl-1H-pyrazol-1-yl. In a particular embodiment W, $R^{1a}$ and $R^{1b}$ complete a 4-methyl-1H-imidazol-1-yl group.

Y1 and Y2 each independently represents N or $CR^2$ where $R^2$ represents H, halogen, CN, $C_{1-6}$alkyl, $C_{1-6}$alkoxy or phenoxy, said alkyl, alkoxy and phenoxy optionally having up to 3 fluorine substituents or a cyclopropyl substituent, but Y1 and Y2 do not both represent N. Very suitably, one of Y1 and Y2 represents CH and the other represents $CR^2$ and $R^2$ very suitably represents H, F, Cl, CN, methyl, methoxy, 2,2,2-trifluoroethoxy, cyclopropylmethoxy or phenoxy, in particular methoxy. In a particular embodiment Y2 represent CH.

In the compounds of formula I, X is connected to the 1,2,3-triazole ring by a linker —$(CR^3CR^4)_m$— where m is 0 or an integer in the range 1-6 and R³ and R⁴ are as defined previously, or the linker has the structure (i), (ii) or (iii):

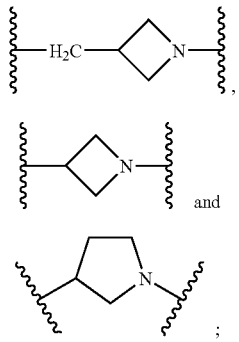

Most suitably, m is 0 or an integer in the range 1-3, or the linker has the structure (i), (ii) or (iii), but when X is connected directly to the triazole ring (i.e. when m=0) or by a linker having the structure (i), (ii) or (iii), X must represent R⁵ which is other than N-heterocyclyl.

When m is other than 0, each R³ and R⁴ is independently H, $C_{1-6}$alkyl, F, $CO_2R^a$ or phenyl, with the proviso that not more than one R³ or R⁴ group may represent $CO_2R^a$ or phenyl; or R³ and R⁴ attached to the same carbon atom may together represent =O (i.e. complete a carbonyl group); or R³ and R⁴ attached to the same carbon atom may together complete a carbocycle of 3 to 6 atoms. In a particular embodiment, when m is 2 or more, not more than one CR³R⁴ group represents CO and not more than one CR³R⁴ group represents a carbocycle. Furthermore, when m is 1 or more, the CR³R⁴ group bonded to the triazole ring is preferably not CO, and when X is SR⁵ or Si(R⁸)₃, the adjacent CR³R⁴ group is preferably not CO.

Specific embodiments of the linker $(CR^3R^4)_m$ include a bond, CH₂, CH₂CH₂, CH₂CH₂CH₂, CF₂, CH₂CO, CF₂CO, CH(CH₃), CH(Ph)CO, CHFCO, (1,1-cyclobutanediyl)CO, CH(CO₂H)CH₂CH₂, CH(CO₂CH₃)CH₂C(CH₃)₂ and the structures (i), (ii) and (iii). In a particular embodiment, $(CR^3R^4)_m$ represents CH₂, CF₂, CH₂CO or CF₂CO. In another particular embodiment, $(CR^3R^4)_m$ represents a bond. In another particular embodiment, $(CR^3R^4)_m$ represents one of the structures (i), (ii) and (iii).

X is selected from H, R⁵, OR⁶, OCOR⁵, SR⁵, NR⁶R⁷, NR⁷COR⁵, NR⁷CO₂R⁸ and Si(R⁸)₃ where R⁵-R⁸ are as defined previously and described in detail below. In a particular embodiment, X is selected from R⁵, OR⁵, SR⁵ and NR⁶R⁷.

In a first sub-embodiment, R⁵ represents $C_{1-10}$alkyl, phenyl$C_{1-4}$alkyl, diphenylmethyl, $C_{3-10}$cycloalkyl or $C_{3-10}$cycloalkenyl, said $C_{3-10}$cycloalkyl or $C_{3-10}$cycloalkenyl optionally having up to 2 benzene rings fused thereto. Within this sub-embodiment, particularly suitable alkyl groups include those containing up to 6 carbon atoms, such as methyl, ethyl, n-propyl, isopropyl, n-butyl, sec-butyl, isobutyl and t-butyl. Within this sub-embodiment, particularly suitable cycloalkyl and cycloalkenyl groups include cyclopentyl, cyclohexyl, cyclooctyl, adamantyl, 9-fluorenyl, cyclohexen-1-yl, 10,11-dihydro-5H-dibenzo[a,d]cyclohepten-5-yl and bicyclo[4.2.0]octa-1,3,5-trien-7-yl. Within this sub-embodiment, particularly suitable phenyl$C_{1-4}$alkyl groups include benzyl. Within this sub-embodiment, when R⁵ represents diphenylmethyl the linker $(CR^3R^4)_m$ very suitably represents a bond or one of the structures (i), (ii) and (iii).

In a second sub-embodiment, R⁵ represents phenyl which optionally forms part of a polycyclic system containing up to 3 additional rings, each of which is independently 5-, 6- or 7-membered and is independently carbocyclic or heterocyclic. Thus, a phenyl group represented by R⁵ may optionally be linked by covalent bonds to one or more 5-, 6- or 7-membered carbocyclic or heterocyclic rings, and/or may be fused to one or more such rings. Said 5-, 6- or 7-membered carbocyclic or heterocyclic rings may themselves be fused and/or covalently to one or more further 5-, 6- or 7-membered carbocyclic or heterocyclic rings, subject to the total number of rings being 4 or less. Heterocyclic rings typically comprise not more than 3 ring atoms selected from N, O and S, the remainder being carbon. Said further rings may be saturated or unsaturated, including aromatic. Examples of 5-, 6- and 7-membered rings to which the phenyl may be fused or covalently linked include benzene, cyclopentane, cyclohexane, pyridine, thiadiazole, oxadiazole, pyrazole, thiophene, pyrrole, 1,4-dioxepane and 5,6-dihydro-2H-pyran-2-one. Within this sub-embodiment, examples of fused polycyclic systems represented by R⁵ include naphthyl, anthracenyl, pyrenyl, phenanthrenyl, 5-indanyl, 1,2,3,4-tetrahydronaphthalen-6-yl, 8-quinolinyl, 1,2,3-benzothiadiazol-5-yl and 3,4-dihydro-2H-1,5-benzodioxepin-7-yl. Within this sub-embodiment, examples of covalently linked polycyclic systems represented by R⁵ include biphenyl, (oxadiazol-3-yl)phenyl, (thiophen-2-yl)phenyl, (pyrazol-1-yl)phenyl, (thiazol-4-yl)phenyl, (pyrrol-1-yl)phenyl, (benzoxazol-2-yl)phenyl and (5-pyridin-4-yl-1,2,4-oxadiazol-3-yl)phenyl. Within this sub-embodiment, examples of polycyclic systems comprising both fused and covalently linked rings include 2-oxo-4-phenyl-2H-chromen-7-yl and 4-phenylquinolin-7-yl.

In a third sub-embodiment, R⁵ represents 4-, 5-, 6- or 7-membered heterocyclic which optionally forms part of a polycyclic system containing up to 3 additional rings, each of which independently comprises 5, 6 or 7 members and is independently carbocyclic or heterocyclic. Thus, a 4-, 5-, 6- or 7-membered heterocyclic ring represented by R⁵ may optionally be linked by covalent bonds to one or more additional 5-, 6- or 7-membered carbocyclic or heterocyclic rings, and/or may be fused to one or more such rings. Said 5-, 6- or 7-membered carbocyclic or heterocyclic rings may themselves be fused and/or covalently to one or more further 5-, 6- or 7-membered carbocyclic or heterocyclic rings, subject to the total number of rings being 4 or less. Said further rings may be saturated or unsaturated, including aromatic. Heterocyclic rings represented by R⁵ or forming part of R⁵ typically comprise not more than 3 ring atoms selected from N, O and S, the remainder being carbon. Within this sub-embodiment, examples of individual heterocyclic rings represented by R⁵ include azetidine, pyrrolidine, piperidine, oxazolidine, morpholine, azepane, 1,4-diazepane, pyrazole, isoxazole, oxazole, thiazole, triazole, pyridine, pyrimidine and oxadiazole. Examples of fused heterocyclic systems represented by R⁵ include imidazo[1,2-a]pyrimidin-2-yl, 2-benzothiazolyl, 2-benzoxazolyl, 2-quinazolinyl, 2-quinolinyl, 2-benzimidazolyl, 9-acridinyl and 4,5,6,7-tetrahydro-2H-indazol-2-yl. Examples of covalently linked heterocyclic systems represented by R⁵ include (1-phenyl)tetrazol-5-yl, (1-phenyl)pyrazol-5-yl, and pyridazin-3-one which bears a phenyl substituent in one or more of the 2-, 4- and 6-positions.

Within this third sub-embodiment there is a class of compounds in which R⁵ represents a 5-, 6- or 7-membered lactam ring in which one of the ring atoms, other than the lactam nitrogen, is optionally O, N or S, said lactam ring optionally being fused to a ring system selected from benzene, naphthalene, biphenyl, $C_{5-10}$cycloalkyl and 5- or 6-membered heteroaryl; and said lactam ring optionally being covalently linked to up to 2 rings selected from phenyl, cyclopentane, cyclohexane and cyclohexene, the total number of rings in the group represented by $R^5$ being not more than 4. Examples of rings and ring systems within this class include:
azepan-2-one,
5-phenylazepan-2-one,
5-cyclohexylazepan-2-one,
2-azabicyclo[3.2.1]octan-3-one,
2-azabicyclo[4.2.1]nonan-3-one,
octahydro-1,5-methanocyclopenta[c]azepin-3(2H)-one,
octahydro-5a,8-methano-1-benzazepin-2(3H)-one,
decahydro-2H-1-benzazepin-2-one,
1,3,4,5-tetrahydro-2H-1-benzazepin-2-one,
1,2,4,5-tetrahydro-3H-2-benzazepin-3-one,
1,3,4,5-tetrahydro-2H-3-benzazepin-2-one,
1-cyclohexyl-1,3,4,5-tetrahydro-2H-1-benzazepin-2-one,
1-cyclohexenyl-1,3,4,5-tetrahydro-2H-1-benzazepin-2-one,
5-phenyl-1,3,4,5-tetrahydro-2H-1-benzazepin-2-one,
6-phenyl-1,3,4,5-tetrahydro-2H-1-benzazepin-2-one,
1,2,3,5-tetrahydro-4H-naphtho[2,1-b]azepin-4-one,
5,11-dihydro-6H-dibenzo[b,e]azepin-6-one,
1,3,4,5-tetrahydro-2H-1,4-benzodiazepin-2-one,
5-phenyl-1,3-dihydro-2H-1,4-benzodiazepin-2-one,
1-phenyl-1H-1,5-benzodiazepin-2,4(3H,5H)-dione,
2,3-dihydro-1,5-benzoxazepin-4(5H)-one,
2H-1,4-benzothiazin-3(4H)-one,
1,3-dihydro-2H-furo[3,2-e]diazepin-2-one,
4,6,7,8-tetrahydro-5H-thieno[3,2-b]azepin-5-one,
5,7,8,9-tetrahydro-6H-pyrido[3,2-b]azepin-6-one,
5,6,7,9-tetrahydro-8H-pyrido[2,3-b]azepin-8-one,
1-phenylpyrrolidin-2-one,
piperidin-2-one,
4-phenylpiperidin-2-one,
octahydroquinolin-2(1H)-one,
2-pyridone,
2-phenylpyridazin-3(2H)-one,
6-phenylpyridazin-3(2H)-one,
4-phenylpyridazin-3(2H)-one,
and 3-phenyloxazolidin-2-one.

Within this class of the third sub-embodiment a particular example of a lactam ring system represented by $R^5$ is 1,3,4,5-tetrahydro-2H-1-benzazepin-2-one.

In all three of the sub-embodiments detailed above, the group $R^5$ optionally bears up to 5 substituents independently selected from halogen, CN, $NO_2$, OH, oxo, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, phenylsulfonyl, benzoyl, benzyl, naphthylmethyl, pyridylmethyl, $SO_2NR_2$, $CONR_2$, $NR_2$ and $R_2N$—$C_{1-4}$alkyl where each R is independently H or $C_{1-4}$alkyl or the two R groups together with the nitrogen to which they are attached complete a ring selected from azetidine, pyrrolidine, piperidine, piperazine and morpholine, and where the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$. Phenyl or heterocyclic embodiments of $R^5$ (i.e. the second and third sub-embodiments detailed above) very suitably bear 0-4 substituents, while $R^5$ in the first sub-embodiment detailed above preferably bears 0-3 substituents, most preferably 0-2 substituents. When more than 2 substituents are present, preferably at least one of the substituents is halogen or $C_{1-4}$alkyl. Particular examples of suitable substituents include halogen (especially F, Cl, Br), CN, $NO_2$, OH, oxo, $C_{1-4}$alkyl (especially methyl, ethyl, n-propyl, isopropyl and t-butyl), polyfluoro$C_{1-4}$alkyl (especially $CF_3$, $CH_2CF_3$, $CH_2CHF_2$ and $CH_2CH_2F$), cyclopropyl, cyclobutyl, cyclopropylmethyl, $C_{1-4}$alkoxy (especially methoxy), and $OCF_3$. It will be readily apparent to those skilled in the art that an oxo substituent cannot be present on an aromatic moiety represented by $R^5$ or forming part of a group represented by $R^5$. However, when a hydroxyl substituent on such an aromatic moiety is capable of tautomerising to the corresponding keto form, both tautomeric forms are included in the invention.

$R^6$ represents H or has the same definition as $R^5$; or when $R^6$ is attached to the same nitrogen atom as $R^7$, $R^6$ and $R^7$ together may complete a heterocyclic ring of up to 6 members, optionally forming part of a fused ring system of up to 20 ring atoms, said ring or fused ring system optionally bearing up to 3 substituents selected from halogen, $C_{1-4}$alkyl, polyfluoro$C_{1-4}$alkyl, $C_{3-4}$cycloalkyl, phenyl, OH, $C_{1-4}$alkoxy, polyfluoro$C_{1-4}$alkoxy, $C_{1-4}$alkylcarbonyl, $C_{1-4}$alkoxycarbonyl $C_{1-4}$alkylthio, $C_{1-4}$alkylsulfonyl, $CONR_2$ and $NR_2$ where each R is independently H or $C_{1-4}$alkyl or the two R groups together with the nitrogen to which they are attached complete a ring selected from azetidine, pyrrolidine, piperidine, piperazine and morpholine. In addition to the nitrogen to which $R^6$ and $R^7$ are mutually attached, a ring or ring system completed by $R^6$ and $R^7$ comprises ring atoms selected from C, N, O and S, but preferably not more than 3 ring atoms in total are selected from N, O and S. A ring completed by $R^6$ and $R^7$ or forming part of a fused system completed by $R^6$ and $R^7$, may be saturated or unsaturated, including aromatic. Examples of monocyclic rings completed by $R^6$ and $R^7$ include pyrrolidine, piperidine, morpholine, piperazine and aza-cyclooctane, and examples of fused ring systems completed by $R^6$ and $R^7$ include tetrahydroquinoline, octahydroquinoline, indoline, 3,4-dihydro-2H-1,4-benzoxazine, 10,11-dihydro-5H-dibenzo[b,f]azepine and 2,3,3a,4,5,6-hexaahydro-1H-pyrazino[3,2,1-jk]carbazole, any of which may bear up to 3 substituents as defined previously. Preferred substituents include halogen, $C_{1-4}$alkyl, OH and $CF_3$.

When $R^6$ takes the same definition as $R^5$, particularly suitable identities include optionally-substituted $C_{1-10}$alkyl, phenyl$C_{1-4}$alkyl, $C_{3-10}$cycloalkyl, phenyl and 5- or 6-membered heteroaryl, wherein the said phenyl and 5- or 6-membered heteroaryl are optionally fused to a further 5- or 6-membered carbocyclic or heterocyclic ring, and wherein "optionally-substituted" refers to optional substitution as defined and discussed above in connection with $R^5$.

$R^7$ represents H or $C_{1-6}$alkyl which optionally bears a substituent selected from halogen, CN, OH, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl; or $R^7$ represents $C_{3-6}$cycloalkyl, benzyl or phenyl, said $C_{3-6}$cycloalkyl, benzyl and phenyl optionally bearing up to 3 substituents selected from halogen, CN, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl; or $R^7$ attached to the same nitrogen atom as $R^6$ may completes a ring as described previously.

When X is $NR^7COR^5$ or $NR^7CO_2R^8$, $R^7$ is very suitably H or optionally substituted $C_{1-6}$alkyl. Specific examples of groups represented by $R^7$ include H, phenyl, 4-fluorophenyl, cyclopentyl, cyclohexyl, benzyl, 4-fluorobenzyl, α-methylbenzyl, methyl, ethyl, and isopropyl, isobutyl and 2,2,2-trifluoroethyl.

$R^8$ represents $C_{1-6}$alkyl (in particular methyl, ethyl, n-propyl, isopropyl or t-butyl), $C_{3-6}$cycloalkyl or phenyl. In a particular embodiment, $R^8$ represents methyl.

A first subset of the compounds of the invention consists of the compounds of formula II:

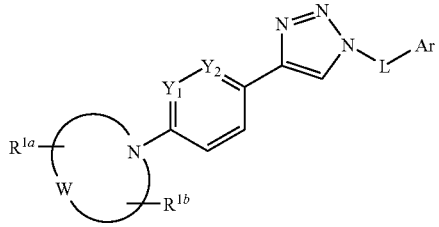

and the pharmaceutically acceptable salts or hydrates thereof; wherein:

L represents $CR^3R^4$, $CH_2CH_2$ or $CH_2CH_2CH_2$;

Ar represents an aromatic moiety selected from:

(a) phenyl which is optionally fused to 1, 2 or 3 additional 5- or 6-membered carbocycles;

(b) phenyl which is fused to a 5- or 6-membered heterocycle;

(c) 5- or 6-membered heteroaryl which is optionally fused to 1 or 2 additional 5- or 6-membered carbocyclic or heterocyclic rings; and (d) a covalently linked bicyclic or tricyclic system represented by the formula Ar1-Ar2-(Ar3)y where Ar1, Ar2 and Ar3 are independently selected from phenyl, 5- or 6-membered heteroaryl and benzofused 5- or 6-membered heteroaryl, and y is 0 or 1;

the moiety Ar bearing 0-4 substituents independently selected from halogen, $NO_2$, CN, OH, $C_{1-4}$alkyl, $CF_3$, cyclopropyl, cyclobutyl, $C_{1-4}$alkoxy, and $OCF_3$;

and W, Y1, Y2, $R^{1a}$, $R^{1b}$, $R^3$ and $R^4$ have the same definitions and preferred identities as before.

In a particular embodiment of this subset, Y2 represents CH, Y1 represents $CR^2$, $R^2$ represents $C_{1-6}$alkoxy, and W, $R^{1a}$ and $R^{1b}$ complete a 1H-imidazol-1-yl group which is optionally substituted in the 4-position with $C_{1-6}$alkyl. Very suitably, Y represents C—OMe and W, $R^{1a}$ and $R^{1b}$ complete a 4-methyl-1H-imidazol-1-yl group.

L very suitably represents $CH_2$, $CF_2$, $CH(CH_3)$ or $CH_2CH_2$.

When Ar bears more than 2 substituents, preferably at least one of them is halogen or $C_{1-4}$alkyl.

Suitable identitities for Ar in accordance with (a) above include optionally substituted phenyl, naphthyl, tetrahydronaphthyl, anthracenyl, pyrenyl and phenanthrenyl.

Suitable identitities for Ar in accordance with (b) above include optionally substituted 8-quinolinyl, 5-benzothiadiazolyl, and 3,4-dihydro-2H-1,5-benzodioxepin-7-yl.

Suitable identitities for Ar in accordance with (c) above include optionally substituted 2-pyridyl, 3-pyridyl, 4-isoxazolyl, 1,2,4-oxadiazol-3-yl, 2-quinolinyl, 9-acridinyl, 2-quinazolinyl, 1H-imidazol-2-yl, 1H-benzimidazol-2-yl, and 1,3-benzoxazol-2-yl.

Suitable identities for Ar in accordance with (d) above include those summarised in the following table.

| Ar1 | Ar2 | y | Ar3 |
|---|---|---|---|
| tetrazol-1,5-diyl | 3-nitrophenyl | 0 | — |
| phenyl-1,4-diyl | phenyl | 0 | — |
| phenyl-1,4-diyl | 5-methyl-1,2,4-oxadiazol-3-yl | 0 | — |
| phenyl-1,3-diyl | 5-methyl-1,2,4-oxadiazol-3-yl | 0 | — |
| phenyl-1,2-diyl | 2-thienyl | 0 | — |
| phenyl-1,4-diyl | 1-pyrazolyl | 0 | — |
| phenyl-1,3-diyl | 2-methylthiazol-4-yl | 0 | — |
| phenyl-1,4-diyl | 1-pyrrolyl | 0 | — |
| phenyl-1,3-diyl | 1-pyrrolyl | 0 | — |
| phenyl-1,4-diyl | 1,2,4-oxadiazol-3,5-diyl | 1 | 4-pyridyl |
| phenyl-1,4-diyl | benzoxazol-2-yl | 0 | — |

| Ar1 | Ar2 | y | Ar3 |
|---|---|---|---|
| | 2-naphthyl | 0 | — |
| | phenyl | 0 | — |
| | phenyl* | 0 | — |

*-attachment point of Ar2 or Ar3 as appropriate.

In a particular embodiment, Ar1 represents phenyl, Ar2 represents 5-membered heteroaryl which is optionally benzofused, and y is 0.

A second subset of the compounds of the invention consists of the compounds of formula III:

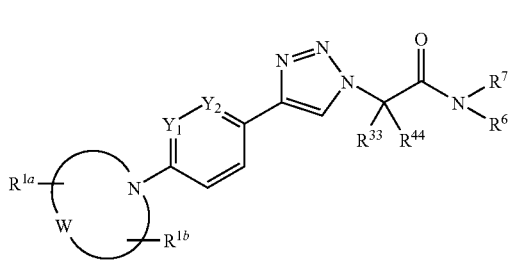

III and the pharmaceutically acceptable salts or hydrates thereof; wherein:

$R^{33}$ and $R^{44}$ independently represent H, $C_{1-6}$alkyl, F or phenyl, with the proviso that not more than one of $R^{33}$ and $R^{44}$ may represent phenyl;

or $R^{33}$ and $R^{44}$ together complete a carbocycle of 3 to 6 atoms;

and W, Y1, Y2, $R^{1a}$, $R^{1b}$, $R^6$ and $R^7$ have the same definitions and preferred identities as before.

In a particular embodiment of this subset, Y2 represents CH, Y1 represents $CR^2$, $R^2$ represents $C_{1-6}$alkoxy, and W, $R^{1a}$ and $R^{1b}$ complete a 1H-imidazol-1-yl group which is optionally substituted in the 4-position with $C_{1-6}$alkyl. Very suitably, Y represents C—OMe and W, $R^{1a}$ and $R^{1b}$ complete a 4-methyl-1H-imidazol-1-yl group.

In a particular embodiment the linker $CR^3R^4$ is selected from $CH_2$, $CF_2$ and $CH(CH_3)$.

Within this subset $R^6$ is preferably selected from optionally-substituted $C_{1-10}$alkyl, phenyl$C_{1-4}$alkyl, $C_{3-10}$cycloalkyl, phenyl and 5- or 6-membered heteroaryl, wherein the said phenyl and 5- or 6-membered heteroaryl are optionally fused to a further 5- or 6-membered carbocyclic or heterocyclic ring, and wherein "optionally-substituted" refers to 0-4 substituents independently selected from halogen, CN, $NO_2$, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl, $C_{1-4}$alkoxycarbonyl, $C_{1-4}$alkylthio, $C_{1-4}$alkylsulfonyl, $CONR_2$ and $NR_2$ where each R is independently H or $C_{1-4}$alkyl or the two R groups together with the nitrogen to which they are attached complete a ring selected from azetidine, pyrrolidine, piperidine, piperazine and morpholine. When more than 2 substituents are present, preferably at least one of the substituents is halogen or $C_{1-4}$alkyl. Particular examples of suitable substituents include halogen (especially F, Cl, Br), CN, $NO_2$, OH, $C_{1-4}$alkyl (especially methyl, ethyl, n-propyl, isopropyl and t-butyl), $CF_3$, cyclopropyl, cyclobutyl, $C_{1-4}$alkoxy (especially methoxy), and $OCF_3$.

When $R^6$ is as defined in the previous paragraph, $R^7$ represents H or $C_{1-6}$alkyl which optionally bears a substituent selected from halogen, CN, OH, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl; or $R^7$ represents $C_{3-6}$cycloalkyl, benzyl or phenyl, said $C_{3-6}$cycloalkyl, benzyl and phenyl optionally bearing up to 3 substituents selected from halogen, CN, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl.

Examples of groups represented by $R^6$ include phenyl, cyclohexyl, 4-fluorobenzyl, 6-methoxy-5-trifluoromethyl-3-pyridyl, cyclooctyl, 2,6-dimethylphenyl, 3-chloro-4-fluorophenyl, 5,7-difluoro-2-benzothiazolyl, 3,5-bis(trifluoromethyl)phenyl, 4-trifluoromethoxyphenyl, benzyl, 3,5-difluorophenyl, adamantyl, naphthyl, 2-methyl-4,5,6,7-tetrahydroindazol-3-yl, 3,5-dimethoxyphenyl, and 8-quinolyl. Further examples of groups represented by $R^6$ include α-methylbenzyl, 2,3,4-trifluorophenyl, 2,3-dihydro-1H-inden-5-yl, 4-t-butylcyclohexyl, 4-fluorophenyl, 2,4,6-trimethylphenyl, 2,4-difluorophenyl, 2,4-dimethoxyphenyl, 2,2,6,6-tetramethylpiperidin-4-yl, and isobutyl.

Examples of groups represented by $R^7$ include H, methyl, isopropyl, cyclohexyl, and phenyl. Further examples of groups represented by $R^7$ include cyclopentyl, benzyl, 4-chlorobenzyl, α-methylbenzyl, 2,2,2-trifluoroethyl, and isobutyl.

Alternatively, $R^6$ and $R^7$ together complete a heterocyclic ring of up to 6 members, optionally forming part of a fused ring system of up to 20 ring atoms, said ring or fused ring system optionally bearing up to 3 substituents selected from halogen, $C_{1-4}$alkyl, polyfluoro$C_{1-4}$alkyl, $C_{3-4}$cycloalkyl, phenyl, $C_{1-4}$alkoxy, polyfluoro$C_{1-4}$alkoxy, $C_{1-4}$alkylcarbonyl, $C_{1-4}$alkoxycarbonyl $C_{1-4}$alkylthio, $C_{1-4}$alkylsulfonyl, $CONR_2$ and $NR_2$ where each R is independently H or $C_{1-4}$alkyl. In addition to the nitrogen to which $R^6$ and $R^7$ are mutually attached, a ring or ring system completed by $R^6$ and $R^7$ comprises ring atoms selected from C, N, O and S, bur preferably not more than 3 ring atoms in total are selected from N, O and S. A ring completed by $R^6$ and $R^7$ or forming part of a fused system completed by $R^6$ and $R^7$ may be saturated or unsaturated, including aromatic. Preferred substituents include halogen, $C_{1-4}$alkyl, phenyl, OH and $CF_3$. Examples of cyclic groups represented by $NR^6R^7$ include octahydroquinolin-1-yl, 4-phenylpiperazin-1-yl, indolin-1-yl, piperidin-1-yl, 1-azacyclooctyl,

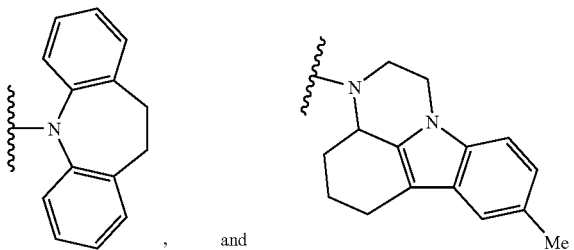

, and

Further examples of cyclic groups represented by $NR^6R^7$ include decahydroquinolin-1-yl, 3,4-dihydro-2H-1,4-benzoxazin-4-yl, and 2,2,4-trimethyl-1,2,3,4-tetrahydroquinolin-1-yl.

A third subset of the compounds of the invention consists of the compounds of formula IV:

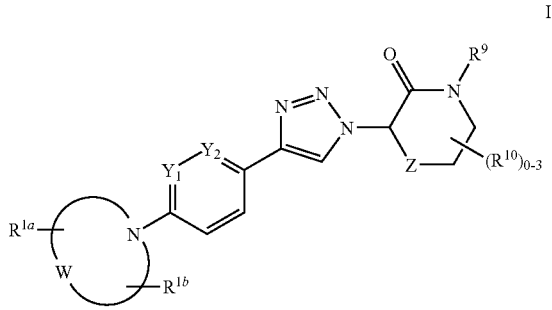

IV and the pharmaceutically acceptable salts or hydrates thereof; wherein:

Z represents $CH_2$, $CH_2$—$CH_2$, O, S, NH, $CH_2$—O, $CH_2$—S or $CH_2$—NH;

$R^9$ represent H, $C_{1-4}$alkyl, $C_{2-4}$alkenyl, polyfluoro$C_{1-4}$alkyl, $C_{3-6}$cycloalkyl, $C_{3-6}$cycloalkyl$C_{1-4}$alkyl, $C_{1-4}$alkoxy$C_{1-4}$alkyl, amino$C_{1-4}$alkyl, $C_{1-4}$alkylcarbonyl, polyfluoro$C_{1-4}$alkylcarbonyl, $C_{1-4}$alkylsulfonyl, phenyl, phenylsulfonyl, benzoyl, benzyl, naphthylmethyl or pyridylmethyl, where said phenyl and the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$;

each $R^{10}$ independently represents halogen, OH, $C_{1-4}$alkyl, $C_{2-4}$alkenyl, polyfluoro$C_{1-4}$alkyl, $C_{3-6}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl or the two R groups together with the nitrogen to which they are attached complete a ring selected from azetidine, pyrrolidine, piperidine, piperazine and morpholine; or phenyl or benzyl either of which optionally is substituted with halogen, $C_{1-4}$alkyl, $C_{1-4}$alkoxy or $CF_3$;

or two $R^{10}$ groups attached to adjacent ring positions optionally complete a fused benzene, naphthalene, cyclopentane, cyclohexane, pyridine, thiophene or furan ring which optionally bears up to 2 substituents independently selected from halogen, $NO_2$, CN, OH, phenyl, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro $C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl;

or two $R^{10}$ groups attached to non-adjacent ring positions optionally complete a $CH_2$ or $CH_2CH_2$ bridge;

and W, Y1, Y2, $R^{1a}$ and $R^{1b}$ have the same definitions and preferred identities as before.

In the compounds of formula IV, specific examples of groups completed by W, $R^{1a}$ and $R^{1b}$ include 4-methyl-1H-imidazol-1-yl, 2-methyl-1H-imidazol-1-yl, 2,4-dimethyl-1H-imidazol-1-yl, 4-trifluoromethyl-1H-imidazol-1-yl, 1H-imidazol-1-yl, 3-methyl-1H-1,2,4-triazol-1-yl and 4-methyl-1H-pyrazol-1-yl.

Very suitably, Y2 represents CH, Y1 represents $CR^2$ where $R^2$ represents H, F, Cl, CN, methyl, methoxy, 2,2,2-trifluoroethoxy, cyclopropylmethoxy or phenoxy, and in a particular embodiment of this subset W, $R^{1a}$ and $R^{1b}$ complete a 4-methyl-1H-imidazol-1-yl group and Y represents C—OMe.

Examples of groups represented by $R^9$ include H, $C_{1-4}$alkyl (including methyl, ethyl, isopropyl, t-butyl and 2,2-dimethylpropyl), polfluoro$C_{1-4}$alkyl (including 2-fluoroethyl, 2,2-difluoroethyl and 2,2,2-trifluoroethyl), cyclohexyl, cyclopropylmethyl, ethoxymethyl, 2-aminoethyl, 2-methylprop-2-en-1-yl, cyclohex-2-en-1-yl, phenyl, benzyl, p-toluenesulfonyl, 2-pyridylmethyl, 3-pyridylmethyl and 4-pyridylmethyl.

Preferred identities for $R^{10}$ include $C_{1-4}$alkyl (especially methyl), polyfluoro$C_{1-4}$alkyl (especially $CF_3$), benzyl, phenyl and cyclohexyl. When more than one $R^{10}$ is present, preferably at least one $R^{10}$ is alkyl or two $R^{10}$ groups complete a ring as described above. Examples of fused rings completed by two $R^{10}$ groups include benzene, naphthalene, cyclopentane, cyclohexane, pyridine, thiophene and furan, any of which is optionally substituted as indicated above. Preferred substituents include halogen, $NO_2$, $C_{1-4}$alkyl, phenyl, polyfluoro$C_{1-4}$alkyl, $C_{1-4}$alkoxy and polyfluoro$C_{1-4}$alkoxy. Preferably not more than one phenyl or $NO_2$ substituent is present.

In a particular embodiment of this subset, two $R^{10}$ groups complete a fused benzene ring optionally substituted with phenyl or $NO_2$ or with up to 2 substituents selected from halogen, $C_{1-4}$alkyl, polyfluoro$C_{1-4}$alkyl, $C_{1-4}$alkoxy and polyfluoro$C_{1-4}$alkoxy. Within this embodiment, A very suitably represents $CH_2CH_2$.

Groups represented by $R^{10}$ and fused rings formed by two adjacent $R^{10}$ groups may be attached at any available position, including positions contained within A and the position to which the triazole ring is attached.

Within the subset of compounds represented by formula IV and the pharmaceutically acceptable salts or hydrates thereof, there is a class of compounds which are represented by formula IV(a):

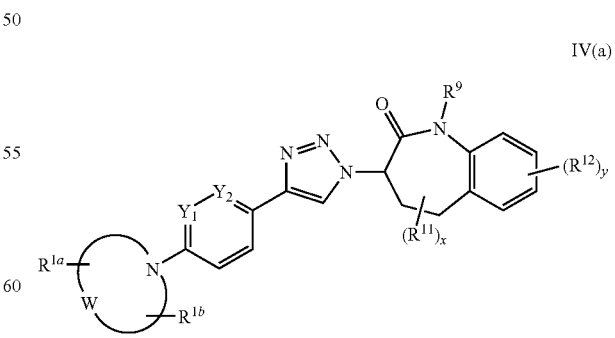

IV(a)

and the pharmaceutically acceptable salts or hydrates thereof; wherein x is 0, 1 or 2;

y is 0, 1 or 2;

$R^{11}$ represents methyl or phenyl with the proviso that x is not 2 when $R^{11}$ is phenyl, each $R^{12}$ is independently selected from phenyl, $NO_2$ halogen, $C_{1-4}$alkyl, polyfluoro$C_{1-4}$alkyl, $C_{1-4}$alkoxy and polyfluoro$C_{1-4}$alkoxy with the provision that not more than one $R^{12}$ represents phenyl or $NO_2$;

and $R^9$, W, Y1, Y2, $R^{1a}$ and $R^{1b}$ have the same definitions and preferred identities as before.

In the compounds of formula IV(a), specific examples of groups completed by W, $R^{1a}$ and $R^{1b}$ include 4-methyl-1H-imidazol-1-yl, 2-methyl-1H-imidazol-1-yl, 2,4-dimethyl-1H-imidazol-1-yl, 4-trifluoromethyl-1H-imidazol-1-yl, 1H-imidazol-1-yl, 3-methyl-1H-1,2,4-triazol-1-yl and 4-methyl-1H-pyrazol-1-yl.

Very suitably, one of Y1 and Y2 represents CH and the other represents $CR^2$ and $R^2$ represents H, F, Cl, CN, methyl, methoxy, 2,2,2-trifluoroethoxy, cyclopropylmethoxy or phenoxy. In certain examples, Y1 is CH, Y2 is $CR^2$ and $R^2$ is H, F, methoxy or cyclopropylmethoxy. In certain other examples Y2 is CH. In a particular embodiment of this subset W, $R^{1a}$ and $R^{1b}$ complete a 4-methyl-1H-imidazol-1-yl group, Y2 is CH and Y1 represents C—OMe.

When x is 2, the methyl groups may be attached at the same or different positions. In a particular embodiment x is 0.

Preferred identities for $R^{12}$ include halogen (especially F, Cl and Br), methyl, methoxy, $CF_3$, and $OCF_3$.

A fourth subset of the compounds of the invention consists of the compounds of formula V:

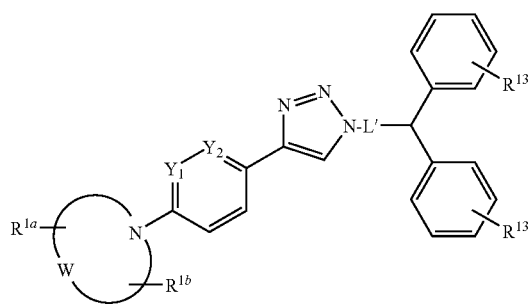

V and the pharmaceutically acceptable salts or hydrates thereof; wherein:

L' represents a bond or a linker selected from:

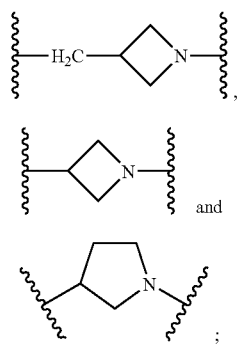

(i)

(ii) and (iii) ;

each $R^{13}$ independently represents H, halogen, $C_{1-4}$alkyl, polyfluoro$C_{1-4}$alkyl, $C_{1-4}$alkoxy or polyfluoro$C_{1-4}$alkoxy;

and W, Y1, Y2, $R^{1a}$ and $R^{1b}$ have the same definitions and preferred identities as before.

In one embodiment of the fourth subset, the $R^{13}$ groups are the same and are selected from H, methyl, F and Cl.

Compounds of formula I may be prepared by reaction of an azide of formula $X—(CR^3R^4)_m—N_3$ (1) with an alkyne of formula (2):

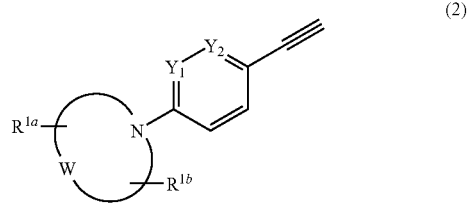

(2)

where W, Y1, Y2, $R^{1a}$, $R^{1b}$, $R^3$, $R^4$, m and X have the same meanings as before. The reaction takes place at ambient temperature in aqueous ethanol or DMF in the presence of copper (II) sulphate and sodium ascorbate.

Azides (1) may be prepared from the corresponding halides by reaction with sodium azide in ethanol or DMF. In the case where m is 0 and X is aromatic, the azide may be prepared by diazotisation of the appropriate aromatic amine followed by treatment with sodium azide. Where they are not commercially available, the relevant halides are obtainable by routes described in the literature or minor variations thereof. Procedures for the halogenation of lactams are described later herein.

Aldehydes (2) are obtainable by reaction of an imidazole, triazole or pyrazole (3) with a fluoro-substituted arylaldehyde (4):

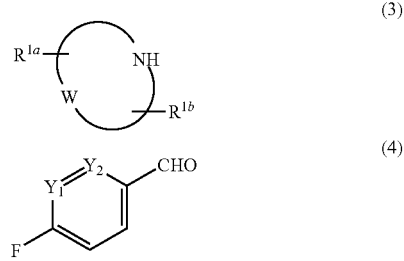

(3)

(4)

where W, Y1, Y2, $R^{1a}$ and $R^{1b}$ have the same meanings as before. The reaction takes place in DMF with heating in the presence of a base such as potassium carbonate.

It will be readily apparent to those skilled in the art that individual compounds in accordance with formula I may be converted to further compounds of formula I using the normal techniques of organic synthesis such as oxidation, reduction, alkylation, condensation and coupling. For example, a compound of formula IV or IV(a) in which $R^9$ is H, may be N-alkylated, N-acylated or N-sulfonylated by conventional techniques to provide the corresponding compounds in which $R^9$ is other than H. As an example there may be cited the treatment of a compound of formula IV or IV(a) in which $R^9$ is H with strong base (such as sodium hydride or caesium carbonate) followed by trifluoroethyl triflate to provide the N-trifluoroethyl derivative. Similar procedures may be carried out on compounds of formula III in which $R^6$ or $R^7$ is H.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt or hydrate thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt or hydrate thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt or hydrate thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt or hydrate thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch. Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ∈4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry,* 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt or hydrate thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a (3-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which inhibits the aggregation of Aβ or otherwise attenuates is neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

EXPERIMENTAL

The ability of the compounds of Formula I to selectively inhibit production of Aβ(1-42) may be determined using the following assay:

Cell-Based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 25 µl and 50 µl media were transferred into a standard Meso avidin-coated 96-well plate for detection of Aβ(40) and Aβ(42) peptides, respectively. 25 µl Meso Assay buffer (PBS, 2% BSA, 0.2% Tween-20) was added to the Aβ(40) wells followed by the addition of 25 µl of the respective antibody premixes to the wells:

Aβ(40) premix: 1 µg/ml ruthenylated G2-10 antibody, 4 µg/ml; and biotinylated 4G8 antibody diluted in Origen buffer Aβ(42) premix: 1 µg/ml ruthenylated G2-11 antibody, 4 µg/ml; and biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Meso Scale Sector 6000 Imager was calibrated according to the manufacturer's instructions. After washing the plates 3 times with 150 µl of PBS per well, 150 µl Meso Scale Discovery read buffer was added to each well and the plates were read on the Sector 6000 Imager according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 µl of 10×MTS/PES was added to the remaining 50 µl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition of less than 5 in most cases less than 1.0 µM, and in many cases less than 0.5 µM. Furthermore, said values were at least 2-fold lower than the corresponding $IC_{50}$ values for Aβ(1-40) inhibition, typically at least 5-fold lower.

Assay for In Vivo Efficacy

APP-YAC transgenic mice (20-30 g; 2-6 months old) and Sprague Dawley rats (200-250 g; 8-10 weeks old) were kept on 12-hr light/dark cycle with unrestricted access to food and water. Mice and rats were fasted overnight and were then dosed orally at 10 ml/kg with test compound formulated in either imwitor:Tween-80 (50:50) or 10% Tween-80, respectively. For compound screening studies, test compounds were administered at a single dose (20 or 100 mg/kg) and blood was taken serially at 1 and 4 hrs via tail bleed from mice and terminally at 7 hrs for mice and rats via cardiac puncture. In dose response studies, compounds were given at 0.1, 3, 10, 30, and 100 mg/kg and blood was taken terminally at 7 hrs from mice and rats via cardiac puncture. Following euthanasia by $CO_2$, forebrain tissue was harvested from animals and stored at −80 degrees. For PD analysis of brain Aβ levels, soluble Aβ was extracted from hemi-forebrains by homogenization in 10 volumes of 0.2% DEA in 50 mM NaCl followed by ultracentrifugation. Levels of Aβ 42/40 were analyzed using Meso Scale technology (electrochemiluminesence) with biotinylated 4G8 capture antibody and ruthenium labeled 12F4 or G210 detection antibodies for Aβ 42 and Aβ 40, respectively. For PK analysis, blood and brain samples were processed using a protein precipitation procedure with the remaining filtrate being analyzed via LC/MS/MS to determine drug exposure levels, brain penetration, and ED50/EC50, where appropriate.

Reductions in Aβ42 levels (relative to vehicle-treated controls) for representative compounds of the invention were in the range 50-90% whereas corresponding reductions in Aβ40 levels for the same compounds were less than 20%.

Syntheses

General Procedure 1 (GP 1)—Halogenation of Lactams

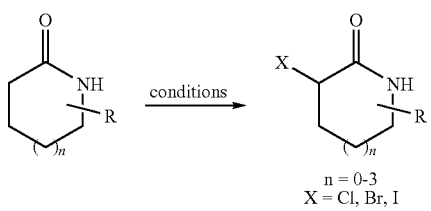

n = 0-3
X = Cl, Br, I

Method a) Chlorination:

Lactam (1 eq) and phosphorus pentachloride (2 eq) were placed in a round bottom flask under nitrogen and benzene (anhydrous, 2.5 M) was added. The reaction mixture was heated to 100° C. for 1.5 h. After cooling to room temperature the volatiles were removed and the remaining solid quenched with ice (caution!). Water was added and the precipitating grey solid collected on a filter frit. The chloro lactam was dried on high vacuum and used as such in the subsequent step.
Method b) Bromination:

To a lactam (1 eq) and phosphorus pentachloride (1 eq) in a round bottom flask was added anhydrous chloroform (~0.25 M) and the resulting solution stirred for 30 minutes. Iodine (0.1 eq) was added and after 5-10 minutes drop-wise bromine (1 eq). The reaction was then stirred for 16 hours. Ice was added and the mixture was extracted with dichloromethane three times. The combined organic fractions were washed with brine, dried ($MgSO_4$), filtered and the solvent was evaporated under reduced pressure. The crude material was used without purification in the subsequent step, but can be purified by chromatography on silica gel.
Method c) Iodination:

To a solution of lactam in dichloromethane (0.2 M) at −15° C. was added N,N,N',N'-tetramethylethylenediamine (4 eq), then at the same temperature, iodotrimethylsilane (4 eq) was added dropwise. The mixture was stirred for 10 min at −15° C. Iodine (2 eq) was added to this mixture in one portion and the mixture was stirred at 0° C. for 2 hours or until complete by LCMS. The mixture was diluted with dichloromethane, washed with sodium thiosulfate (sat. aqueous), dried over magnesium sulfate, filtered and concentrated to afford crude product, which was purified on silica gel (EtOAc/hexane) to afford desired product.

General Procedure 2 (GP 2)—Preparation of Alkyl Azides

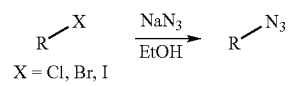

X = Cl, Br, I

Alkyl halide (1.0 eq) and sodium azide (1.2-3 eq; caution, very toxic) were placed in a round bottom flask and ethanol or DMF (DMA, DMPU for unactivated and hindered substrates) were added to give an approximately 0.2 M solution. The mixture was stirred for 16 h at room temperature or up to 80° C. for less reactive electrophiles. The reaction mixture was then alternatively filtered through a 0.45 µM filter and used directly or more commonly worked-up according to the following procedure: water was added and the mixture extracted with methylene chloride twice. The combined organic layers were evaporated under reduced pressure without heating (caution: organic azides are explosive). The crude azide was used directly without further purification in the subsequent step according to GP4.

General Procedure 3 (GP 3)—Preparation of Aryl Azides

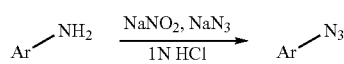

Aromatic amine (1 eq) was placed in a round bottom flask and aqueous 1N HCl was added to give an approximately 0.07M solution. The solution was cooled to 0° C. and an aqueous solution of $NaNO_2$ (1 eq, approx. 0.5M) was added dropwise under nitrogen. The reaction mixture was allowed to stir for 2 h at 0° C. An aqueous solution of $NaN_3$ (1.5 eq, approx. 0.5M) was added and the solution was warmed to room temperature and allowed to stir overnight (18 h). Water and methylene chloride were added the pH was adjusted to pH 9 by addition of aqueous 1N sodium hydroxide solution. The product was extracted into the organic layer, which was washed with brine twice, dried with magnesium sulfate, and evaporated under reduced pressure in the absence of heat (caution: azides are explosive). The crude azide was used directly without further purification in the subsequent step according to GP4.

Synthesis of
3-methoxy-4-(4-methyl-imidazol-1-yl)-benzaldehyde

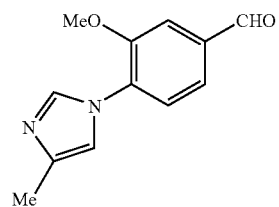

4-Fluoro-3-methoxybenzaldehyde (140 g, 0.91 mol) and 4-methylimidazole (154 g, 1.88 mol) were combined in 2200 mL of dry DMF, degassed by bubbling nitrogen through for 20 min, and then potassium carbonate (189 g, 1.37 mol) was added, and the mixture was warmed to 100° C. (internal temperature), with mechanical stirring. After 22 h, the nearly black, heterogeneous mixture was cooled to room temperature and partitioned between water (3000 mL) and EtOAc (6000 mL). Extracted aqueous layer with additional EtOAc (3×2000 mL), and the combined EtOAc extracts were washed with saturated brine (2×2000 mL), dried ($Na_2SO_4$) and concentrated to afford 215 g of a red, gummy oil. Dissolved in a minimum amount of $CH_2Cl_2$ and purified on a 1.5-kg plug of silica gel (eluting sequentially with 4 L each of 20%, 40%, 60% and 80% EtOAc-hexanes, then with 16 L of EtOAc); fractions containing product (mixture of two isomers) were combined and concentrated to afford 92 g (47%) of a yellow-orange solid (mixture of isomers), which was dissolved (with warming) in a minimum amount of DMF (120 mL) and treated with water (1000 mL) portionwise (with mechanical stirring) at room temperature. Stirred suspension for 10 min, then collected precipitate (w/water washes) to afford a slightly orange solid, which was recrystallized from 250 mL absolute EtOH and 1000 mL of water to afford (after drying under high vacuum overnight) 67.8 g of the title compound as a light orange, fluffy solid.

$^1$H (600 MHz, $CDCl_3$): 2.28 (s, 3H), 3.87 (s, 3H), 6.92 (s, 1H), 6.99 (d, J=16.8 Hz, 1H), 7.16 (s, 1H), 7.17 (d, J=8.1 Hz, 1H), 7.23 (d, J=8.1 Hz, 1H), 7.31 (t, J=7.5 Hz, 1H), 7.39 (t, J=7.5 Hz, 2H), 7.52 (d, J=16.8 Hz, 1H), 7.72 (s, 1H), 7.74 (d, J=7.8 Hz, 2H), 7.88 (s, 1H).

LCMS (ESI): calcd for $C_{22}H_{20}N_3O_2$ $[M+H]^+$ 358.2. found 358.2

Synthesis of 1-(4-ethynyl-2-methoxy-phenyl)-4-methyl-1H-imidazole

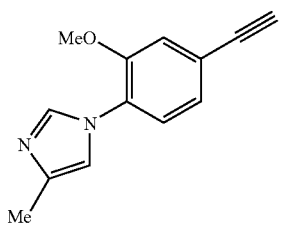

3-Methoxy-4-(4-methyl-imidazol-1-yl)-benzaldehyde (2.00 g, 9.25 mmol) and anhydrous potassium carbonate (2.56 g, 18.5 mmol) were placed in a 250-mL flask and placed on high vacuum for 10 minutes. Under nitrogen, anhydrous MeOH (60 ml) was added via syringe. To the yellowish suspension was added dimethyl(1-diazo-2-oxopropyl) phosphonate (2.132 g, 11.10 mmol). The reaction was stirred at room temperature for 22 h. The reaction was quenched with aqueous sodium hydrogen carbonate (5%, 100 mL), and the mixture was diluted with diethyl ether (250 mL). The combined organic fractions were washed with brine (saturated, 2×100 mL), dried over MgSO4, filtered and evaporated. The residue was dried on high vacuum to give the title compound as a yellow solid (1.71 g, 87%). The product was pure enough by LCMS and NMR and not further purified.

$^1$H (600 MHz, $CDCl_3$): 2.30 (s, 3H), 3.13 (s, 1H), 3.86 (s, 3H), 6.91 (t, J=1.1 Hz, 1H), 7.13-7.20 (m, 3H), 7.71 (d, J=1.1 Hz, 1H).

LCMS (ESI): calcd for $C_{13}H_{13}N_2O$ $[M+H]^+$ 213.2. found 213.2

The following representative and related alkynes were prepared via synthetic routes analogous to 1-(4-ethynyl-2-methoxyphenyl)-4-methyl-1H-imidazole, and were then coupled to azides employing typical cycloaddition conditions (see GP4 below).

1-(4-Ethynyl-2-methoxyphenyl)-3-methyl-4H-1,2,4-triazole

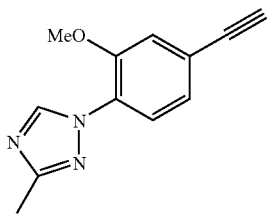

A mixture of 4-fluoro-3-methoxybenzaldehyde (3.0 g, 19 mmol) and 5-methyl 1,2,4-triazole (2.0 g, 24 mmol) in 10 mL of DMF was treated with $K_2CO_3$ (5.0 g, 36 mmol) and stirred at 130° C. overnight. Diluted with DCM, washed with sat'd $NaHCO_3$, dried, concentrated. Chromatography on $SiO_2$ (0-15% MeOH/DCM) gave a 4:1 mixture of regioisomers (1.3 g, 6.0 mmol; 31%). Dissolved intermediate oily aldehyde in 10 mL of MeOH, treated with $K_2CO_3$ (2.0 g, 14 mmol) and dimethyl (1-diazo-2-oxopropyl)phosphonate (1.5 g, 7.8 mmol). Stirred at RT overnight, diluted with DCM, extracted with water, dried ($Na_2SO_4$), concentrated. Chromatography on $SiO_2$ (0-10% MeOH/DCM) gave product as a 4:1 mixture of regioisomers. Reverse phase LC (10-100% MeCN/water with 0.025% TFA) was used to separate regioisomers; fractions were neutralized with DCM/sat'd $NaHCO_3$, the organic layer was dried ($Na_2SO_4$), concentrated to yield 420 mg (10% overall yield) of triazolyl alkyne:

$^1$H NMR (600 MHz, DMSO-$d_6$) δ 8.82 (s, 1H), 7.62 (d, J=8.2 Hz, 1H), 7.32 (s, 1H), 7.17 (d, J=7.9 Hz, 1H), 4.30 (s, 1H), 3.88 (s, 3H), 2.30 (s, 3H); MS (EI) $[M+1]^+$ calc'd 214.1. found 214.3.

5-Ethynyl-2-(4-methyl-1H-imidazol-1-yl)benzonitrile

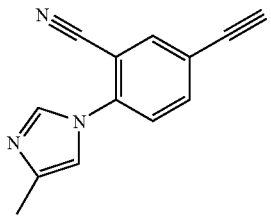

A mixture of 4-fluoro-3-cyanobenzaldehyde (3.0 g, 20 mmol) in 20 mL of DMF was treated with 4-methylimidazole (3.0 g, 37 mmol) and warmed to 100° C. Stirred overnight. Diluted with EtOAc, washed with sat'd $NaHCO_3$, dried ($Na_2SO_4$), concentrated. Triturated with MeOH and filtered to give a single regioisomer (1.3 g, 6.1 mmol; 31%). Suspended in 20 mL of MeOH, treated with $K_2CO_3$ (1.4 g, 10 mmol) and dimethyl (1-diazo-2-oxopropyl)phosphonate (1.4 g, 7.3 mmol) and stirred overnight. Diluted with DCM and washed with water. Dried ($Na_2SO_4$), conc. Chromatography on silica (0-20% MeOH/DCM) gave the desired alkyne (606 mg; 15% overall yield):

¹H NMR (600 MHz, CDCl₃) δ 7.87 (s, 1H), 7.76 (d, J=7.3 Hz, 1H), 7.75 (s, 1H), 7.37 (d, J=8.5 Hz, 1H), 7.24 (d, J=1.1 Hz, 1H), 7.06 (s, 1H), 3.25 (s, 1H), 2.29 (s, 3H).

1-(4-Ethynyl-2-phenoxyphenyl)-4-methyl-1H-imidazole

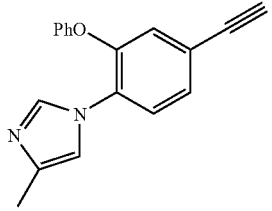

A mixture of 4-fluoro-3-phenoxybenzaldehyde (1.0 g, 4.6 mmol) in 10 mL of DMF was treated with 4-methylimidazole (1.0 g, 12 mmol) and warmed to 100° C. Stirred overnight. Diluted with EtOAc, washed with sat'd NaHCO₃, dried (Na₂SO₄), concentrated. Dissolved in 10 mL of MeOH, treated with K₂CO₃ (1.0 g, 7.2 mmol) and dimethyl (1-diazo-2-oxopropyl)phosphonate (1.0 g, 5.2 mmol) and stirred overnight. Diluted with DCM and washed with water. Dried (Na₂SO₄), conc. Chromatography on silica (0-20% MeOH/DCM) gave the desired alkyne (1.1 g; 87% overall yield):

¹H NMR (600 MHz, CDCl₃) δ 7.23-7.31 (m, 4H), 7.11-7.12 (m, 2H), 6.88-6.95 (m, 4H), 3.11 (s, 1H), 2.29 (s, 3H).

1-(4-Ethynyl-2-methoxyphenyl)-1H-imidazole

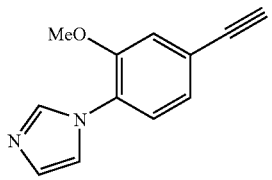

A mixture of 4-fluoro-3-methoxybenzaldehyde (1.0 g, 6.5 mmol) in 20 mL of DMF was treated with 4-methylimidazole (1.0 g, 15 mmol) and warmed to 130° C. Stirred overnight. Diluted with EtOAc, washed with sat'd NaHCO₃, dried (Na₂SO₄), concentrated. Dissolved in 20 mL of MeOH, treated with K₂CO₃ (2.0 g, 14 mmol) and dimethyl (1-diazo-2-oxopropyl)phosphonate (1.5 g, 7.8 mmol) and stirred overnight. Diluted with DCM and washed with water. Dried (Na₂SO₄), conc. Chromatography on silica (0-20% MeOH/DCM) gave the desired alkyne:

¹H NMR (600 MHz, CDCl₃) δ 7.79 (s, 1H), 7.18 (t, J=1.2 Hz, 1H), 7.16 (d, J=1.8 Hz, 1H), 7.15 (m, 2H), 7.13 (d, J=1.5 Hz, 1H).

1-(4-Ethynylphenyl)-4-methyl-1H-imidazole

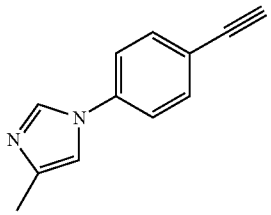

A mixture of 4-fluorobenzaldehyde (5.0 g, 40 mmol) in 60 mL of DMF was treated with 4-methylimidazole (6.6 g, 81 mmol) and K₂CO₃ (8.4 g, 60 mmol) and warmed to 100° C. Stirred overnight. Diluted with EtOAc, washed with sat'd NaHCO₃, dried (Na₂SO₄), concentrated to give a 4:1 mixture of imidazole regioisomers. Recrystallization from EtOH gave a single regioisomer. A portion of the aldehyde (500 mg, 2.69 mmol) was dissolved in 10 mL of MeOH, treated with K₂CO₃ (740 mg, 5.4 mmol) and dimethyl (1-diazo-2-oxopropyl)phosphonate (620 mg, 3.2 mmol) and stirred overnight. Diluted with DCM and washed with water. Dried (Na₂SO₄), conc. Chromatography on silica (0-20% MeOH/DCM) gave the desired alkyne (400 mg; 82%):

¹H NMR (600 MHz, CDCl₃) δ 7.75 (s, 1H), 7.55-7.56 (m, 2H), 7.29-7.30 (m, 2H), 7.24 (s, 1H), 6.99 (s, 1H), 3.12 (s, 1H), 2.27 (s, 3H); MS (EI) [M+1]⁺ calc'd 183.1. found 183.3.

5-Ethynyl-2-(4-methyl-1H-imidazol-1-yl)pyridine

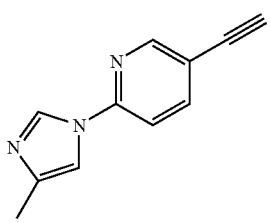

A mixture of 6-chloronicotinaldehyde (5.0 g, 35 mmol) in 60 mL of DMF was treated with 4-methylimidazole (5.8 g, 71 mmol) and K₂CO₃ (7.3 g, 53 mmol) and warmed to 100° C. Stirred overnight. Diluted with EtOAc, washed with sat'd NaHCO₃, dried (Na₂SO₄), concentrated to give a 4:1 mixture of imidazole regioisomers. Recrystallization from EtOH gave a single regioisomer. A portion of the aldehyde (500 mg, 2.67 mmol) was dissolved in 10 mL of MeOH, treated with K₂CO₃ (740 mg, 5.4 mmol) and dimethyl (1-diazo-2-oxopropyl) phosphonate (620 mg, 3.2 mmol) and stirred overnight. Diluted with DCM and washed with water. Dried (Na₂SO₄), conc. Chromatography on silica (0-20% MeOH/DCM) gave the desired alkyne (276 mg; 56%):

¹H NMR (600 MHz, DMSO-d₆) δ8.54 (s, 1H), 8.40 (s, 1H), 8.05 (dd, J=8.5, 2.3 Hz, 1H), 7.74 (d, J=8.5 Hz, 1H); 7.64 (s, 1H), 4.44 (s, 1H), 2.13 (s, 3H); MS (EI) [M+1]⁺ calc'd 184.1. found 184.2.

1-(4-Ethynyl-2-methoxyphenyl)-4-(trifluoromethyl)-1H-imidazole

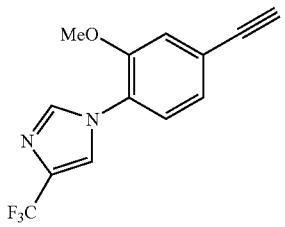

4-Fluoro-3-methoxybenzaldehyde (2.57 g, 16.7 mmol), 4-trifluoromethylimidazole (4.54 g, 33.4 mmol), and K₂CO₃ (3.46 g, 25 mmol) were dissolved in 15 ml of DMF and stirred at 100° C. overnight. Cooled to room temperature and DMF removed in vacuo. The concentrated mass was taken up in EtOAc and water. Layers were separated and the aqueous layer was extracted twice with EtOAc. The organic extracts were combined, dried (Na₂SO₄), and concentrated. Chromatography on SiO₂ (0-50% EtOAc/CH₂Cl₂) gave a cream-colored solid (1.67 g, 6.2 mmol, 37%). A solution of aldehyde intermediate (445 mg, 2.32 mmol) in 20 ml of MeOH was treated with K₂CO₃ (534 mg, 3.86 mmol) and a solution of dimethyl (1-diazo-2-oxopropyl)phosphonate (522 mg, 1.93 mmol) in 5 ml of MeOH and stirred at room temperature overnight. MeOH was removed in vacuo and the concentrated mass was dissolved in EtOAc and washed sequentially with water, sat'd NaHCO₃, and water. The organic layer was dried (Na₂SO₄) and concentrated to a yellow solid (493.2 mg, 1.9 mmol, 96%).

¹H NMR (600 MHz, CDCl₃) δ 7.77 (s, 1H), 7.51 (t, J=1.2 Hz, 1H), 7.22 (d, J=7.9 Hz, 1H), 7.18 (dd, J=7.9, 1.4 Hz, 1H), 7.16 (d, J=1.5 Hz, 1H), 3.86 (s, 3H), 3.16 (s, 1H); MS (EI) [M+1]⁺ calc'd 267.1. found 267.2.

1-(4-Ethynyl-2-fluorophenyl)-4-methyl-1H-imidazole

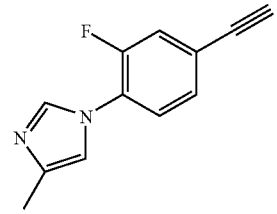

3,4-Difluorobenzaldehyde (4.82 g, 33.9 mmol), 4-methylimidazole (5.57 g, 67.8 mmol), and K₂CO₃ (7.03 g, 50.9 mmol) were dissolved in 35 ml of DMF and stirred at 100° C. overnight. Cooled to room temperature and DMF removed in vacuo. The concentrated mass was taken up in EtOAc and water. Layers were separated and the aqueous layer was extracted twice with EtOAc. The organic extracts were combined, dried (Na₂SO₄), and concentrated. Chromatography on SiO₂ (0-75% EtOAc/CH₂Cl₂) gave a cream-colored solid (mixture of isomers). This mass was taken up in a minimum amount of EtOH and treated with water until the formation of a precipitate. The precipitate was collected as a white solid and yielded 522.5 mg (2.6 mmol, 8%) after drying under high vacuum overnight. A solution of aldehyde intermediate (516 mg, 2.53 mmol) in 20 ml of MeOH was treated with K₂CO₃ (698 mg, 5.05 mmol) and a solution of dimethyl (1-diazo-2-oxopropyl)phosphonate (583 mg, 3.03 mmol) in 10 ml of MeOH and stirred at room temperature for 2.5 hours. MeOH was removed in vacuo and the concentrated mass was dissolved in aqueous NaHCO₃ and EtOAc. Layers were separated and the aqueous layer was extracted twice with EtOAc. The organic extracts were combined, dried (Na₂SO₄), and concentrated to a yellow powder (506 mg, 2.5 mmol, 100%).

¹H NMR (600 MHz, CDCl₃) δ 7.74 (s, 1H), 7.33 (m, 3H), 6.96 (s, 1H), 3.16 (s, 1H), 2.29 (s, 3H); MS (EI) [M+1]⁺ calc'd 201.1. found 201.2.

4-Fluoro-3-(2,2,2-trifluoroethoxy)benzaldehyde

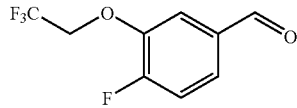

Methyl 4-fluoro-3-hydroxybenzoate (10 g, 58.8 mmol), 2,2,2-trifluoroethyl trifluoromethanesulfonate (20.4 g, 88 mmol), and Cs₂CO₃ (51 g, 157 mmol) were dissolved in 200 ml of THF and stirred at 65° C. overnight. Cooled to room temperature and diluted with EtOAc and brine. Layers were separated and the aqueous layer was extracted twice with EtOAc. The organic extracts were combined, dried (Na₂SO₄), and concentrated to yield 14.82 g (58.8 mmol, 100%). A solution of hydroxybenzoate intermediate (14.82 g, 58.8 mmol) in 150 ml of THF was cooled to 0° C., treated with LiAlH₄ (3.95 g, 104 mmol), and allowed to warm to room temperature over 1 hour. Reaction quenched sequentially with 4 ml of water, 4 ml of 1 N NaOH, and 12 ml of water and left to stir for thirty minutes. Reaction was filtered and the filtrate concentrated to a yellow oil (13.33 g, 59 mmol, 100%). A solution of DMSO (10.26 ml, 145 mmol) in 10 ml of dry CH₂Cl₂ was added dropwise to a solution of oxalyl chloride (33.3 ml, 66.6 mmol) in an additional 100 ml of dry CH₂Cl₂ and stirred at −78° C. for 20 minutes. A solution of alcohol intermediate (13.33 g, 59 mmol) in 50 ml dry CH₂Cl₂ was then added and the reaction was stirred at −78° C. for 30 minutes. The reaction was treated with triethylamine (30.8 ml, 221 mmol) and stirred at −78° C. for 30 minutes. The reaction was warmed to 0° C., stirred for 30 minutes, and then allowed to warm to room temperature. Diluted with 1 N HCl and CH₂Cl₂. The aqueous layer was separated and extracted once with CH₂Cl₂. The organic layers were combined and washed sequentially with sat'd NaHCO₃, 10 vol % bleach in water, and brine. The organic layer was dried (Na₂SO₄) and concentrated to a yellow solid (12.37 g, 55.7 mmol, 94%).

¹H NMR (600 MHz, CDCl₃) δ 9.90 (s, 1H), 7.56 (ddd, J=8.2, 4.4, 1.7 Hz, 1H), 7.54 (dd, J=7.9, 2.1 Hz, 1H), 7.28 (dd, J=10.2, 8.2 Hz, 1H), 7.28 (q, J=8.0 Hz, 2H); MS (EI) [M+1]⁺ calc'd 223.0. found 223.2.

1-[4-Ethynyl-2-(2,2,2-trifluoroethoxy)phenyl]-4-methyl-1H-imidazole

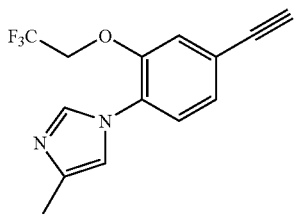

A solution of 4-fluoro-3-(2,2,2-trifluoroethoxy)benzaldehyde (12.88 g, 58 mmol) and 4-methylimidazole (10 g, 122 mmol) in 150 ml of DMF was stirred at 100° C. overnight and then stirred at 130° C. an additional 24 hours. Cooled to room temperature and DMF removed in vacuo. The concentrated mass was taken up in EtOAc and washed twice with water to yield two aqueous layers. Each aqueous layer was separately extracted twice with EtOAc. The organic extracts were combined, dried (Na₂SO₄), and concentrated to a brown solid (mixture of isomers). This mass was dissolved in a minimum amount of CH₂Cl₂ and filtered. The filter cake was collected as a yellow solid (6.275 g, 22.1 mmol, 38%). A solution of aldehyde intermediate (1 g, 3.5 mmol) in 30 ml MeOH was treated with K₂CO₃ (972 mg, 7.04 mmol) and a solution of dimethyl (1-diazo-2-oxopropyl)phosphonate (879 mg, 4.57 mmol) in 5 ml dry MeOH and stirred at room temperature for 8 hours. MeOH was removed in vacuo and the concentrated mass was dissolved in aqueous NaHCO₃ and EtOAc. Layers were separated and the aqueous layer was extracted twice with EtOAc. The organic extracts were combined, dried (Na₂SO₄), and concentrated to a yellow solid (986 mg, 3.5 mmol, 100%).

¹H NMR (600 MHz, CDCl₃) δ 7.70 (d, J=1.2 Hz, 1H), 7.25 (2s, 2H), 7.13 (s, 1H), 6.92 (s, 1H), 4.33 (q, J=8.0 Hz, 2H), 3.15 (s, 1H), 2.27 (d, J=0.6 Hz, 3H); MS (EI) [M+1]⁺ calc'd 281.1. found 281.2.

General Procedure 4 (GP 4)—Preparation of Triazoles

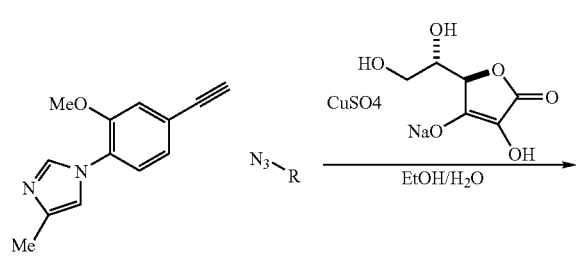

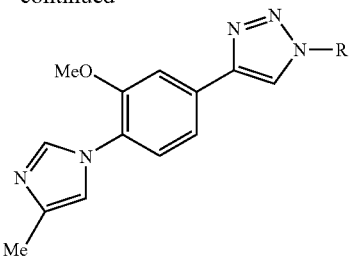

1-(4-ethynyl-2-methoxy-phenyl)-4-methyl-1H-imidazole (or another alkyne described above), azide, water and ethanol (or DMF) were placed in a round bottom flask and aqueous copper sulfate solution (1M, 10-100 mol %) and aqueous sodium ascorbate solution (1M, 20-60 mol %) was added. The reaction mixture was stirred at room temperature until complete (more copper sulfate solution and sodium ascorbate solution were added as needed), then the solvents were removed under reduced pressure. The residue was purified by reversed phase chromatography (C18, acetonitrile/water with 0.1% TFA).

General Procedure 5 (GP 5)—Alkylation of Amides and Lactams

Method a):

An amide or lactam (1 eq) and caesium carbonate (3 eq) were added to a round-bottom flask under nitrogen and THF (0.05-0.1 M) was added. Alkyl halide or triflate (e.g. trifluoroethyl trifluoromethane sulfonate, 1-1.1 eq) was added and the suspension heated to 65° C. for 1-2 hr. The mixture was cooled, water (10 mL) was added and the mixture was extracted with dichloromethane three times. The combined organic fractions were washed with brine, dried (MgSO₄), filtered and the solvent was evaporated under reduced pressure. The residue was purified by preparative HPLC Reverse phase (C-18), eluting with Acetonitrile/Water+0.1% TFA, to give the desired alkylated product as the trifluoroacetate salt.

Method b):

An amide or lactam (1 eq) and potassium hexamethyldisilazide (1.2 eq) were added to a round-bottom flask under nitrogen and DMF (0.05-0.1 M) was added. Alkyl halide or triflate (e.g. trifluoroethyl trifluoromethane sulfonate, 1.2-1.5 eq) was added and the suspension stirred at room temperature for 16 h (or stirred at slightly elevated temperature, caution: overalkylation). The residue was purified by preparative HPLC Reverse phase (C-18), eluting with Acetonitrile/Water+0.1% TFA, to give the desired alkylated product as the trifluoroacetate salt.

Method c):

An amide or lactam (1 eq) and sodium hydride (60% mineral oil dispersion, 1.2 eq) were dissolved in DMF (0.01-0.1 M) at 0° C. and stirred for 20 min. Alkyl halide or triflate (e.g. trifluoroethyl trifluoromethane sulfonate, 1.1-1.5 eq) was then added dropwise and the reaction stirred at room temperature to 40° C. until complete by LCMS. The reaction was worked up using Brine (2×, 100 mL) and EtOAc (100 mL). The organic layer was dried using MgSO4 and evaporated under reduced pressure. The residue was purified by preparative HPLC Reverse Phase (C-18), eluting with Acetonitrile/Water w/0.1% TFA, to give the product as a yellow solid. It was then freebased using Sat. K-card solution, extracting into EtAOc, and the organic layer was dried with MgSO4 and evaporated under reduced pressure to give a yellow solid.

Example 1

N-cyclohexyl-2-{4-[3-methoxy-4-(4-methyl-imidazol-1-yl)-phenyl]-1,2,3-triazol-1-yl}-N-phenyl-acetamide

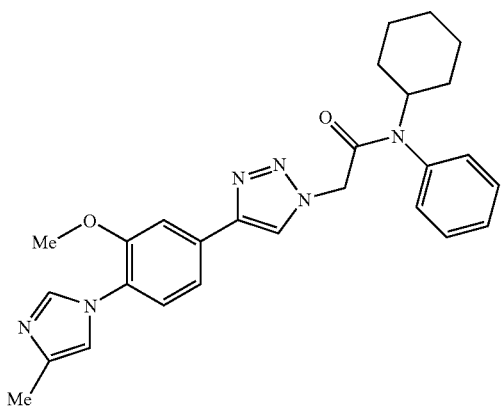

Alkyne (100 mg, 0.47 mmol), azide (146 mg, 0.57 mmol) as a solution in DMF (6 mL), ethanol (12 mL), and water (12 mL) were added to a 50-mL flask. To the cloudy solution was added copper sulfate solution (0.05 mL) and sodium ascorbate solution (0.11 mL) according to GP4. The green suspension was stirred for 16 h at room temperature and further copper sulfate solution (0.05 mL) and sodium ascorbate solution (0.11 mL) was added. After another 6 h stirring at room temperature the solvents were evaporated and the residue purified. The product (205 mg) was obtained as a colorless solid.

$^1$H (600 MHz, dmso-d6): 1.41 (s, 9H), 2.13 (s, 3H), 3.88 (s, 3H), 7.14 (s, 1H), 7.38 (d, J=7.9 Hz, 1H), 7.41-7.43 (m, 3H), 7.63-7.66 (m, 2H), 7.79 (d, J=1.5 Hz, 1H).

LCMS (ESI): calcd for $C_{27}H_{31}N_6O_2$ [M+H]$^+$ 471.2. found 471.1

Example 2

(R) and (S)-3-{4-[3-methoxy-4-(4-methyl-imidazol-1-yl)-phenyl]-1,2,3-triazol-1-yl}-1,3,4,5-tetrahydro-1-benzazepin-2-one

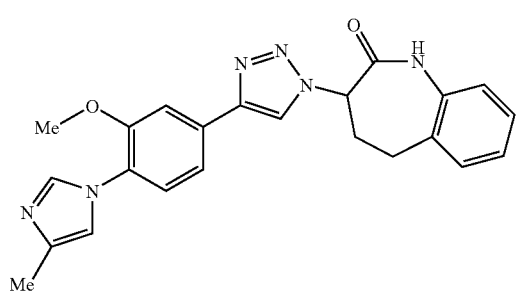

Alkyne (50 mg, 0.24 mmol), azide (1.7 mL, 0.17 M in DMF, 0.28 mmol), ethanol (8 mL), and water (8 mL) were added to a 50-mL flask. To the cloudy solution was added copper sulfate solution (0.024 mL) and sodium ascorbate solution (0.059 mL) according to GP4. The green suspension was stirred for 16 h at room temperature and further copper sulfate solution (0.024 mL) and sodium ascorbate solution (0.059 mL) was added. After another 16 h stirring at room temperature the solvents were evaporated and the residue purified. The racemic product (50 mg) as the TFA salt was obtained as a colorless solid. After freebasing with $Na_2CO_3$ the material was resolved: 50% ethanol/heptane Column: Chiralcel OJ-H 2 cm×25 cm (5 uM); 12 mL/min; 254 nm detection; enantiomer 1 $t_r$=15.29 min, enantiomer 2 $t_r$=20.57 min $^1$H (600 MHz, dmso-d6): 2.14 (s, 3H), 3.90 (s, 3H), 7.15-7.17 (m, 3H), 7.29-7.34 (m, 3H), 7.39-7.41 (m, 3H), 7.66 (d, J=16.4 Hz, 1H), 7.80 (s, 1H).

LCMS (ESI): calcd for $C_{23}H_{23}N_6O_2$ [M+H]$^+$ 415.1. found 415.0

Example 3

1-(4-tert-butyl-benzyl)-4-[3-methoxy-4-(4-methyl-imidazole-1-yl)-phenyl]-1H-[1,2,3]triazole trifluoroacetate salt

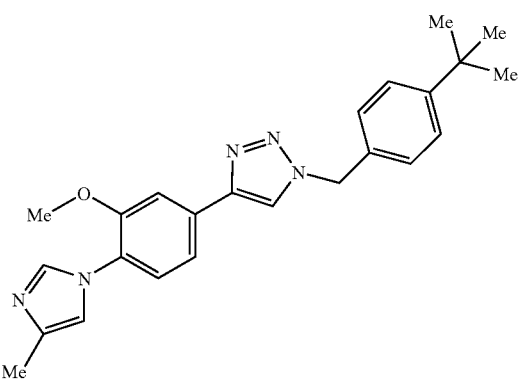

Alkyne (100 mg, 0.47 mmol) and azide (89 mg, 0.47 mmol) as a solution in dimethyl sulfoxide (52 mL, used in place of ethanol) and water (25 mL) were added to a 250-mL flask. To the clear solution was added copper sulfate solution (0.47 mL) and sodium ascorbate solution (0.16 mL) according to GP4. The yellow suspension was stirred for 46 h at room temperature and the solution was quenched with water (100 mL) and an F-frit was used to collect the green precipitate. The residue was purified and the product (120 mg) was obtained as a yellow oil.

$^1$H (600 MHz, dmso-d6): 1.22 (s, 9H), 2.31 (s, 3H), 3.90 (s, 3H), 5.60 (s, 2H), 7.26-7.28 (m, 2H), 7.38-7.39 (m, 2H), 7.61 (m, 2H), 7.71-7.73 (m, 2H), 8.79 (s, 1H), 79.32 (d, J=1.4 Hz, 1H).

In the following examples "alkyne" refers to 1-(4-ethynyl-2-methoxy-phenyl)-4-methyl-1H-imidazole and "azide" to the appropriate alkyl or aryl azide.

LCMS (ESI): calcd for $C_{24}H_{27}N_5O$ [M+H]+ 402.2. found 402.2

Example 4

4-[3-Methoxy-4-(4-methyl-imidazol-1-yl)-phenyl]-1-phenylsulfanylmethyl-1H-[1,2,3]triazole trifluoroacetate salt

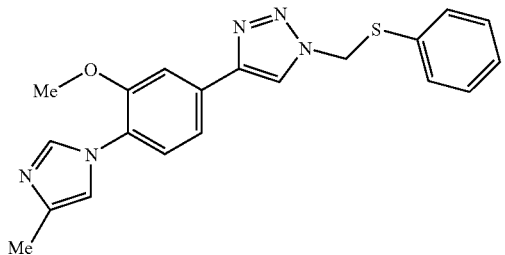

Alkyne (100 mg, 0.47 mmol), azide (78 mg, 0.47 mmol), ethanol (7.5 mL), and water (7.5 mL) were added to a 100-mL flask. To the clear solution was added copper sulfate solution (0.47 mL) and sodium ascorbate solution (0.09 mL) according to GP4. The yellow suspension was stirred for 72 h at room temperature and the solvents were evaporated and the residue purified. The product (160 mg) was obtained as green crystals.

$^1$H (600 MHz, dmso-d6): 2.32 (s, 3H), 3.92 (s, 3H), 6.02 (s, 2H), 7.33-7.38 (m, 3H), 7.41-7.42 (m, 2H), 7.60-7.61 (m, 2H), 7.72-7.75 (m, 2H), 8.80 (s, 1H), 9.33 (d, J=1.5 Hz, 1H).

LCMS (ESI): calcd for $C_{20}H_{19}N_5OS$ [M+H]+ 378.1. found 378.1

Example 5

4-[3-Methoxy-4-(4-methyl-imidazol-1-yl)-phenyl]-1-(1-phenyl-ethyl)-1H-[1,2,3]triazole trifluoroacetate salt

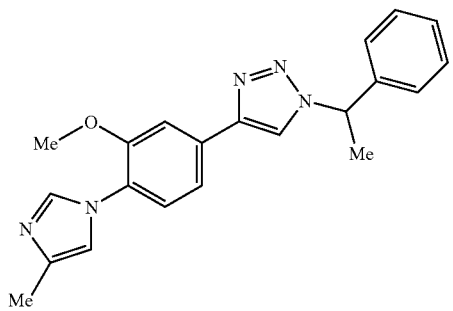

Alkyne (115 mg, 0.54 mmol), azide (10.0 mL, 0.054 M in DMF, 0.54 mmol), ethanol (7.5 mL) and water (7.5 mL) were added to a 100-mL flask. To the clear solution was added copper sulfate solution (0.54 mL) and sodium ascorbate solution (0.11 mL) according to GP4. The yellow suspension was stirred for 11 days at room temperature and the solvents were evaporated and the residue purified. The product (190 mg) was obtained as a yellow oil.

$^1$H (600 MHz, dmso-d6): 1.91 (s, 3H), 2.31 (s, 3H), 3.91 (s, 3H), 5.98-6.02 (m, 1H), 7.29-7.38 (m, 5H), 7.62-7.63 (m, 2H), 7.72-7.74 (m, 2H), 8.92 (s, 1H), 9.33 (d, J=1.5 Hz, 1H).

LCMS (ESI): calcd for $C_{21}H_{21}N_5O$ [M+H]+ 360.2. found 360.1

Example 6

2-(4-{4-[3-Methoxy-4-(4-methyl-imidazol-1-yl)-phenyl]-[1,2,3]triazol-1-ylmethyl}-phenyl)-benzooxazole trifluoroacetate salt

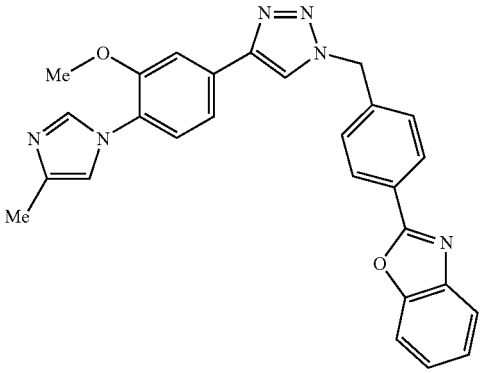

Alkyne (42.4 mg, 0.20 mmol), azide (10.0 mL, 0.02 M in DMF, 0.20 mmol), ethanol (10 mL), and water (10 mL) were added to a 100-mL flask. To the clear solution was added copper sulfate solution (0.20 mL) and sodium ascorbate solution (0.04 mL) according to GP4. The yellow suspension was stirred for 20 h at room temperature and the solvents were evaporated and the residue purified. The product (100 mg) was obtained as a brown solid.

$^1$H (600 MHz, dmso-d6): 2.31 (s, 3H), 3.91 (s, 3H), 5.81 (s, 2H), 7.38-7.43 (m, 2H), 7.54-7.80 (m, 8H), 8.21-8.22 (m, 2H), 8.86 (s, 1H), 9.31 (s, 1H).

LCMS (ESI): calcd for $C_{27}H_{22}N_6O_2$ [M+H]+ 463.2. found 463.1

Example 7

1-[(4-Difluoromethyl-phenyl)-difluoro-methyl]-4-[3-methoxy-4-(4-methyl-imidazol-1-yl)-phenyl]-1H-[1,2,3]triazole trifluoracetate salt

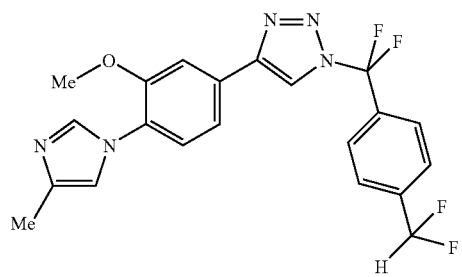

Alkyne (48.4 mg, 0.23 mmol), azide (10.0 mL, 0.023 M in DMF, 0.23 mmol), ethanol (10 mL), and water (10 mL) were added to a 100-mL flask. To the clear solution was added copper sulfate solution (0.23 mL) and sodium ascorbate solution (0.05 mL) according to GP4. The yellow suspension was stirred for 20 h at room temperature and the solvents were evaporated and the residue purified. The product (66 mg) was obtained as a yellow solid.

¹H (600 MHz, dmso-d6): 2.31 (s, 3H), 3.92 (s, 3H), 7.07-7.34 (m, 1H), 7.67-7.91 (m, 8H), 9.35 (s, 1H), 9.48 (s, 1H).
LCMS (ESI): calcd for $C_{21}H_{17}F_5N_5O$ [M+H]⁺ 432.1. found 432.0

Example 8

2-{4-[3-Methoxy-4-(4-methyl-imidazol-1-yl)-phenyl]-[1,2,3]triazol-1-yl}-1-(octahydro-quinolin-1-yl)-ethanone trifluoroacetate salt

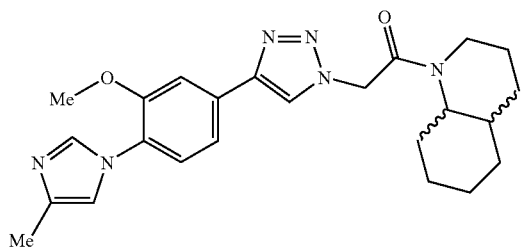

Alkyne (90 mg, 0.42 mmol), azide (10.0 mL, 0.042 M in DMF, 0.42 mmol), ethanol (10 mL), and water (10 mL) were added to a 100-mL flask. To the clear solution was added copper sulfate solution (0.42 mL) and sodium ascorbate solution (0.09 mL) according to GP4. The yellow suspension was stirred for 20 h at room temperature and the solvents were evaporated and the residue purified. The product (135 mg) was obtained as a colorless powder.
¹H (600 MHz, dmso-d6): 0.97-1.10 (m, 2H), 1.20-1.40 (m, 4H), 1.48-1.72 (m, 6H), 1.73-1.8 (m, 1H), 1.95-2.03 (m, 1H), 2.31 (s, 3H), 3.20-3.25 (m, 2H), 3.92 (s, 3H), 5.42-5.60 (m, 2H), 7.61-7.64 (m, 2H), 7.72 (s, 1H), 7.76 (s, 1H), 8.66 (s, 1H), 9.32 (d, J=1.5 Hz), 1H).
LCMS (ESI): calcd for $C_{24}H_{30}N_6O_2$ [M+H]⁺ 435.2. found 435.2

Example 9

2,2-Difluoro-N-(4-fluoro-benzyl)-2-{4-[3-methoxy-4-(4-methyl-imidazol-1-yl)-phenyl]-[1,2,3]triazol-1-yl}-acetamide trifluoroacetate salt

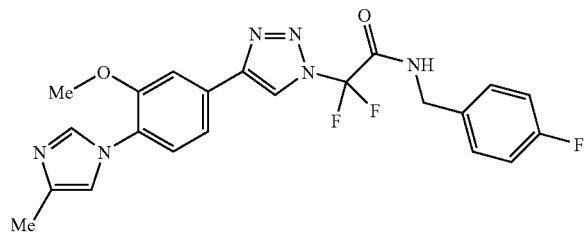

Alkyne (40.6 mg, 0.19 mmol), azide (10.0 mL, 0.019 M in DMF, 0.19 mmol), ethanol (10 mL), and water (10 mL) were added to a 100-mL flask. To the clear solution was added copper sulfate solution (0.19 mL) and sodium ascorbate solution (0.04 mL) according to GP4. The yellow suspension was stirred for 20 h at room temperature and the solvents were evaporated and the residue purified. The product (32 mg) was obtained as a colorless solid.
¹H (600 MHz, CD₃OD): 2.31 (s, 3H), 3.99 (s, 3H), 4.52 (s, 1H), 7.04-7.07 (m, 2H), 7.37-7.39 (m, 2H), 7.58-7.71 (m, 3H), 7.84 (m, 2H), 9.11 (s, 1H), 9.15 (s, 1H).
LCMS (ESI): calcd for $C_{22}H_{19}F_3N_6O_2$ [M+H]⁺ 457.1. found 457.0

Example 10

(R) and (S)-3-{4-[3-methoxy-4-(4-methyl-1H-imidazol-1-yl)phenyl]-1H-1,2,3-triazol-1-yl}-6,8-dimethyl-1-(2,2,2-trifluoroethyl)-1,3,4,5-tetrahydro-2H-1-benzazepin-2-one

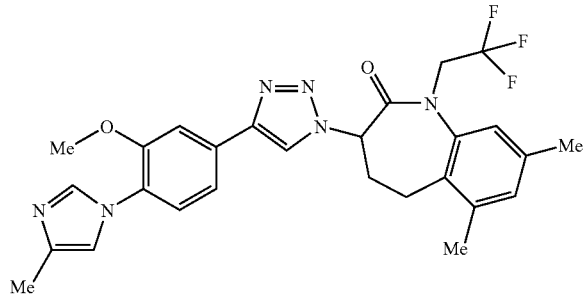

6,8-dimethyl-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one (300 mg, 0.678 mmol) and sodium hydride (60% mineral oil dispersion, 32.5 mg, 0.814 mmol) were dissolved in DMF (60 ml) at 0° C. and stirred for 20 min. Trifluoroethyl triflate (0.108 ml, 0.746 mmol) was then added dropwise and the reaction stirred at 40° C. for 4 h. Water was added and the reaction mixture extracted with EtOAc (100 mL). The organic layer was washed with brine (2×100 mL) dried over MgSO4 and evaporated under reduced pressure. The residue was purified by preparative HPLC Reverse Phase (C-18), eluting with Acetonitrile/Water w/0.1% TFA, to give the product as a yellow solid. The free base was obtained by washing an EtOAc solution with potassium carbonate solution (aqueous, saturated). The organic layer was dried over MgSO4 and evaporated under reduced pressure to give the free base (302 mg) as a yellow solid.
Resolution: SFC: OD-H, 20×250 mm, 25% Methanol/CO2, 70 ml/min, 9 min runtime, 220 nm, 254 nm; enantiomer 1 $t_r$=3.97 min, enantiomer 2 $t_r$=6.00 min
¹H (500 MHz, CD₃OD): 2.24 (s, 3H), 2.38 (s, 3H), 2.38 (s, 3H), 2.42 (s, 3H), 2.65 (m, 1H), 2.87 (m, 1H), 2.96 (m, 1H), 3.95 (s, 3H), 4.34 (m, 1H), 5.08 (m, 1H), 5.39 (m, 1H), 7.09 (s, 1H), 7.11 (s, 1H), 7.20 (s, 1H), 7.41 (d, J=7.9 Hz), 7.51 (dd, J=1.7, 8.0 Hz, 1H), 7.69 (d, J=1.7 Hz, 1H), 7.81 (d, J=1.5 Hz), 8.68 (s, 1H).

LCMS (ESI): calcd for $C_{27}H_{28}F_3N_6O_2$ [M+H]$^+$ 524.2. found 524.2

Example 11

(R) and (S)-6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one

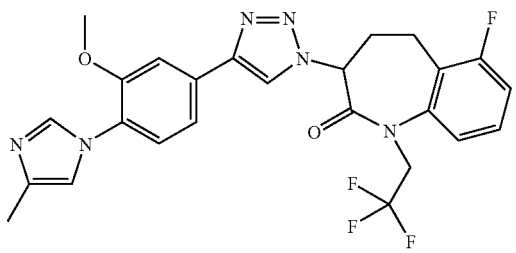

6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one (1.24 mg, 2.87 mmol) and sodium hydride (60% mineral oil dispersion, 103 mg, 4.3 mmol) were dissolved in DMF (30 ml) at 0° C. and stirred for 30 min. Trifluoroethyl triflate (666 mg, 2.87 mmol) was then added dropwise and the reaction mixture warmed to room temperature. After 3 hours water was added and the reaction mixture extracted with dichloromethane (50 mL). The organic layer was dried over MgSO4 and evaporated under reduced pressure. The residue was purified by preparative HPLC Reverse Phase (C-18), eluting with Acetonitrile/Water w/0.1% TFA, to give the product as a yellow solid.

Resolution (of the free base):75% ethanol/25% heptane Column: Chiralcel OJ-H; 254 nm detection; enantiomer 1 (465 mg), enantiomer 2 (489 mg).

$^1$H (600 MHz, CD$_3$OD): 2.22 (s, 3H), 2.65-2.72 (m, 1H), 2.75-2.80 (m, 1H), 2.99-3.05 (m, 1H), 3.34-3.38 (m, 1H), 3.93 (s, 3H), 4.34-4.40 (m, 1H), 5.08-5.12 (m, 1H), 5.48-5.52 (m, 1H), 7.07 (s, 1H), 7.18-7.23 (m, 1H), 7.38-7.40 (m, 2H), 7.46-7.50 (m, 2H), 7.66 (s, 1H), 7.79 (s, 1H), 8.66 (s, 1H).

LCMS (ESI): calcd for $C_{25}H_{23}F_4N_6O_2$ [M+H]$^+$ 515.2. found 515.2

Example 12

N-(3-chloro-4-fluorophenyl)-2-{4-[3-methoxy-4-(4-methyl-1H-imidazol-1-yl)phenyl]-1H-1,2,3-triazol-1-yl}-N-(2,2,2-trifluoroethyl)acetamide trifluoroacetate salt

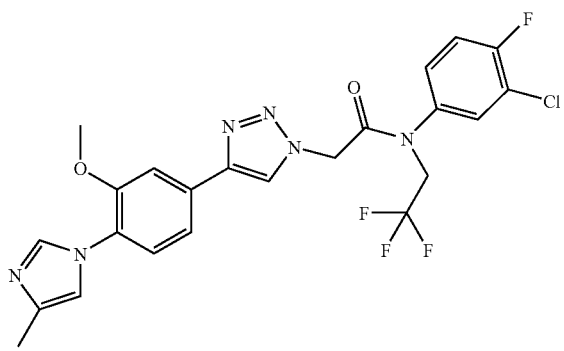

N-(3-chloro-4-fluorophenyl)-2-{-4-[3-methoxy-4-(4-methyl-1H-imidazol-1-yl)phenyl]-1H-1,2,3-triazol-1-yl}acetamide (50 mg, 0.113 mmol) and KHMDS (27.1 mg, 0.136 mmol) were added to a 25-mL flask under nitrogen and DMF (3 ml) was added. Trifluoroethyl triflate (0.023 ml, 0.159 mmol) was added and the suspension stirred at room temperature for 16 h. The residue was purified by preparative HPLC Reverse phase (C-18), eluting with Acetonitrile/Water+0.1% TFA, to give the product (25 mg) as a yellow solid.

$^1$H (500 MHz, DMSO-d6): 1.33 (s, 3H), 3.94 (s, 3H), 4.57 (q, J=9.0 Hz, 2H), 5.28 (s, 2H), 7.61-7.64 (m, 4H), 7.74 (s, 1H), 7.76 (s, 1H), 7.93 (m, 1H), 8.62 (s, 1H), 9.33 (s, 1H).

LCMS (ESI): calcd for $C_{23}H_{20}ClF_4N_6O_2$ [M+H]$^+$ 523.1. found 523.1

Example 13

(R) and (S)-6,8-difluoro-3-{4-[3-methoxy-4-(4-methyl-1H-imidazol-1-yl)phenyl]-1H-1,2,3-triazol-1-yl}-1-(2,2,2-trifluoro ethyl)-1,3,4,5-tetrahydro-2H-1-benzazepin-2-one

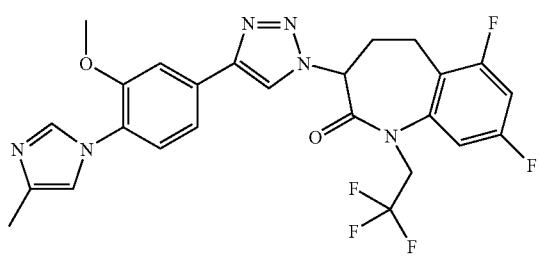

6,8-difluoro-3-{-4-[3-methoxy-4-(4-methyl-1H-imidazol-1-yl)phenyl]-1H-1,2,3-triazol-1-yl}-1,3,4,5-tetrahydro-2H-1-benzazepin-2-one (45 mg, 0.08 mmol) and caesium carbonate (46.1 mg, 0.239 mmol) were suspended in THF (3 ml) at room temperature and trifluoroethyl triflate (0.014 ml, 0.096 mmol) added according to GP5 method c. The product (40 mg) was obtained as TFA salt. The free base was obtained by washing an EtOAc solution with potassium carbonate solution (aqueous, saturated). The organic layer was dried over MgSO4 and evaporated under reduced pressure to give the free base as a yellow solid.

Resolution: 50% iso-propanol/heptane Column: Chiral Technology OD 2×25 cm, 10 uM; 10 mL/min, 45 minute run; 254 nm detection; enantiomer 1 t$_r$=10.71 min, enantiomer 2 t$_r$=15.07 min $^1$H (500 MHz, TFA salt, DMSO-d6): 2.33 (s, 3H), 2.50 (m, 1H), 2.68 (m, 1H), 2.95 (m, 1H), 3.23 (m, 1H), 3.94 (s, 3H), 4.66 (m, 1H), 5.05 (m, 1H), 5.59 (m, 1H), 7.38 (m, 1H), 7.56 (d, J=9.8 Hz), 7.62-7.66 (m, 2H), 7.76 (dd, J=1.0, 9.8 Hz, 1H), 9.03 (s, 1H), 9.33 (s, 1H).

LCMS (ESI): calcd for $C_{25}H_{22}F_5N_6O_2$ [M+H]$^+$ 533.2. found 533.2

Biological Activity

Using the cell-based assay described previously, the following results were obtained:

| Example | Aβ42 IC$_{50}$ (nM) |
|---|---|
| 1 | 616 |
| 2 | 386/1330 * |
| 3 | 310 |
| 4 | 529 |
| 5 | 2662 |
| 6 | 177 |
| 7 | 2245 |

-continued

| Example | Aβ42 IC$_{50}$ (nM) |
|---|---|
| 8 | 1071 |
| 9 | 933 |
| 10 | 21/490 * |
| 11 | 35/1903 * |

-continued

| Example | Aβ42 IC$_{50}$ (nM) |
|---|---|
| 12 | 84 |
| 13 | 44/456 * |

* results for individual enantiomers.

Using analogous methods, the compounds shown in Tables I-IV were also prepared and were found to inhibit Aβ42 production with an IC$_{50}$ of less than 5.0 μM, in most cases less than 1.0 μM, and with at least a two-fold selectivity for Aβ42 over Aβ40.

TABLE I

| EX. | Structure | Name | [M + H]$^+$ |
|---|---|---|---|
| 14 | 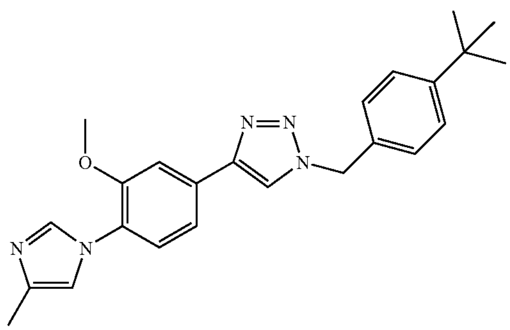 | 1-(4-tert-butylbenzyl)-4-[3-methoxy-4-(4-methyl-1H-imidazol-1-yl)phenyl]-1H-1,2,3-triazole | Calc'd 402.2, found 402.0 |
| 15 | 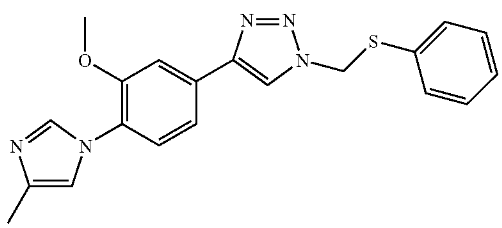 | 4-[3-methoxy-4-{4-methyl-1H-imidazol-1-yl)phenyl]-1-[(phenylthio)methyl]-1H-1,2,3-triazole | Calc'd 378.1, found 378.1 |
| 16 | 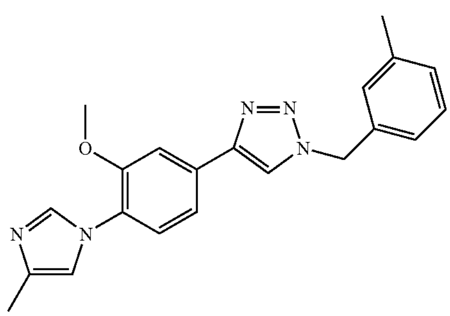 | 4-[3-methoxy-4-(4-methyl-1H-imidazol-1-yl)phenyl]-1-(3-methylbenzyl)-1H-1,2,3-triazole | Calc'd 360.2, found 360.2 |
| 17 | 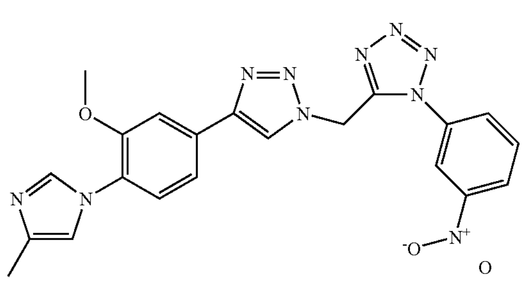 | 5-({4-[3-methoxy-4-(4-methyl-1H-imidazol-1-yl)phenyl]-1H-1,2,3-triazol-1-yl}methyl)-1-(3-nitrophenyl)-1H-tetrazole | Calc'd 459.2, found 459.1 |

TABLE I-continued

| EX. | Structure | Name | [M + H]+ |
|---|---|---|---|
| 18 | 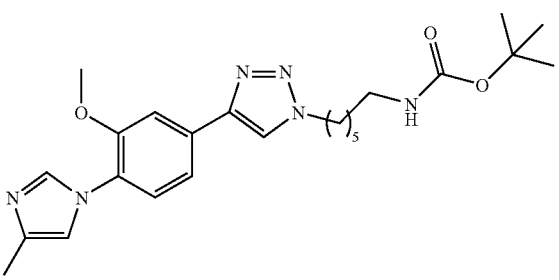 | tert-butyl (6-{4-[3-methoxy-4-(4-methyl-1H-imidazol-1-yl)phenyl]-1H-1,2,3-triazol-1-yl}hexyl)carbamate | Calc'd 455.3, found 455.2 |
| 19 | 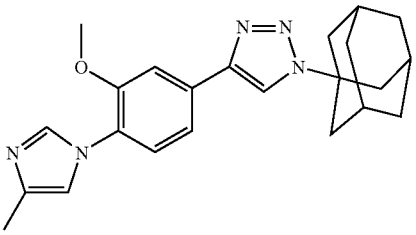 | 1-(1-adamantyl)-4-[3-methoxy-4-(4-methyl-1H-imidazol-1-yl)phenyl]-1H-1,2,3-triazole | Calc'd 390.2, found 390.2 |
| 20 | 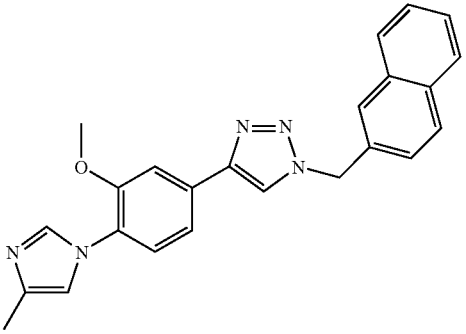 | 4-[3-methoxy-4-(4-methyl-1H-imidazol-1-yl)phenyl]-1-(2-naphthylmethyl)-1H-1,2,3-triazole | Calc'd 396.2, found 396.1 |
| 21 | 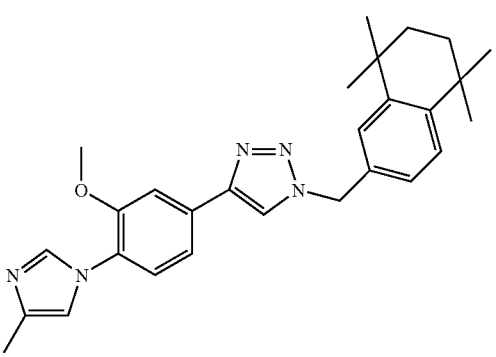 | 4-[3-methoxy-4-(4-methyl-1H-imidazol-1-yl)phenyl]-1-[(5,5,8,8-tetramethyl-5,6,7,8-tetrahydronaphthalen-2-yl)methyl]-1H-1,2,3-triazole | Calc'd 456.3, found 456.2 |
| 22 | 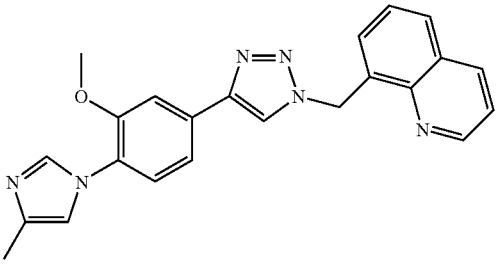 | 8-({4-[3-methoxy-4-(4-methyl-1H-imidazol-1-yl)phenyl]-1H-1,2,3-triazol-1-yl}methyl)quinoline | Calc'd 397.2, found 397.1 |

TABLE I-continued

| EX. | Structure | Name | [M + H]⁺ |
|---|---|---|---|
| 23 | 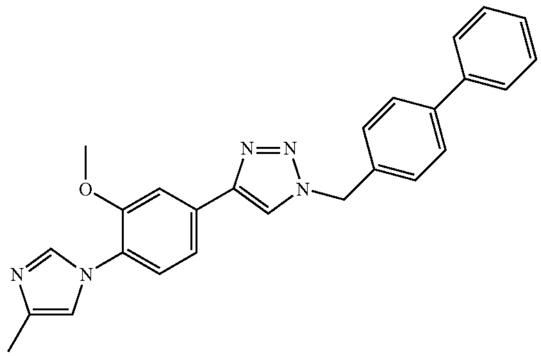 | 1-(biphenyl-4-ylmethyl)-4-[3-methoxy-4-(4-methyl-1H-imidazol-1-yl)phenyl]-1H-1,2,3-triazole | Calc'd 422.2, found 422.2 |
| 24 | 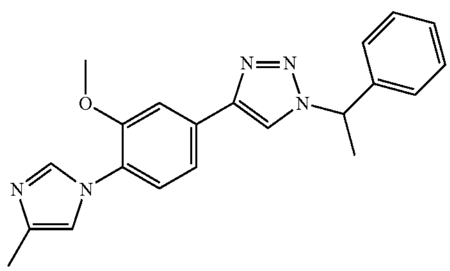 | 4-[3-methoxy-4-(4-methyl-1H-imidazol-1-yl)phenyl]-1-(1-phenylethyl)-1H-1,2,3-triazole | Calc'd 360.2, found 360.1 |
| 25 | 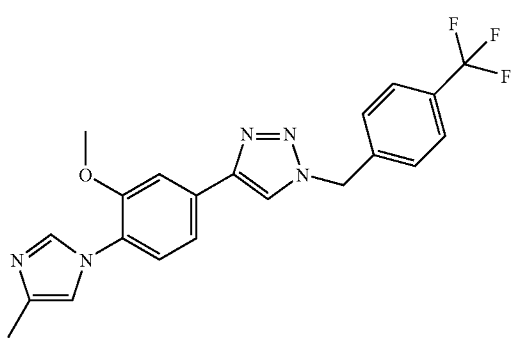 | 4-[3-methoxy-4-(4-methyl-1H-imidazol-1-yl)phenyl]-1-[4-(trifluoromethyl)benzyl]-1H-1,2,3-triazole | Calc'd 414.2, found 414.1 |
| 26 | 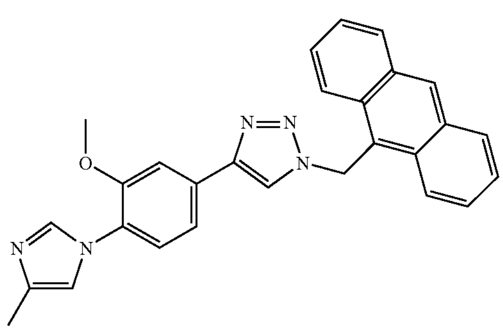 | 1-(9-anthrylmethyl)-4-[3-methoxy-4-(4-methyl-1H-imidazol-1-yl)phenyl]-1H-1,2,3-triazole | Calc'd 446.2, found 446.1 |

TABLE I-continued

| EX. | Structure | Name | [M + H]+ |
|---|---|---|---|
| 27 | 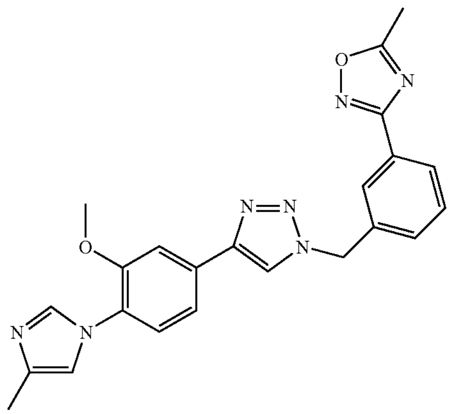 | 3-[3-({4-[3-methoxy-4-(4-methyl-1H-imidazol-1-yl)phenyl]-1H-1,2,3-triazol-1-yl}methyl)phenyl]-5-methyl-1,2,4-oxadiazole | Calc'd 428.2, found 428.1 |
| 28 | 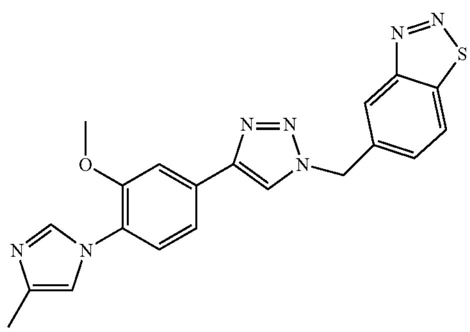 | 5-({4-[3-methoxy-4-(4-methyl-1H-imidazol-1-yl)phenyl]-1H-1,2,3-triazol-1-yl}methyl)-1,2,3-benzothiadiazole | Calc'd 404.1, found 404.0 |
| 29 | 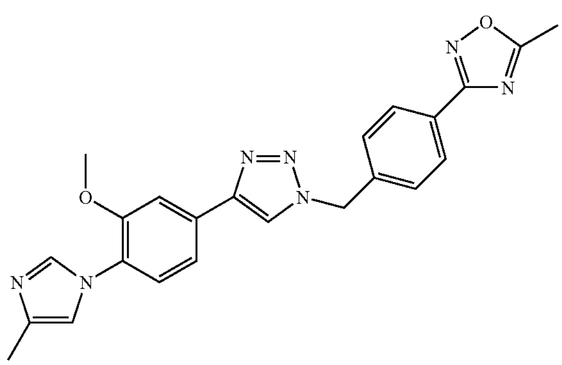 | 3-[4-({4-[3-methoxy-4-(4-methyl-1H-imidazol-1-yl)phenyl]-1H-1,2,3-triazol-1-yl}methyl)phenyl]-5-methyl-1,2,4-oxadiazole | Calc'd 428.2, found 428.0 |
| 30 | 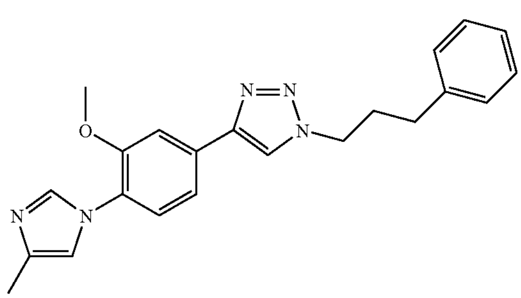 | 4-[3-methoxy-4-(4-methyl-1H-imidazol-1-yl)phenyl]-1-(3-phenylpropyl)-1H-1,2,3-triazole | Calc'd 374.2, found 374.2 |

TABLE I-continued

| EX. | Structure | Name | [M + H]+ |
|---|---|---|---|
| 31 | 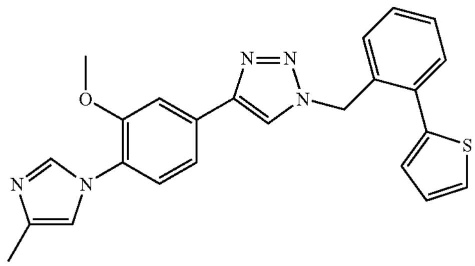 | 4-[3-methoxy-4-(4-methyl-1H-imidazol-1-yl)phenyl]-1-[2-(2-thienyl)benzyl]-1H-1,2,3-triazole | Calc'd 428.2, found 428.1 |
| 32 | 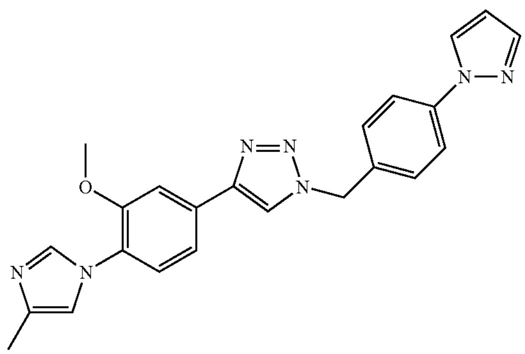 | 4-[3-methoxy-4-(4-methyl-1H-imidazol-1-yl)phenyl]-1-[4-(1H-pyrazol-1-yl)benzyl]-1H-1,2,3-triazole | Calc'd 412.2, found 412.2 |
| 33 | 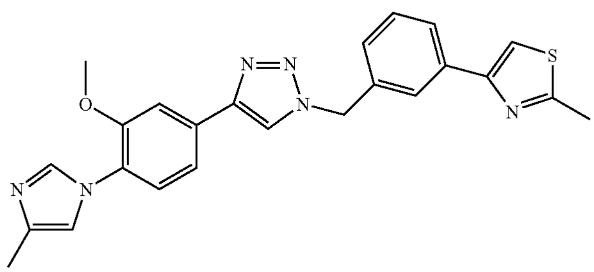 | 4-[3-methoxy-4-(4-methyl-1H-imidazol-1-yl)phenyl]-1-[3-(2-methyl-1,3-thiazol-4-yl)benzyl]-1H-1,2,3-triazole | Calc'd 443.2, found 443.1 |
| 34 | 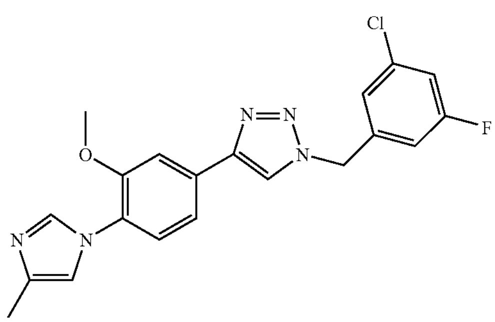 | 1-(3-chloro-5-fluorobenzyl)-4-[3-methoxy-4-(4-methyl-1H-imidazol-1-yl)phenyl]-1H-1,2,3-triazole | Calc'd 398.1, found 398.1 |
| 35 | 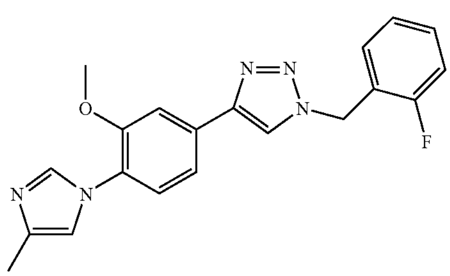 | 1-(2-fluorobenzyl)-4-[3-methoxy-4-(4-methyl-1H-imidazol-1-yl)phenyl]-1H-1,2,3-triazole | Calc'd 364.2, found 364.1 |

TABLE I-continued

| EX. | Structure | Name | [M + H]⁺ |
|---|---|---|---|
| 36 | 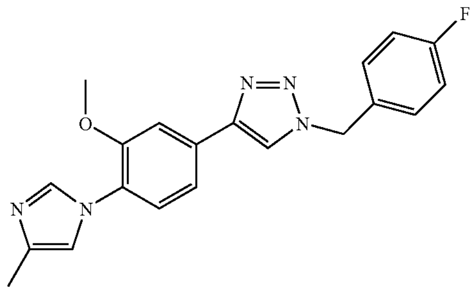 | 1-(4-fluorobenzyl)-4-[3-methoxy-4-(4-methyl-1H-imidazol-1-yl)phenyl]-1H-1,2,3-triazole | Calc'd 364.2, found 364.1 |
| 37 | 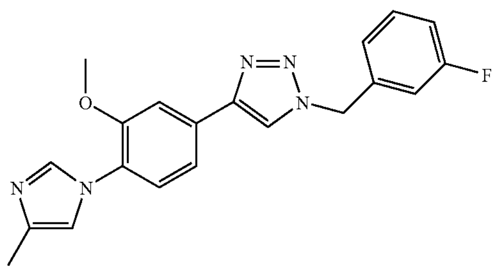 | 1-(3-fluorobenzyl)-4-[3-methoxy-4-(4-methyl-1H-imidazol-1-yl)phenyl]-1H-1,2,3-triazole | Calc'd 364.2, found 364.1 |
| 38 | 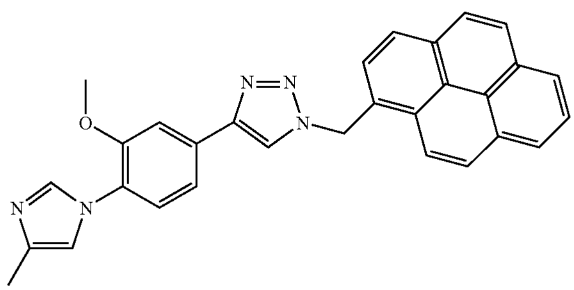 | 4-[3-methoxy-4-(4-methyl-1H-imidazol-1-yl)phenyl]-1-(pyren-1-ylmethyl)-1H-1,2,3-triazole | Calc'd 470.2, found 470.1 |
| 39 | 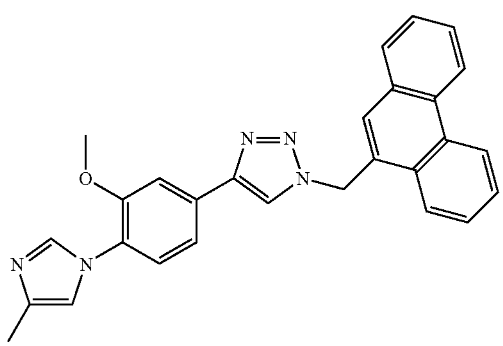 | 4-[3-methoxy-4-(4-methyl-1H-imidazol-1-yl)phenyl]-1-(9-phenanthrylmethyl)-1H-1,2,3-triazole | Calc'd 446.2, found 446.1 |
| 40 | 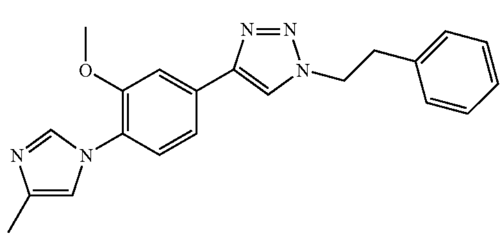 | 4-[3-methoxy-4-(4-methyl-1H-imidazol-1-yl)phenyl]-1-(2-phenylethyl)-1H-1,2,3-triazole | Calc'd 360.2, found 360.2 |

TABLE I-continued

| EX. | Structure | Name | [M + H]+ |
|---|---|---|---|
| 41 | 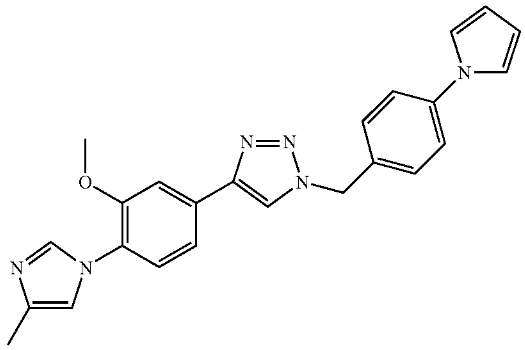 | 4-[3-methoxy-4-(4-methyl-1H-imidazol-1-yl)phenyl]-1-[4-(1H-pyrrol-1-yl)benzyl]-1H-1,2,3-triazole | Calc'd 411.2, found 411.2 |
| 42 | 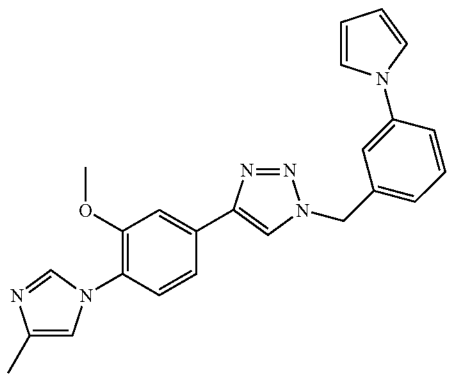 | 4-[3-methoxy-4-(4-methyl-1H-imidazol-1-yl)phenyl]-1-[3-(1H-pyrrol-1-yl)benzyl]-1H-1,2,3-triazole | Calc'd 411.2, found 411.2 |
| 43 | 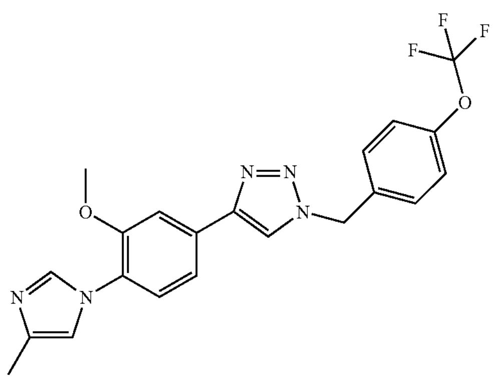 | 4-[3-methoxy-4-(4-methyl-1H-imidazol-1-yl)phenyl]-1-[4-(trifluoromethoxy)benzyl]-1H-1,2,3-triazole | Calc'd 430.1, found 429.9 |
| 44 | 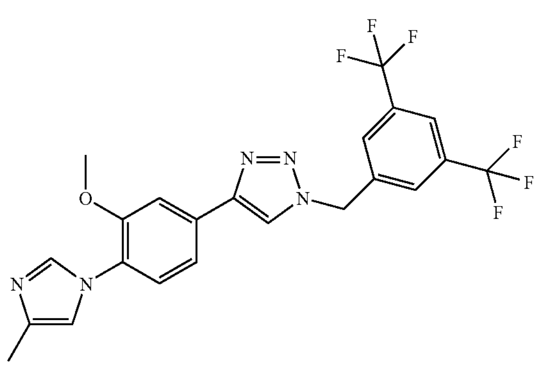 | 1-[3,5-bis(trifluoromethyl)benzyl]-4-[3-methoxy-4-(4-methyl-1H-imidazol-1-yl)phenyl]-1H-1,2,3-triazole | Calc'd 482.1, found 481.9 |

TABLE I-continued

| EX. | Structure | Name | [M + H]+ |
|---|---|---|---|
| 45 | 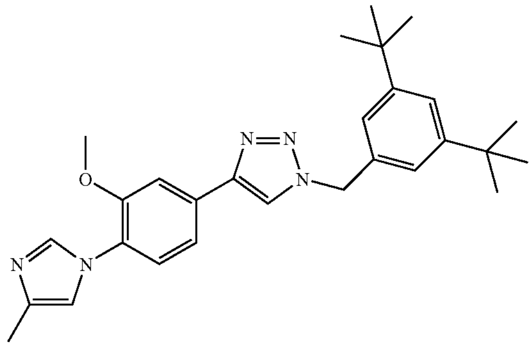 | 1-(3,5-di-tert-butylbenzyl)-4-[3-methoxy-4-(4-methyl-1H-imidazol-1-yl)phenyl]-1H-1,2,3-triazole | Calc'd 458.3, found 458.0 |
| 46 | 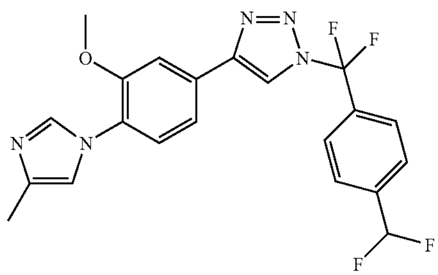 | 1-{[4-(difluoromethyl)phenyl](difluoro)methyl}-4-[3-methoxy-4-(4-methyl-1H-imidazol-1-yl)phenyl]-1H-1,2,3-triazole | Calc'd 432.1, found 432.0 |
| 47 | 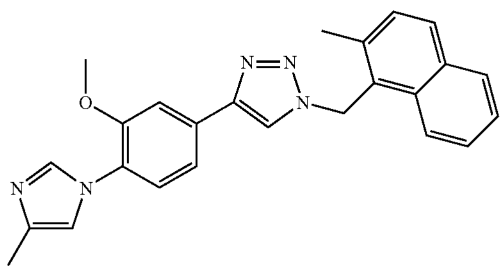 | 4-[3-methoxy-4-(4-methyl-1H-imidazol-1-yl)phenyl]-1-[(2-methyl-1-naphthyl)methyl]-1H-1,2,3-triazole | Calc'd 410.2, found 410.0 |
| 48 | 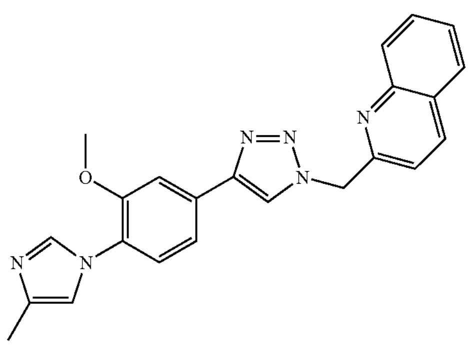 | 2-({4-[3-methoxy-4-(4-methyl-1H-imidazol-1-yl)phenyl]-1H-1,2,3-triazol-1-yl}methyl)quinoline | Calc'd 397.2, found 397.0 |
| 49 | 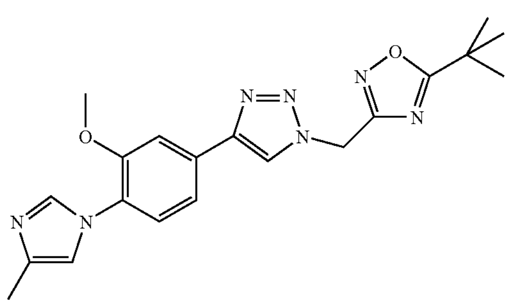 | 5-tert-butyl-3-({4-[3-methoxy-4-(4-methyl-1H-imidazol-1-yl)phenyl]-1H-1,2,3-triazol-1-yl}methyl)-1,2,4-oxadiazole | Calc'd 394.2, found 394.0 |

TABLE I-continued

| EX. | Structure | Name | [M + H]+ |
|---|---|---|---|
| 50 | 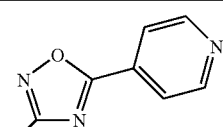 | 4-{3-[4-({4-[3-methoxy-4-(4-methyl-1H-imidazol-1-yl)phenyl]-1H-1,2,3-triazol-1-yl}methyl)phenyl]-1,2,4-oxadiazol-5-yl}pyridine | Calc'd 491.2, found 491.0 |
| 51 | 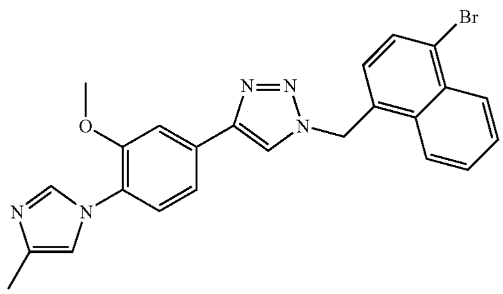 | 1-[(4-bromo-1-naphthyl)methyl]-4-[3-methoxy-4-(4-methyl-1H-imidazol-1-yl)phenyl]-1H-1,2,3-triazole | Calc'd 474.1, found 473.9 |
| 52 | 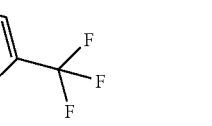 | 4-[3-methoxy-4-(4-methyl-1H-imidazol-1-yl)phenyl]-1-[3-(trifluoromethyl)benzyl]-1H-1,2,3-triazole | Calc'd 414.2, found 413.9 |
| 53 | 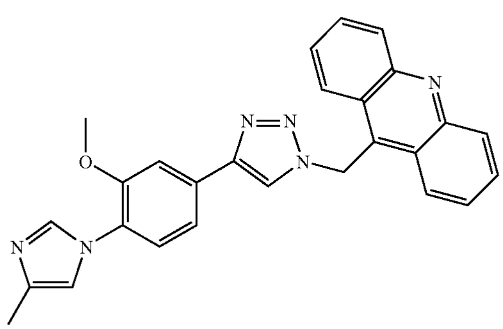 | 9-({4-[3-methoxy-4-(4-methyl-1H-imidazol-1-yl)phenyl]-1H-1,2,3-triazol-1-yl}methyl)acridine | Calc'd 447.2, found 447.0 |

TABLE I-continued

| EX. | Structure | Name | [M + H]+ |
|---|---|---|---|
| 54 | 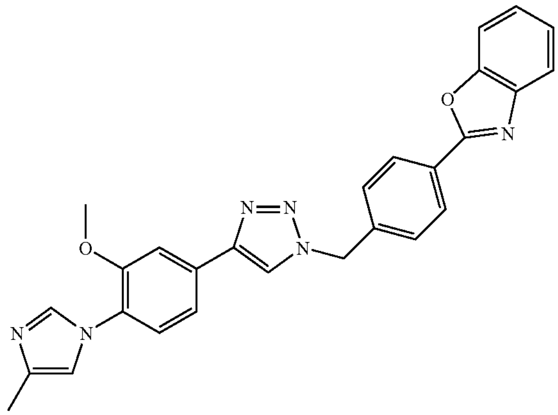 | 2-[4-({4-[3-methoxy-4-(4-methyl-1H-imidazol-1-yl)phenyl]-1H-1,2,3-triazol-1-yl}methyl)phenyl]-1,3-benzoxazole | Calc'd 463.2, found 463.0 |
| 55 | 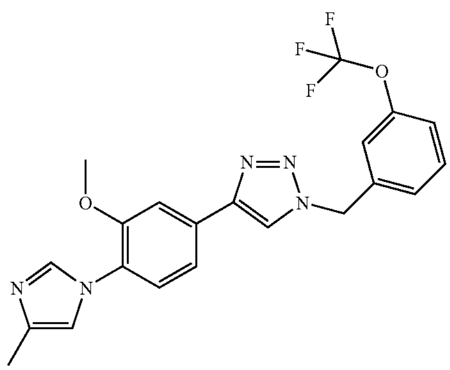 | 4-[3-methoxy-4-(4-methyl-1H-imidazol-1-yl)phenyl]-1-[3-(trifluoromethoxy)benzyl]-1H-1,2,3-triazole | Calc'd 430.1, found 429.9 |
| 56 | 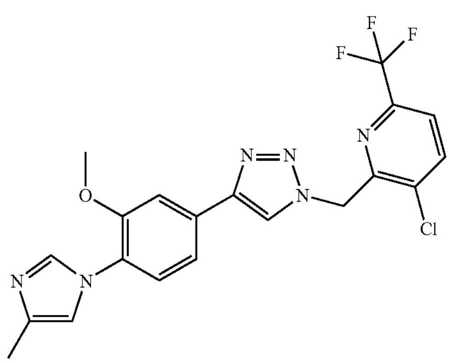 | 3-chloro-2-({4-[3-methoxy-4-(4-methyl-1H-imidazol-1-yl)phenyl]-1H-1,2,3-triazol-1-yl}methyl)-6-(trifluoromethyl)pyridine | Calc'd 449.1, found 448.9 |
| 57 | 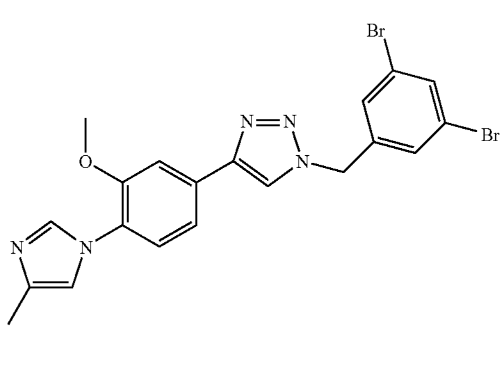 | 1-(3,5-dibromobenzyl)-4-[3-methoxy-4-(4-methyl-1H-imidazol-1-yl)phenyl]-1H-1,2,3-triazole | Calc'd 502.0, found 503.7 |

TABLE I-continued

| EX. | Structure | Name | [M + H]+ |
|---|---|---|---|
| 58 | 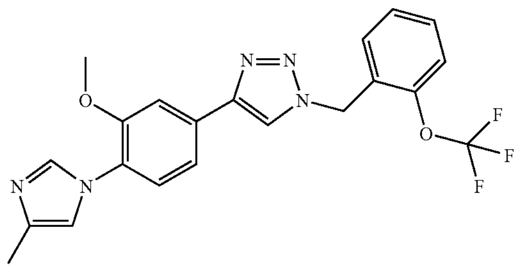 | 4-[3-methoxy-4-(4-methyl-1H-imidazol-1-yl)phenyl]-1-[2-(trifluoromethoxy)benzyl]-1H-1,2,3-triazole | Calc'd 430.1, found 429.9 |
| 59 | 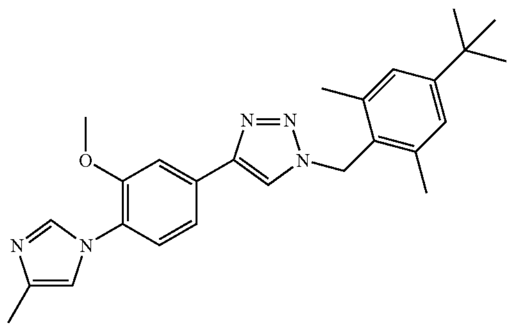 | 1-(4-tert-butyl-2,6-dimethylbenzyl)-4-[3-methoxy-4-(4-methyl-1H-imidazol-1-yl)phenyl]-1H-1,2,3-triazole | Calc'd 430.3, found 430.1 |
| 60 | 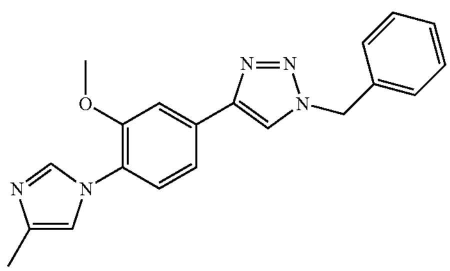 | 1-benzyl-4-[3-methoxy-4-(4-methyl-1H-imidazol-1-yl)phenyl]-1H-1,2,3-triazole | Calc'd 346.2, found 346.1 |
| 61 | 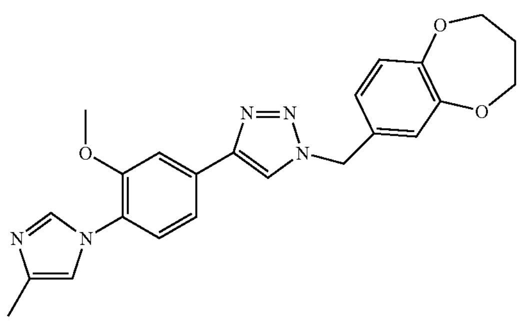 | 1-(3,4-dihydro-2H-1,5-benzodioxepin-7-ylmethyl)-4-[3-methoxy-4-(4-methyl-1H-imidazol-1-yl)phenyl]-1H-1,2,3-triazole | Calc'd 418.2, found 418.2 |
| 62 | 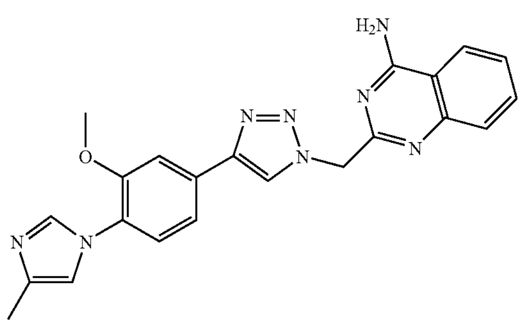 | 2-({4-[3-methoxy-4-(4-methyl-1H-imidazol-1-yl)phenyl]-1H-1,2,3-triazol-1-yl}methyl)quinazolin-4-amine | Calc'd 413.2, found 413.2 |

TABLE I-continued

| EX. | Structure | Name | [M + H]+ |
|---|---|---|---|
| 63 | 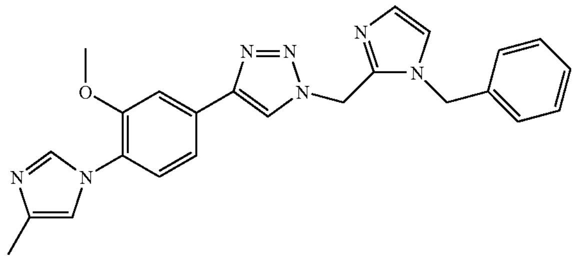 | 1-[(1-benzyl-1H-imidazol-2-yl)methyl]-4-[3-methoxy-4-(4-methyl-1H-imidazol-1-yl)phenyl]-1H-1,2,3-triazole | Calc'd 426.2, found 426.2 |
| 64 | 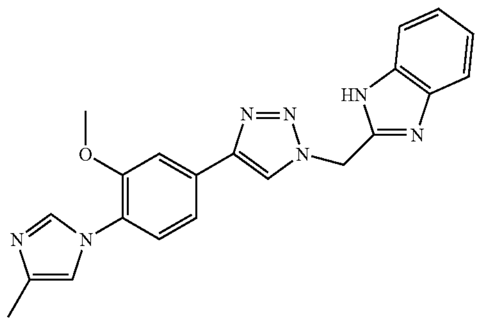 | 2-({4-[3-methoxy-4-(4-methyl-1H-imidazol-1-yl)phenyl]-1H-1,2,3-triazol-1-yl}methyl)-1H-benzimidazole | Calc'd 386.2, found 386.2 |
| 65 | 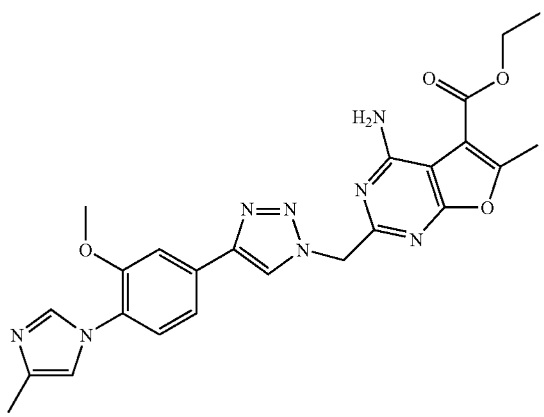 | ethyl 4-amino-2-({4-[3-methoxy-4-(4-methyl-1H-imidazol-1-yl)phenyl]-1H-1,2,3-triazol-1-yl}methyl)-6-methylfuro[2,3-d]pyrimidine-5-carboxylate | Calc'd 489.2, found 489.2 |
| 66 | 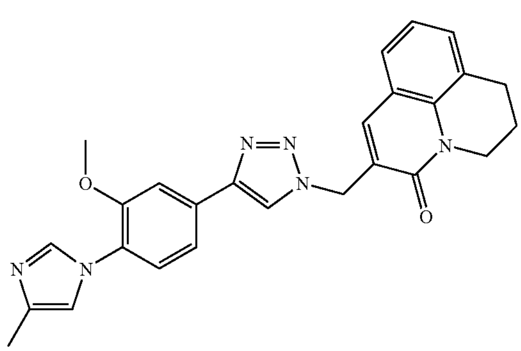 | 6-({4-[3-methoxy-4-(4-methyl-1H-imidazol-1-yl)phenyl]-1H-1,2,3-triazol-1-yl}methyl)-2,3-dihydro-1H,5H-pyrido[3,2,1-ij]quinolin-5-one | Calc'd 453.2, found 453.2 |

TABLE I-continued

| EX. | Structure | Name | [M + H]⁺ |
|---|---|---|---|
| 67 | 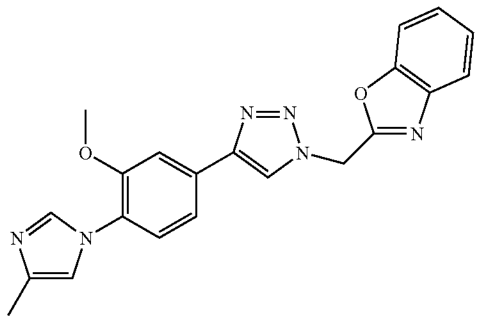 | 2-({4-[3-methoxy-4-(4-methyl-1H-imidazol-1-yl)phenyl]-1H-1,2,3-triazol-1-yl}methyl)-1,3-benzoxazole | Calc'd 387.2, found 387.1 |
| 68 | 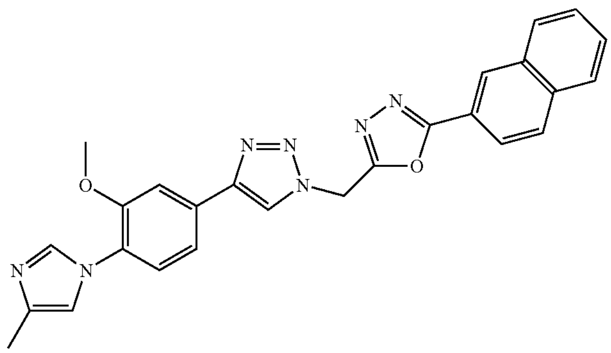 | 2-({4-[3-methoxy-4-(4-methyl-1H-imidazol-1-yl)phenyl]-1H-1,2,3-triazol-1-yl}methyl)-5-(2-naphthyl)-1,3,4-oxadiazole | Calc'd 464.2, found 464.2 |
| 69 | 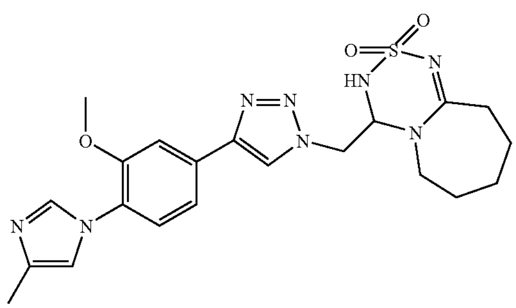 | 4-({4-[3-methoxy-4-(4-methyl-1H-imidazol-1-yl)phenyl]-1H-1,2,3-triazol-1-yl}methyl)-3,4,7,8,9,10-hexahydro-6H-[1,2,4,6]thiatriazino[4,3-a]azepine 2,2-dioxide | Calc'd 471.2, found 471.2 |
| 70 | 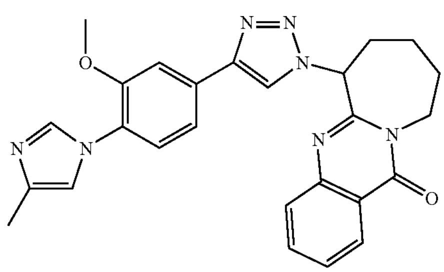 | 6-{4-[3-methoxy-4-(4-methyl-1H-imidazol-1-yl)phenyl]-1H-1,2,3-triazol-1-yl}-7,8,9,10-tetrahydroazepine[2,1-b]quinazolin-12(6H)-one | Calc'd 468.2, found 468.2 |
| 71 | 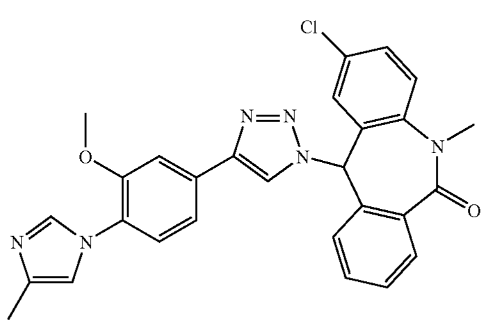 | 2-chloro-11-{4-[3-methoxy-4-(4-methyl-1H-imidazol-1-yl)phenyl]-1H-1,2,3-triazol-1-yl}-5-methyl-5,11-dihydro-6H-dibenzo[b,e]azepin-6-one | Calc'd 511.2, found 511.2 |

TABLE I-continued

| EX. | Structure | Name | [M + H]+ |
|---|---|---|---|
| 72 | | 1-[(2,4-diphenyl-1,3-thiazol-5-yl)methyl]-4-[3-methoxy-4-(4-methyl-1H-imidazol-1-yl)phenyl]-1H-1,2,3-triazole | Calc'd 505.2, found 505.2 |
| 72 | | 4-[3-methoxy-4-(4-methyl-1H-imidazol-1-yl)phenyl]-1-[(1-phenyl-1H-1,2,3-triazol-4-yl)methyl]-1H-1,2,3-triazole | Calc'd 413.2, found 413.2 |
| 73 | 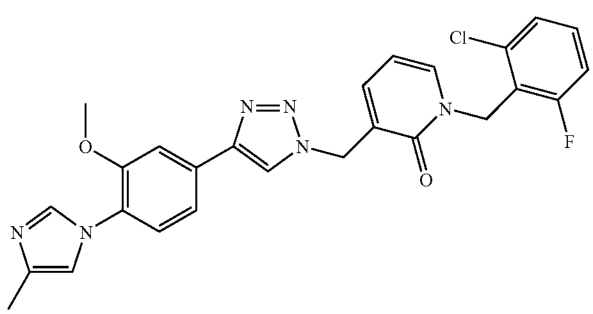 | 1-(2-chloro-6-fluorobenzyl)-3-({4-[3-methoxy-4-(4-methyl-1H-imidazol-1-yl)phenyl]-1H-1,2,3-triazol-1-yl}methyl)pyridin-2(1H)-one | Calc'd 505.2, found 505.2 |
| 74 | 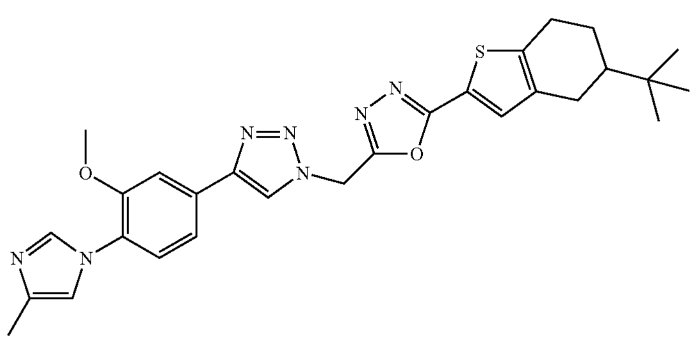 | 2-(5-tert-butyl-4,5,6,7-tetrahydro-1-benzothien-2-yl)-5-({4-[3-methoxy-4-(4-methyl-1H-imidazol-1-yl)phenyl]-1H-1,2,3-triazol-1-yl}methyl)-1,3,4-oxadiazole | Calc'd 530.2, found 530.2 |

TABLE I-continued

| EX. | Name | [M + H]+ |
|---|---|---|
| 75 | 2-({4-[3-methoxy-4-(4-methyl-1H-imidazol-1-yl)phenyl]-1H-1,2,3-triazol-1-yl}methyl)-1H-perimidine | Calc'd 436.2, found 436.2 |
| 76 | 2-[3-({4-[3-methoxy-4-(4-methyl-1H-imidazol-1-yl)phenyl]-1H-1,2,3-triazol-1-yl}methyl)-1H-1,2,4-triazol-5-yl]aniline | Calc'd 428.2, found 214.7 |
| 77 | 11-{4-[3-methoxy-4-(4-methyl-1H-imidazol-1-yl)phenyl]-1H-1,2,3-triazol-1-yl}-6,11-dihydrodibenzo[b,e]oxepine-2-carbonitrile | Calc'd 475.2, found 475.2 |
| 78 | 1-bicyclo[4.2.0]octa-1,3,5-trien-7-yl-4-[3-methoxy-4-(4-methyl-1H-imidazol-1-yl)phenyl]-1H-1,2,3-triazole | Calc'd 358.2, found 358.2 |
| 79 | 4-({4-[3-methoxy-4-(4-methyl-1H-imidazol-1-yl)phenyl]-1H-1,2,3-triazol-1-yl}methyl)-3,4,7,8,9,10-hexahydro-6H-[1,2,4,6]thiatriazino[4,3-a]azepine 2,2-dioxide | Calc'd 471.2, found 471.2 |

TABLE I-continued

| EX. | Structure | Name | [M + H]+ |
|---|---|---|---|
| 80 | 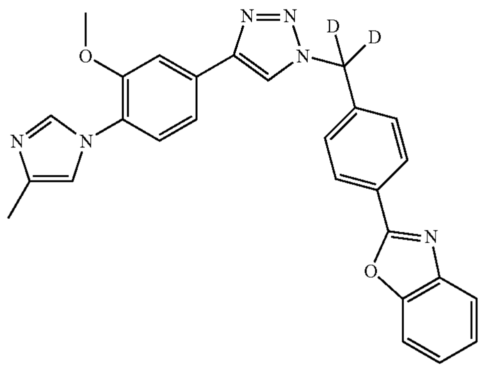 | 2-[4-({4-[3-methoxy-4-(4-methyl-1H-imidazol-1-yl)phenyl]-1H-1,2,3-triazol-1-yl}methyl)phenyl]-1,3-benzoxazole-d_2_ | Calc'd 465.2, found 465.2 |
| 81 | 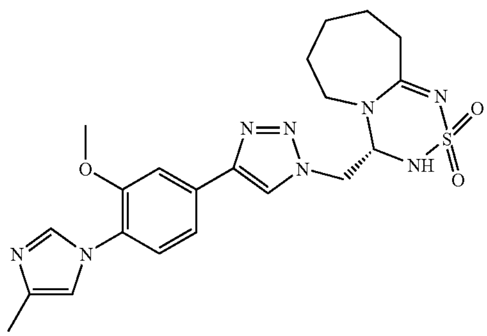 | (4R)-4-({4-[3-methoxy-4-(4-methyl-1H-imidazol-1-yl)phenyl]-1H-1,2,3-triazol-1-yl}methyl)-3,4,7,8,9,10-hexahydro-6H-[1,2,4,6]thiatriazino[4,3-a]azepine 2,2-dioxide | Calc'd 471.2, found 471.2 |
| 82 | 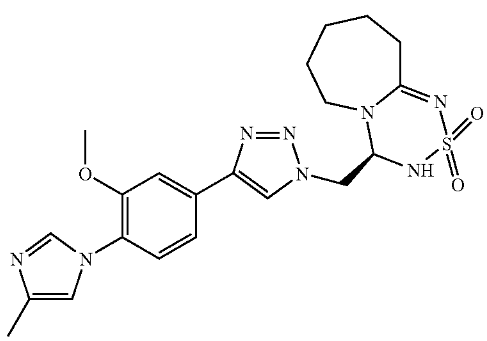 | (4S)-4-({4-[3-methoxy-4-(4-methyl-1H-imidazol-1-yl)phenyl]-1H-1,2,3-triazol-1-yl}methyl)-3,4,7,8,9,10-hexahydro-6H-[1,2,4,6]thiatriazino[4,3-a]azepine 2,2-dioxide | Calc'd 471.2, found 471.2 |
| 83 | 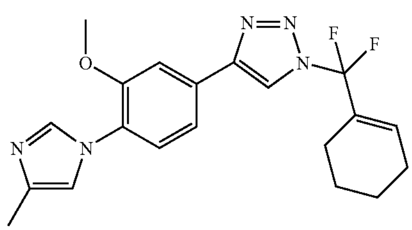 | 1-[cyclohex-1-en-1-yl(difluoro)methyl]-4-[3-methoxy-4-(4-methyl-1H-imidazol-1-yl)phenyl]-1H-1,2,3-triazole | Calc'd 386.2, found 386.2 |
| 84 | 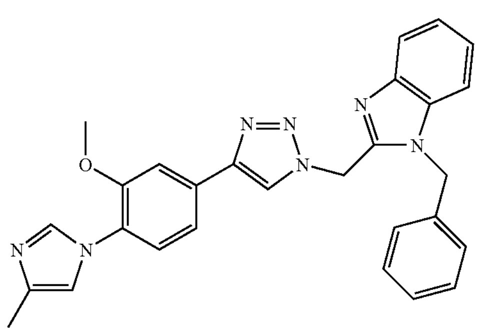 | 1-benzyl-2-({4-[3-methoxy-4-(4-methyl-1H-imidazol-1-yl)phenyl]-1H-1,2,3-triazol-1-yl}methyl)-1H-benzimidazole | Calc'd 476.2, found 476.2 |

| EX. | Structure | Name | [M + H]⁺ |
|---|---|---|---|
| 85 | 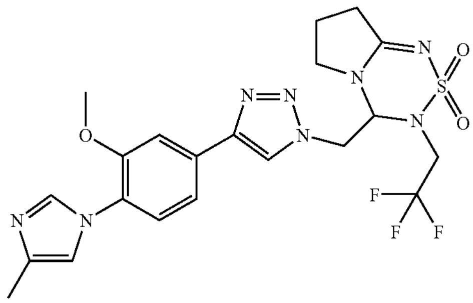 | 4-({4-[3-methoxy-4-(4-methyl-1H-imidazol-1-yl)phenyl]-1H-1,2,3-triazol-1-yl}methyl)-3-(2,2,2-trifluoroethyl)-3,4,7,8-tetrahydro-6H-pyrrolo[2,1-c][1,2,4,6]thiatriazine 2,2-dioxide | Calc'd 525.2, found 525.2 |
| 86 | 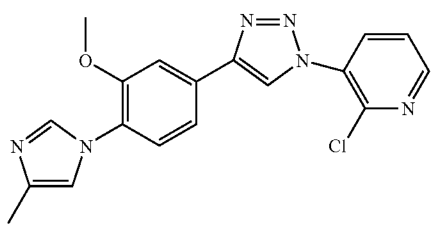 | 2-chloro-3-{4-[3-methoxy-4-(4-methyl-1H-imidazol-1-yl)phenyl]-1H-1,2,3-triazol-1-yl}pyridine | Calc'd 367.1, found 367.1 |
| 87 | 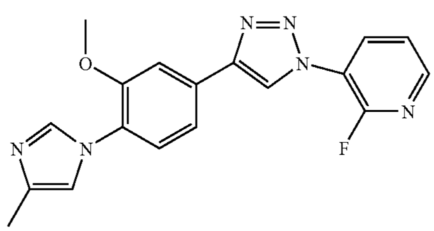 | 2-fluoro-3-{4-[3-methoxy-4-(4-methyl-1H-imidazol-1-yl)phenyl]-1H-1,2,3-triazol-1-yl}pyridine | Calc'd 351.1, found 351.1 |
| 88 | 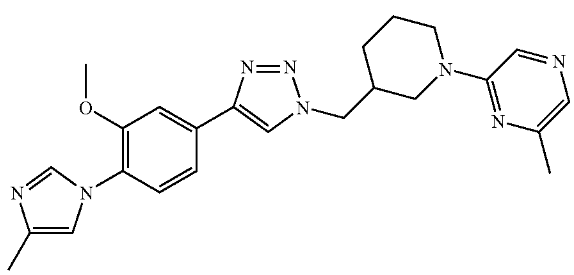 | 2-[3-({4-[3-methoxy-4-(4-methyl-1H-imidazol-1-yl)phenyl]-1H-1,2,3-triazol-1-yl}methyl)piperidin-1-yl]-6-methylpyrazine | Calc'd 445.2, found 445.2 |
| 89 | 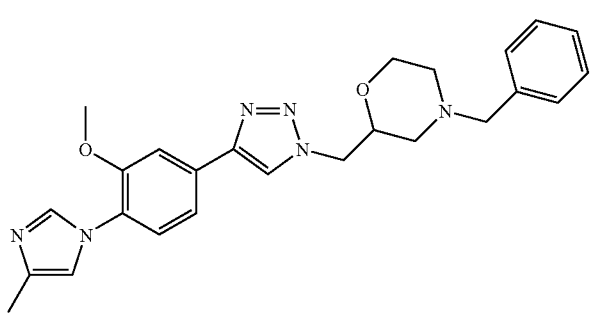 | 4-benzyl-2-({4-[3-methoxy-4-(4-methyl-1H-imidazol-1-yl)phenyl]-1H-1,2,3-triazol-1-yl}methyl)morpholine | Calc'd 445.2, found 445.2 |

TABLE I-continued

| EX. | Structure | Name | [M + H]+ |
|---|---|---|---|
| 90 | 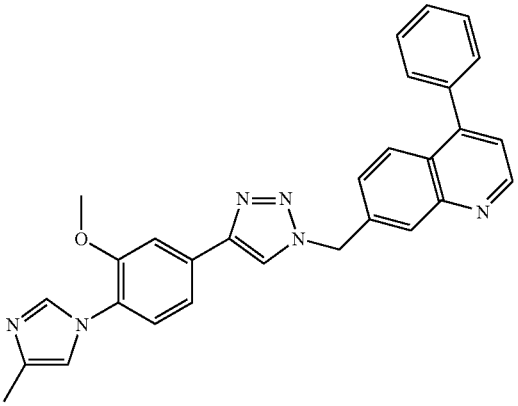 | 7-({4-[3-methoxy-4-(4-methyl-1H-imidazol-1-yl)phenyl]-1H-1,2,3-triazol-1-yl}methyl)-4-phenylquinoline | Calc'd 473.2, found 473.2 |
| 91 | 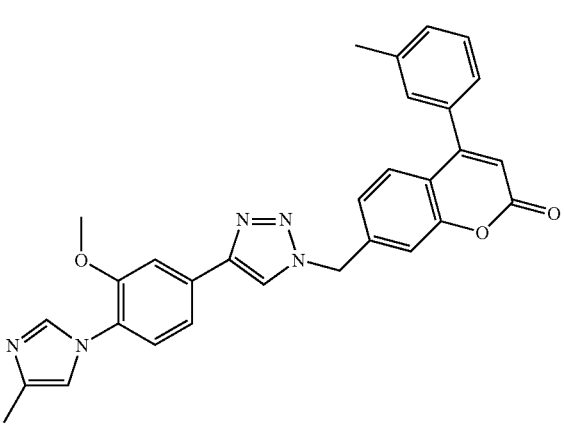 | 7-({4-[3-methoxy-4-(4-methyl-1H-imidazol-1-yl)phenyl]-1H-1,2,3-triazol-1-yl}methyl)-4-(3-methylphenyl)-2H-chromen-2-one | Calc'd 504.2, found 504.2 |
| 92 | 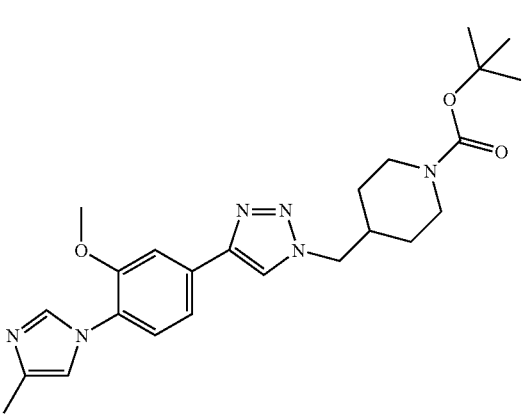 | tert-butyl 4-({4-[3-methoxy-4-(4-methyl-1H-imidazol-1-yl)phenyl]-1H-1,2,3-triazol-1-yl}methyl)piperidine-1-carboxylate | Calc'd 453.3, found 453.3 |
| 93 | 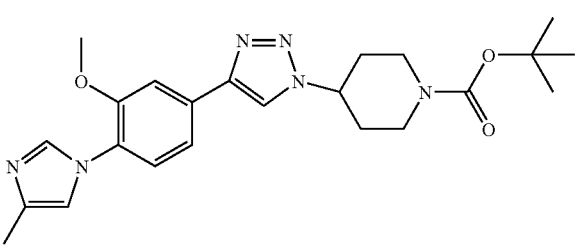 | tert-butyl 4-{4-[3-methoxy-4-(4-methyl-1H-imidazol-1-yl)phenyl]-1H-1,2,3-triazol-1-yl}piperidine-1-carboxylate | Calc'd 439.2, found 439.3 |

TABLE I-continued

| EX. | Structure | Name | [M + H]⁺ |
|---|---|---|---|
| 94 | 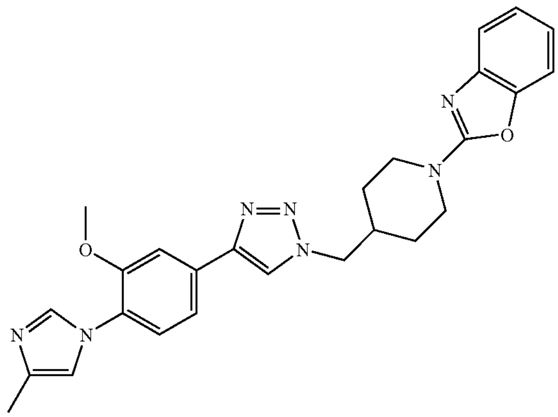 | 2-[4-({4-[3-methoxy-4-(4-methyl-1H-imidazol-1-yl)phenyl]-1H-1,2,3-triazol-1-yl}methyl)piperidin-1-yl]-1,3-benzoxazole | Calc'd 470.2, found 470.2 |
| 95 | 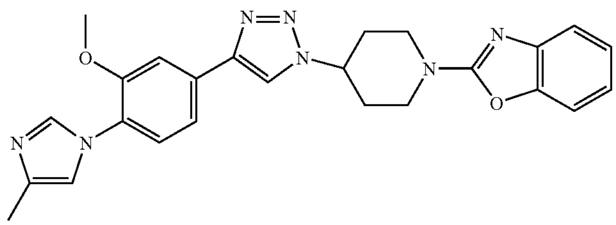 | 2-(4-{4-[3-methoxy-4-(4-methyl-1H-imidazol-1-yl)phenyl]-1H-1,2,3-triazol-1-yl}piperidin-1-yl)-1,3-benzoxazole | Calc'd 456.2, found 456.2 |
| 96 | 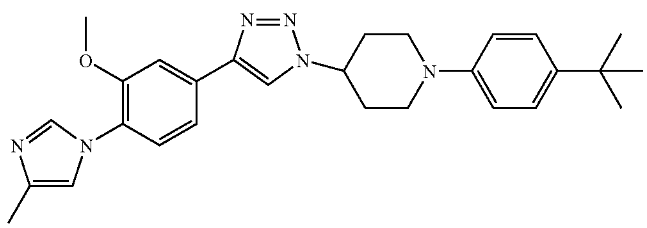 | 1-(4-tert-butylphenyl)-4-{4-[3-methoxy-4-(4-methyl-1H-imidazol-1-yl)phenyl]-1H-1,2,3-triazol-1-yl}piperidine | Calc'd 471.3, found 471.3 |
| 97 | 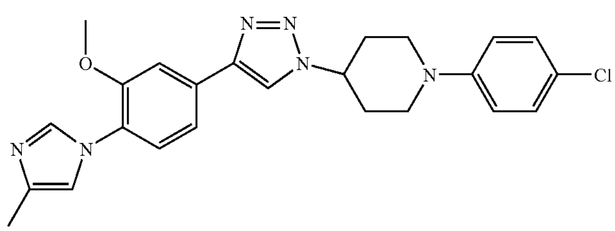 | 1-(4-chlorophenyl)-4-{4-[3-methoxy-4-(4-methyl-1H-imidazol-1-yl)phenyl]-1H-1,2,3-triazol-1-yl}piperidine | Calc'd 449.2, found 449.2 |
| 98 | 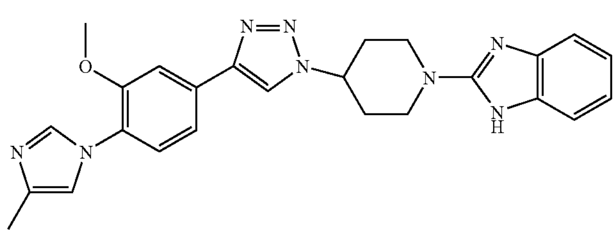 | 2-(4-{4-[3-methoxy-4-(4-methyl-1H-imidazol-1-yl)phenyl]-1H-1,2,3-triazol-1-yl}piperidin-1-yl)-1H-benzimidazole | Calc'd 455.2, found 455.2 |

TABLE I-continued

| EX. | Structure | Name | [M + H]⁺ |
|---|---|---|---|
| 99 | 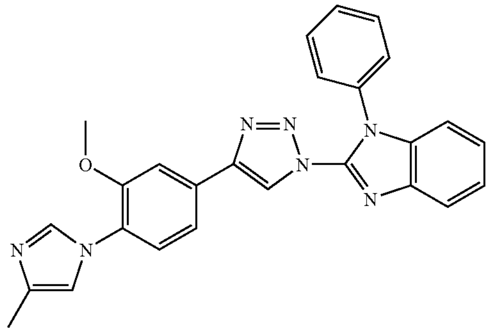 | 2-{4-[3-methoxy-4-(4-methyl-1H-imidazol-1-yl)phenyl]-1H-1,2,3-triazol-1-yl}-1-phenyl-1H-benzimidazole | Calc'd 448.2, found 448.2 |
| 100 | 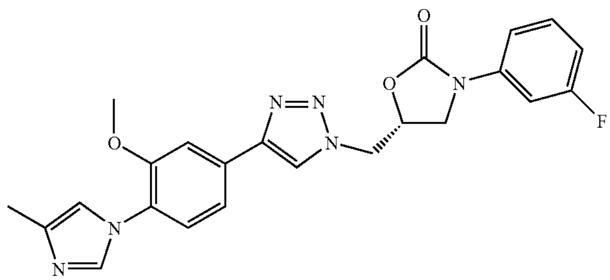 | (5R)-3-(3-fluorophenyl)-5-({4-[3-methoxy-4-(4-methyl-1H-imidazol-1-yl)phenyl]-1H-1,2,3-triazol-1-yl}methyl)-1,3-oxazolidin-2-one | Calc'd 449.2, found 449.2 |
| 101 | 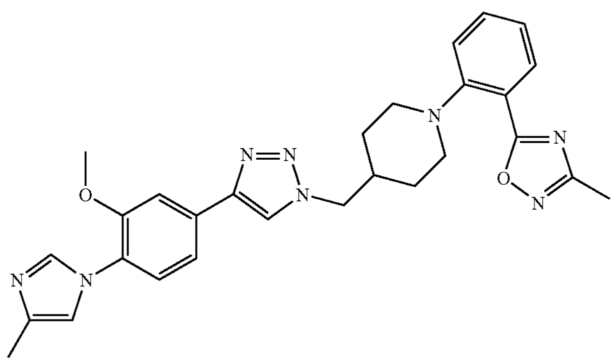 | 4-({4-[3-methoxy-4-(4-methyl-1H-imidazol-1-yl)phenyl]-1H-1,2,3-triazol-1-yl}methyl)-1-[2-(3-methyl-1,2,4-oxadiazol-5-yl)phenyl]piperidine | Calc'd 511.3, found 511.3 |
| 102 | 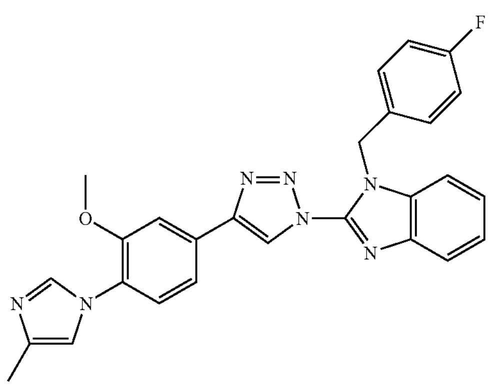 | 1-(4-fluorobenzyl)-2-{4-[3-methoxy-4-(4-methyl-1H-imidazol-1-yl)phenyl]-1H-1,2,3-triazol-1-yl}-1H-benzimidazole | Calc'd 480.2, found 480.2 |
| 103 | 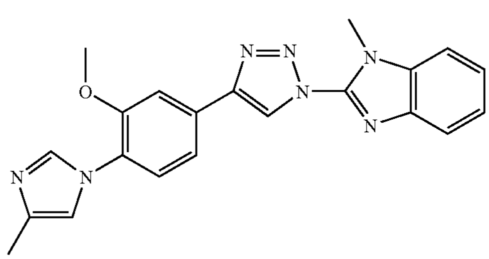 | 2-{4-[3-methoxy-4-(4-methyl-1H-imidazol-1-yl)phenyl]-1H-1,2,3-triazol-1-yl}-1-methyl-1H-benzimidazole | Calc'd 386.2, found 386.2 |

TABLE I-continued

| EX. | Structure | Name | [M + H]⁺ |
|---|---|---|---|
| 104 | 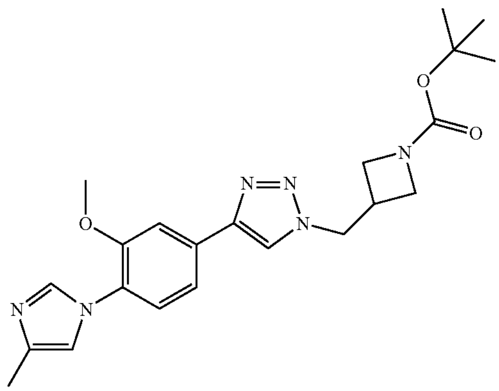 | tert-butyl 3-({4-[3-methoxy-4-(4-methyl-1H-imidazol-1-yl)phenyl]-1H-1,2,3-triazol-1-yl}methyl)azetidine-1-carboxylate | Calc'd 425.2, found 425.3 |
| 105 | 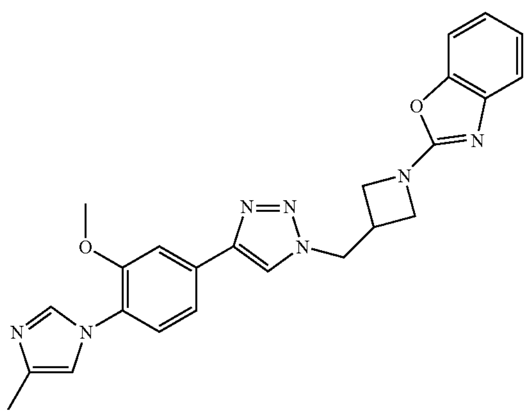 | 2-[3-({4-[3-methoxy-4-(4-methyl-1H-imidazol-1-yl)phenyl]-1H-1,2,3-triazol-1-yl}methyl)azetidin-1-yl]-1,3-benzoxazole | Calc'd 442.2, found 442.2 |
| 106 | 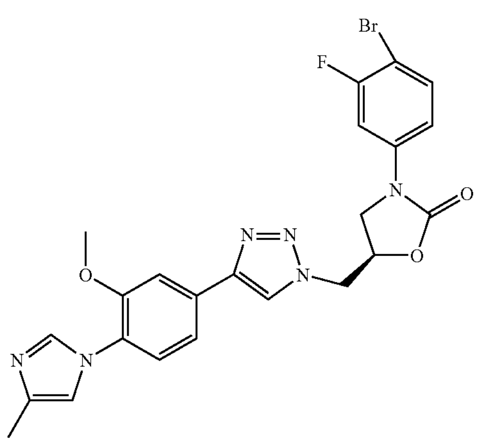 | (5R)-3-(4-bromo-3-fluorophenyl)-5-({4-[3-methoxy-4-(4-methyl-1H-imidazol-1-yl)phenyl]-1H-1,2,3-triazol-1-yl}methyl)-1,3-oxazolidin-2-one | Calc'd 527.1, found 527.0 |

TABLE I-continued

| EX. | Structure | Name | [M + H]+ |
|---|---|---|---|
| 107 | 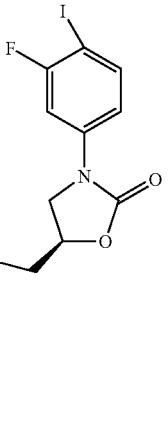 | (5R)-3-(3-fluoro-4-iodophenyl)-5-({4-[3-methoxy-4-(4-methyl-1H-imidazol-1-yl)phenyl]-1H-1,2,3-triazol-1-yl}methyl)-1,3-oxazolidin-2-one | Calc'd 575.1, found 575.0 |
| 108 | 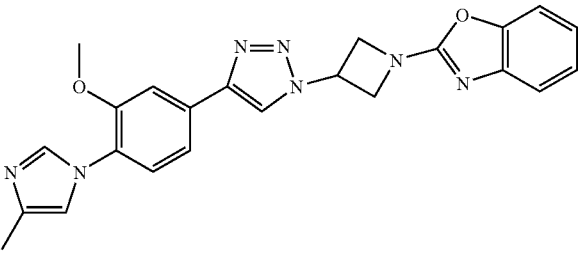 | 2-(3-{4-[3-methoxy-4-(4-methyl-1H-imidazol-1-yl)phenyl]-1H-1,2,3-triazol-1-yl}azetidin-1-yl)-1,3-benzoxazole | Calc'd 428.2, found 428.2 |
| 109 | 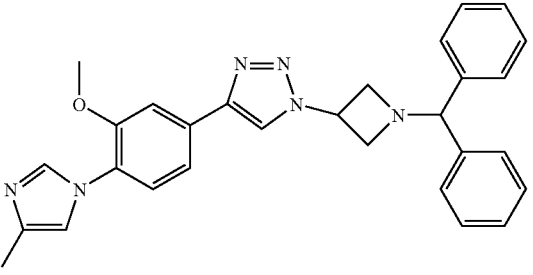 | 1-[1-(diphenylmethyl)azetidin-3-yl]-4-[3-methoxy-4-(4-methyl-1H-imidazol-1-yl)phenyl]-1H-1,2,3-triazole | Calc'd 477.2, found 477.2 |
| 110 | 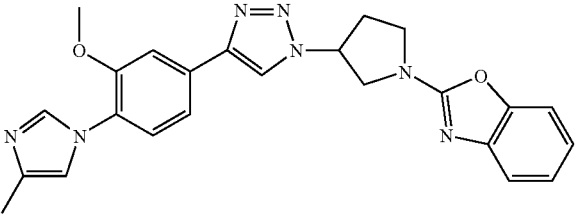 | 2-(3-{4-[3-methoxy-4-(4-methyl-1H-imidazol-1-yl)phenyl]-1H-1,2,3-triazol-1-yl}pyrrolidin-1-yl)-1,3-benzoxazole | Calc'd 442.2, found 442.2 |
| 111 | 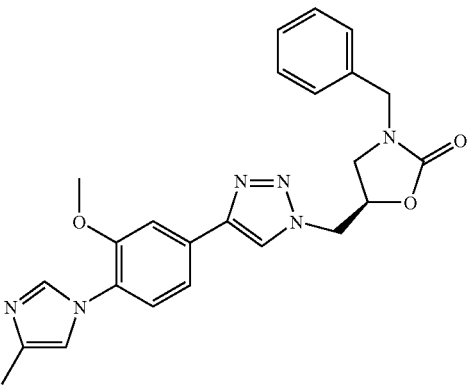 | (5R)-3-benzyl-5-({4-[3-methoxy-4-methyl-1H-imidazol-1-yl)phenyl]-1H-1,2,3-triazol-1-yl}methyl)-1,3-oxazolidin-2-one | Calc'd 445.2, found 445.2 |

TABLE I-continued

| EX. | Structure | Name | [M + H]+ |
|---|---|---|---|
| 112 | 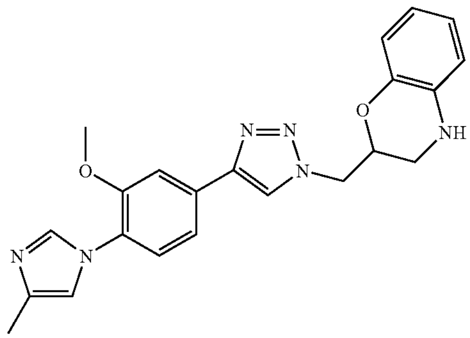 | 2-({4-[3-methoxy-4-(4-methyl-1H-imidazol-1-yl)phenyl]-1H-1,2,3-triazol-1-yl}methyl)-3,4-dihydro-2H-1,4-benzoxazine | Calc'd 403.2, found 403.2 |
| 113 | 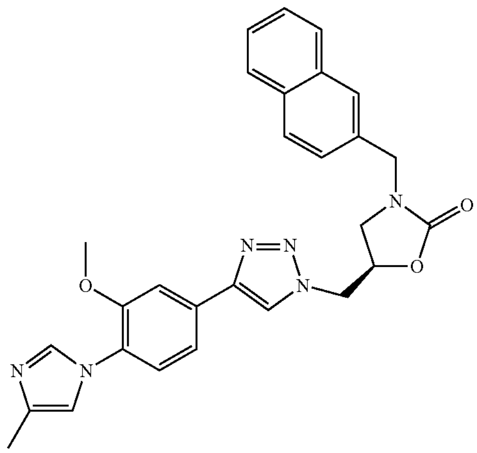 | (5R)-5-({4-[3-methoxy-4-(4-methyl-1H-imidazol-1-yl)phenyl]-1H-1,2,3-triazol-1-yl}methyl)-3-(2-naphthylmethyl)-1,3-oxazolidin-2-one | Calc'd 495.2, found 495.2 |
| 114 | 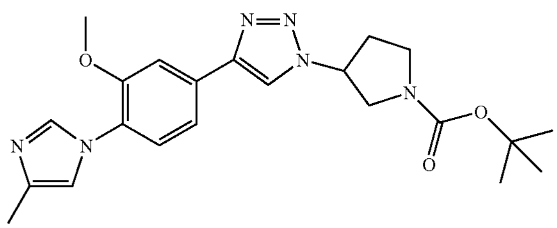 | tert-butyl 3-{4-[3-methoxy-4-(4-methyl-1H-imidazol-1-yl)phenyl]-1H-1,2,3-triazol-1-yl}pyrrolidine-1-carboxylate | Calc'd 425.2, found 425.3 |
| 115 | 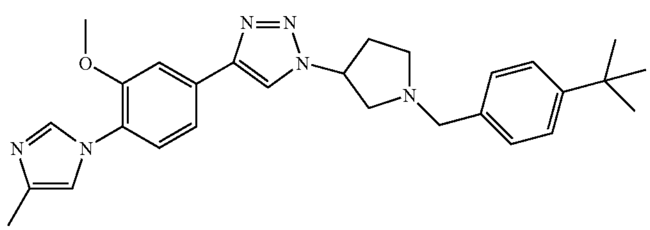 | 1-[1-(4-tert-butylbenzyl)pyrrolidin-3-yl]-4-[3-methoxy-4-(4-methyl-1H-imidazol-1-yl)phenyl]-1H-1,2,3-triazole | Calc'd 471.3, found 471.3 |
| 116 | 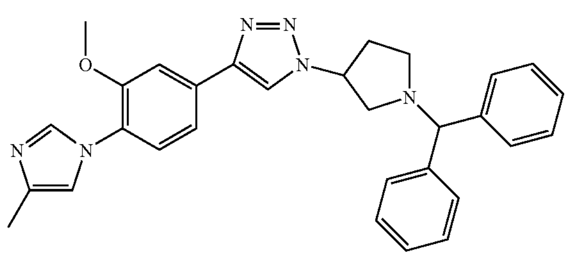 | 1-[1-(diphenylmethyl)pyrrolidin-3-yl]-4-[3-methoxy-4-(4-methyl-1H-imidazol-1-yl)phenyl]-1H-1,2,3-triazole | Calc'd 491.3, found 491.3 |

TABLE I-continued

| EX. | Structure | Name | [M + H]⁺ |
|---|---|---|---|
| 117 | 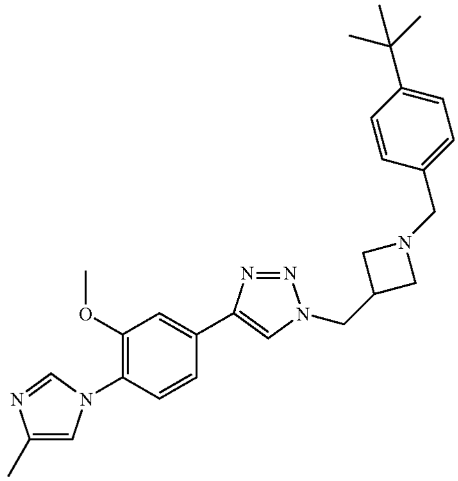 | 1-{[1-(4-tert-butylbenzyl)azetidin-3-yl]methyl}-4-[3-methoxy-4-(4-methyl-1H-imidazol-1-yl)phenyl]-1H-1,2,3-triazole | Calc'd 471.3, found 471.3 |
| 118 | 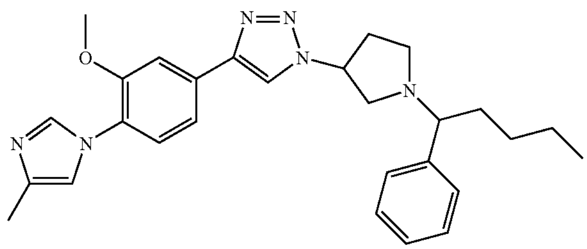 | 4-[3-methoxy-4-(4-methyl-1H-imidazol-1-yl)phenyl]-1-[1-(1-phenylpentyl)pyrrolidin-3-yl]-1H-1,2,3-triazole | Calc'd 471.3, found 471.3 |
| 119 | 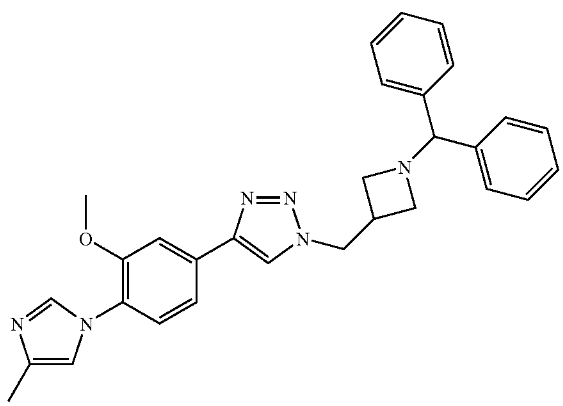 | 1-{[1-(diphenylmethyl)azetidin-3-yl]methyl}-4-[3-methoxy-4-(4-methyl-1H-imidazol-1-yl)phenyl]-1H-1,2,3-triazole | Calc'd 491.3, found 491.3 |
| 120 | 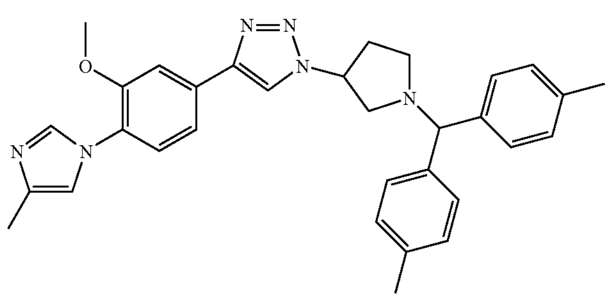 | 1-{1-[bis(4-methylphenyl)methyl]pyrrolidin-3-yl}-4-[3-methoxy-4-(4-methyl-1H-imidazol-1-yl)phenyl]-1H-1,2,3-triazole | Calc'd 519.3, found 519.3 |

TABLE I-continued

| EX. | Name | [M + H]⁺ |
|---|---|---|
| 121 | 1-{1-[bis(4-methylphenyl)methyl]azetidin-3-yl}-4-[3-methoxy-4-(4-methyl-1H-imidazol-1-yl)phenyl]-1H-1,2,3-triazole | Calc'd 505.3, found 505.3 |
| 122 | 1-[1-(4,4-dimethyl-1,2,3,4-tetrahydronaphthalen-1-yl)pyrrolidin-3-yl]-4-[3-methoxy-4-(4-methyl-1H-imidazol-1-yl)phenyl]-1H-1,2,3-triazole | Calc'd 483.3, found 483.3 |
| 123 | 1-{1-[bis(4-chlorophenyl)methyl]pyrrolidin-3-yl}-4-[3-methoxy-4-(4-methyl-1H-imidazol-1-yl)phenyl]-1H-1,2,3-triazole | Calc'd 559.2, found 559.1 |
| 124 | 1-{1-[bis(4-fluorophenyl)methyl]pyrrolidin-3-yl}-4-[3-methoxy-4-(4-methyl-1H-imidazol-1-yl)phenyl]-1H-1,2,3-triazole | Calc'd 527.2, found 527.2 |
| 125 | 1-[1-(diphenylmethyl)pyrrolidin-3-yl]-4-[3-methoxy-4-(4-methyl-1H-imidazol-1-yl)phenyl]-1H-1,2,3-triazole | Calc'd 491.3, found 491.3 |

TABLE I-continued

| EX. | Structure | Name | [M + H]+ |
|---|---|---|---|
| 126 | 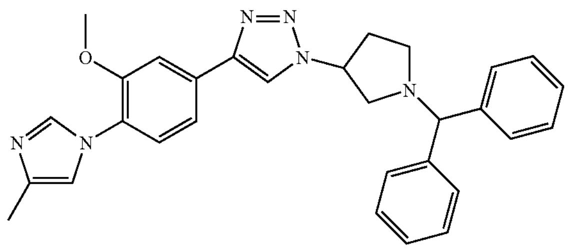 | 1-[1-(diphenylmethyl)pyrrolidin-3-yl]-4-[3-methoxy-4-(4-methyl-1H-imidazol-1-yl)phenyl]-1H-1,2,3-triazole | Calc'd 491.3, found 491.3 |
| 127 | 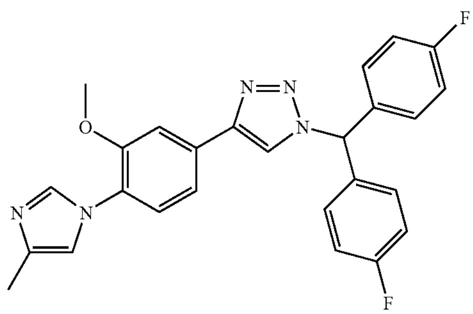 | 1-[bis(4-fluorophenyl)methyl]-4-[3-methoxy-4-(4-methyl-1H-imidazol-1-yl)phenyl]-1H-1,2,3-triazole | Calc'd 458.2, found 458.2 |
| 128 | 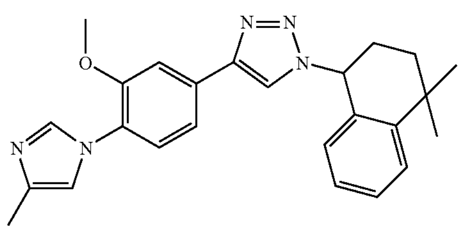 | 1-(4,4-dimethyl-1,2,3,4-tetrahydronaphthalen-1-yl)-4-[3-methoxy-4-(4-methyl-1H-imidazol-1-yl)phenyl]-1H-1,2,3-triazole | Calc'd 414.2, found 414.3 |
| 129 | 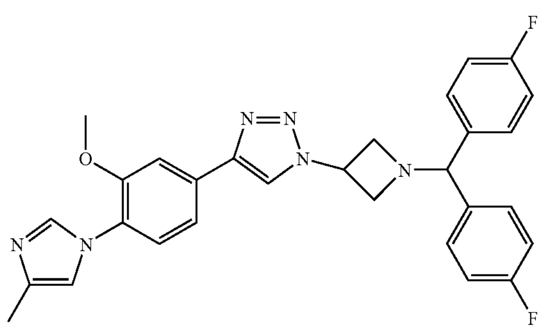 | 1-{1-[bis(4-fluorophenyl)methyl]azetidin-3-yl}-4-[3-methoxy-4-(4-methyl-1H-imidazol-1-yl)phenyl]-1H-1,2,3-triazole | Calc'd 513.2, found 513.2 |
| 130 | 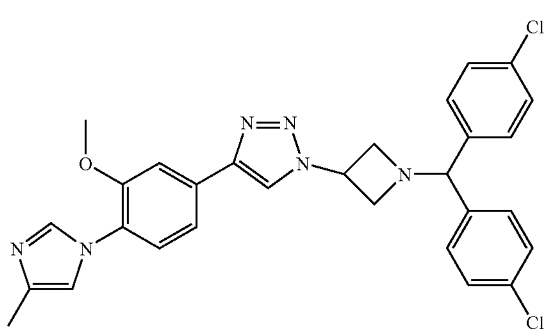 | 1-{1-[bis(4-chlorophenyl)methyl]azetidin-3-yl}-4-[3-methoxy-4-(4-methyl-1H-imidazol-1-yl)phenyl]-1H-1,2,3-triazole | Calc'd 545.2, found 545.1 |

TABLE I-continued

| EX. | Structure | Name | [M + H]+ |
|---|---|---|---|
| 131 | 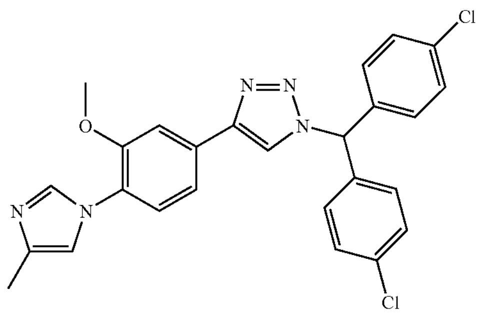 | 1-[bis(4-chlorophenyl)methyl]-4-[3-methoxy-4-(4-methyl-1H-imidazol-1-yl)phenyl]-1H-1,2,3-triazole | Calc'd 490.1, found 490.1 |
| 132 | 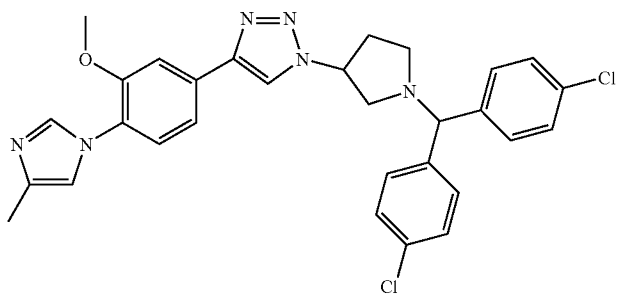 | 1-{1-[bis(4-chlorophenyl)methyl]pyrrolidin-3-yl}-4-[3-methoxy-4-(4-methyl-1H-imidazol-1-yl)phenyl]-1H-1,2,3-triazole | Calc'd 559.2, found 559.1 |
| 133 | 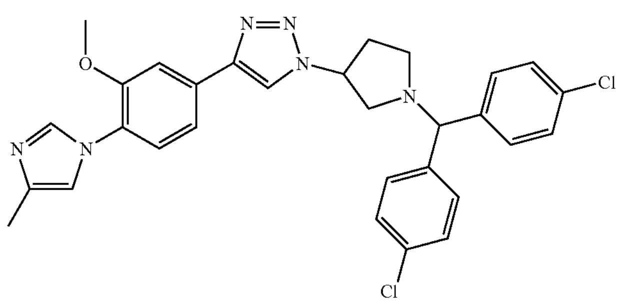 | 1-{1-[bis(4-chlorophenyl)methyl]pyrrolidin-3-yl}-4-[3-methoxy-4-(4-methyl-1H-imidazol-1-yl)phenyl]-1H-1,2,3-triazole | Calc'd 559.2, found 559.1 |
| 134 | 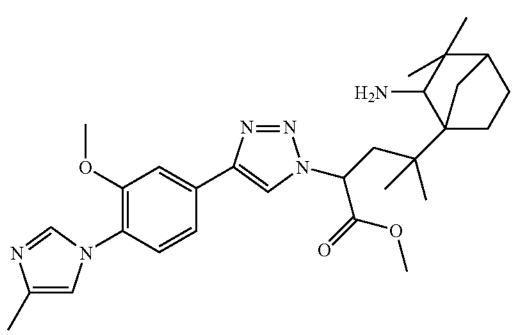 | methyl 4-(2-amino-3,3-dimethylbicyclo[2.2.1]hept-1-yl)-2-{4-[3-methoxy-4-(4-methyl-1H-imidazol-1-yl)phenyl]-1H-1,2,3-triazol-1-yl}-4-methylpentanoate | Calc'd 521.3, found 521.2 |

TABLE II

| EX. | Structure | Name | [M + H]+ |
|---|---|---|---|
| 135 | 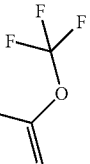 | 2-{4-[3-methoxy-4-(4-methyl-1H-imidazol-1-yl)phenyl]-1H-1,2,3-triazol-1-yl}-N-[4-(trifluoromethoxy)phenyl]acetamide | Calc'd 473.2, found 473.0 |
| 136 | 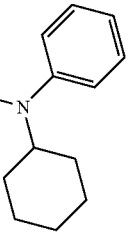 | N-cyclohexyl-2-{4-[3-methoxy-4-(4-methyl-1H-imidazol-1-yl)phenyl]-1H-1,2,3-triazol-1-yl}-N-phenylacetamide | Calc'd 471.3, found 471.1 |
| 137 | 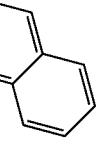 | 2-{4-[3-methoxy-4-(4-methyl-1H-imidazol-1-yl)phenyl]-1H-1,2,3-triazol-1-yl}-N-1-naphthylacetamide | Calc'd 439.2, found 439.2 |
| 138 | 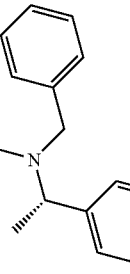 | N-benzyl-2-{4-[3-methoxy-4-(4-methyl-1H-imidazol-1-yl)phenyl]-1H-1,2,3-triazol-1-yl}-N-[(1S)-1-phenylethyl]acetamide | Calc'd 507.3, found 507.3 |
| 139 | 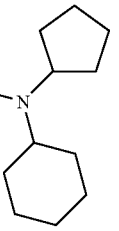 | N-cyclohexyl-N-cyclopentyl-2-{4-[3-methoxy-4-(4-methyl-1H-imidazol-1-yl)phenyl]-1H-1,2,3-triazol-1-yl}acetamide | Calc'd 463.3, found 463.3 |

TABLE II-continued

| EX. | Structure | Name | [M + H]⁺ |
| --- | --- | --- | --- |
| 140 | 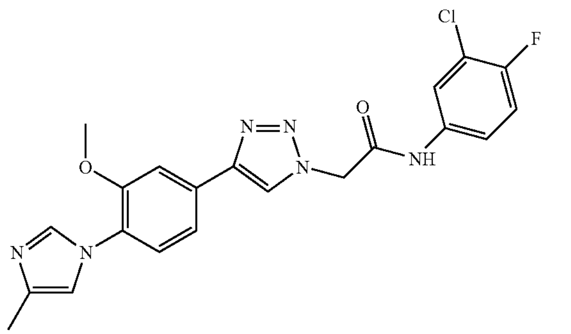 | N-(3-chloro-4-fluorophenyl)-2-{4-[3-methoxy-4-(4-methyl-1H-imidazol-1-yl)phenyl]-1H-1,2,3-triazol-1-yl}acetamide | Calc'd 441.1, found 441.1 |
| 141 | 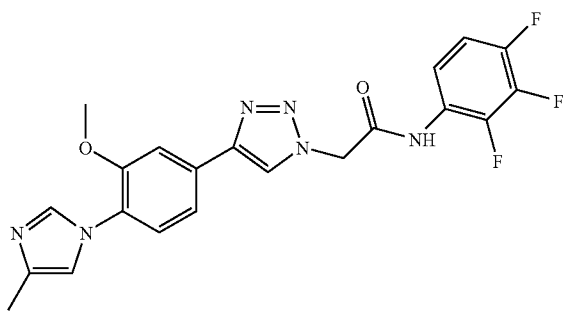 | 2-{4-[3-methoxy-4-(4-methyl-1H-imidazol-1-yl)phenyl]-1H-1,2,3-triazol-1-yl}-N-(2,3,4-trifluorophenyl)acetamide | Calc'd 443.1, found 443.1 |
| 142 | 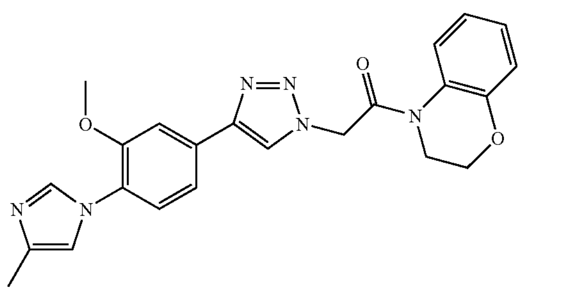 | 4-({4-[3-methoxy-4-(4-methyl-1H-imidazol-1-yl)phenyl]-1H-1,2,3-triazol-1-yl}acetyl)-3,4-dihydro-2H-1,4-benzoxazine | Calc'd 431.2, found 431.2 |
| 143 | 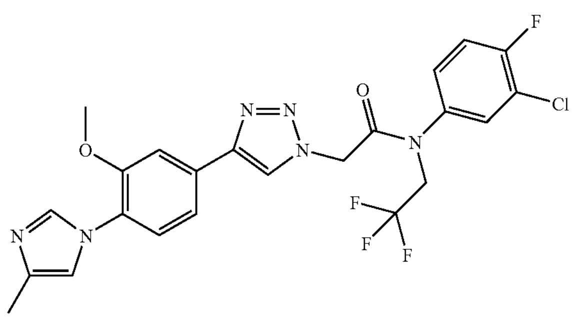 | N-(3-chloro-4-fluorophenyl)-2-{4-[3-methoxy-4-(4-methyl-1H-imidazol-1-yl)phenyl]-1H-1,2,3-triazol-1-yl}-N-(2,2,2-trifluoroethyl)acetamide | Calc'd 523.1, found 523.1 |
| 144 | 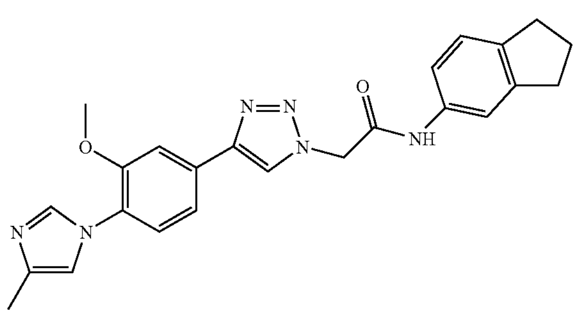 | N-(2,3-dihydro-1H-inden-5-yl)-2-{4-[3-methoxy-4-(4-methyl-1H-imidazol-1-yl)phenyl]-1H-1,2,3-triazol-1-yl}acetamide | Calc'd 429.2, found 429.2 |

TABLE II-continued

| EX. | Name | [M + H]+ |
|---|---|---|
| 145 | N-(4-tert-butylcyclohexyl)-2-{4-[3-methoxy-4-(4-methyl-1H-imidazol-1-yl)phenyl]-1H-1,2,3-triazol-1-yl}acetamide | Calc'd 451.3, found 451.3 |
| 146 | 2-{4-[3-methoxy-4-(4-methyl-1H-imidazol-1-yl)phenyl]-1H-1,2,3-triazol-1-yl}-N-(2,2,2-trifluoroethyl)-N-(2,3,4-trifluorophenyl)acetamide | Calc'd 525.1, found 525.1 |
| 147 | 1-({4-[3-methoxy-4-(4-methyl-1H-imidazol-1-yl)phenyl]-1H-1,2,3-triazol-1-yl}acetyl)-2,2,4-trimethyl-1,2,3,4-tetrahydroquinoline | Calc'd 471.3, found 471.2 |
| 148 | N-(2,3-dihydro-1H-inden-5-yl)-2-{4-[3-methoxy-4-(4-methyl-1H-imidazol-1-yl)phenyl]-1H-1,2,3-triazol-1-yl}-N-(2,2,2-trifluoroethyl)acetamide | Calc'd 511.2, found 511.2 |
| 149 | N-2-adamantyl-N-(4-chlorobenzyl)-2-{4-[3-methoxy-4-(4-methyl-1H-imidazol-1-yl)phenyl]-1H-1,2,3-triazol-1-yl}acetamide | Calc'd 571.3, found 571.2 |

TABLE II-continued

| EX. | Structure | Name | [M + H]+ |
|---|---|---|---|
| 150 | 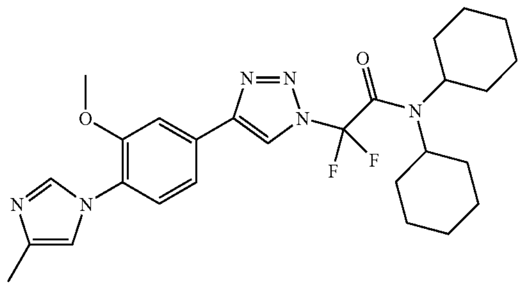 | N,N-dicyclohexyl-2,2-difluoro-2-{4-[3-methoxy-4-(4-methyl-1H-imidazol-1-yl)phenyl]-1H-1,2,3-triazol-1-yl}acetamide | Calc'd 513.3, found 513.3 |
| 151 | 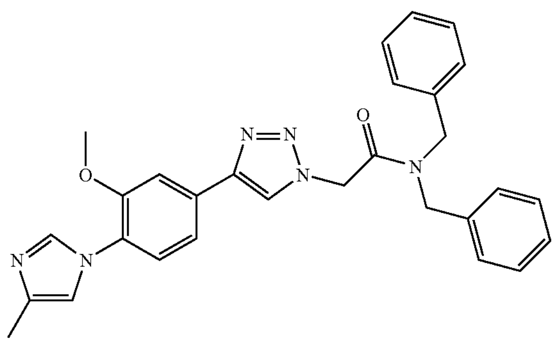 | N,N-dibenzyl-2-{4-[3-methoxy-4-(4-methyl-1H-imidazol-1-yl)phenyl]-1H-1,2,3-triazol-1-yl}acetamide | Calc'd 493.2, found 493.2 |
| 152 | 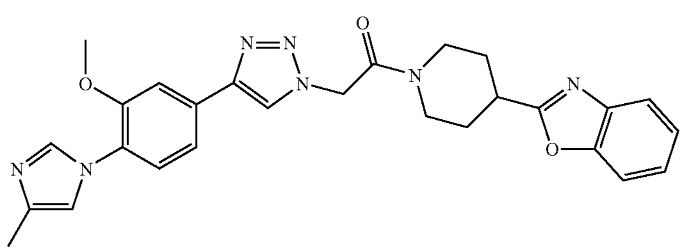 | 2-[1-({4-[3-methoxy-4-(4-methyl-1H-imidazol-1-yl)phenyl]-1H-1,2,3-triazol-1-yl}acetyl)piperidin-4-yl]-1,3-benzoxazole | Calc'd 498.2, found 498.2 |
| 153 | 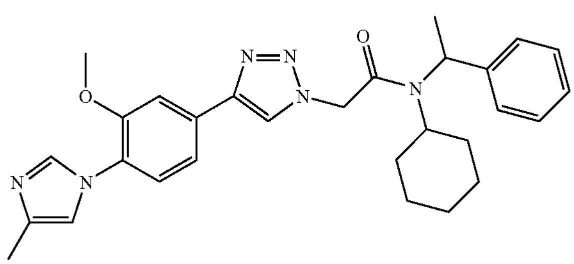 | N-cyclohexyl-2-{4-[3-methoxy-4-(4-methyl-1H-imidazol-1-yl)phenyl]-1H-1,2,3-triazol-1-yl}-N-(1-phenylethyl)acetamide | Calc'd 499.3, found 499.3 |
| 154 | 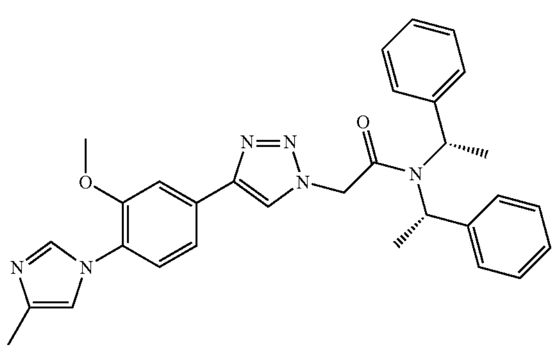 | 2-{4-[3-methoxy-4-(4-methyl-1H-imidazol-1-yl)phenyl]-1H-1,2,3-triazol-1-yl}-N,N-bis[(1S)-1-phenylethyl]acetamide | Calc'd 521.3, found 521.3 |

TABLE II-continued

| EX. | Structure | Name | [M + H]+ |
|---|---|---|---|
| 155 | 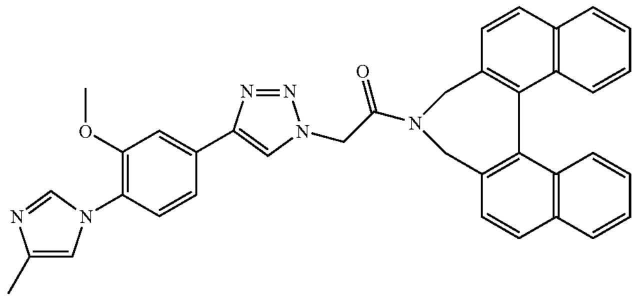 | 4-({4-[3-methoxy-4-(4-methyl-1H-imidazol-1-yl)phenyl]-1H-1,2,3-triazol-1-yl}acetyl)-4,5-dihydro-3H-dinaphtho[1,2-e:2',1'-c]azepine | Calc'd 591.3, found 591.2 |
| 156 | 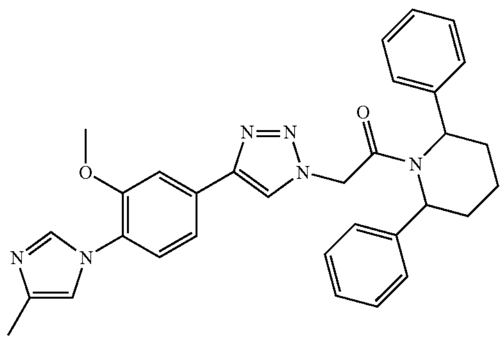 | 1-({4-[3-methoxy-4-(4-methyl-1H-imidazol-1-yl)phenyl]-1H-1,2,3-triazol-1-yl}acetyl)-2,6-diphenylpiperidine | Calc'd 533.3, found 533.2 |
| 157 | 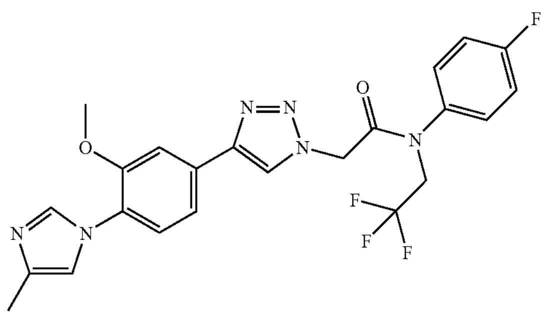 | N-(4-fluorophenyl)-2-{4-[3-methoxy-4-(4-methyl-1H-imidazol-1-yl)phenyl]-1H-1,2,3-triazol-1-yl}-N-(2,2,2-trifluoroethyl)acetamide | Calc'd 489.2, found 489.1 |
| 158 | 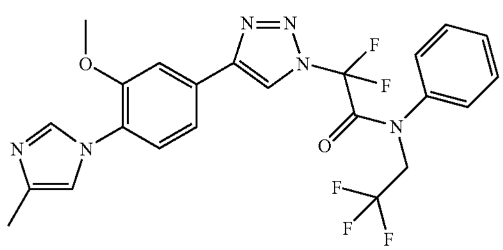 | 2,2-difluoro-2-{4-[3-methoxy-4-(4-methyl-1H-imidazol-1-yl)phenyl]-1H-1,2,3-triazol-1-yl}-N-phenyl-N-(2,2,2-trifluoroethyl)acetamide | Calc'd 507.2, found 507.1 |
| 159 | 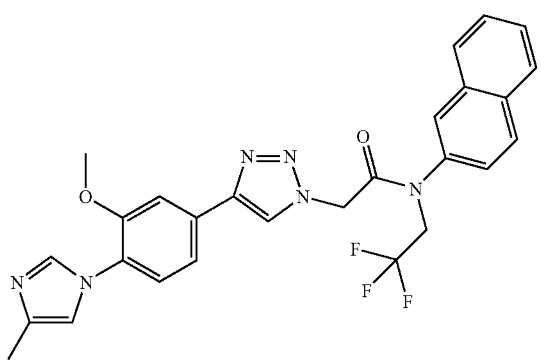 | 2-{4-[3-methoxy-4-(4-methyl-1H-imidazol-1-yl)phenyl]-1H-1,2,3-triazol-1-yl}-N-2-naphthyl-N-(2,2,2-trifluoroethyl)acetamide | Calc'd 521.2, found 521.1 |

TABLE II-continued

| EX. | Structure | Name | [M + H]+ |
|---|---|---|---|
| 160 | 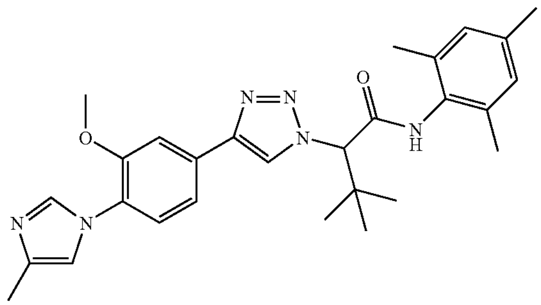 | N-mesityl-2-{4-[3-methoxy-4-(4-methyl-1H-imidazol-1-yl)phenyl]-1H-1,2,3-triazol-1-yl}-3,3-dimethylbutanamide | Calc'd 487.3, found 487.2 |
| 161 | 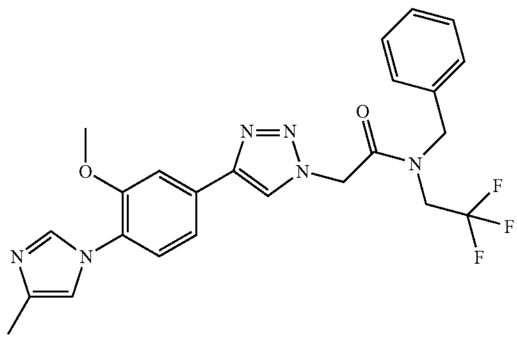 | N-benzyl-2-{4-[3-methoxy-4-(4-methyl-1H-imidazol-1-yl)phenyl]-1H-1,2,3-triazol-1-yl}-N-(2,2,2-trifluoroethyl)acetamide | Calc'd 485.2, found 485.1 |
| 162 | 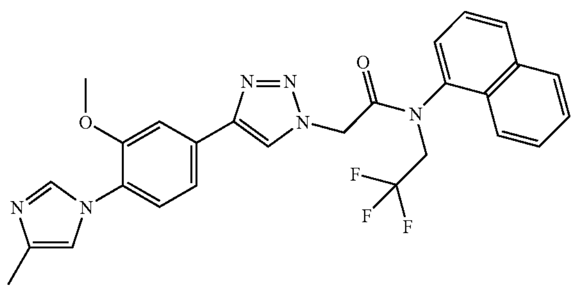 | 2-{4-[3-methoxy-4-(4-methyl-1H-imidazol-1-yl)phenyl]-1H-1,2,3-triazol-1-yl}-N-1-naphthyl-N-(2,2,2-trifluoroethyl)acetamide | Calc'd 521.2, found 521.1 |
| 163 | 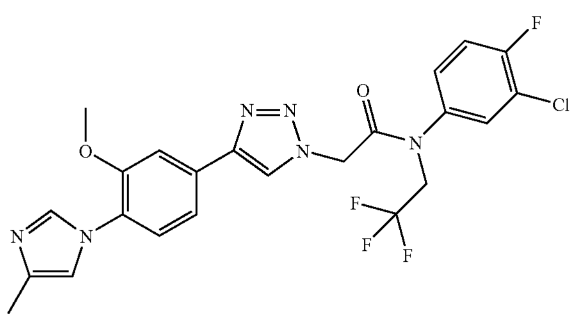 | N-(3-chloro-4-fluorophenyl)-2-{4-[3-methoxy-4-(4-methyl-1H-imidazol-1-yl)phenyl]-1H-1,2,3-triazol-1-yl}-N-(2,2,2-trifluoroethyl)acetamide | Calc'd 523.1, found 523.0 |
| 164 | 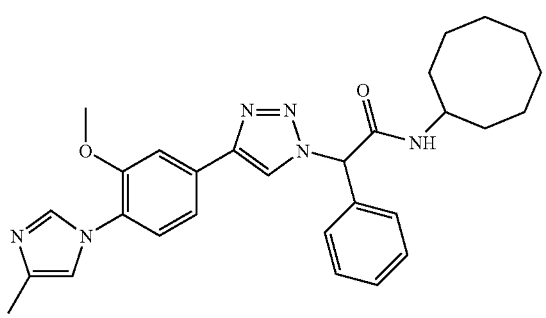 | N-cyclooctyl-2-{4-[3-methoxy-4-(4-methyl-1H-imidazol-1-yl)phenyl]-1H-1,2,3-triazol-1-yl}-2-phenylacetamide | Calc'd 499.3, found 499.2 |

TABLE II-continued

| EX. | Structure | Name | [M + H]+ |
|---|---|---|---|
| 165 | 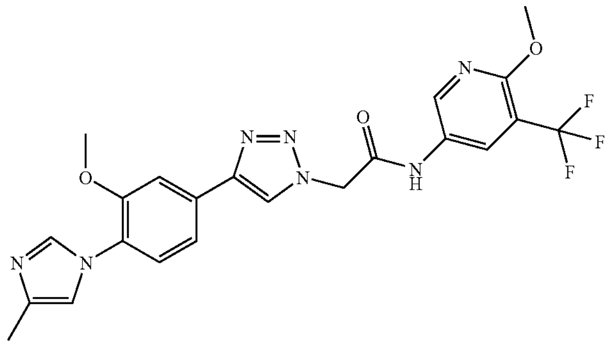 | 2-{4-[3-methoxy-4-(4-methyl-1H-imidazol-1-yl)phenyl]-1H-1,2,3-triazol-1-yl}-N-[6-methoxy-5-(trifluoromethyl)pyridin-3-yl]acetamide | Calc'd 488.2, found 488.1 |
| 166 | 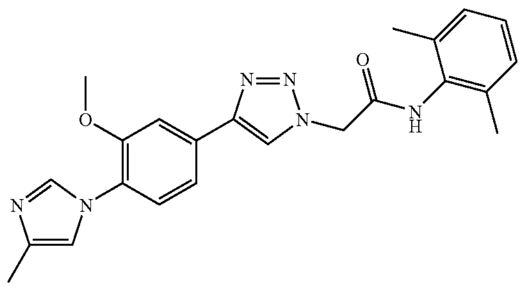 | N-(2,6-dimethylphenyl)-2-{4-[3-methoxy-4-(4-methyl-1H-imidazol-1-yl)phenyl]-1H-1,2,3-triazol-1-yl}acetamide | Calc'd 417.2, found 417.0 |
| 167 | 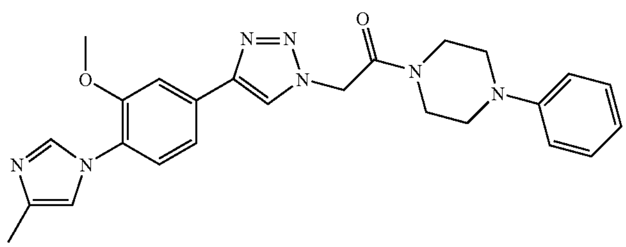 | 1-({4-[3-methoxy-4-(4-methyl-1H-imidazol-1-yl)phenyl]-1H-1,2,3-triazol-1-yl}acetyl)-4-phenylpiperazine | Calc'd 458.2, found 458.0 |
| 168 | 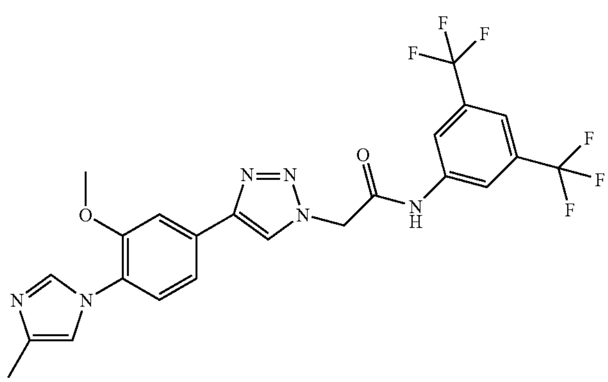 | N-[3,5-bis(trifluoromethyl)phenyl]-2-{4-[3-methoxy-4-(4-methyl-1H-imidazol-1-yl)phenyl]-1H-1,2,3-triazol-1-yl}acetamide | Calc'd 525.1, found 524.9 |
| 169 | 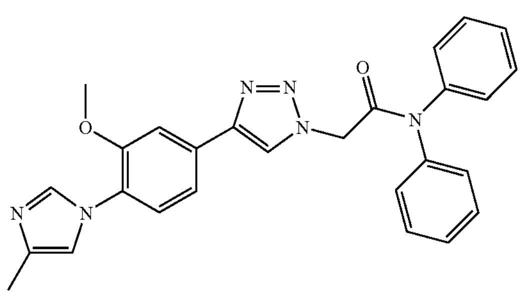 | 2-{4-[3-methoxy-4-(4-methyl-1H-imidazol-1-yl)phenyl]-1H-1,2,3-triazol-1-yl}-N,N-diphenylacetamide | Calc'd 465.2, found 465.0 |

TABLE II-continued

| EX. | Structure | Name | [M + H]+ |
|---|---|---|---|
| 170 | 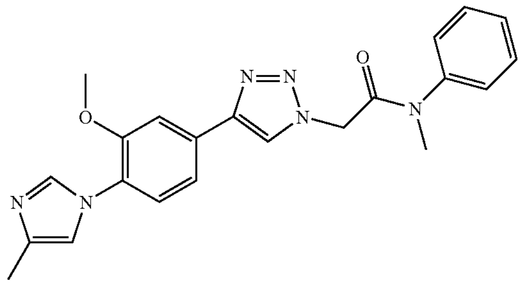 | 2-{4-[3-methoxy-4-(4-methyl-1H-imidazol-1-yl)phenyl]-1H-1,2,3-triazol-1-yl}-N-methyl-N-phenylacetamide | Calc'd 403.2, found 403.0 |
| 171 | 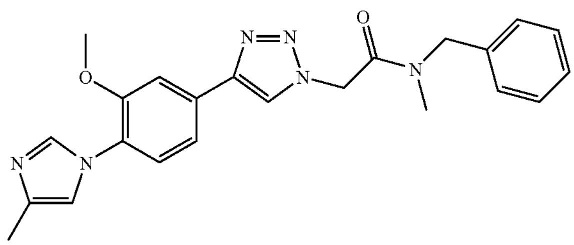 | N-benzyl-2-{4-[3-methoxy-4-(4-methyl-1H-imidazol-1-yl)phenyl]-1H-1,2,3-triazol-1-yl}-N-methylacetamide | Calc'd 417.2, found 417.0 |
| 172 | 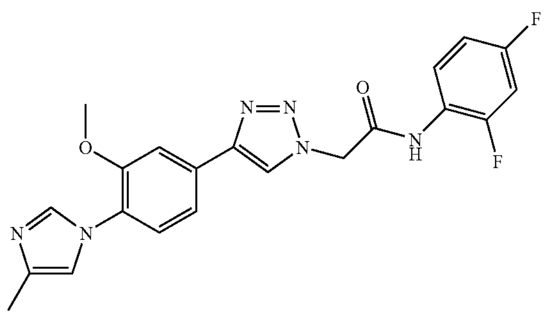 | N-(2,4-difluorophenyl)-2-{4-[3-methoxy-4-(4-methyl-1H-imidazol-1-yl)phenyl]-1H-1,2,3-triazol-1-yl}acetamide | Calc'd 425.2, found 425.0 |
| 173 | 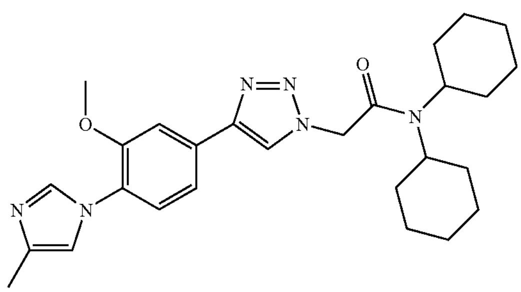 | N,N-dicyclohexyl-2-{4-[3-methoxy-4-(4-methyl-1H-imidazol-1-yl)phenyl]-1H-1,2,3-triazol-1-yl}acetamide | Calc'd 477.3, found 477.1 |
| 174 | 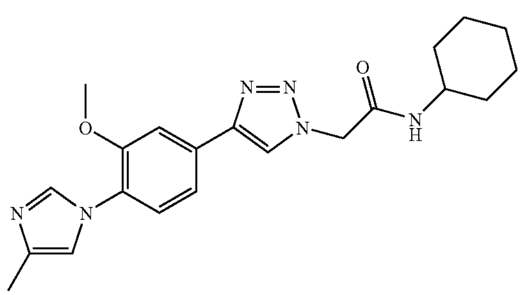 | N-cyclohexyl-2-{4-[3-methoxy-4-(4-methyl-1H-imidazol-1-yl)phenyl]-1H-1,2,3-triazol-1-yl}acetamide | Calc'd 395.2, found 395.0 |

TABLE II-continued

| EX. | Structure | Name | [M + H]+ |
|---|---|---|---|
| 175 | 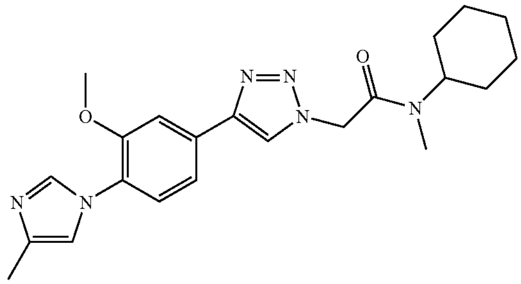 | N-cyclohexyl-2-{4-[3-methoxy-4-(4-methyl-1H-imidazol-1-yl)phenyl]-1H-1,2,3-triazol-1-yl}-N-methylacetamide | Calc'd 409.2, found 409.0 |
| 176 | 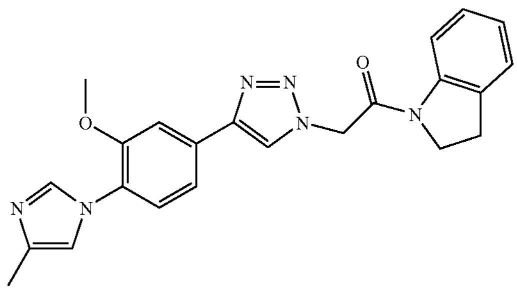 | 1-({4-[3-methoxy-4-(4-methyl-1H-imidazol-1-yl)phenyl]-1H-1,2,3-triazol-1-yl}acetyl)indoline | Calc'd 415.2, found 415.0 |
| 177 | 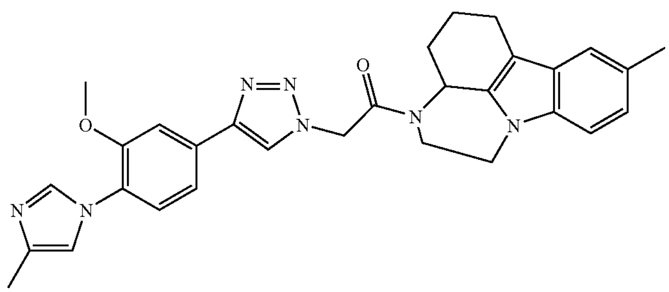 | 3-({4-[3-methoxy-4-(4-methyl-1H-imidazol-1-yl)phenyl]-1H-1,2,3-triazol-1-yl}acetyl)-8-methyl-2,3,3a,4,5,6-hexahydro-1H-pyrazino[3,2,1-jk]carbazole | Calc'd 522.3, found 522.0 |
| 178 | 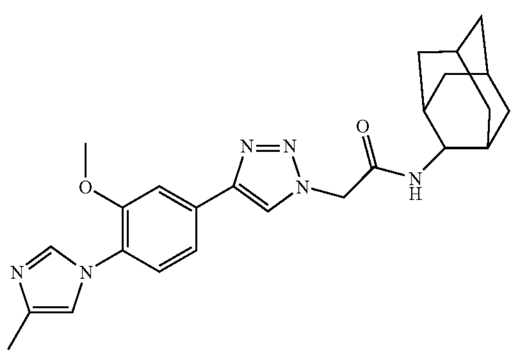 | N-2-adamantyl-2-{4-[3-methoxy-4-(4-methyl-1H-imidazol-1-yl)phenyl]-1H-1,2,3-triazol-1-yl}acetamide | Calc'd 447.3, found 447.0 |
| 179 | 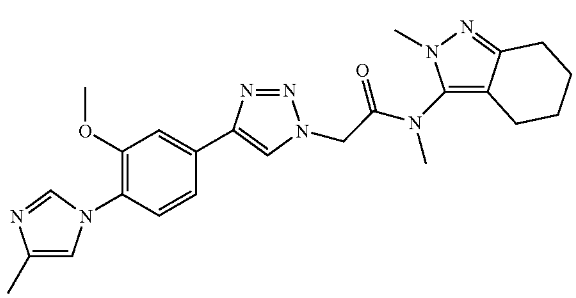 | 2-{4-[3-methoxy-4-(4-methyl-1H-imidazol-1-yl)phenyl]-1H-1,2,3-triazol-1-yl}-N-methyl-N-(2-methyl-4,5,6,7-tetrahydro-2H-indazol-3-yl)acetamide | Calc'd 461.2, found 461.0 |

TABLE II-continued

| EX. | Structure | Name | [M + H]+ |
|---|---|---|---|
| 180 | 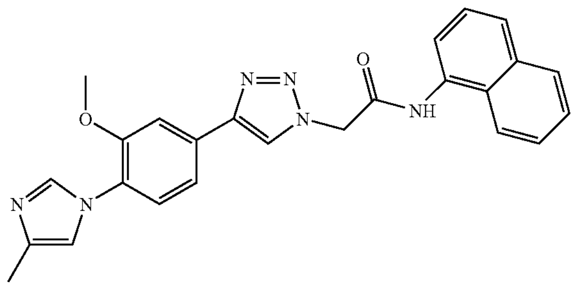 | 2-{4-[3-methoxy-4-(4-methyl-1H-imidazol-1-yl)phenyl]-1H-1,2,3-triazol-1-yl}-N-1-naphthylacetamide | Calc'd 439.2, found 439.0 |
| 181 | 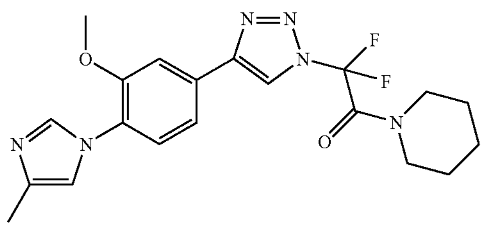 | 1-(difluoro{4-[3-methoxy-4-(4-methyl-1H-imidazol-1-yl)phenyl]-1H-1,2,3-triazol-1-yl}acetyl)piperidine | Calc'd 417.2, found 417.0 |
| 182 | 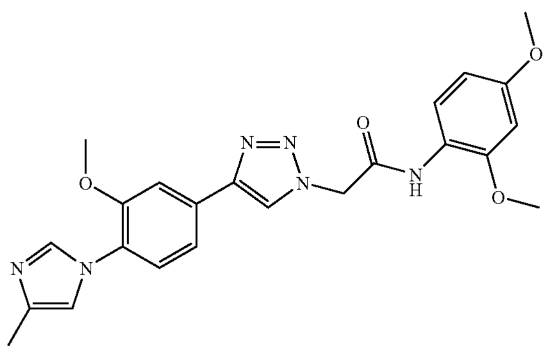 | N-(2,4-dimethoxyphenyl)-2-{4-[3-methoxy-4-(4-methyl-1H-imidazol-1-yl)phenyl]-1H-1,2,3-triazol-1-yl}acetamide | Calc'd 449.2, found 449.0 |
| 183 | 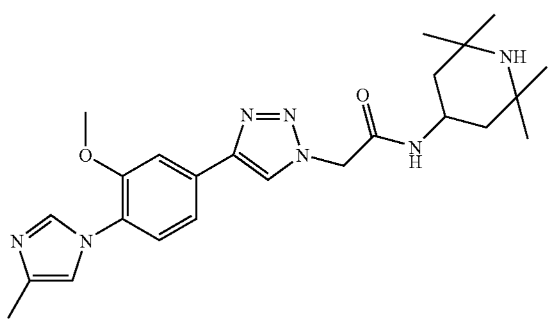 | 2-{4-[3-methoxy-4-(4-methyl-1H-imidazol-1-yl)phenyl]-1H-1,2,3-triazol-1-yl}-N-(2,2,6,6-tetramethylpiperidin-4-yl)acetamide | Calc'd 452.3, found 452.1 |
| 184 | 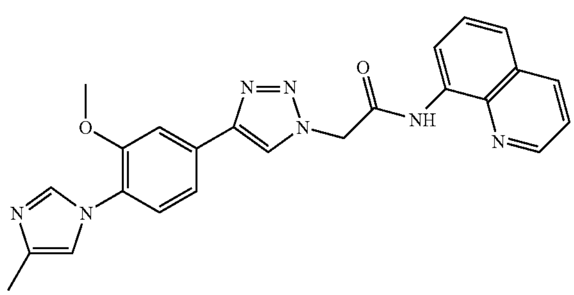 | 2-{4-[3-methoxy-4-(4-methyl-1H-imidazol-1-yl)phenyl]-1H-1,2,3-triazol-1-yl}-N-quinolin-8-ylacetamide | Calc'd 440.2, found 440.0 |

TABLE II-continued

| EX. | Structure | Name | [M + H]+ |
|---|---|---|---|
| 185 | 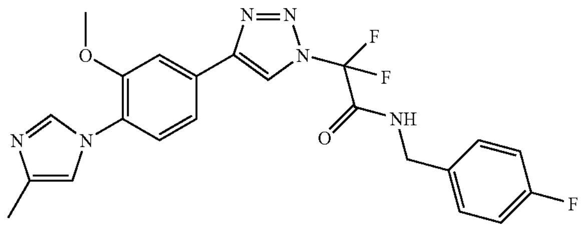 | 2,2-difluoro-N-(4-fluorobenzyl)-2-{4-[3-methoxy-4-(4-methyl-1H-imidazol-1-yl)phenyl]-1H-1,2,3-triazol-1-yl}acetamide | Calc'd 457.2, found 457.0 |
| 186 | 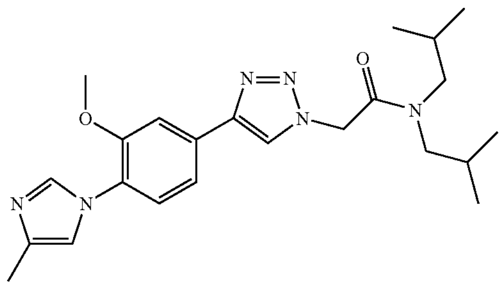 | N,N-diisobutyl-2-{4-[3-methoxy-4-(4-methyl-1H-imidazol-1-yl)phenyl]-1H-1,2,3-triazol-1-yl}acetamide | Calc'd 425.3, found 425.2 |
| 187 | 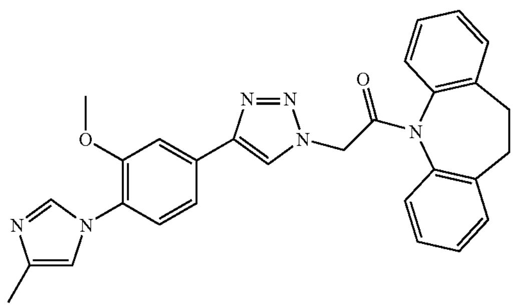 | 5-({4-[3-methoxy-4-(4-methyl-1H-imidazol-1-yl)phenyl]-1H-1,2,3-triazol-1-yl}acetyl)-10,11-dihydro-5H-dibenzo[b,f]azepine | Calc'd 491.2, found 491.2 |
| 188 | 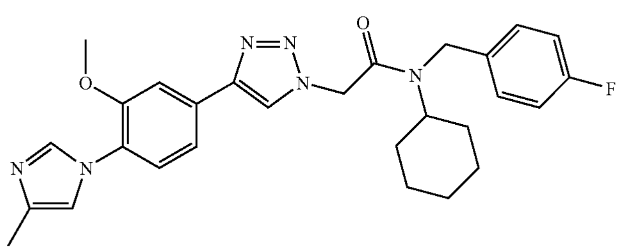 | N-cyclohexyl-N-(4-fluorobenzyl)-2-{4-[3-methoxy-4-(4-methyl-1H-imidazol-1-yl)phenyl]-1H-1,2,3-triazol-1-yl}acetamide | Calc'd 503.3, found 503.2 |
| 189 | 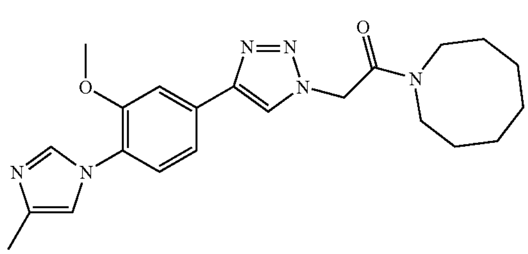 | 1-({4-[3-methoxy-4-(4-methyl-1H-imidazol-1-yl)phenyl]-1H-1,2,3-triazol-1-yl}acetyl)azocane | Calc'd 409.2, found 409.2 |

TABLE II-continued

| EX. | Structure | Name | [M + H]+ |
|---|---|---|---|
| 190 | 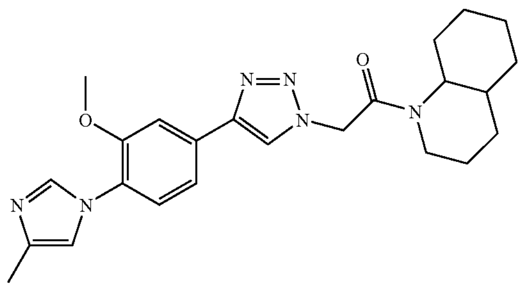 | 1-({4-[3-methoxy-4-(4-methyl-1H-imidazol-1-yl)phenyl]-1H-1,2,3-triazol-1-yl}acetyl)decahydroquinoline | Calc'd 435.3, found 435.2 |
| 191 | 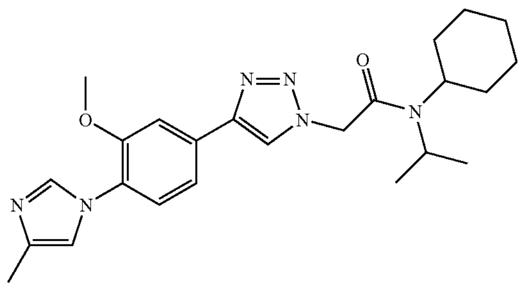 | N-cyclohexyl-N-isopropyl-2-{4-[3-methoxy-4-(4-methyl-1H-imidazol-1-yl)phenyl]-1H-1,2,3-triazol-1-yl}acetamide | Calc'd 437.3, found 437.3 |
| 192 | 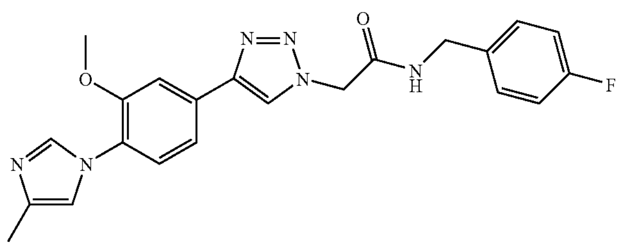 | N-(4-fluorobenzyl)-2-{4-[3-methoxy-4-(4-methyl-1H-imidazol-1-yl)phenyl]-1H-1,2,3-triazol-1-yl}acetamide | Calc'd 421.2, found 421.1 |

TABLE III

| EX. | Structure | Name | [M + H]+ |
|---|---|---|---|
| 193 | 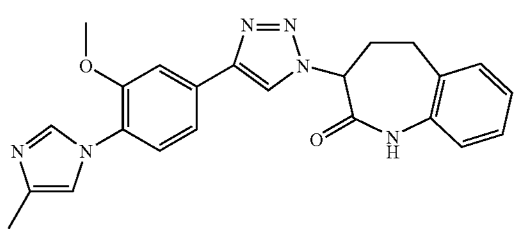 | 3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 415.2, found 415.0 |
| 194 | 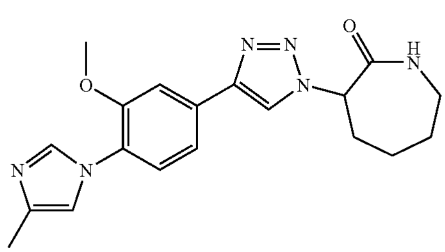 | 3-{4-[3-methoxy-4-(4-methyl-1H-imidazol-1-yl)phenyl]-1H-1,2,3-triazol-1-yl}azepan-2-one | Calc'd 367.2, found 367.2 |

TABLE III-continued

| EX. | Structure | Name | [M + H]+ |
|---|---|---|---|
| 195 | 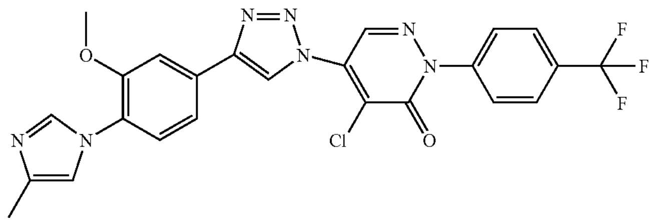 | 4-chloro-5-{4-[3-methoxy-4-(4-methyl-1H-imidazol-1-yl)phenyl]-1H-1,2,3-triazol-1-yl}-2-[4-(trifluoromethyl)phenyl]pyridazin-3(2H)-one | Calc'd 528.1, found 528.1 |
| 196 | 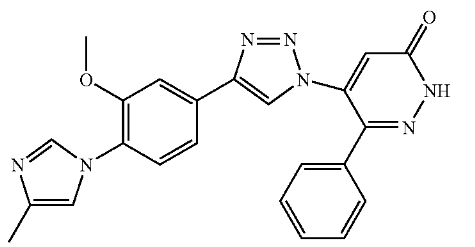 | 5-{4-[3-methoxy-4-(4-methyl-1H-imidazol-1-yl)phenyl]-1H-1,2,3-triazol-1-yl}-6-phenylpyridazin-3(2H)-one | Calc'd 426.2, found 426.2 |
| 197 | 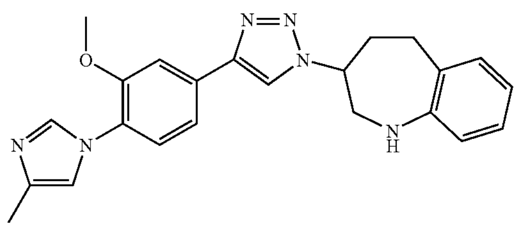 | 3-{4-[3-methoxy-4-(4-methyl-1H-imidazol-1-yl)phenyl]-1H-1,2,3-triazol-1-yl}-2,3,4,5-tetrahydro-1H-1-benzazepine | Calc'd 401.2, found 401.2 |
| 198 | 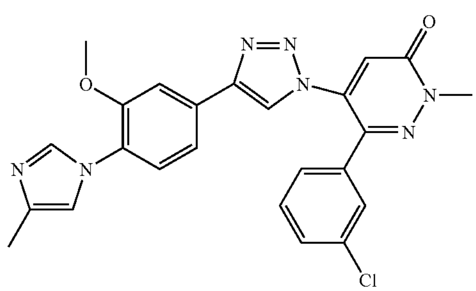 | 6-(3-chlorophenyl)-5-{4-[3-methoxy-4-(4-methyl-1H-imidazol-1-yl)phenyl]-1H-1,2,3-triazol-1-yl}-2-methylpyridazin-3(2H)-one | Calc'd 474.1, found 474.2 |
| 199 | 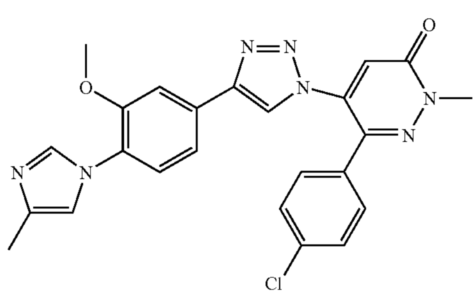 | 6-(4-chlorophenyl)-5-{4-[3-methoxy-4-(4-methyl-1H-imidazol-1-yl)phenyl]-1H-1,2,3-triazol-1-yl}-2-methylpyridazin-3(2H)-one | Calc'd 474.1, found 474.1 |
| 200 | 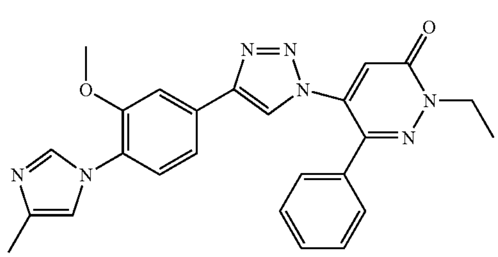 | 2-ethyl-5-{4-[3-methoxy-4-(4-methyl-1H-imidazol-1-yl)phenyl]-1H-1,2,3-triazol-1-yl}-6-phenylpyridazin-3(2H)-one | Calc'd 454.2, found 454.2 |

TABLE III-continued

| EX. | Structure | Name | [M + H]+ |
|---|---|---|---|
| 201 | 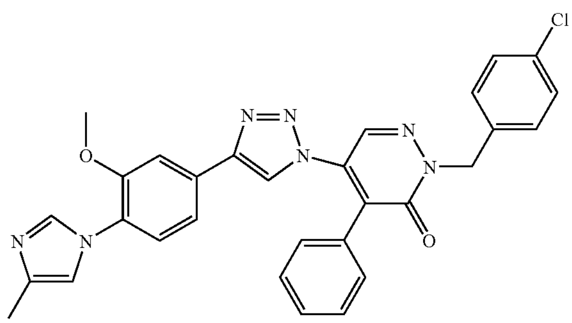 | 2-(4-chlorobenzyl)-5-{4-[3-methoxy-4-(4-methyl-1H-imidazol-1-yl)phenyl]-1H-1,2,3-triazol-1-yl}-4-phenylpyridazin-3(2H)-one | Calc'd 550.2, found 550.2 |
| 202 | 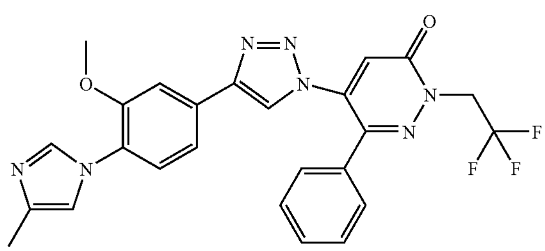 | 5-{4-[3-methoxy-4-(4-methyl-1H-imidazol-1-yl)phenyl]-1H-1,2,3-triazol-1-yl}-6-phenyl-2-(2,2,2-trifluoroethyl)pyridazin-3(2H)-one | Calc'd 508.2, found 508.2 |
| 203 | 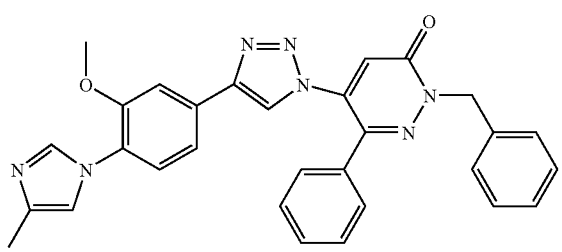 | 2-benzyl-5-{4-[3-methoxy-4-(4-methyl-1H-imidazol-1-yl)phenyl]-1H-1,2,3-triazol-1-yl}-6-phenylpyridazin-3(2H)-one | Calc'd 516.2, found 516.2 |
| 204 | 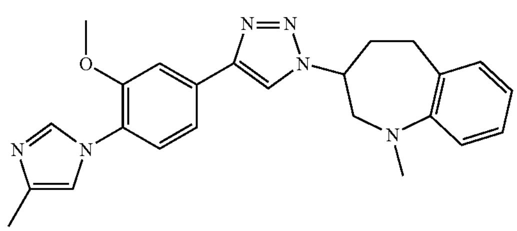 | 3-{4-[3-methoxy-4-(4-methyl-1H-imidazol-1-yl)phenyl]-1H-1,2,3-triazol-1-yl}-1-methyl-2,3,4,5-tetrahydro-1H-1-benzazepine | Calc'd 415.2, found 415.2 |
| 205 | 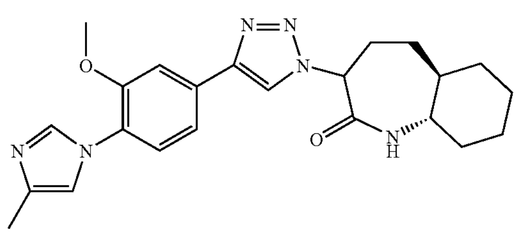 | 3-{4-[3-methoxy-4-(4-methyl-1H-imidazol-1-yl)phenyl]-1H-1,2,3-triazol-1-yl}decahydro-2H-1-benzazepin-2-one | Calc'd 421.2, found 421.2 |
| 206 | 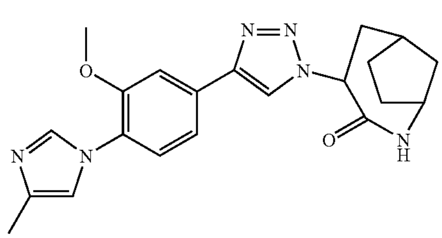 | 4-{4-[3-methoxy-4-(4-methyl-1H-imidazol-1-yl)phenyl]-1H-1,2,3-triazol-1-yl}-2-azabicyclo[4.2.1]nonan-3-one | Calc'd 393.2, found 393.2 |

TABLE III-continued

| EX. | Structure | Name | [M + H]+ |
|---|---|---|---|
| 207 | 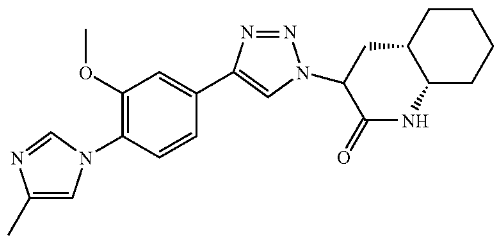 | 3-{4-[3-methoxy-4-(4-methyl-1H-imidazol-1-yl)phenyl]-1H-1,2,3-triazol-1-yl}octahydroquinolin-2(1H)-one | Calc'd 407.2, found 407.2 |
| 208 | 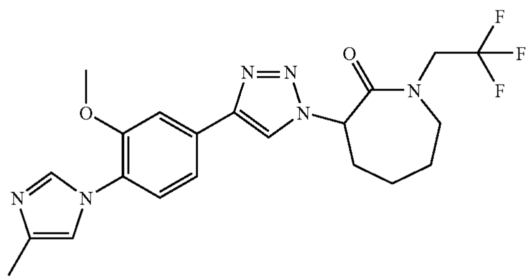 | 3-{4-[3-methoxy-4-(4-methyl-1H-imidazol-1-yl)phenyl]-1H-1,2,3-triazol-1-yl}-1-(2,2,2-trifluoroethyl)azepan-2-one | Calc'd 449.2, found 449.2 |
| 209 | 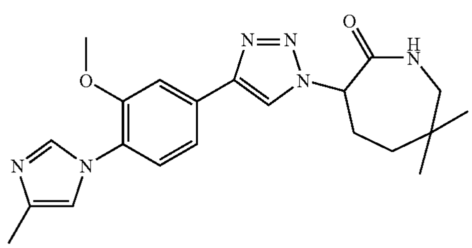 | 3-{4-[3-methoxy-4-(4-methyl-1H-imidazol-1-yl)phenyl]-1H-1,2,3-triazol-1-yl}-6,6-dimethylazepan-2-one | Calc'd 395.2, found 395.2 |
| 210 | 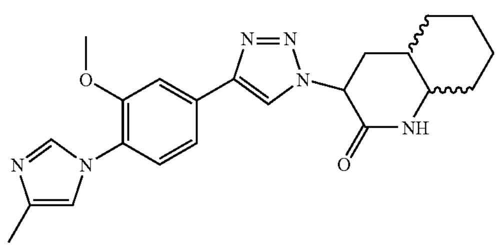 | 3-{4-[3-methoxy-4-(4-methyl-1H-imidazol-1-yl)phenyl]-1H-1,2,3-triazol-1-yl}octahydroquinolin-2(1H)-one | Calc'd 407.2, found 407.2 |
| 211 | 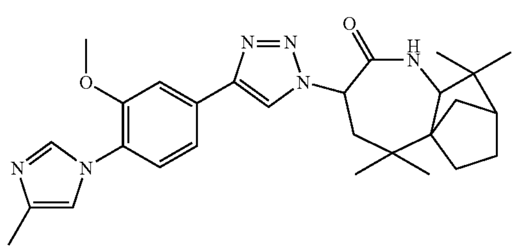 | 3-{4-[3-methoxy-4-(4-methyl-1H-imidazol-1-yl)phenyl]-1H-1,2,3-triazol-1-yl}-5,5,9,9-tetramethyloctahydro-5a,8-methano-1-benzazepin-2(3H)-one | Calc'd 489.3, found 489.3 |
| 212 | 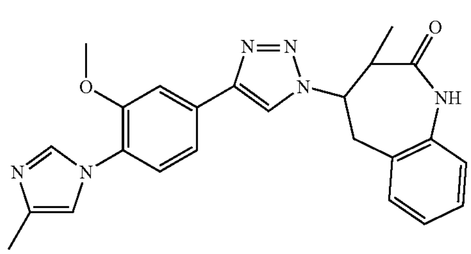 | 3-{4-[3-methoxy-4-(4-methyl-1H-imidazol-1-yl)phenyl]-1H-1,2,3-triazol-1-yl}-3-methyl-1,3,4,5-tetrahydro-2H-1-benzazepin-2-one | Calc'd 429.2, found 429.2 |

TABLE III-continued

| EX. | Structure | Name | [M + H]+ |
|---|---|---|---|
| 213 | 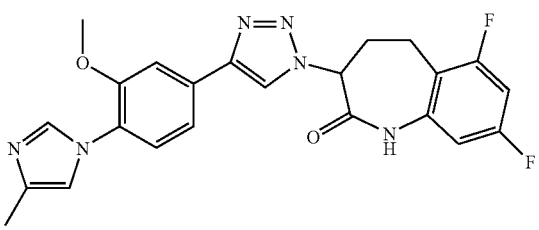 | 6,8-difluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 451.2, found 451.1 |
| 214 | 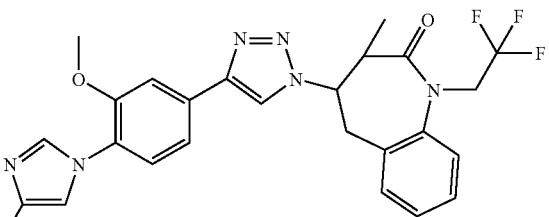 | 3-{4-[3-methoxy-4-(4-methyl-1H-imidazol-1-yl)phenyl]-1H-1,2,3-triazol-1-yl}-3-methyl-1-(2,2,2-trifluoroethyl)-1,3,4,5-tetrahydro-2H-1-benzazepin-2-one | Calc'd 511.2, found 511.2 |
| 215 | 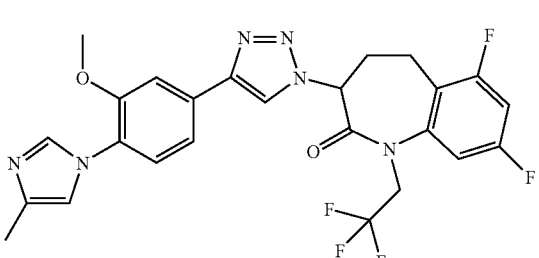 | 6,8-difluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 533.2, found 533.2 |
| 216 | 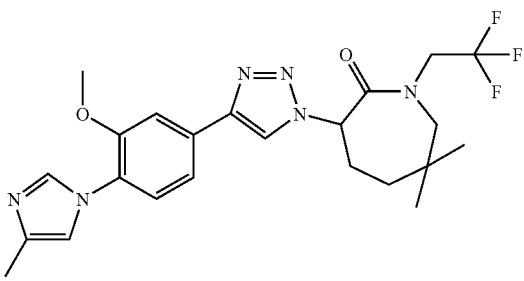 | 3-{4-[3-methoxy-4-(4-methyl-1H-imidazol-1-yl)phenyl]-1H-1,2,3-triazol-1-yl}-6,6-dimethyl-1-(2,2,2-trifluoroethyl)azepan-2-one | Calc'd 477.2, found 477.2 |
| 217 | 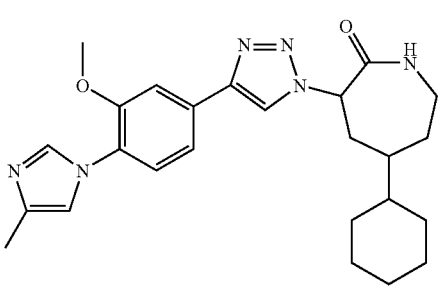 | 5-cyclohexyl-3-{4-[3-methoxy-4-(4-methyl-1H-imidazol-1-yl)phenyl]-1H-1,2,3-triazol-1-yl}azepan-2-one | Calc'd 449.3, found 449.2 |
| 218 | 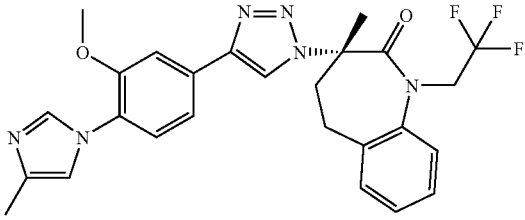 | (3S)-3-{4-[3-methoxy-4-(4-methyl-1H-imidazol-1-yl)phenyl]-1H-1,2,3-triazol-1-yl}-3-methyl-1-(2,2,2-trifluoroethyl)-1,3,4,5-tetrahydro-2H-1-benzazepin-2-one | Calc'd 511.2, found 511.2 |

TABLE III-continued

| EX. | Structure | Name | [M + H]+ |
|---|---|---|---|
| 219 | 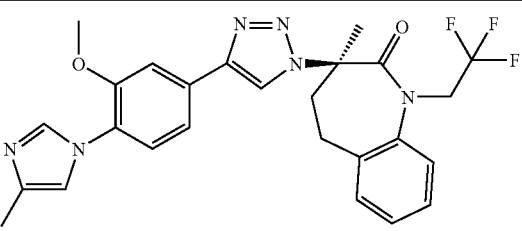 | (3R)-3-{4-[3-methoxy-4-(4-methyl-1H-imidazol-1-yl)phenyl]-1H-1,2,3-triazol-1-yl}-3-methyl-1-(2,2,2-trifluoroethyl)-1,3,4,5-tetrahydro-2H-1-benzazepin-2-one | Calc'd 511.2, found 511.2 |
| 220 | 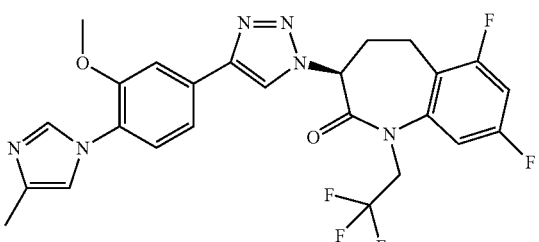 | (3S)-6,8-difluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 533.2, found 533.2 |
| 221 | 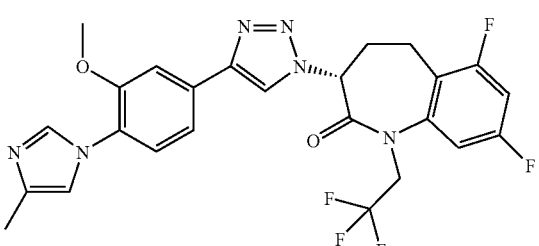 | (3R)-6,8-difluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 533.2, found 533.2 |
| 222 | 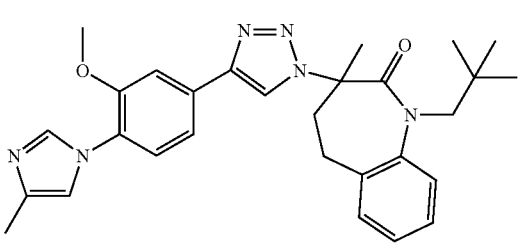 | 1-(2,2-dimethylpropyl)-3-{4-[3-methoxy-4-(4-methyl-1H-imidazol-1-yl)phenyl]-1H-1,2,3-triazol-1-yl}-3-methyl-1,3,4,5-tetrahydro-2H-1-benzazepin-2-one | Calc'd 499.3, found 499.3 |
| 223 | 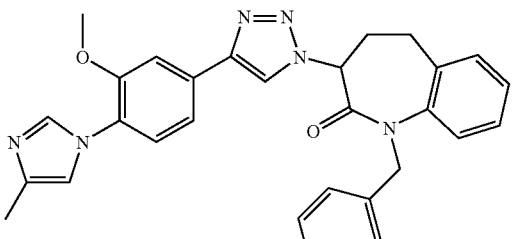 | 1-benzyl-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 505.2, found 505.2 |
| 224 | 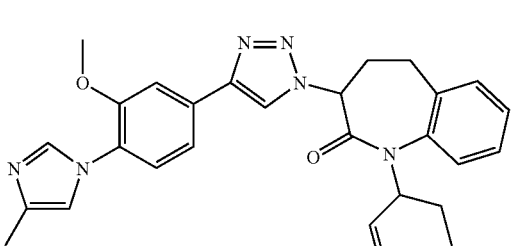 | 1-cyclohex-2-en-1-yl-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 495.3, found 495.2 |

TABLE III-continued

| EX. | Structure | Name | [M + H]+ |
|---|---|---|---|
| 225 | 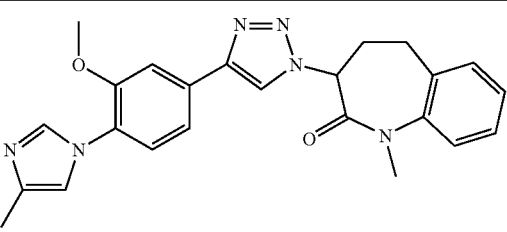 | 3-{4-[3-methoxy-4-(4-methyl-1H-imidazol-1-yl)phenyl]-1H-1,2,3-triazol-1-yl}-1-methyl-1,3,4,5-tetrahydro-2H-1-benzazepin-2-one | Calc'd 429.2, found 429.2 |
| 226 | 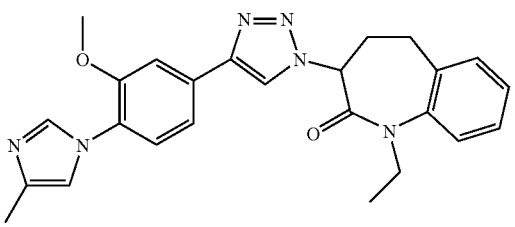 | 1-ethyl-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 443.2, found 443.2 |
| 227 | 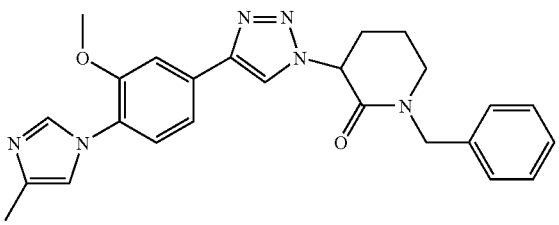 | 1-benzyl-3-{4-[3-methoxy-4-(4-methyl-1H-imidazol-1-yl)phenyl]-1H-1,2,3-triazol-1-yl}piperidin-2-one | Calc'd 443.2, found 443.2 |
| 228 | 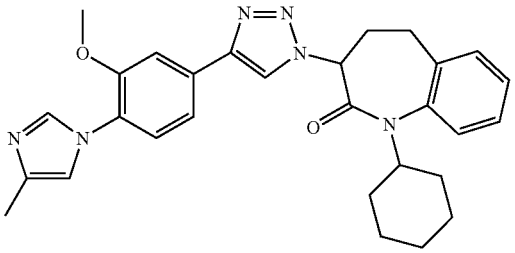 | 1-cyclohexyl-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 497.3, found 497.2 |
| 229 | 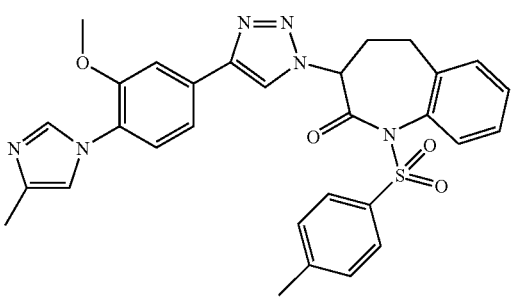 | 3-{4-[3-methoxy-4-(4-methyl-1H-imidazol-1-yl)phenyl]-1H-1,2,3-triazol-1-yl}-1-[(4-methylphenyl)sulfonyl]-1,3,4,5-tetrahydro-2H-1-benzazepin-2-one | Calc'd 569.2, found 569.1 |
| 230 | 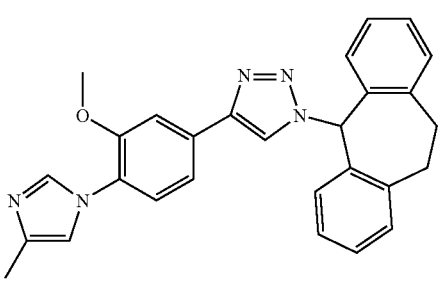 | 1-(10,11-dihydro-5H-dibenzo[a,d][7]annulen-5-yl)-4-[3-methoxy-4-(4-methyl-1H-imidazol-1-yl)phenyl]-1H-1,2,3-triazole | Calc'd 448.2, found 448.2 |

TABLE III-continued

| EX. | Structure | Name | [M + H]+ |
|---|---|---|---|
| 231 | 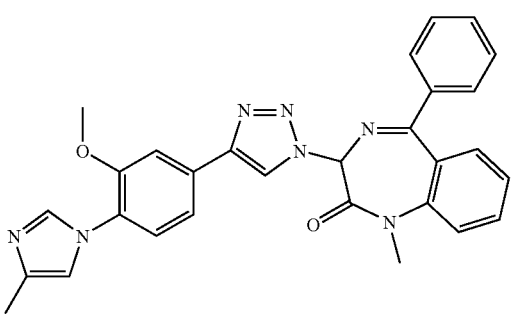 | 3-{4-[3-methoxy-4-(4-methyl-1H-imidazol-1-yl)phenyl]-1H-1,2,3-triazol-1-yl}-1-methyl-5-phenyl-1,3-dihydro-2H-1,4-benzodiazepin-2-one | Calc'd 504.2, found 504.2 |
| 232 | 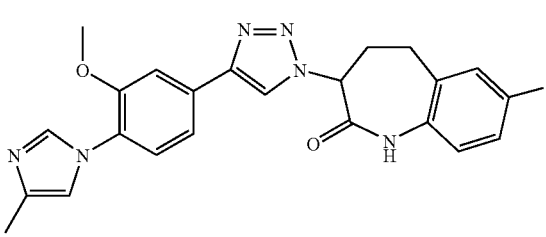 | 7-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 433.2, found 433.2 |
| 234 | 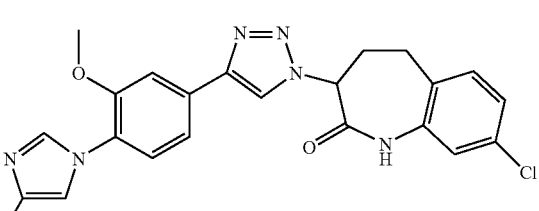 | 8-chloro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 449.1, found 449.1 |
| 235 | 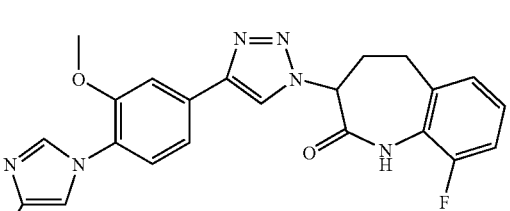 | 9-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 433.2, found 433.1 |
| 236 | 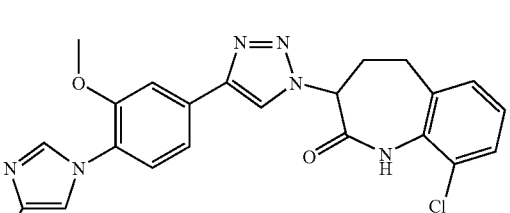 | 9-chloro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 449.1, found 449.1 |
| 237 | 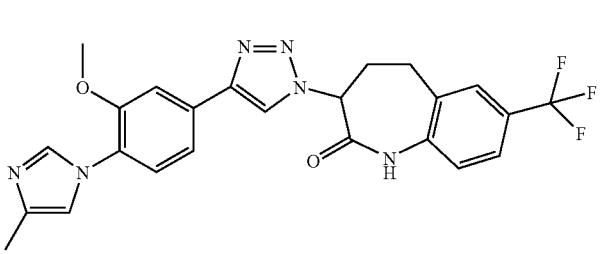 | 3-{4-[3-methoxy-4-(4-methyl-1H-imidazol-1-yl)phenyl]-1H-1,2,3-triazol-1-yl}-7-(trifluoromethyl)-1,3,4,5-tetrahydro-2H-1-benzazepin-2-one | Calc'd 483.2, found 483.1 |

TABLE III-continued

| EX. | Structure | Name | [M + H]+ |
|---|---|---|---|
| 238 | 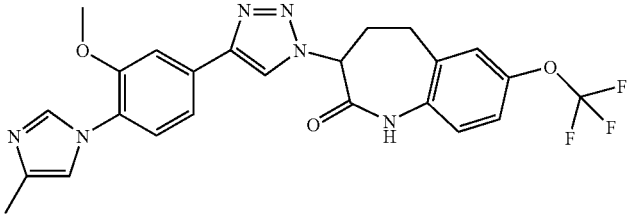 | 3-{4-[3-methoxy-4-(4-methyl-1H-imidazol-1-yl)phenyl]-1H-1,2,3-triazol-1-yl}-7-(trifluoromethoxy)-1,3,4,5-tetrahydro-2H-1-benzazepin-2-one | Calc'd 499.2, found 499.2 |
| 239 | 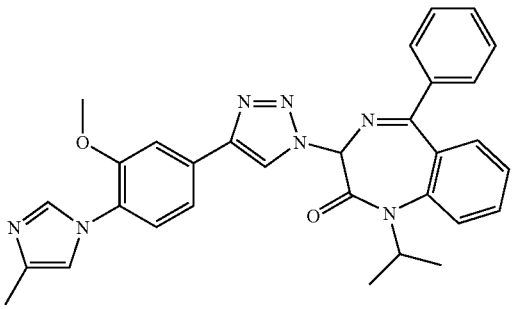 | 1-isopropyl-3-{4-[3-methoxy-4-(4-methyl-1H-imidazol-1-yl)phenyl]-1H-1,2,3-triazol-1-yl}-5-phenyl-1,3-dihydro-2H-1,4-benzodiazepin-2-one | Calc'd 532.2, found 532.2 |
| 240 | 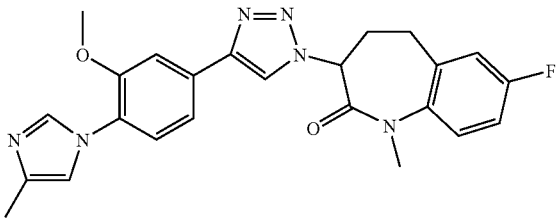 | 7-fluoro-3-{4-[3-methoxy-4-(4-methyl-1H-imidazol-1-yl)phenyl]-1H-1,2,3-triazol-1-yl}-1-methyl-1,3,4,5-tetrahydro-2H-1-benzazepin-2-one | Calc'd 447.2, found 447.2 |
| 241 | 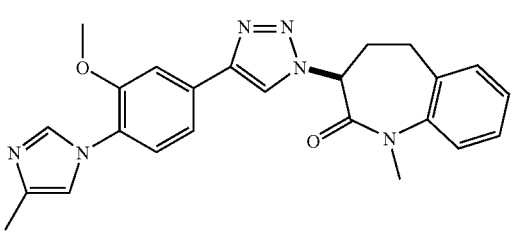 | 3-{4-[3-methoxy-4-(4-methyl-1H-imidazol-1-yl)phenyl]-1H-1,2,3-triazol-1-yl}-1-methyl-1,3,4,5-tetrahydro-2H-1-benzazepin-2-one | Calc'd 429.2, found 429.2 |
| 242 | 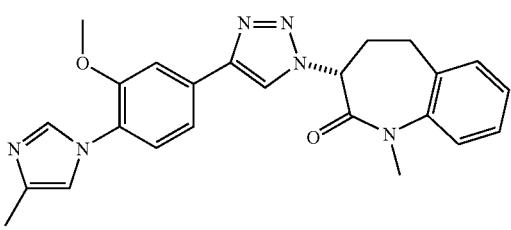 | 3-{4-[3-methoxy-4-(4-methyl-1H-imidazol-1-yl)phenyl]-1H-1,2,3-triazol-1-yl}-1-methyl-1,3,4,5-tetrahydro-2H-1-benzazepin-2-one | Calc'd 429.2, found 429.2 |
| 243 | 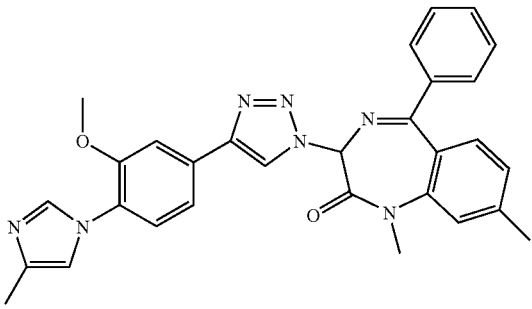 | 3-{4-[3-methoxy-4-(4-methyl-1H-imidazol-1-yl)phenyl]-1H-1,2,3-triazol-1-yl}-1,8-dimethyl-5-phenyl-1,3-dihydro-2H-1,4-benzodiazepin-2-one | Calc'd 518.2, found 518.2 |

TABLE III-continued

| EX. | Structure | Name | [M + H]+ |
|---|---|---|---|
| 245 | 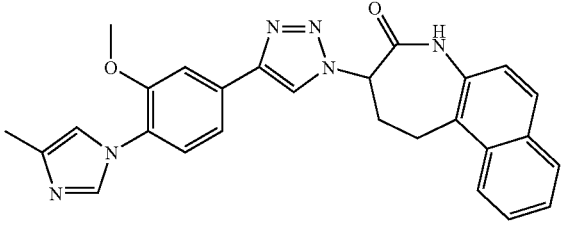 | 3-{4-[3-methoxy-4-(4-methyl-1H-imidazol-1-yl)phenyl]-1H-1,2,3-triazol-1-yl}-1,2,3,5-tetrahydro-4H-naphtho[2,1-b]azepin-4-one | Calc'd 465.2, found 465.2 |
| 246 | 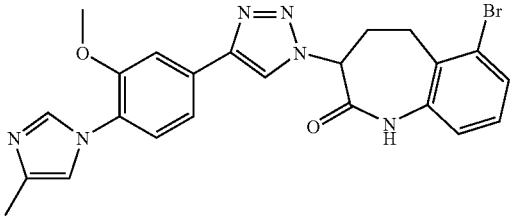 | 6-bromo-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 493.1, found 493.1 |
| 247 | 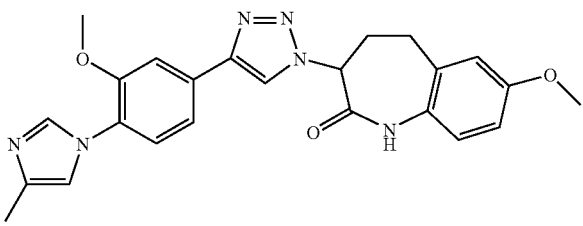 | 7-methoxy-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 445.2, found 445.2 |
| 248 | 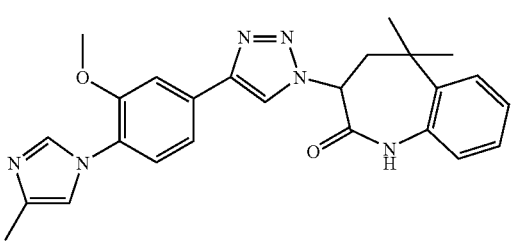 | 3-{4-[3-methoxy-4-(4-methyl-1H-imidazol-1-yl)phenyl]-1H-1,2,3-triazol-1-yl}-5,5-dimethyl-1,3,4,5-tetrahydro-2H-1-benzazepin-2-one | Calc'd 443.2, found 443.2 |
| 249 | 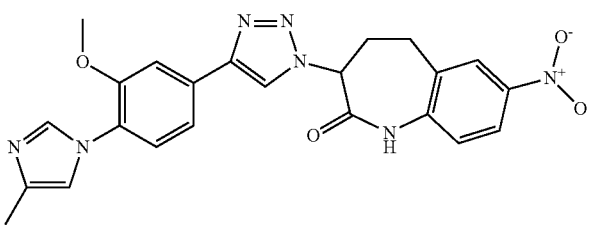 | 3-{4-[3-methoxy-4-(4-methyl-1H-imidazol-1-yl)phenyl]-1H-1,2,3-triazol-1-yl}-7-nitro-1,3,4,5-tetrahydro-2H-1-benzazepin-2-one | Calc'd 460.2, found 460.1 |
| 250 | 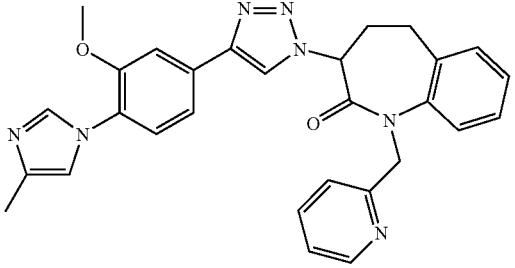 | 3-{4-[3-methoxy-4-(4-methyl-1H-imidazol-1-yl)phenyl]-1H-1,2,3-triazol-1-yl}-1-(pyridin-2-ylmethyl)-1,3,4,5-tetrahydro-2H-1-benzazepin-2-one | Calc'd 506.2, found 506.2 |

TABLE III-continued

| EX. | Structure | Name | [M + H]+ |
|---|---|---|---|
| 251 | 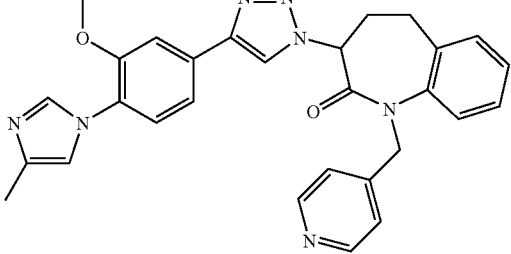 | 3-{4-[3-methoxy-4-(4-methyl-1H-imidazol-1-yl)phenyl]-1H-1,2,3-triazol-1-yl}-1-(pyridin-4-ylmethyl)-1,3,4,5-tetrahydro-2H-1-benzazepin-2-one | Calc'd 506.2, found 506.2 |
| 252 | 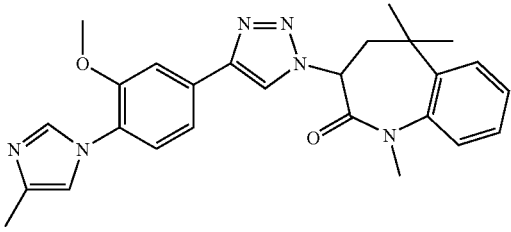 | 3-{4-[3-methoxy-4-(4-methyl-1H-imidazol-1-yl)phenyl]-1H-1,2,3-triazol-1-yl}-1,5,5-trimethyl-1,3,4,5-tetrahydro-2H-1-benzazepin-2-one | Calc'd 457.2, found 457.2 |
| 253 | 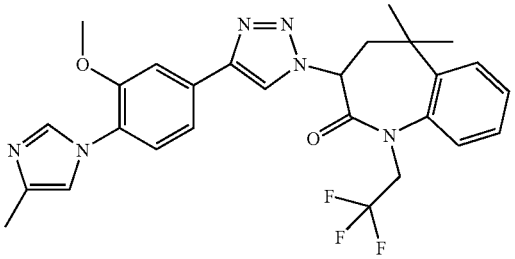 | 3-{4-[3-methoxy-4-(4-methyl-1H-imidazol-1-yl)phenyl]-1H-1,2,3-triazol-1-yl}-5,5-dimethyl-1-(2,2,2-trifluoroethyl)-1,3,4,5-tetrahydro-2H-1-benzazepin-2-one | Calc'd 525.2, found 525.2 |
| 254 | 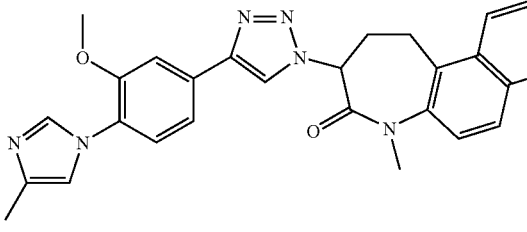 | 3-{4-[3-methoxy-4-(4-methyl-1H-imidazol-1-yl)phenyl]-1H-1,2,3-triazol-1-yl}-5-methyl-1,2,3,5-tetrahydro-4H-naphtho[2,1-b]azepin-4-one | Calc'd 479.2, found 479.2 |
| 255 | 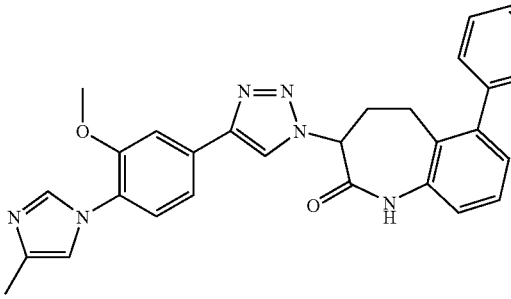 | 3-{4-[3-methoxy-4-(4-methyl-1H-imidazol-1-yl)phenyl]-1H-1,2,3-triazol-1-yl}-6-phenyl-1,3,4,5-tetrahydro-2H-1-benzazepin-2-one | Calc'd 491.2, found 491.2 |
| 256 | 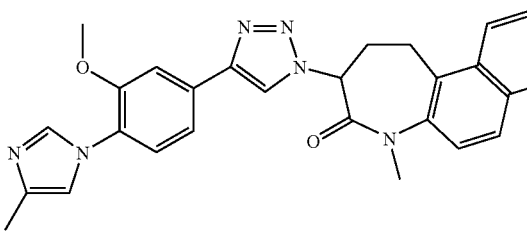 | 3-{4-[3-methoxy-4-(4-methyl-1H-imidazol-1-yl)phenyl]-1H-1,2,3-triazol-1-yl}-5-methyl-1,2,3,5-tetrahydro-4H-naphtho[2,1-b]azepin-4-one | Calc'd 479.2, found 479.2 |

TABLE III-continued

| EX. | Structure | Name | [M + H]+ |
|---|---|---|---|
| 257 | 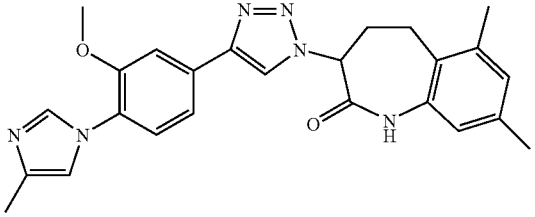 | 3-{4-[3-methoxy-4-(4-methyl-1H-imidazol-1-yl)phenyl]-1H-1,2,3-triazol-1-yl}-6,8-dimethyl-1,3,4,5-tetrahydro-2H-1-benzazepin-2-one | Calc'd 443.2, found 443.2 |
| 258 | 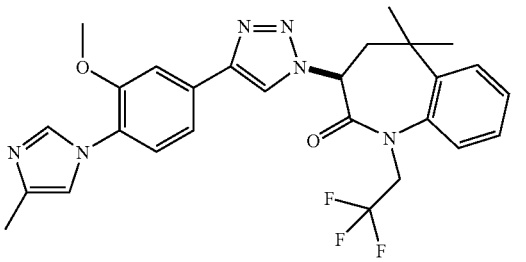 | 3-{4-[3-methoxy-4-(4-methyl-1H-imidazol-1-yl)phenyl]-1H-1,2,3-triazol-1-yl}-5,5-dimethyl-1-(2,2,2-trifluoroethyl)-1,3,4,5-tetrahydro-2H-1-benzazepin-2-one | Calc'd 525.2, found 525.2 |
| 259 | 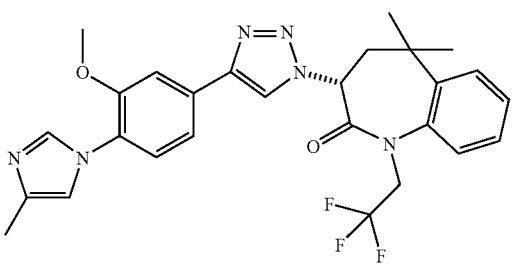 | 3-{4-[3-methoxy-4-(4-methyl-1H-imidazol-1-yl)phenyl]-1H-1,2,3-triazol-1-yl}-5,5-dimethyl-1-(2,2,2-trifluoroethyl)-1,3,4,5-tetrahydro-2H-1-benzazepin-2-one | Calc'd 525.2, found 525.2 |
| 260 | 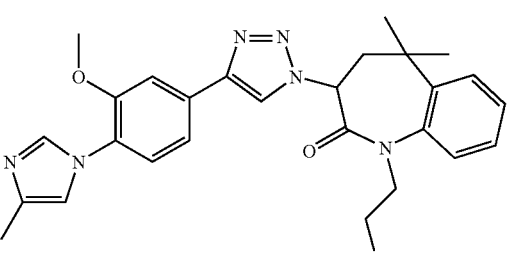 | 1-(2-fluoroethyl)-3-{4-{3-methoxy-4-(4-methyl-1H-imidazol-1-yl)phenyl]-1H-1,2,3-triazol-1-yl}-5,5-dimethyl-1,3,4,5-tetrahydro-2H-1-benzazepin-2-one | Calc'd 489.2, found 489.2 |
| 261 | 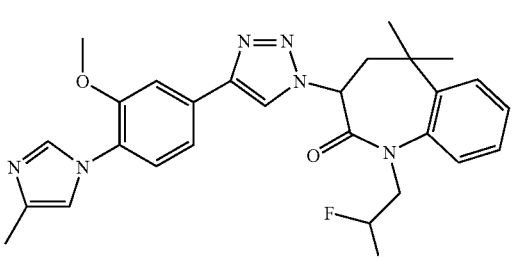 | 1-(2,2-difluoroethyl)-3-{4-[3-methoxy-4-(4-methyl-1H-imidazol-1-yl)phenyl]-1H-1,2,3-triazol-1-yl}-5,5-dimethyl-1,3,4,5-tetrahydro-2H-1-benzazepin-2-one | Calc'd 507.2, found 507.2 |
| 262 | 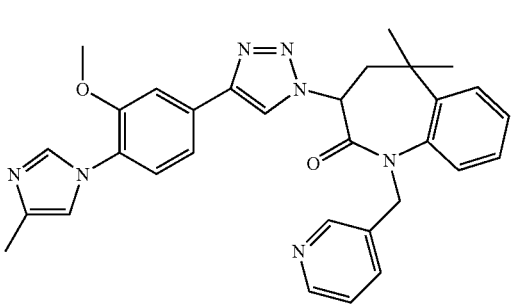 | 3-{4-[3-methoxy-4-(4-methyl-1H-imidazol-1-yl)phenyl]-1H-1,2,3-triazol-1-yl}-5,5-dimethyl-1-(pyridin-3-ylmethyl)-1,3,4,5-tetrahydro-2H-1-benzazepin-2-one | Calc'd 534.3, found 534.2 |

TABLE III-continued

| EX. | Structure | Name | [M + H]+ |
|---|---|---|---|
| 263 | 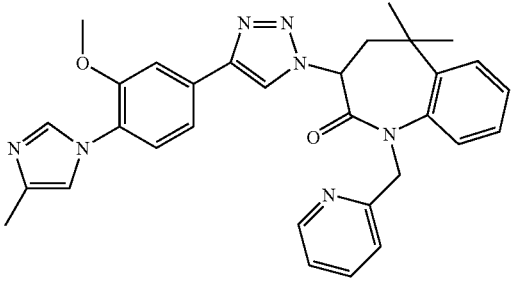 | 3-{4-[3-methoxy-4-(4-methyl-1H-imidazol-1-yl)phenyl]-1H-1,2,3-triazol-1-yl}-5,5-dimethyl-1-(pyridin-2-ylmethyl)-1,3,4,5-tetrahydro-2H-1-benzazepin-2-one | Calc'd 534.3, found 534.2 |
| 264 | 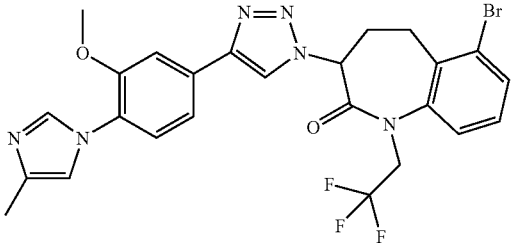 | 6-bromo-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 575.1, found 575.1 |
| 265 | 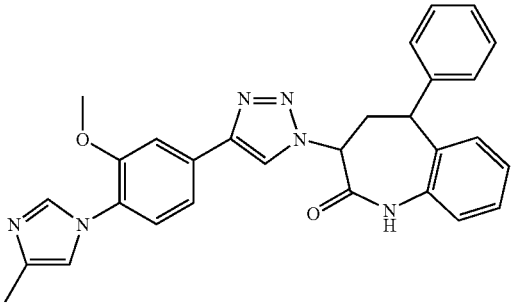 | 3-(4-[3-methoxy-4-(4-methyl-1H-imidazol-1-yl)phenyl]-1H-1,2,3-triazol-1-yl}-5-phenyl-1,3,4,5-tetrahydro-2H-1-benzazepin-2-one | Calc'd 491.2, found 491.2 |
| 267 | 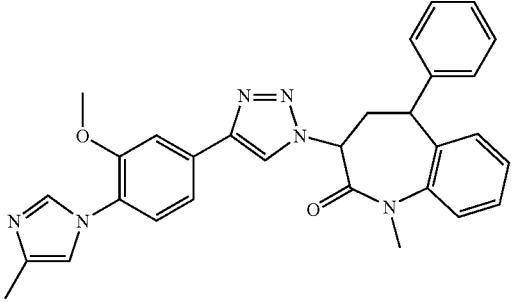 | 3-{4-[3-methoxy-4-(4-methyl-1H-imidazol-1-yl)phenyl]-1H-1,2,3-triazol-1-yl}-1-methyl-5-phenyl-1,3,4,5-tetrahydro-2H-1-benzazepin-2-one | Calc'd 505.2, found 505.2 |
| 268 | 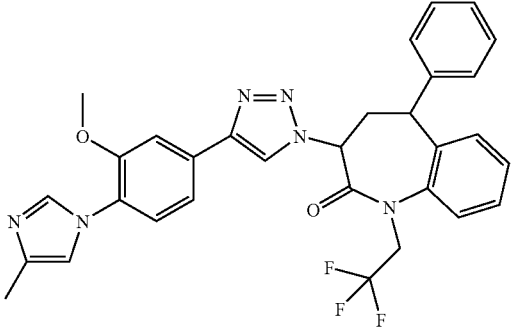 | 3-{4-[3-methoxy-4-(4-methyl-1H-imidazol-1-yl)phenyl]-1H-1,2,3-triazol-1-yl}-5-phenyl-1-(2,2,2-trifluoroethyl)-1,3,4,5-tetrahydro-2H-1-benzazepin-2-one | Calc'd 573.2, found 573.2 |

| EX. | Structure | Name | [M + H]+ |
|---|---|---|---|
| 269 | 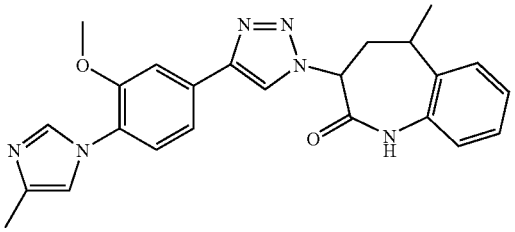 | 3-{4-[3-methoxy-4-(4-methyl-1H-imidazol-1-yl)phenyl]-1H-1,2,3-triazol-1-yl}-5-methyl-1,3,4,5-tetrahydro-2H-1-benzazepin-2-one | Calc'd 429.2, found 429.2 |
| 270 | 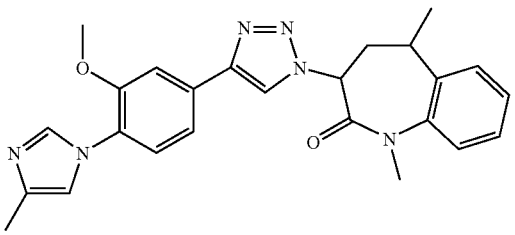 | 3-{4-[3-methoxy-4-(4-methyl-1H-imidazol-1-yl)phenyl]-1H-1,2,3-triazol-1-yl}-1,5-dimethyl-1,3,4,5-tetrahydro-2H-1-benzazepin-2-one | Calc'd 443.2, found 443.2 |
| 271 | 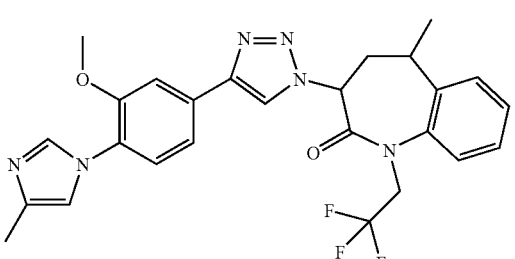 | 3-{4-[3-methoxy-4-(4-methyl-1H-imidazol-1-yl)phenyl]-1H-1,2,3-triazol-1-yl}-5-methyl-1-(2,2,2-trifluoroethyl)-1,3,4,5-tetrahydro-2H-1-benzazepin-2-one | Calc'd 511.2, found 511.2 |
| 272 | 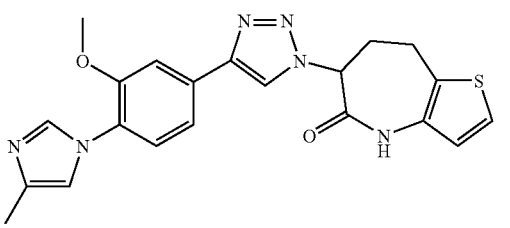 | 6-{4-[3-methoxy-4-(4-methyl-1H-imidazol-1-yl)phenyl]-1H-1,2,3-triazol-1-yl}-4,6,7,8-tetrahydro-5H-thieno[3,2-b]azepin-5-one | Calc'd 421.1, found 421.1 |
| 273 | 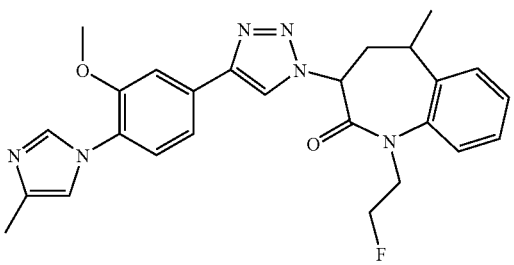 | 1-(2-fluoroethyl)-3-{4-[3-methoxy-4-(4-methyl-1H-imidazol-1-yl)phenyl]-1H-1,2,3-triazol-1-yl}-5-methyl-1,3,4,5-tetrahydro-2H-1-benzazepin-2-one | Calc'd 475.2, found 475.2 |
| 274 | 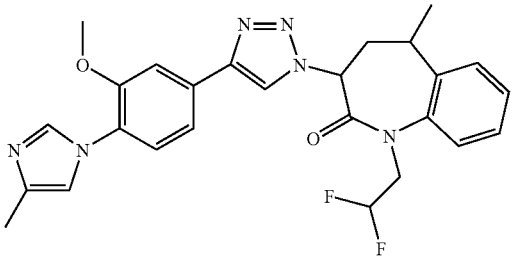 | 1-(2,2-difluoroethyl)-3-{4-[3-methoxy-4-(4-methyl-1H-imidazol-1-yl)phenyl]-1H-1,2,3-triazol-1-yl}-5-methyl-1,3,4,5-tetrahydro-2H-1-benzazepin-2-one | Calc'd 493.2, found 493.2 |

TABLE III-continued

| EX. | Structure | Name | [M + H]+ |
|---|---|---|---|
| 275 | 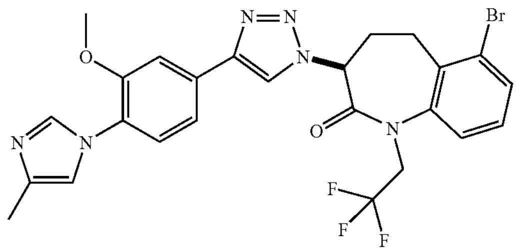 | 6-bromo-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 575.1, found 575.1 |
| 276 | 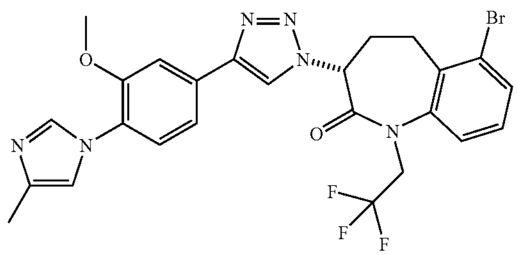 | 6-bromo-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 575.1, found 575.1 |
| 277 | 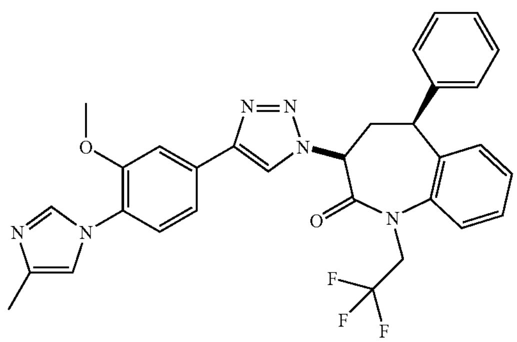 | (5S)-3-{4-[3-methoxy-4-(4-methyl-1H-imidazol-1-yl)phenyl]-1H-1,2,3-triazol-1-yl}-5-phenyl-1-(2,2,2-trifluoroethyl)-1,3,4,5-tetrahydro-2H-1-benzazepin-2-one | Calc'd 573.2, found 573.2 |
| 278 | 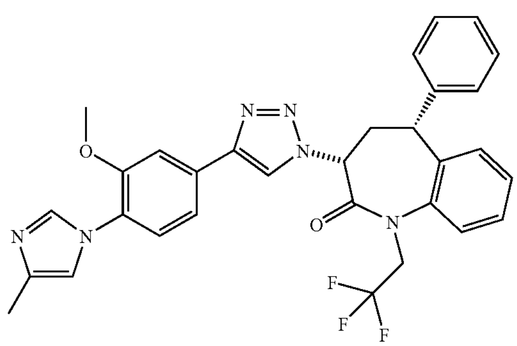 | (5R)-3-{4-[3-methoxy-4-(4-methyl-1H-imidazol-1-yl)phenyl]-1H-1,2,3-triazol-1-yl}-5-phenyl-1-(2,2,2-trifluoroethyl)-1,3,4,5-tetrahydro-2H-1-benzazepin-2-one | Calc'd 573.2, found 573.2 |
| 279 | 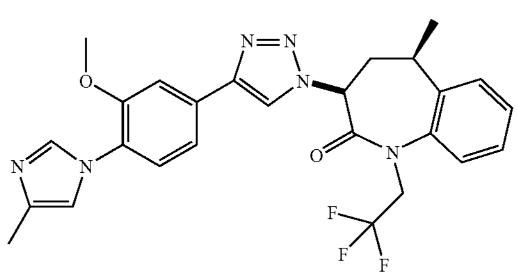 | (5R)-3-{4-[3-methoxy-4-(4-methyl-1H-imidazol-1-yl)phenyl]-1H-1,2,3-triazol-1-yl}-5-methyl-1-(2,2,2-trifluoroethyl)-1,3,4,5-tetrahydro-2H-1-benzazepin-2-one | Calc'd 511.2, found 511.2 |

TABLE III-continued

| EX. | Structure | Name | [M + H]+ |
|---|---|---|---|
| 280 | 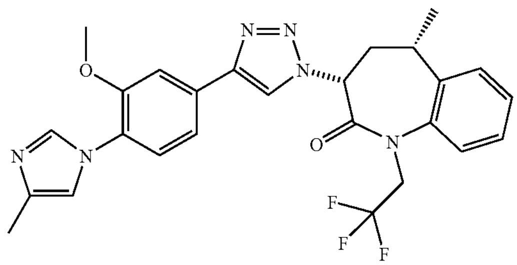 | (5S)-3-{4-[3-methoxy-4-(4-methyl-1H-imidazol-1-yl)phenyl]-1H-1,2,3-triazol-1-yl}-5-methyl-1-(2,2,2-trifluoroethyl)-1,3,4,5-tetrahydro-2H-1-benzazepin-2-one | Calc'd 511.2, found 511.2 |
| 281 | 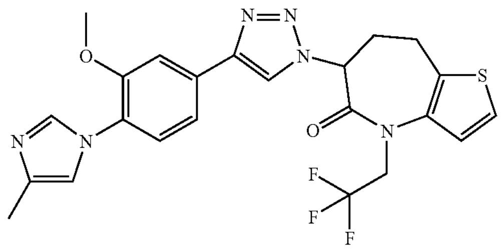 | 6-{4-[3-methoxy-4-(4-methyl-1H-imidazol-1-yl)phenyl]-1H-1,2,3-triazol-1-yl}-4-(2,2,2-trifluoroethyl)-4,6,7,8-tetrahydro-5H-thieno[3,2-b]azepin-5-one | Calc'd 503.1, found 503.1 |
| 282 | 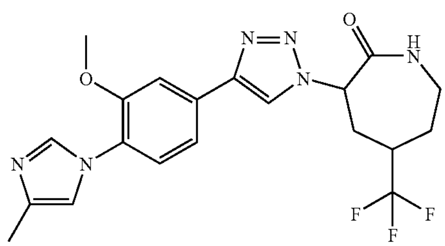 | 3-{4-[3-methoxy-4-(4-methyl-1H-imidazol-1-yl)phenyl]-1H-1,2,3-triazol-1-yl}-5-(trifluoromethyl)azepan-2-one | Calc'd 435.2, found 435.2 |
| 283 | 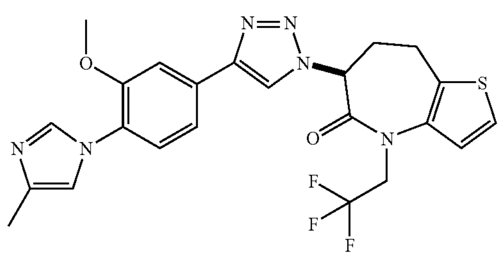 | 6-{4-[3-methoxy-4-(4-methyl-1H-imidazol-1-yl)phenyl]-1H-1,2,3-triazol-1-yl}-4-(2,2,2-trifluoroethyl)-4,6,7,8-tetrahydro-5H-thieno[3,2-b]azepin-5-one | Calc'd 503.1, found 503.1 |
| 284 | 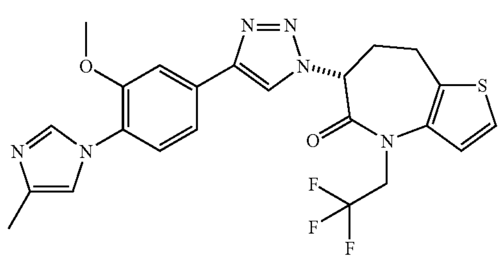 | 6-{4-[3-methoxy-4-(4-methyl-1H-imidazol-1-yl)phenyl]-1H-1,2,3-triazol-1-yl}-4-(2,2,2-trifluoroethyl)-4,6,7,8-tetrahydro-5H-thieno[3,2-b]azepin-5-one | Calc'd 503.1, found 503.1 |
| 285 | 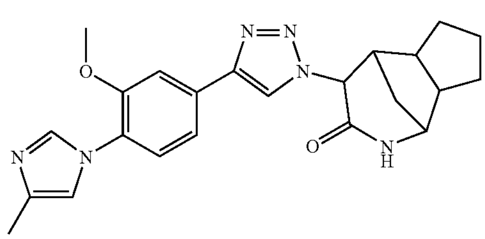 | 4-{4-[3-methoxy-4-(4-methyl-1H-imidazol-1-yl)phenyl]-1H-1,2,3-triazol-1-yl}octahydro-1,5-methanocyclopenta[c]azepin-3(2H)-one | Calc'd 419.2, found 419.2 |

TABLE III-continued

| EX. | Structure | Name | [M + H]+ |
|---|---|---|---|
| 286 | 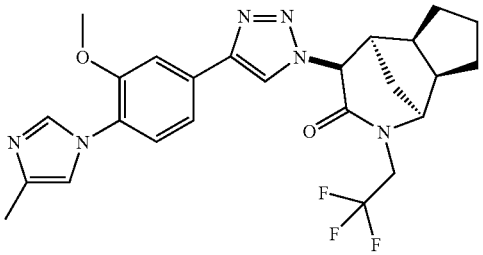 | (1S,5R,5aS,8aR)-4-{4-[3-methoxy-4-(4-methyl-1H-imidazol-1-yl)phenyl]-1H-1,2,3-triazol-1-yl}-2-(2,2,2-trifluoroethyl)octahydro-1,5-methanocyclopenta[c]azepin-3(2H)-one | Calc'd 501.2, found 501.2 |
| 287 | 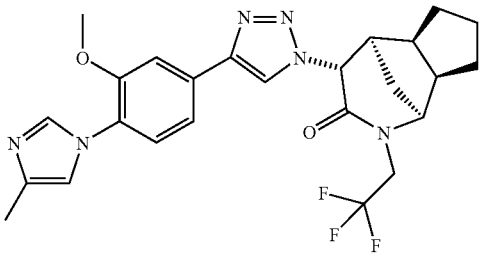 | (1S,5R,5aS,8aR)-4-{4-[3-methoxy-4-(4-methyl-1H-imidazol-1-yl)phenyl]-1H-1,2,3-triazol-1-yl}-2-(2,2,2-trifluoroethyl)octahydro-1,5-methanocyclopenta[c]azepin-3(2H)-one | Calc'd 501.2, found 501.2 |
| 288 | 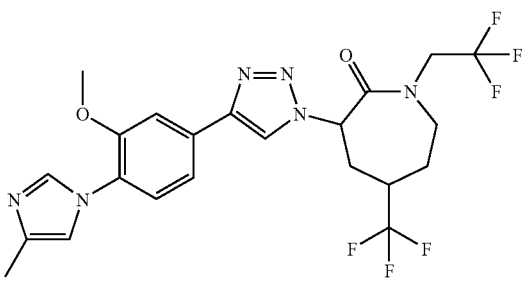 | 3-{4-[3-methoxy-4-(4-methyl-1H-imidazol-1-yl)phenyl]-1H-1,2,3-triazol-1-yl}-1-(2,2,2-trifluoroethyl)-5-(trifluoromethyl)azepan-2-one | Calc'd 517.2, found 517.1 |
| 289 | 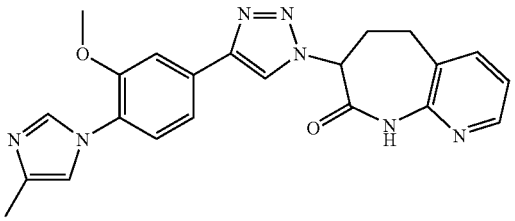 | 7-{4-[3-methoxy-4-(4-methyl-1H-imidazol-1-yl)phenyl]-1H-1,2,3-triazol-1-yl}-5,6,7,9-tetrahydro-8H-pyrido[2,3-b]azepin-8-one | Calc'd 416.2, found 416.2 |
| 290 | 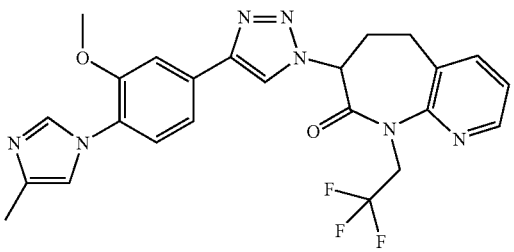 | 7-{4-[3-methoxy-4-(4-methyl-1H-imidazol-1-yl)phenyl]-1H-1,2,3-triazol-1-yl}-9-(2,2,2-trifluoroethyl)-5,6,7,9-tetrahydro-8H-pyrido[2,3-b]azepin-8-one | Calc'd 498.2, found 498.2 |
| 291 | 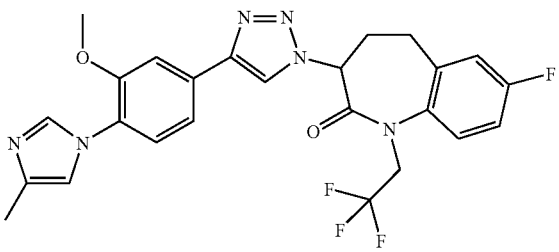 | 7-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.2 |

TABLE III-continued

| EX. | Structure | Name | [M + H]+ |
|---|---|---|---|
| 292 | 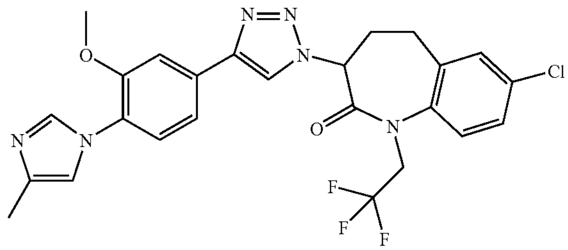 | 7-chloro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 531.2, found 531.2 |
| 293 | 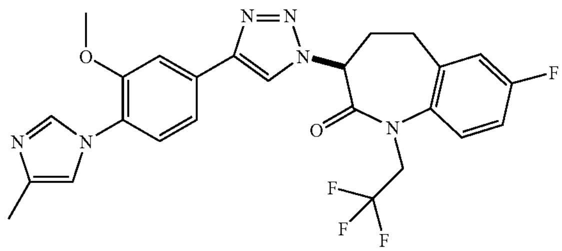 | 7-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 294 | 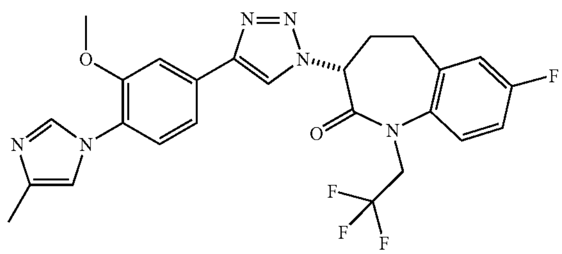 | 7-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 295 | 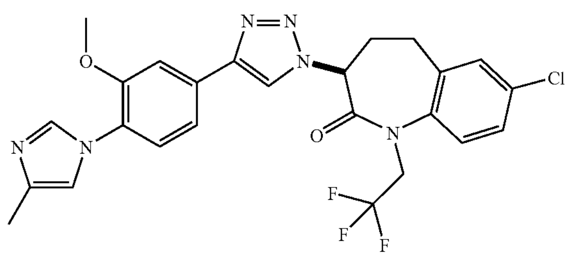 | 7-chloro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 531.2, found 531.2 |
| 296 | 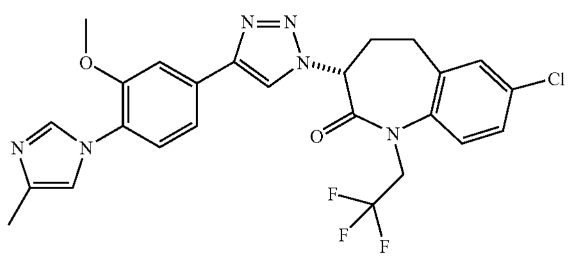 | 7-chloro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 531.2, found 531.2 |
| 297 | 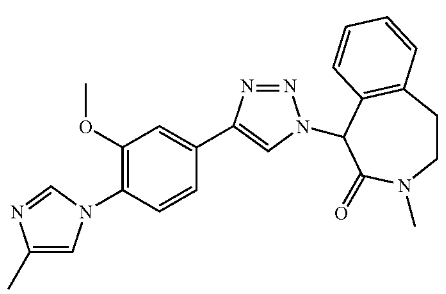 | 1-{4-[3-methoxy-4-(4-methyl-1H-imidazol-1-yl)phenyl]-1H-1,2,3-triazol-1-yl}-3-methyl-1,3,4,5-tetrahydro-2H-3-benzazepin-2-one | Calc'd 429.2, found 429.1 |

TABLE III-continued

| EX. | Name | [M + H]+ |
|---|---|---|
| 298 | (1R)-4-{4-[3-methoxy-4-(4-methyl-1H-imidazol-1-yl)phenyl]-1H-1,2,3-triazol-1-yl}-1,8,8-trimethyl-2-azabicyclo[3.2.1]octan-3-one | Calc'd 421.2, found 421.2 |
| 299 | 7-{4-[3-methoxy-4-(4-methyl-1H-imidazol-1-yl)phenyl]-1H-1,2,3-triazol-1-yl}-9-(2,2,2-trifluoroethyl)-5,6,7,9-tetrahydro-8H-pyrido[2,3-b]azepin-8-one | Calc'd 498.2, found 498.1 |
| 300 | 7-{4-[3-methoxy-4-(4-methyl-1H-imidazol-1-yl)phenyl]-1H-1,2,3-triazol-1-yl}-9-(2,2,2-trifluoroethyl)-5,6,7,9-tetrahydro-8H-pyrido[2,3-b]azepin-8-one | Calc'd 498.2, found 498.1 |
| 301 | 3-{4-[3-methoxy-4-(4-methyl-1H-imidazol-1-yl)phenyl]-1H-1,2,3-triazol-1-yl}-5,5-dimethyl-2,3,4,5-tetrahydro-1H-1-benzazepine | Calc'd 429.2, found 429.2 |
| 302 | 3-{4-[3-methoxy-4-(4-methyl-1H-imidazol-1-yl)phenyl]-1H-1,2,3-triazol-1-yl}-1-(2,2,2-trifluoroethyl)-5-(trifluoromethyl)azepan-2-one | Calc'd 517.2, found 517.1 |

TABLE III-continued

| EX. | Structure | Name | [M + H]⁺ |
|---|---|---|---|
| 303 | 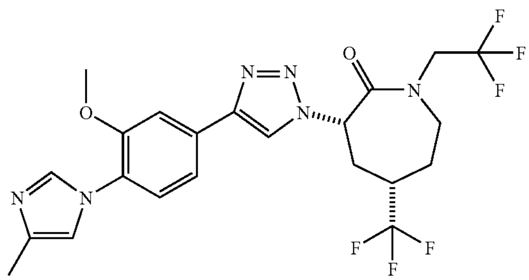 | 3-{4-[3-methoxy-4-(4-methyl-1H-imidazol-1-yl)phenyl]-1H-1,2,3-triazol-1-yl}-1-(2,2,2-trifluoroethyl)-5-(trifluoromethyl)azepan-2-one | Calc'd 517.2, found 517.1 |
| 304 | 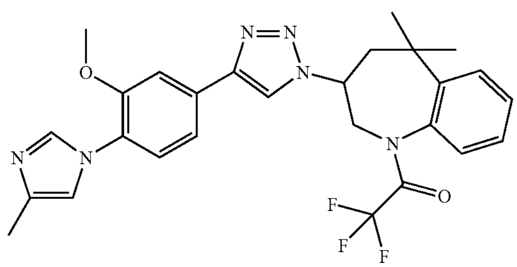 | 3-{4-[3-methoxy-4-(4-methyl-1H-imidazol-1-yl)phenyl]-1H-1,2,3-triazol-1-yl}-5,5-dimethyl-1-(trifluoroacetyl)-2,3,4,5-tetrahydro-1H-1-benzazepine | Calc'd 525.2, found 525.2 |
| 305 | 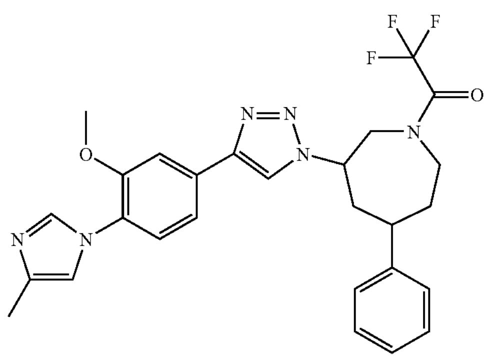 | 3-{4-[3-methoxy-4-(4-methyl-1H-imidazol-1-yl)phenyl]-1H-1,2,3-triazol-1-yl}-5-phenyl-1-(trifluoroacetyl)azepane | Calc'd 525.2, found 525.2 |
| 306 | 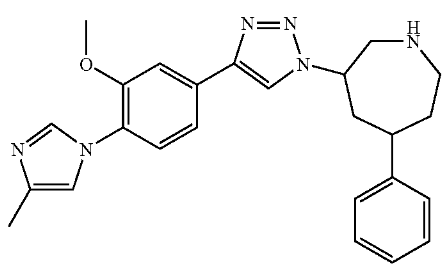 | 3-{4-[3-methoxy-4-(4-methyl-1H-imidazol-1-yl)phenyl]-1H-1,2,3-triazol-1-yl}-5-phenylazepane | Calc'd 429.2, found 429.1 |
| 307 | 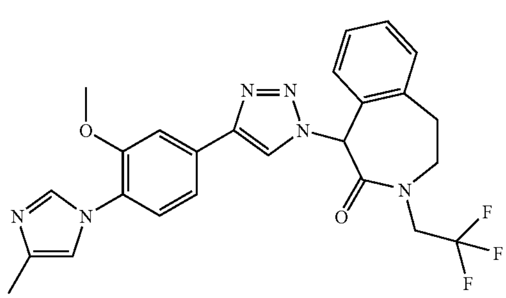 | 1-{4-[3-methoxy-4-(4-methyl-1H-imidazol-1-yl)phenyl]-1H-1,2,3-triazol-1-yl}-3-(2,2,2-trifluoroethyl)-1,3,4,5-tetrahydro-2H-3-benzazepin-2-one | Calc'd 497.2, found 497.1 |

TABLE III-continued

| EX. | Structure | Name | [M + H]+ |
|---|---|---|---|
| 308 | 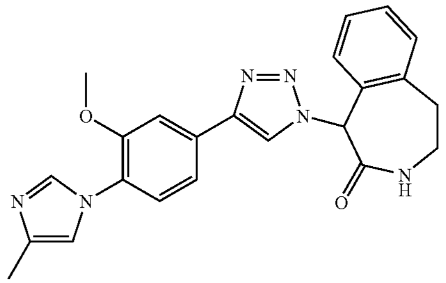 | 1-{4-[3-methoxy-4-(4-methyl-1H-imidazol-1-yl)phenyl]-1H-1,2,3-triazol-1-yl}-1,3,4,5-tetrahydro-2H-3-benzazepin-2-one | Calc'd 415.2, found 415.1 |
| 309 | 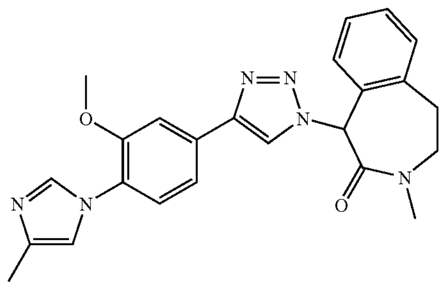 | 1-{4-[3-methoxy-4-(4-methyl-1H-imidazol-1-yl)phenyl]-1H-1,2,3-triazol-1-yl}-3-methyl-1,3,4,5-tetrahydro-2H-3-benzazepin-2-one | Calc'd 429.2, found 429.1 |
| 310 | 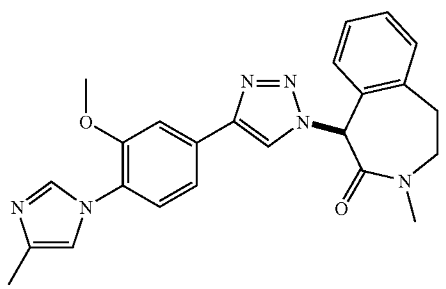 | 1-{4-[3-methoxy-4-(4-methyl-1H-imidazol-1-yl)phenyl]-1H-1,2,3-triazol-1-yl}-3-methyl-1,3,4,5-tetrahydro-2H-3-benzazepin-2-one | Calc'd 429.2, found 429.1 |
| 311 | 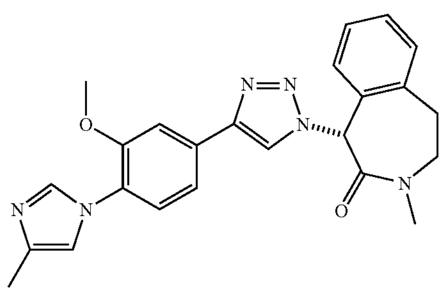 | 1-{4-[3-methoxy-4-(4-methyl-1H-imidazol-1-yl)phenyl]-1H-1,2,3-triazol-1-yl}-3-methyl-1,3,4,5-tetrahydro-2H-3-benzazepin-2-one | Calc'd 429.2, found 429.1 |
| 312 | 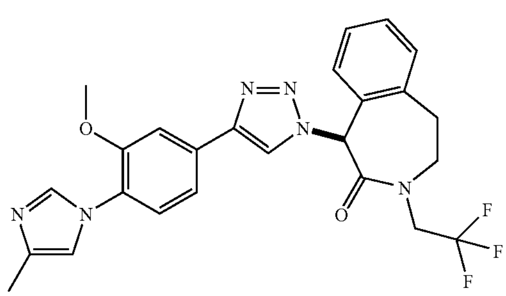 | 1-{4-[3-methoxy-4-(4-methyl-1H-imidazol-1-yl)phenyl]-1H-1,2,3-triazol-1-yl}-3-(2,2,2-trifluoroethyl)-1,3,4,5-tetrahydro-2H-3-benzazepin-2-one | Calc'd 497.2, found 497.1 |

TABLE III-continued

| EX. | Structure | Name | [M + H]+ |
|---|---|---|---|
| 313 | 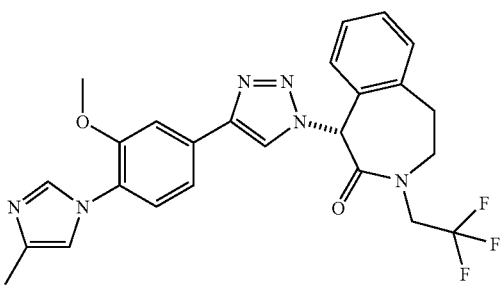 | 1-{4-[3-methoxy-4-(4-methyl-1H-imidazol-1-yl)phenyl]-1H-1,2,3-triazol-1-yl}-3-(2,2,2-trifluoroethyl)-1,3,4,5-tetrahydro-2H-3-benzazepin-2-one | Calc'd 497.2, found 497.1 |
| 314 | 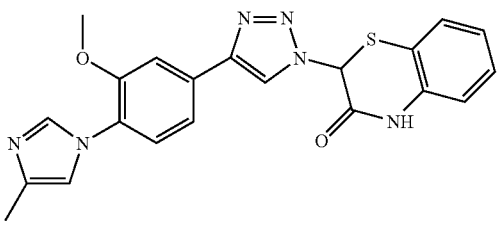 | 2-{4-[3-methoxy-4-(4-methyl-1H-imidazol-1-yl)phenyl]-1H-1,2,3-triazol-1-yl}-2H-1,4-benzothiazin-3(4H)-one | Calc'd 419.1, found 419.1 |
| 315 | 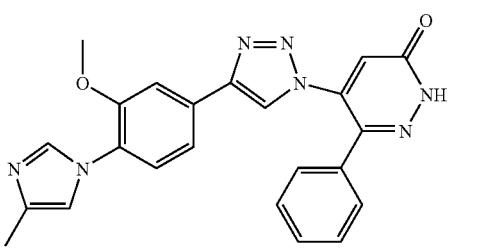 | 5-{4-[3-methoxy-4-(4-methyl-1H-imidazol-1-yl)phenyl]-1H-1,2,3-triazol-1-yl}-6-phenylpyridazin-3(2H)-one | Calc'd 426.2, found 426.1 |
| 316 | 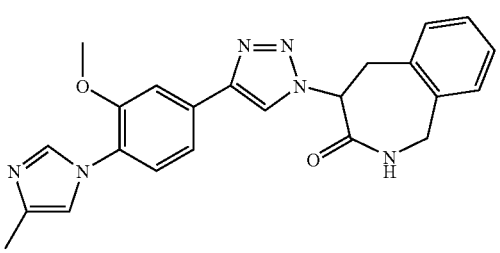 | 4-{4-[3-methoxy-4-(4-methyl-1H-imidazol-1-yl)phenyl]-1H-1,2,3-triazol-1-yl}-1,2,4,5-tetrahydro-3H-2-benzazepin-3-one | Calc'd 415.2, found 415.1 |
| 317 | 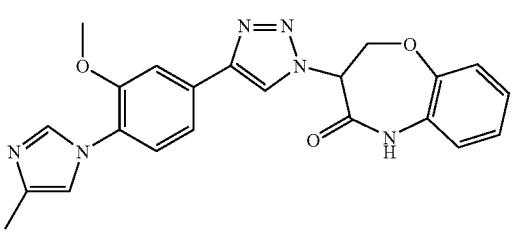 | 3-{4-[3-methoxy-4-(4-methyl-1H-imidazol-1-yl)phenyl]-1H-1,2,3-triazol-1-yl}-2,3-dihydro-1,5-benzoxazepin-4(5H)-one | Calc'd 417.2, found 417.1 |
| 318 | 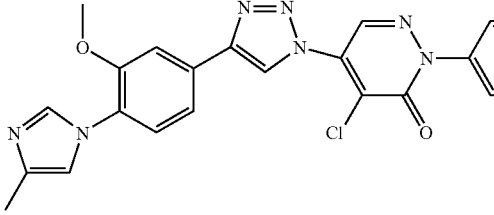 | 4-chloro-5-{4-[3-methoxy-4-(4-methyl-1H-imidazol-1-yl)phenyl]-1H-1,2,3-triazol-1-yl}-2-phenylpyridazin-3(2H)-one | Calc'd 460.1, found 460.1 |

TABLE III-continued

| EX. | Structure | Name | [M + H]+ |
|---|---|---|---|
| 319 | 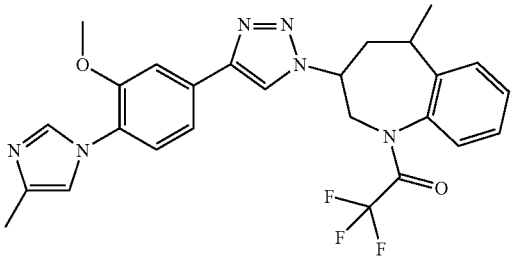 | 3-{4-[3-methoxy-4-(4-methyl-1H-imidazol-1-yl)phenyl]-1H-1,2,3-triazol-1-yl}-5-methyl-1-(trifluoroacetyl)-2,3,4,5-tetrahydro-1H-1-benzazepine | Calc'd 511.2, found 511.1 |
| 320 | 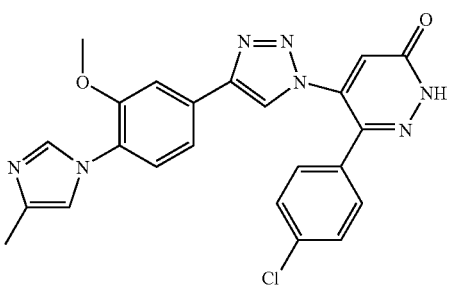 | 6-(4-chlorophenyl)-5-{4-[3-methoxy-4-(4-methyl-1H-imidazol-1-yl)phenyl]-1H-1,2,3-triazol-1-yl}pyridazin-3(2H)-one | Calc'd 460.1, found 460.1 |
| 321 | 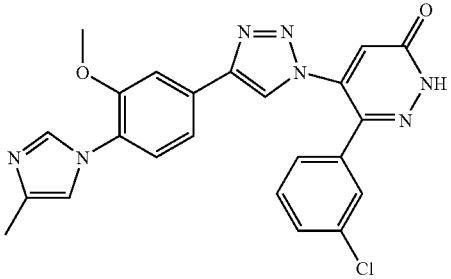 | 6-(3-chlorophenyl)-5-{4-[3-methoxy-4-(4-methyl-1H-imidazol-1-yl)phenyl]-1H-1,2,3-triazol-1-yl}pyridazin-3(2H)-one | Calc'd 460.1, found 460.1 |
| 322 | 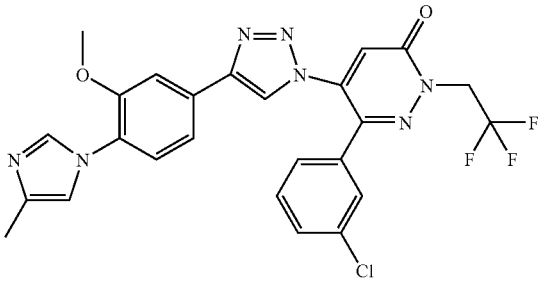 | 6-(3-chlorophenyl)-5-{4-[3-methoxy-4-(4-methyl-1H-imidazol-1-yl)phenyl]-1H-1,2,3-triazol-1-yl}-2-(2,2,2-trifluoroethyl)pyridazin-3(2H)-one | Calc'd 542.1, found 542.0 |
| 323 | 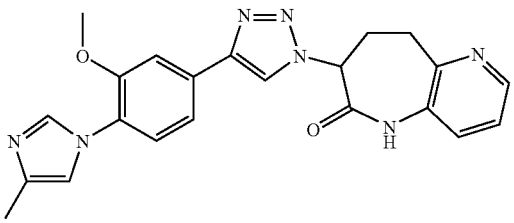 | 7-{4-[3-methoxy-4-(4-methyl-1H-imidazol-1-yl)phenyl]-1H-1,2,3-triazol-1-yl}-5,7,8,9-tetrahydro-6H-pyrido[3,2-b]azepin-6-one | Calc'd 416.2, found 416.1 |

TABLE III-continued

| EX. | Structure | Name | [M + H]+ |
|---|---|---|---|
| 324 | 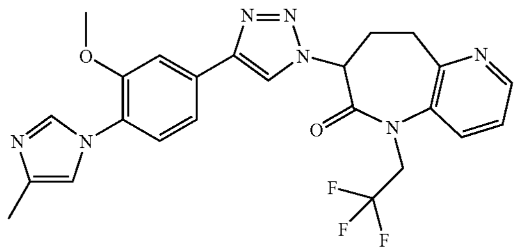 | 7-{4-[3-methoxy-4-(4-methyl-1H-imidazol-1-yl)phenyl]-1H-1,2,3-triazol-1-yl}-5-(2,2,2-trifluoroethyl)-5,7,8,9-tetrahydro-6H-pyrido[3,2-b]azepin-6-one | Calc'd 498.2, found 498.1 |
| 325 | 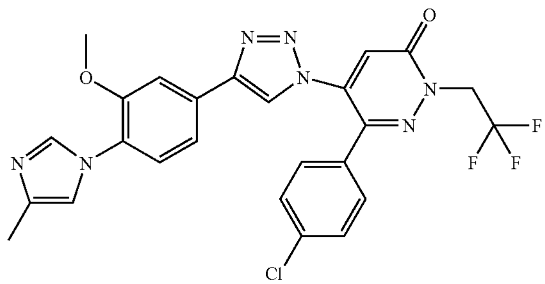 | 6-(4-chlorophenyl)-5-{4 [3-methoxy-4-(4-methyl-1H-imidazol-1-yl)phenyl]-1H-1,2,3-triazol-1-yl}-2-(2,2,2-trifluoroethyl)pyridazin-3(2H)-one | Calc'd 542.1, found 542.0 |
| 326 | 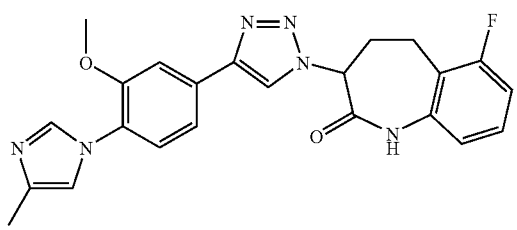 | 6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 433.2, found 433.1 |
| 327 | 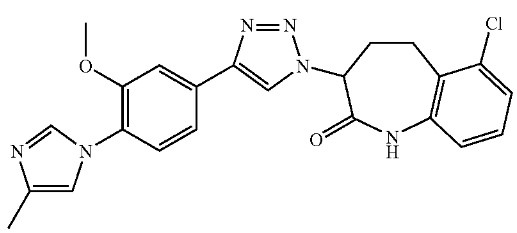 | 6-chloro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 449.1, found 449.1 |
| 328 | 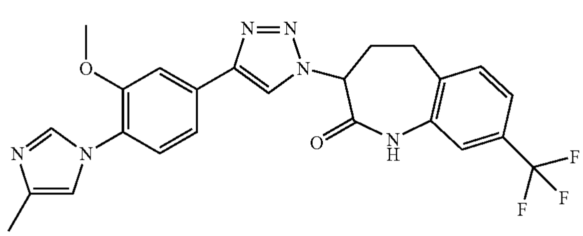 | 3-{4-[3-methoxy-4-(4-methyl-1H-imidazol-1-yl)phenyl]-1H-1,2,3-triazol-1-yl}-8-(trifluoromethyl)-1,3,4,5-tetrahydro-2H-1-benzazepin-2-one | Calc'd 483.2, found 483.2 |
| 329 | 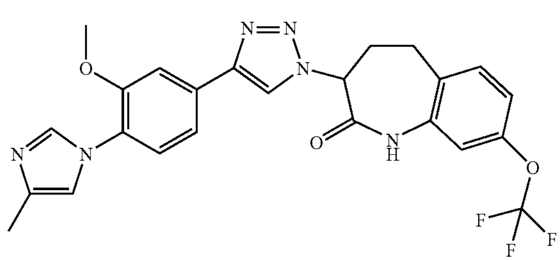 | 3-{4-[3-methoxy-4-(4-methyl-1H-imidazol-1-yl)phenyl]-1H-1,2,3-triazol-1-yl}-8-(trifluoromethoxy)-1,3,4,5-tetrahydro-2H-1-benzazepin-2-one | Calc'd 499.2, found 499.2 |

TABLE III-continued

| EX. | Structure | Name | [M + H]+ |
|---|---|---|---|
| 330 | 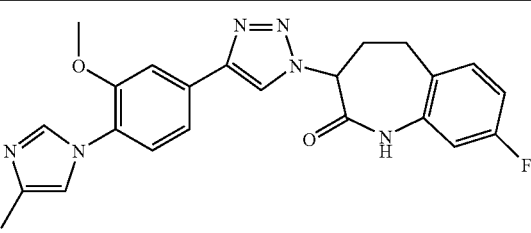 | 8-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 433.2, found 433.1 |
| 331 | 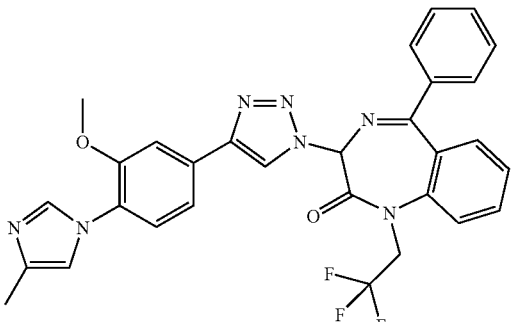 | 3-{4-[3-methoxy-4-(4-methyl-1H-imidazol-1-yl)phenyl]-1H-1,2,3-triazol-1-yl}-5-phenyl-1-(2,2,2-trifluoroethyl)-1,3-dihydro-2H-1,4-benzodiazepin-2-one | Calc'd 572.2, found 572.2 |
| 332 | 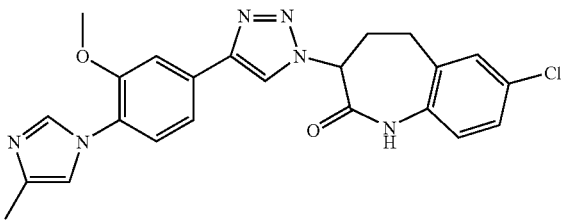 | 7-chloro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 449.1, found 449.1 |
| 333 | 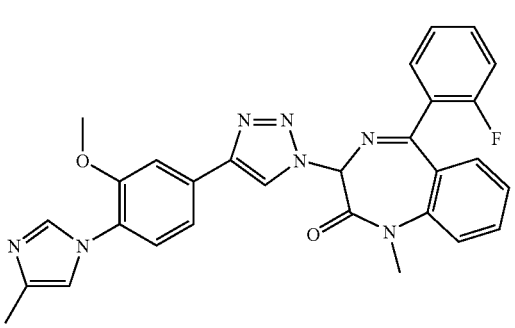 | 5-(2-fluorophenyl)-3-{4-[3-methoxy-4-(4-methyl-1H-imidazol-1-yl)phenyl]-1H-1,2,3-triazol-1-yl}-1-methyl-1,3-dihydro-2H-1,4-benzodiazepin-2-one | Calc'd 522.2, found 522.2 |
| 334 | 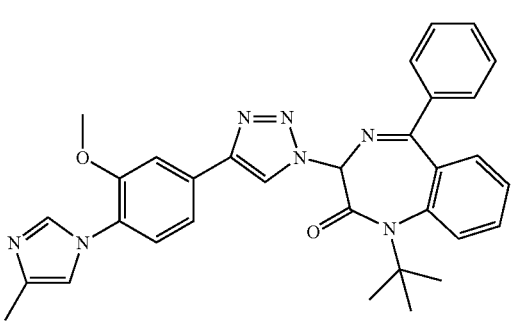 | 1-tert-butyl-3-{4-[3-methoxy-4-(4-methyl-1H-imidazol-1-yl)phenyl]-1H-1,2,3-triazol-1-yl}-5-phenyl-1,3-dihydro-2H-1,4-benzodiazepin-2-one | Calc'd 546.3, found 526.2 |

TABLE III-continued

| EX. | Structure | Name | [M + H]⁺ |
|---|---|---|---|
| 335 | 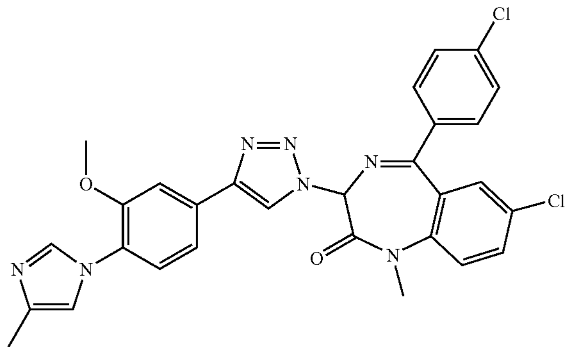 | 7-chloro-5-(4-chlorophenyl)-3-{4-[3-methoxy-4-(4-methyl-1H-imidazol-1-yl)phenyl]-1H-1,2,3-triazol-1-yl}-1-methyl-1,3-dihydro-2H-1,4-benzodiazepin-2-one | Calc'd 572.1, found 572.1 |
| 336 | 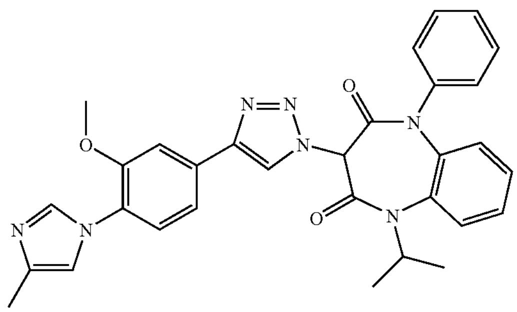 | 1-isopropyl-3-{4-[3-methoxy-4-(4-methyl-1H-imidazol-1-yl)phenyl]-1H-1,2,3-triazol-1-yl}-5-phenyl-1H-1,5-benzodiazepine-2,4(3H,5H)-dione | Calc'd 548.2, found 548.2 |
| 337 | 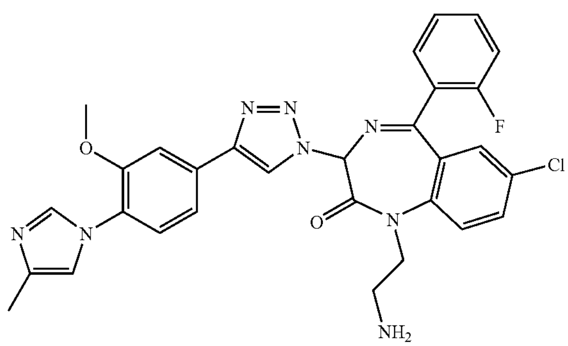 | 1-(2-aminoethyl)-7-chloro-5-(2-fluorophenyl)-3-{4-[3-methoxy-4-(4-methyl-1H-imidazol-1-yl)phenyl]-1H-1,2,3-triazol-1-yl}-1,3-dihydro-2H-1,4-benzodiazepin-2-one | Calc'd 585.2, found 585.2 |
| 338 | 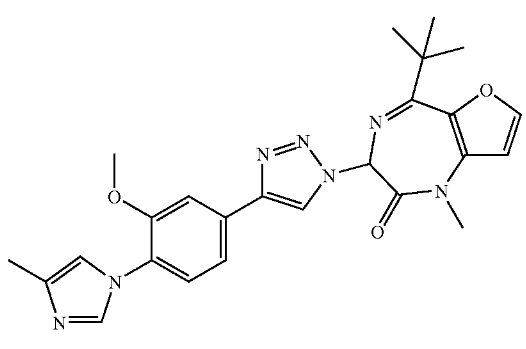 | 5-tert-butyl-3-{4-[3-methoxy-4-(4-methyl-1H-imidazol-1-yl)phenyl]-1H-1,2,3-triazol-1-yl}-1-methyl-1,3-dihydro-2H-furo[3,2-e][1,4]diazepin-2-one | Calc'd 474.2, found 474.2 |
| 339 | 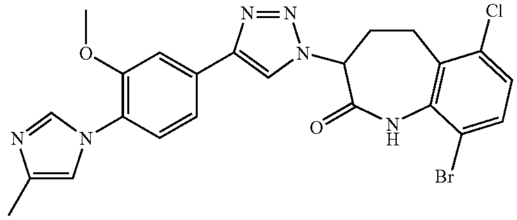 | 9-bromo-6-chloro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 527.1, found 527.0 |

TABLE III-continued

| EX. | Structure | Name | [M + H]+ |
|---|---|---|---|
| 340 | 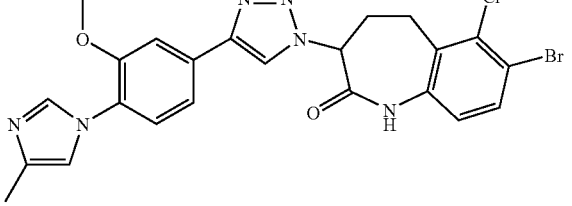 | 7-bromo-6-chloro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 527.1, found 527.0 |
| 341 | 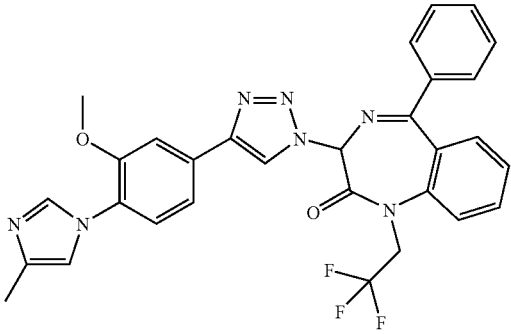 | 3-{4-[3-methoxy-4-(4-methyl-1H-imidazol-1-yl)phenyl]-1H-1,2,3-triazol-1-yl}-5-phenyl-1-(2,2,2-trifluoroethyl)-1,3-dihydro-2H-1,4-benzodiazepin-2-one | Calc'd 572.2, found 572.2 |
| 342 | 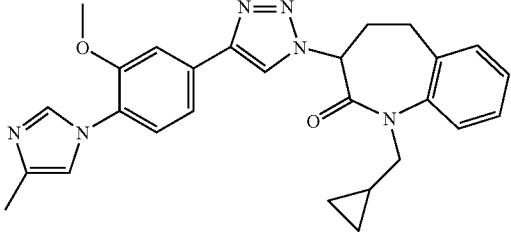 | 1-(cyclopropylmethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 469.2, found 469.2 |
| 343 | 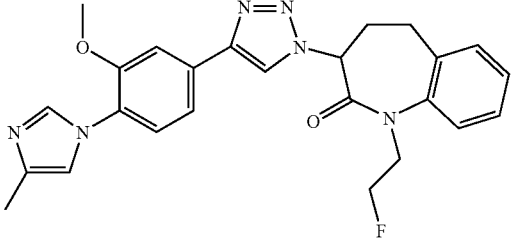 | 1-(2-fluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 461.2, found 461.2 |
| 344 | 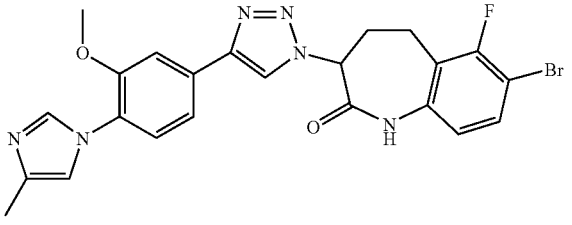 | 7-bromo-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 511.1, found 511.1 |
| 345 | 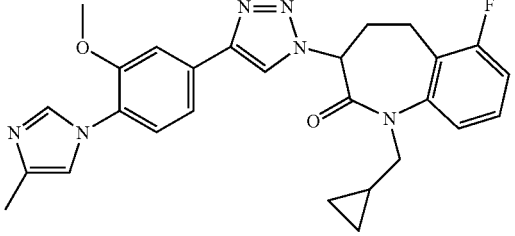 | 1-(cyclopropylmethyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 487.2, found 487.2 |

TABLE III-continued

| EX. | Structure | Name | [M + H]+ |
|---|---|---|---|
| 346 | 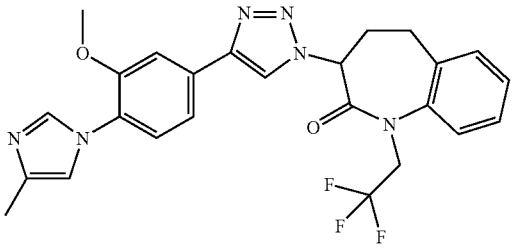 | 3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 497.2, found 497.2 |
| 347 | 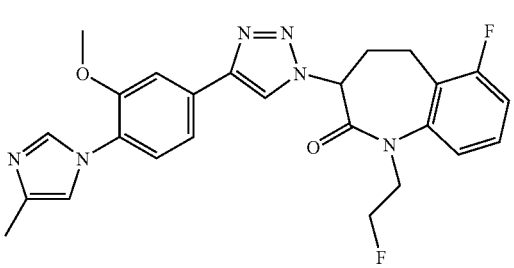 | 6-fluoro-1-(2-fluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |
| 348 | 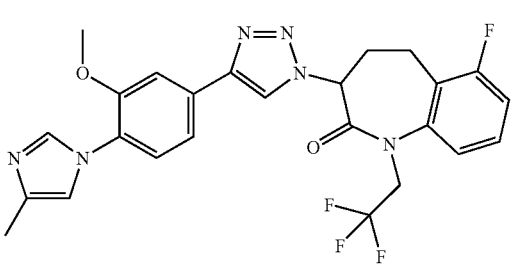 | 6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.2 |
| 349 | 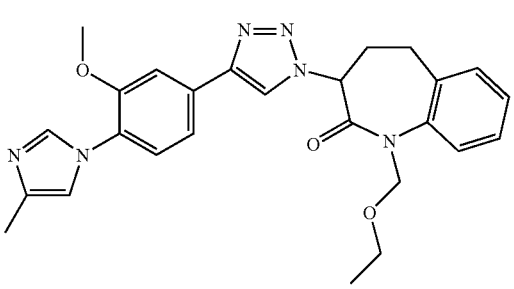 | 1-(ethoxymethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 473.2, found 473.2 |
| 350 | 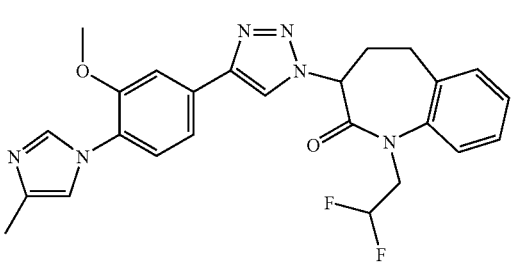 | 1-(2,2-difluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |
| 351 | 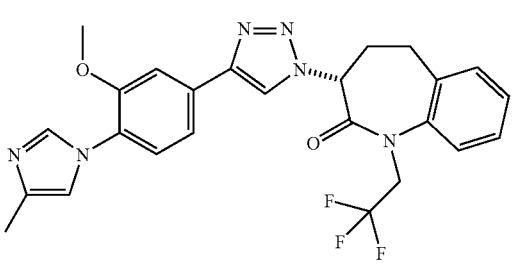 | (3R)-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 497.2, found 497.2 |

TABLE III-continued

| EX. | Structure | Name | [M + H]+ |
|---|---|---|---|
| 352 | 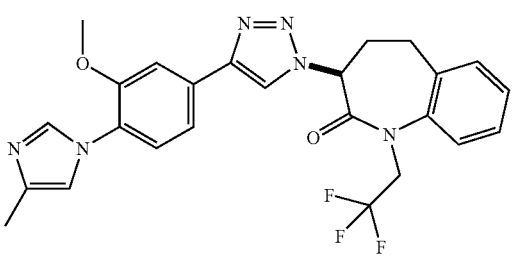 | (3S)-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 497.2, found 497.2 |
| 353 | 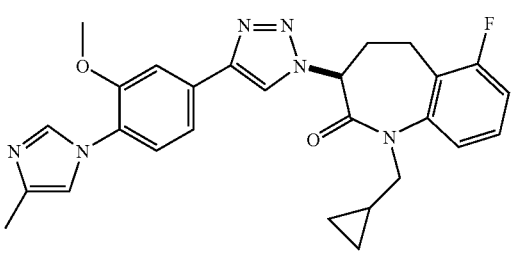 | (3S)-1-(cyclopropylmethyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 487.2, found 487.2 |
| 354 | 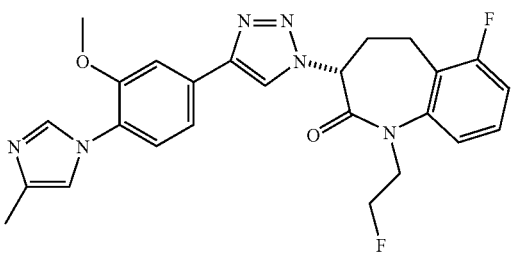 | (3R)-6-fluoro-1-(2-fluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |
| 355 | 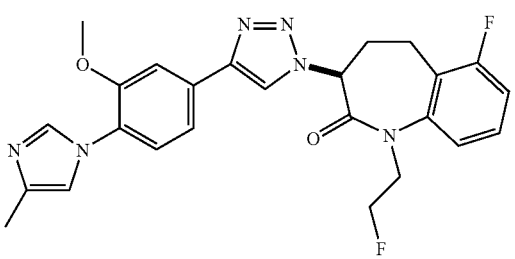 | (3S)-6-fluoro-1-(2-fluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |
| 356 | 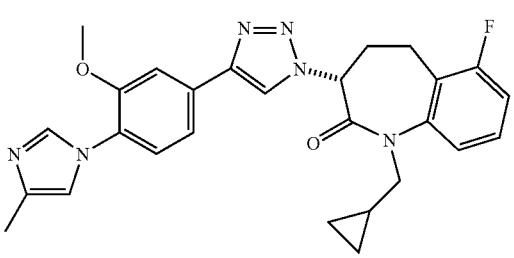 | (3R)-1-(cyclopropylmethyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 487.2, found 487.2 |
| 357 | 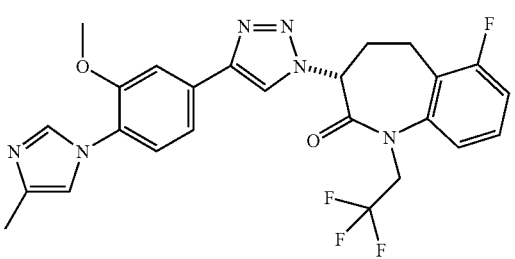 | (3R)-6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.2 |

TABLE III-continued

| EX. | Structure | Name | [M + H]+ |
|---|---|---|---|
| 358 | 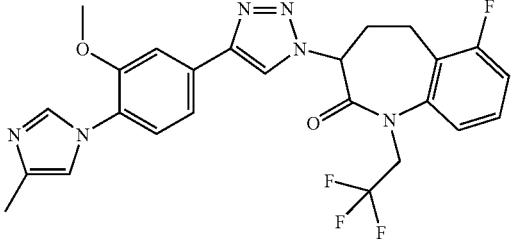 | (3S)-6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.2 |
| 359 | 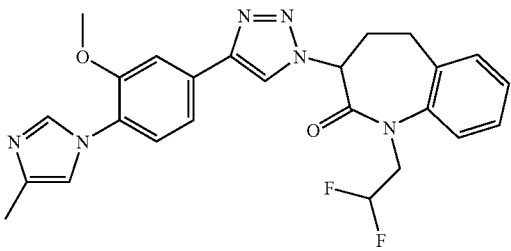 | 1-(2,2-difluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |
| 360 | 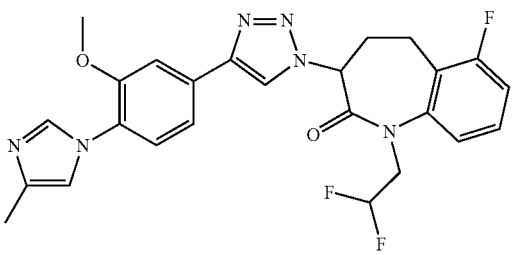 | 1-(2,2-difluoroethyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 497.2, found 497.2 |
| 361 | 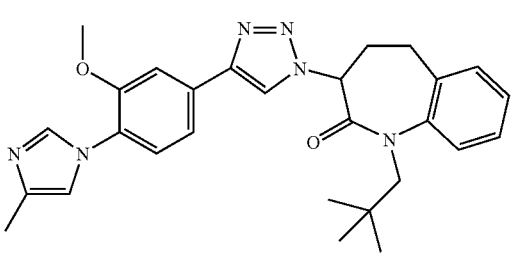 | 1-(2,2-dimethylpropyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 485.3, found 485.2 |
| 362 | 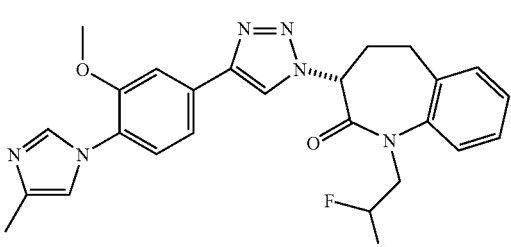 | (3R)-1-(2,2-difluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |
| 363 | 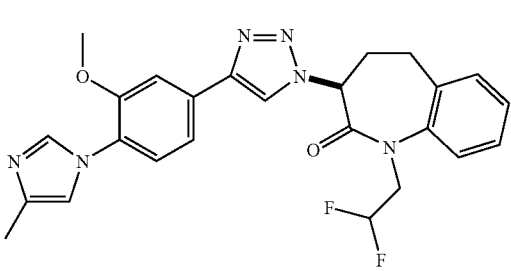 | (3S)-1-(2,2-difluoroethyl)-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 479.2, found 479.2 |

TABLE III-continued

| EX. | Structure | Name | [M + H]+ |
|---|---|---|---|
| 364 | 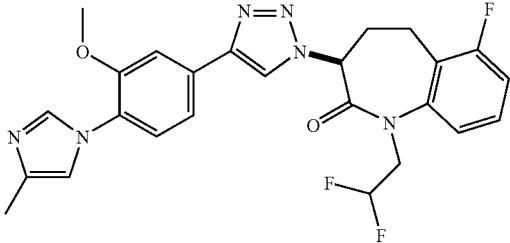 | (3S)-1-(2,2-difluoroethyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 497.2, found 497.2 |
| 365 | 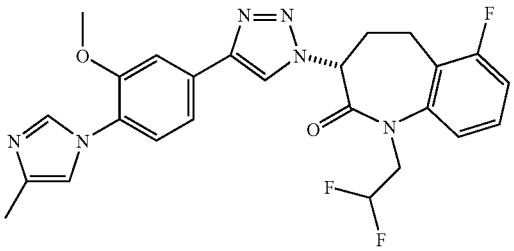 | (3R)-1-(2,2-difluoroethyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 497.2, found 497.2 |
| 366 | 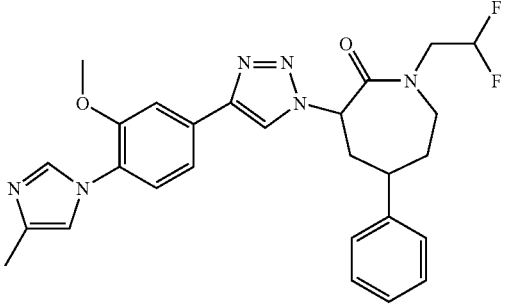 | 1-(2,2-difluoroethyl)-3-{4-[3-methoxy-4-(4-methyl-1H-imidazol-1-yl)phenyl]-1H-1,2,3-triazol-1-yl}-5-phenylazepan-2-one | Calc'd 507.2, found 507.2 |
| 367 | 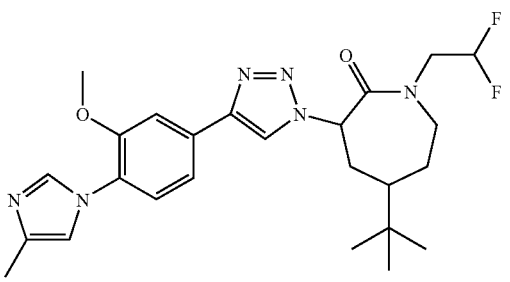 | 5-tert-butyl-1-(2,2-difluoroethyl)-3-{4-[3-methoxy-4-(4-methyl-1H-imidazol-1-yl)phenyl]-1H-1,2,3-triazol-1-yl}azepan-2-one | Calc'd 487.3, found 487.2 |
| 368 | 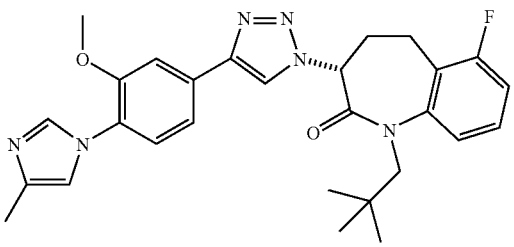 | (3R)-1-(2,2-dimethylpropyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 503.3, found 503.2 |

TABLE III-continued

| EX. | Structure | Name | [M + H]+ |
|---|---|---|---|
| 369 | 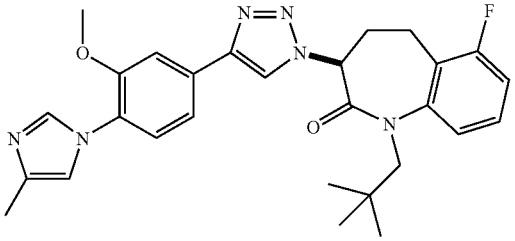 | (3S)-1-(2,2-dimethylpropyl)-6-fluoro-3-{4-[3-methoxy-4-(4-methyl-1H-imidazol-1-yl)phenyl]-1H-1,2,3-triazol-1-yl}-1,3,4,5-tetrahydro-2H-1-benzazepin-2-one | Calc'd 503.3, found 503.2 |
| 370 | 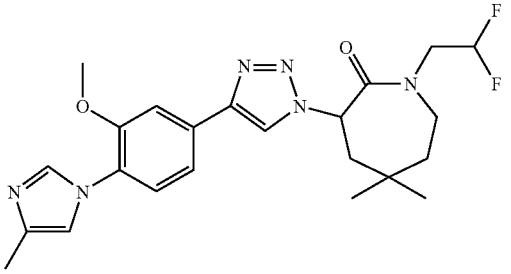 | 1-(2,2-difluoroethyl)-3-{4-[3-methoxy-4-(4-methyl-1H-imidazol-1-yl)phenyl]-1H-1,2,3-triazol-1-yl}-5,5-dimethylazepan-2-one | Calc'd 459.2, found 459.2 |
| 371 | 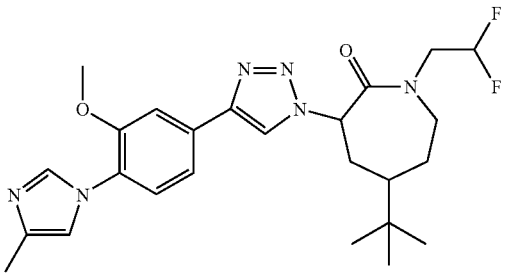 | 5-tert-butyl-1-(2,2-difluoroethyl)-3-{4-[3-methoxy-4-(4-methyl-1H-imidazol-1-yl)phenyl]-1H-1,2,3-triazol-1-yl}azepan-2-one | Calc'd 487.3, found 487.3 |
| 372 | 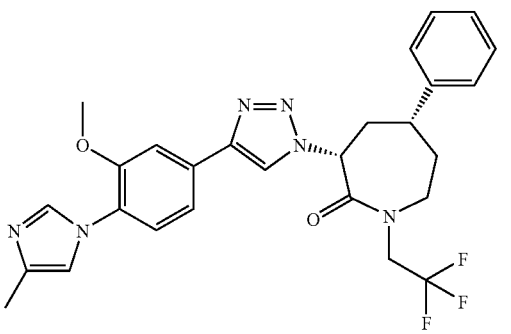 | (3R,5R)-3-{4-[3-methoxy-4-(4-methyl-1H-imidazol-1-yl)phenyl]-1H-1,2,3-triazol-1-yl}-5-phenyl-1-(2,2,2-trifluoroethyl)azepan-2-one | Calc'd 525.2, found 525.2 |
| 373 | 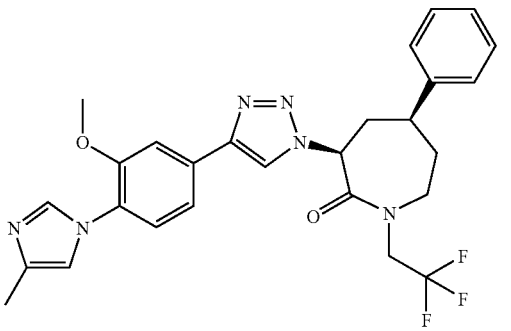 | (3S,5S)-3-{4-[3-methoxy-4-(4-methyl-1H-imidazol-1-yl)phenyl]-1H-1,2,3-triazol-1-yl}-5-phenyl-1-(2,2,2-trifluoroethyl)azepan-2-one | Calc'd 525.2, found 525.2 |

TABLE III-continued

| EX. | Structure | Name | [M + H]+ |
|---|---|---|---|
| 374 | 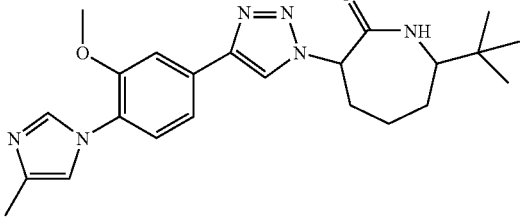 | 7-tert-butyl-3-{4-[3-methoxy-4-(4-methyl-1H-imidazol-1-yl)phenyl]-1H-1,2,3-triazol-1-yl}azepan-2-one | Calc'd 423.3, found 423.3 |
| 375 | 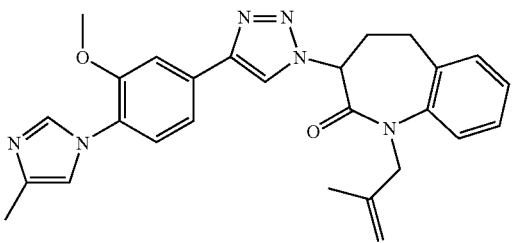 | 3-{4-[3-methoxy-4-(4-methyl-1H-imidazol-1-yl)phenyl]-1H-1,2,3-triazol-1-yl}-1-(2-methylprop-2-en-1-yl)-1,3,4,5-tetrahydro-2H-1-benzazepin-2-one | Calc'd 469.2, found 469.2 |
| 376 | 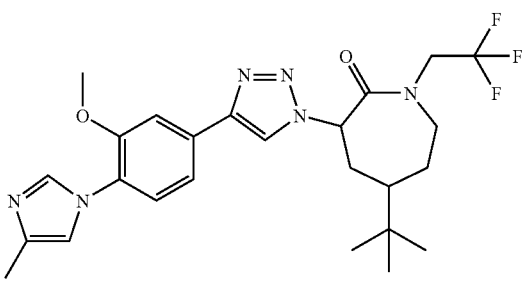 | 5-tert-butyl-3-{4-[3-methoxy-4-(4-methyl-1H-imidazol-1-yl)phenyl]-1H-1,2,3-triazol-1-yl}-1-(2,2,2-trifluoroethyl)azepan-2-one | Calc'd 505.3, found 505.2 |
| 377 | 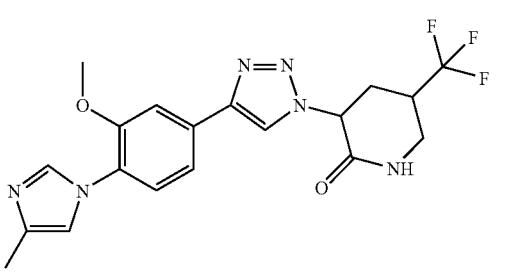 | 3-{4-[3-methoxy-4-(4-methyl-1H-imidazol-1-yl)phenyl]-1H-1,2,3-triazol-1-yl}-5-(trifluoromethyl)piperidin-2-one | Calc'd 421.2, found 421.1 |
| 378 | 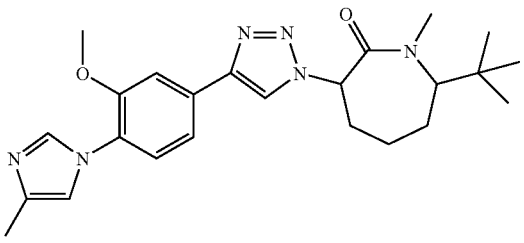 | 7-tert-butyl-3-{4-[3-methoxy-4-(4-methyl-1H-imidazol-1-yl)phenyl]-1H-1,2,3-triazol-1-yl}-1-methylazepan-2-one | Calc'd 437.3, found 437.2 |
| 379 | 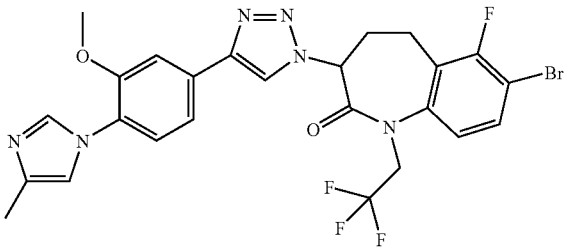 | 7-bromo-6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 593.1, found 593.0 |

TABLE III-continued

| EX. | Structure | Name | [M + H]+ |
|---|---|---|---|
| 380 | 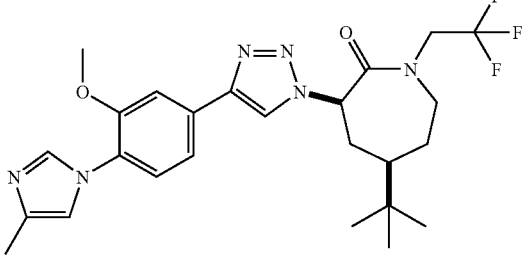 | (3R,5R)-5-tert-butyl-3-{4-[3-methoxy-4-(4-methyl-1H-imidazol-1-yl)phenyl]-1H-1,2,3-triazol-1-yl}-1-(2,2,2-trifluoroethyl)azepan-2-one | Calc'd 505.3, found 505.2 |
| 381 | 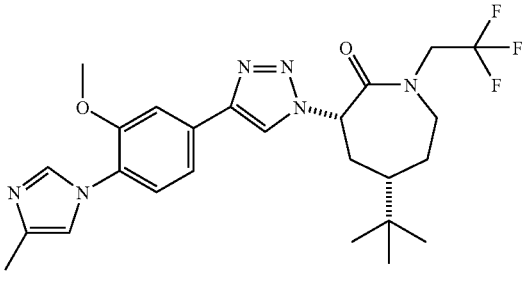 | (3S,5S)-5-tert-butyl-3-{4-[3-methoxy-4-(4-methyl-1H-imidazol-1-yl)phenyl]-1H-1,2,3-triazol-1-yl}-1-(2,2,2-trifluoroethyl)azepan-2-one | Calc'd 505.3, found 505.2 |
| 382 | 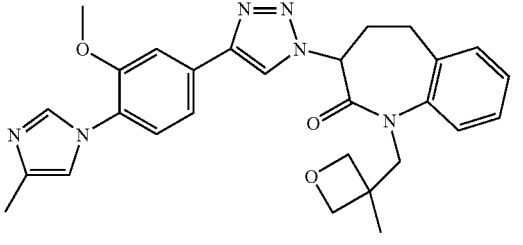 | 3-{4-[3-methoxy-4-(4-methyl-1H-imidazol-1-yl)phenyl]-1H-1,2,3-triazol-1-yl}-1-[(3-methyloxetan-3-yl)methyl]-1,3,4,5-tetrahydro-2H-1-benzazepin-2-one | Calc'd 499.2, found 499.2 |
| 383 | 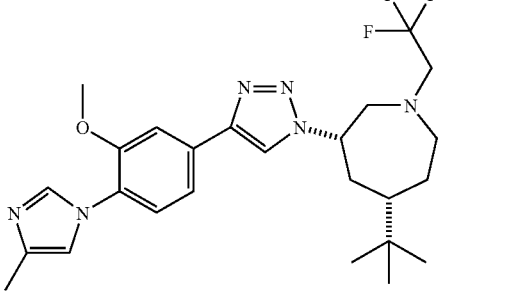 | (3S,5S)-5-tert-butyl-3-{4-[3-methoxy-4-(4-methyl-1H-imidazol-1-yl)phenyl]-1H-1,2,3-triazol-1-yl}-1-(2,2,2-trifluoroethyl)azepane | Calc'd 491.3, found 489.2 |
| 384 | 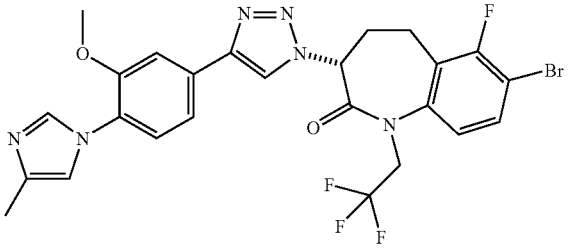 | (3R)-7-bromo-6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 593.1, found 595.0 |

TABLE III-continued

| EX. | Structure | Name | [M + H]+ |
|---|---|---|---|
| 385 | 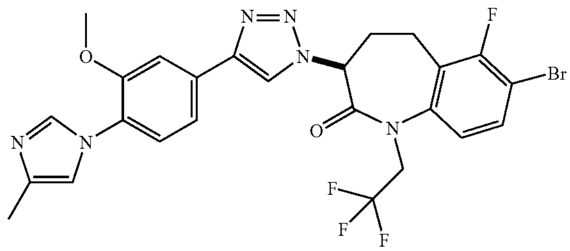 | (3S)-7-bromo-6-fluoro-3-{4-[3-methoxy-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 593.1, found 595.0 |
| 386 | 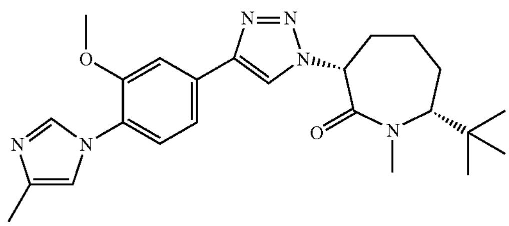 | (3R,7R)-7-tert-butyl-3-{4-[3-methoxy-4-(4-methyl-1H-imidazol-1-yl)phenyl]-1H-1,2,3-triazol-1-yl}-1-methylazepan-2-one | Calc'd 437.3, found 437.2 |
| 387 | 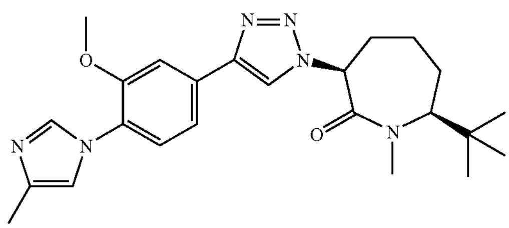 | (3S,7S)-7-tert-butyl-3-{4-[3-methoxy-4-(4-methyl-1H-imidazol-1-yl)phenyl]-1H-1,2,3-triazol-1-yl}-1-methylazepan-2-one | Calc'd 437.3, found 437.2 |
| 388 | 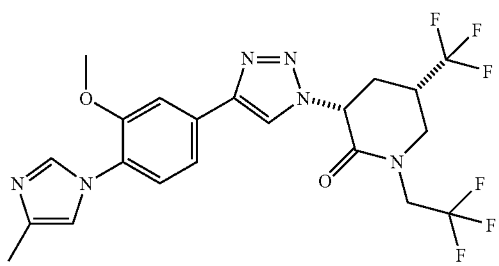 | (3R,5S)-3-{4-[3-methoxy-4-(4-methyl-1H-imidazol-1-yl)phenyl]-1H-1,2,3-triazol-1-yl}-1-(2,2,2-trifluoroethyl)-5-(trifluoromethyl)piperidin-2-one | Calc'd 503.2, found 503.1 |
| 389 | 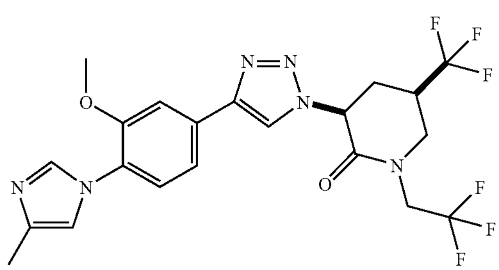 | (3S,5R)-3-{4-[3-methoxy-4-(4-methyl-1H-imidazol-1-yl)phenyl]-1H-1,2,3-triazol-1-yl}-1-(2,2,2-trifluoroethyl)-5-(trifluoromethyl)piperidin-2-one | Calc'd 503.2, found 503.1 |
| 390 | 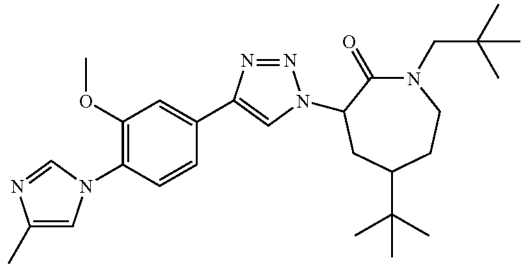 | 5-tert-butyl-1-(2,2-dimethylpropyl)-3-{4-[3-methoxy-4-(4-methyl-1H-imidazol-1-yl)phenyl]-1H-1,2,3-triazol-1-yl}azepan-2-one | Calc'd 493.3, found 493.3 |

TABLE III-continued

| EX. | Structure | Name | [M + H]+ |
|---|---|---|---|
| 391 | 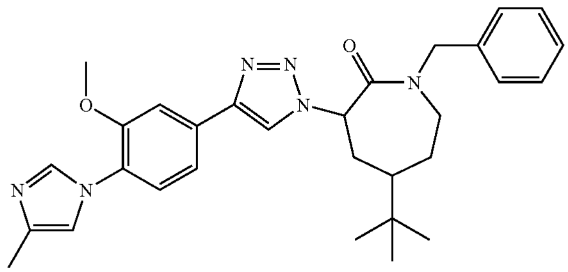 | 1-benzyl-5-tert-butyl-3-{4-[3-methoxy-4-(4-methyl-1H-imidazol-1-yl)phenyl]-1H-1,2,3-triazol-1-yl}azepan-2-one | Calc'd 513.3, found 513.2 |
| 392 | 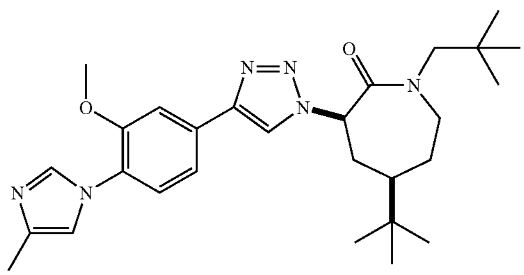 | (3R,5R)-5-tert-butyl-1-(2,2-dimethylpropyl)-3-{4-[3-methoxy-4-(4-methyl-1H-imidazol-1-yl)phenyl]-1H-1,2,3-triazol-1-yl}azepan-2-one | Calc'd 493.3, found 493.3 |
| 393 | 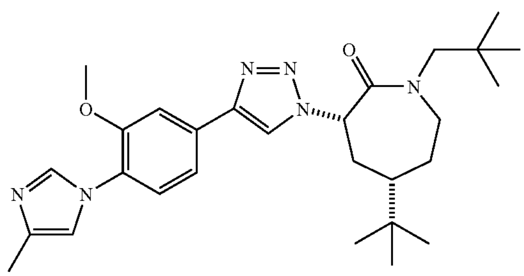 | (3S,5S)-5-tert-butyl-1-(2,2-dimethylpropyl)-3-{4-[3-methoxy-4-(4-methyl-1H-imidazol-1-yl)phenyl]-1H-1,2,3-triazol-1-yl}azepan-2-one | Calc'd 493.3, found 493.3 |
| 394 | 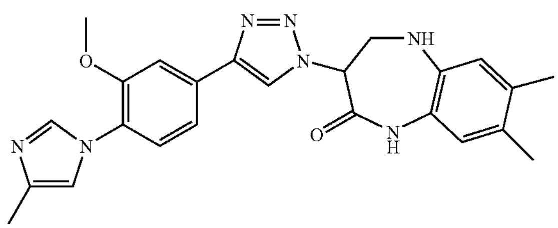 | 3-{4-[3-methoxy-4-(4-methyl-1H-imidazol-1-yl)phenyl]-1H-1,2,3-triazol-1-yl}-7,8-dimethyl-1,3,4,5-tetrahydro-2H-1,5-benzodiazepin-2-one | Calc'd 444.2, found 442.1 |
| 395 | 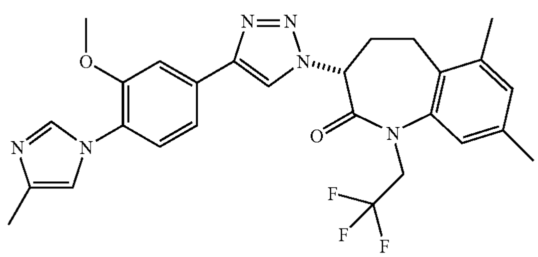 | (3R)-3-{4-[3-methoxy-4-(4-methyl-1H-imidazol-1-yl)phenyl]-1H-1,2,3-triazol-1-yl}-6,8-dimethyl-1-(2,2,2-trifluoroethyl)-1,3,4,5-tetrahydro-2H-1-benzazepin-2-one | Calc'd 525.2, found 525.2 |
| 396 | 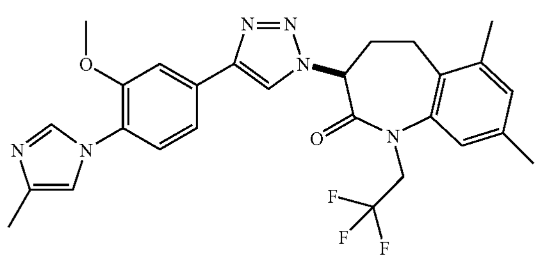 | (3S)-3-{4-[3-methoxy-4-(4-methyl-1H-imidazol-1-yl)phenyl]-1H-1,2,3-triazol-1-yl}-6,8-dimethyl-1-(2,2,2-trifluoroethyl)-1,3,4,5-tetrahydro-2H-1-benzazepin-2-one | Calc'd 525.2, found 525.2 |

TABLE III-continued

| EX. | Structure | Name | [M + H]+ |
|---|---|---|---|
| 397 | 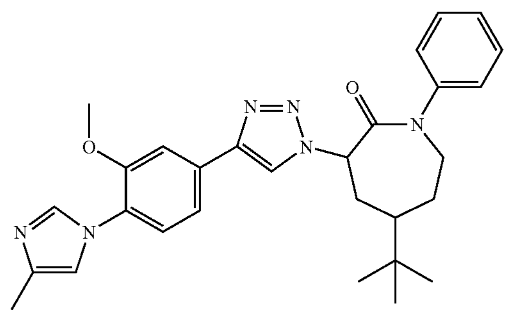 | 5-tert-butyl-3-{4-[3-methoxy-4-(4-methyl-1H-imidazol-1-yl)phenyl]-1H-1,2,3-triazol-1-yl}-1-phenylazepan-2-one | Calc'd 499.3, found 499.3 |
| 398 | 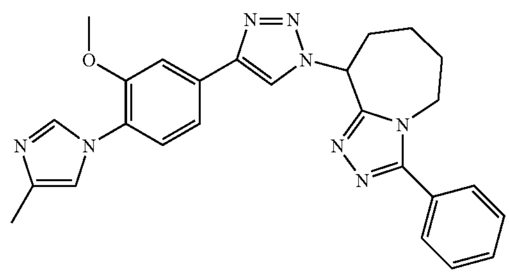 | 9-{4-[3-methoxy-4-(4-methyl-1H-imidazol-1-yl)phenyl]-1H-1,2,3-triazol-1-yl}-3-phenyl-6,7,8,9-tetrahydro-5H-[1,2,4]triazolo[4,3-a]azepine | Calc'd 467.2, found 467.2 |
| 399 | 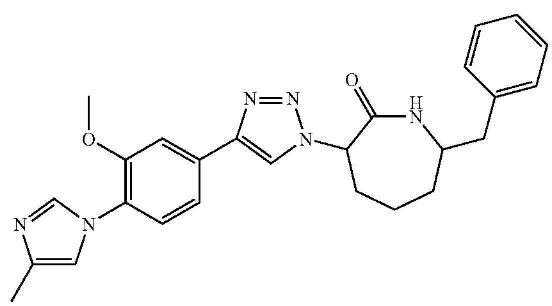 | 7-benzyl-3-{4-[3-methoxy-4-(4-methyl-1H-imidazol-1-yl)phenyl]-1H-1,2,3-triazol-1-yl}azepan-2-one | Calc'd 457.2, found 457.2 |
| 400 | 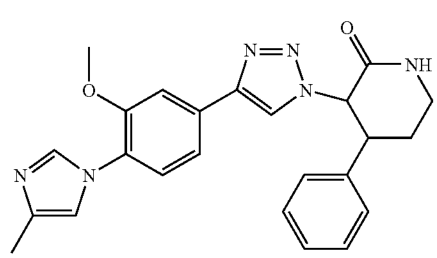 | 3-{4-[3-methoxy-4-(4-methyl-1H-imidazol-1-yl)phenyl]-1H-1,2,3-triazol-1-yl}-4-phenylpiperidin-2-one | Calc'd 429.2, found 429.3 |

TABLE IV

| EX. | Structure | Name | [M + H]+ |
|---|---|---|---|
| 401 | 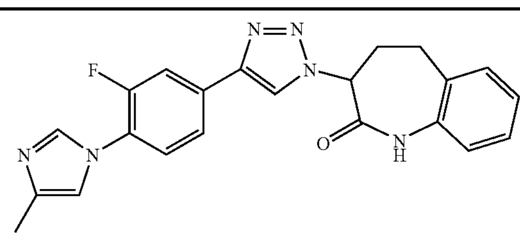 | 3-{4-[3-fluoro-4-(4-methyl-1H-imidazol-1-yl)phenyl]-1H-1,2,3-triazol-1-yl}-1,3,4,5-tetrahydro-2H-1-benzazepin-2-one | Calc'd 403.2, found 403.2 |

TABLE IV-continued

| EX. | Name | [M + H]⁺ |
|---|---|---|
| 402 | 3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |
| 403 | 3-{4-[3-fluoro-4-(4-methyl-1H-imidazol-1-yl)phenyl]-1H-1,2,3-triazol-1-yl}-1-methyl-1,3,4,5-tetrahydro-2H-1-benzazepin-2-one | Calc'd 417.2, found 417.2 |
| 404 | 1-(2,2-difluoroethyl)-3-{4-[3-fluoro-4-(4-methyl-1H-imidazol-1-yl)phenyl]-1H-1,2,3-triazol-1-yl}-1,3,4,5-tetrahydro-2H-1-benzazepin-2-one | Calc'd 467.2, found 467.2 |
| 405 | 3-{4-[4-(4-methyl-1H-imidazol-1-yl)phenyl]-1H-1,2,3-triazol-1-yl}-1,3,4,5-tetrahydro-2H-1-benzazepin-2-one | Calc'd 385.2, found 385.2 |
| 406 | 3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 467.2, found 467.2 |
| 407 | 1-(2,2-difluoroethyl)-3-{4-[4-(4-methyl-1H-imidazol-1-yl)phenyl]-1H-1,2,3-triazol-1-yl}-1,3,4,5-tetrahydro-2H-1-benzazepin-2-one | Calc'd 449.2, found 449.2 |

TABLE IV-continued

| EX. | Structure | Name | [M + H]+ |
|---|---|---|---|
| 408 | 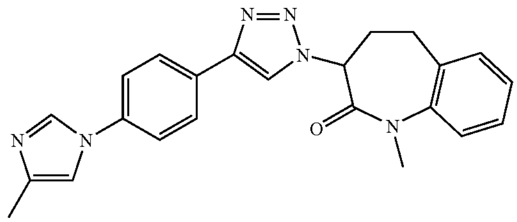 | 1-methyl-3-{4-[4-(4-methyl-1H-imidazol-1-yl)phenyl]-1H-1,2,3-triazol-1-yl}-1,3,4,5-tetrahydro-2H-1-benzazepin-2-one | Calc'd 399.2, found 399.2 |
| 409 | 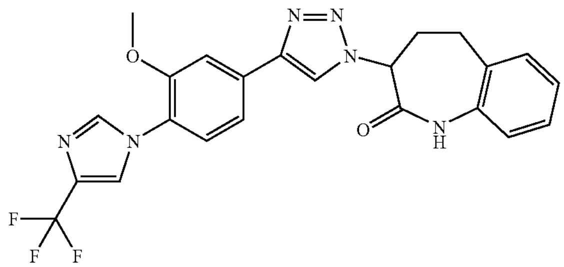 | 3-(4-{3-methoxy-4-[4-(trifluoromethyl)-1H-imidazol-1-yl]phenyl}-1H-1,2,3-triazol-1-yl)-1,3,4,5-tetrahydro-2H-1-benzazepin-2-one | Calc'd 469.2, found 469.2 |
| 410 | 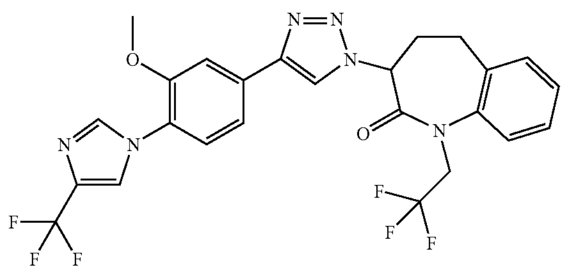 | 3-(4-{3-methoxy-4-[4-(trifluoromethyl)-1H-imidazol-1-yl]phenyl}-1H-1,2,3-triazol-1-yl)-1-(2,2,2-trifluoroethyl)-1,3,4,5-tetrahydro-2H-1-benzazepin-2-one | Calc'd 551.2, found 551.1 |
| 411 | 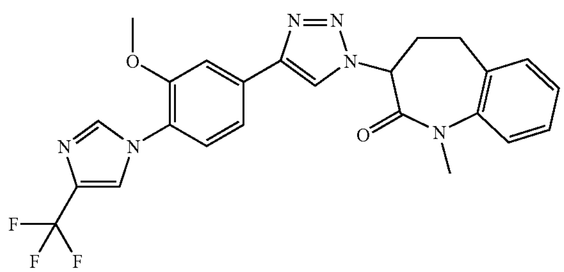 | 3-(4-{3-methoxy-4-[4-(trifluoromethyl)-1H-imidazol-1-yl]phenyl}-1H-1,2,3-triazol-1-yl)-1-methyl-1,3,4,5-tetrahydro-2H-1-benzazepin-2-one | Calc'd 483.2, found 483.2 |
| 412 | 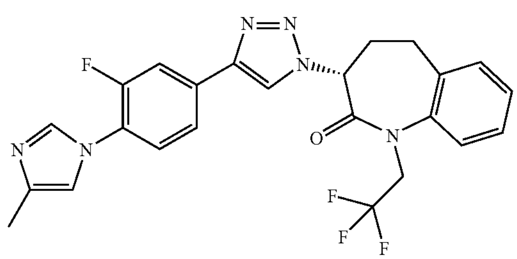 | (3R)-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |
| 413 | 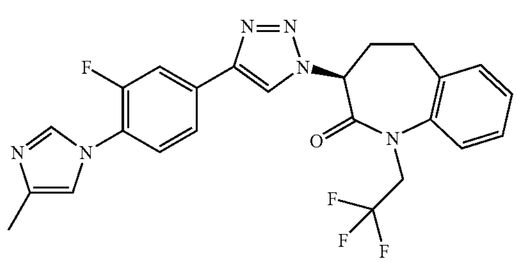 | (3S)-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |

TABLE IV-continued

| EX. | Name | [M + H]+ |
|---|---|---|
| 414 | 3-{4-[6-(4-methyl-1H-imidazol-1-yl)pyridin-3-yl]-1H-1,2,3-triazol-1-yl}-1-(2,2,2-trifluoroethyl)-1,3,4,5-tetrahydro-2H-1-benzazepin-2-one | Calc'd 468.2, found 468.2 |
| 415 | 1-(2,2-difluoroethyl)-3-{4-[6-(4-methyl-1H-imidazol-1-yl)pyridin-3-yl]-1H-1,2,3-triazol-1-yl}-1,3,4,5-tetrahydro-2H-1-benzazepin-2-one | Calc'd 450.2, found 450.2 |
| 416 | (3R)-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 467.2, found 467.2 |
| 417 | (3S)-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 467.2, found 467.2 |
| 418 | 6-fluoro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 503.2, found 503.1 |
| 419 | 6-fluoro-3-{4-[3-fluoro-4-(4-methyl-1H-imidazol-1-yl)phenyl]-1H-1,2,3-triazol-1-yl}-1,3,4,5-tetrahydro-2H-1-benzazepin-2-one | Calc'd 421.2, found 421.2 |

TABLE IV-continued

| EX. | Structure | Name | [M + H]+ |
|---|---|---|---|
| 420 | 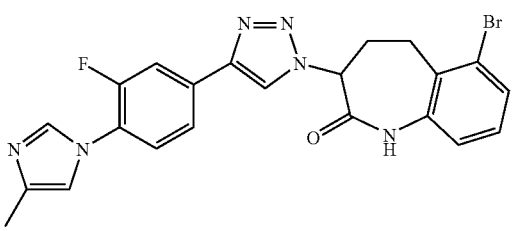 | 6-bromo-3-{4-[3-fluoro-4-(4-methyl-1H-imidazol-1-yl)phenyl]-1H-1,2,3-triazol-1-yl}-1,3,4,5-tetrahydro-2H-1-benzazepin-2-one | Calc'd 481.1, found 483.1 |
| 421 | 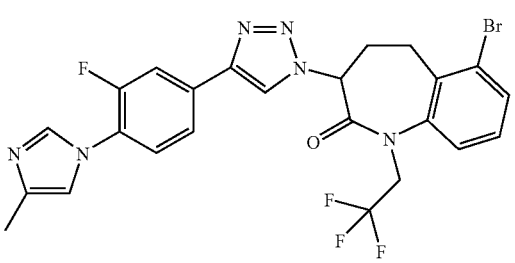 | 6-bromo-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 563.1, found 563.1 |
| 422 | 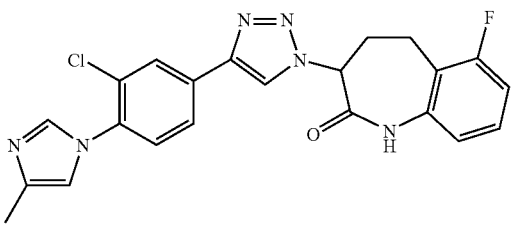 | 3-{4-[3-chloro-4-(4-methyl-1H-imidazol-1-yl)phenyl]-1H-1,2,3-triazol-1-yl}-6-fluoro-1,3,4,5-tetrahydro-2H-1-benzazepin-2-one | Calc'd 437.1, found 437.1 |
| 423 | 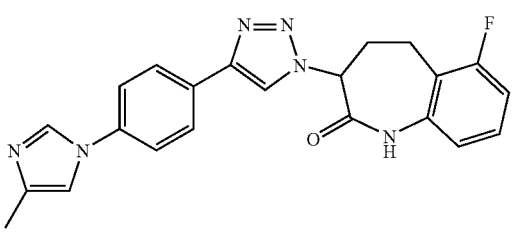 | 6-fluoro-3-{4-[4-(4-methyl-1H-imidazol-1-yl)phenyl]-1H-1,2,3-triazol-1-yl}-1,3,4,5-tetrahydro-2H-1-benzazepin-2-one | Calc'd 403.2, found 403.2 |
| 424 | 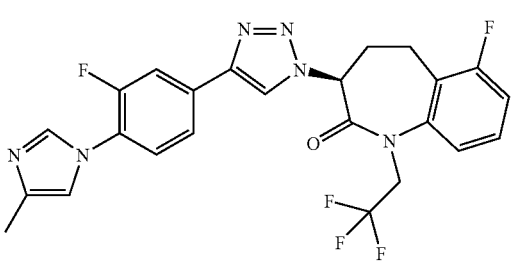 | (3S)-6-fluoro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 503.2, found 503.1 |
| 425 | 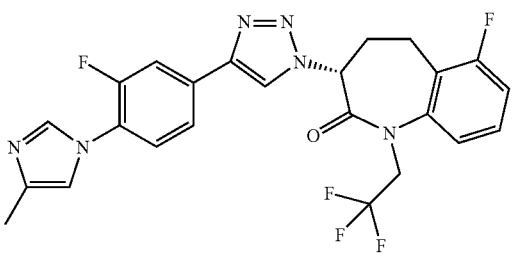 | (3R)-6-fluoro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 503.2, found 503.1 |

TABLE IV-continued

| EX. | Name | [M + H]+ |
|---|---|---|
| 426 | 6-fluoro-3-{4-[4-(4-methyl-1H-imidazol-1-yl)-3-(trifluoromethyl)phenyl]-1H-1,2,3-triazol-1-yl}-1-(2,2,2-trifluoroethyl)-1,3,4,5-tetrahydro-2H-1-benzazepin-2-one | Calc'd 553.2, found 553.1 |
| 427 | 3-{4-[3-chloro-4-(4-methyl-1H-imidazol-1-yl)phenyl]-1H-1,2,3-triazol-1-yl}-6-fluoro-1-(2,2,2-trifluoroethyl)-1,3,4,5-tetrahydro-2H-1-benzazepin-2-one | Calc'd 519.1, found 519.1 |
| 428 | 6-fluoro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 516.2, found 516.2 |
| 429 | 3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 498.2, found 498.2 |
| 430 | 3-{4-[3-chloro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 501.1, found 501.2 |
| 431 | (3R)-6-bromo-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 563.1, found 563.1 |

TABLE IV-continued

| EX. | Structure | Name | [M + H]+ |
|---|---|---|---|
| 432 | 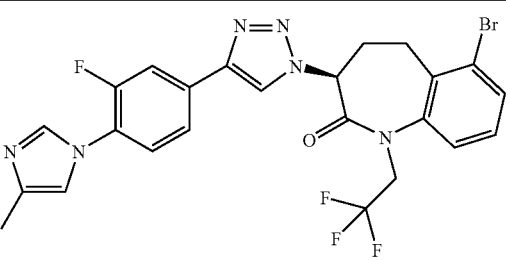 | (3S)-6-bromo-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 563.1, found 563.1 |
| 433 | 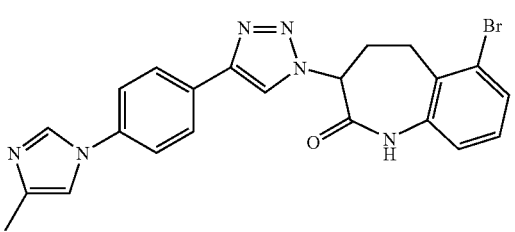 | 6-bromo-3-{4-[4-(4-methyl-1H-imidazol-1-yl)phenyl]-1H-1,2,3-triazol-1-yl}-1,3,4,5-tetrahydro-2H-1-benzazepin-2-one | Calc'd 463.1, found 463.1 |
| 434 | 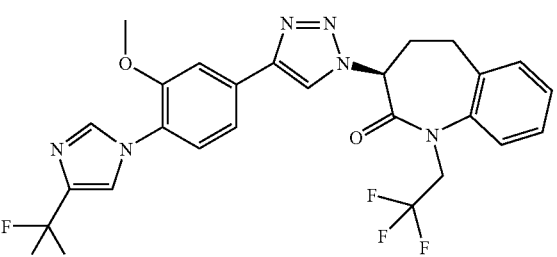 | (3S)-3-(4-{3-methoxy-4-[4-(trifluoromethyl)-1H-imidazol-1-yl]phenyl}-1H-1,2,3-triazol-1-yl)-1-(2,2,2-trifluoroethyl)-1,3,4,5-tetrahydro-2H-1-benzazepin-2-one | Calc'd 551.2, found 551.1 |
| 435 | 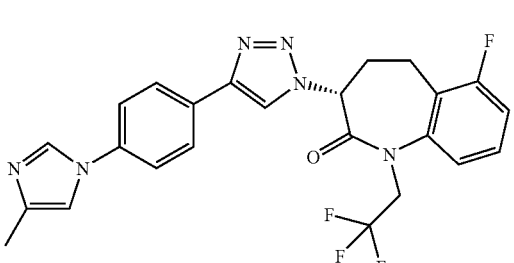 | (3R)-6-fluoro-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |
| 436 | 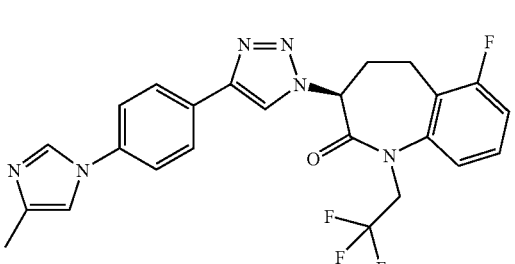 | (3S)-6-fluoro-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |
| 437 | 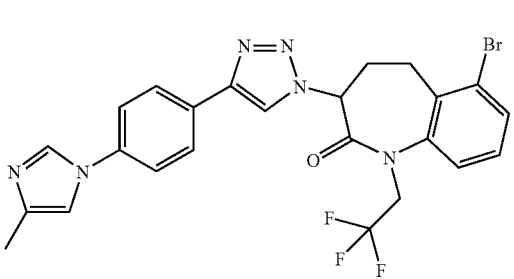 | 6-bromo-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 545.1, found 545.1 |

TABLE IV-continued

| EX. | Structure | Name | [M + H]+ |
|---|---|---|---|
| 438 | 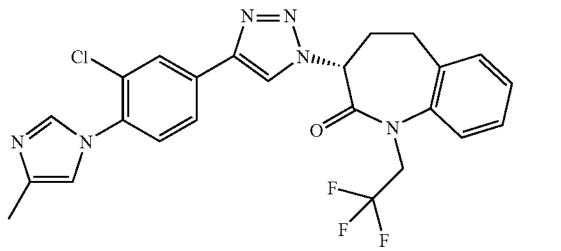 | (3R)-3-{4-[3-chloro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 501.1, found 501.2 |
| 439 | 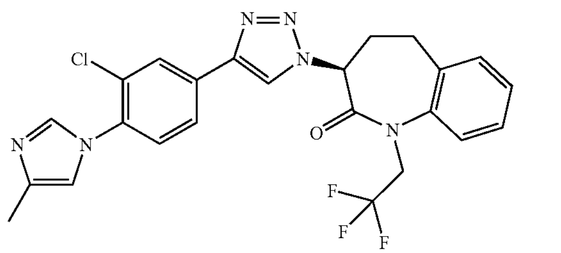 | (3S)-3-{4-[3-chloro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 501.1, found 501.2 |
| 440 | 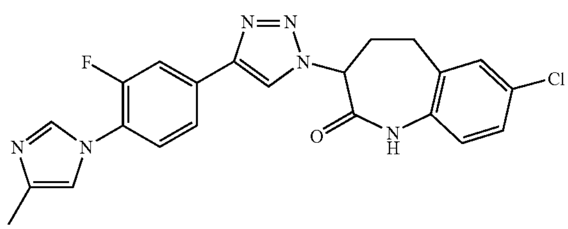 | 7-chloro-3-{4-[3-fluoro-4-(4-methyl-1H-imidazol-1-yl)phenyl]-1H-1,2,3-triazol-1-yl}-1,3,4,5-tetrahydro-2H-1-benzazepin-2-one | Calc'd 437.1, found 437.1 |
| 441 | 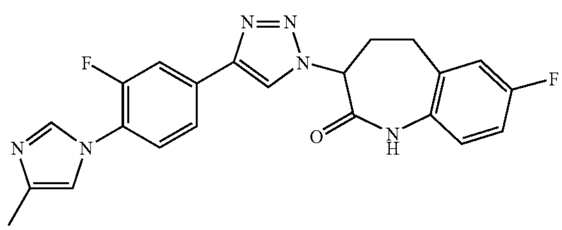 | 7-fluoro-3-{4-[3-fluoro-4-(4-methyl-1H-imidazol-1-yl)phenyl]-1H-1,2,3-triazol-1-yl}-1,3,4,5-tetrahydro-2H-1-benzazepin-2-one | Calc'd 421.2, found 421.2 |
| 442 | 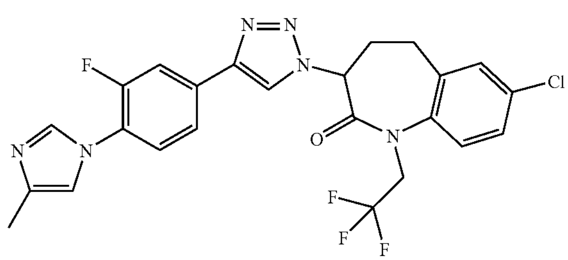 | 7-chloro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 519.1, found 519.1 |
| 443 | 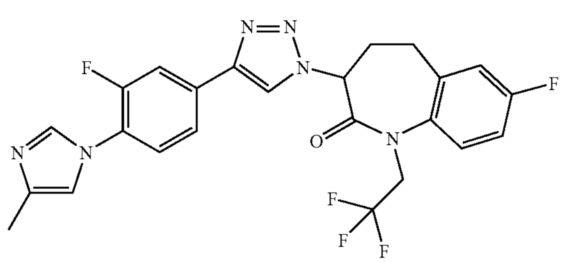 | 7-fluoro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 503.2, found 503.2 |

TABLE IV-continued

| EX. | Name | [M + H]+ |
|---|---|---|
| 444 | 6-bromo-3-(4-{3-methoxy-4-[4-(trifluoromethyl)-1H-imidazol-1-yl]phenyl}-1H-1,2,3-triazol-1-yl)-1,3,4,5-tetrahydro-2H-1-benzazepin-2-one | Calc'd 547.1, found 549.0 |
| 445 | (3R)-6-fluoro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 516.2, found 516.2 |
| 446 | (3S)-6-fluoro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 516.2, found 516.2 |
| 447 | (3R)-7-fluoro-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |
| 448 | (3S)-7-fluoro-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 485.2, found 485.2 |
| 449 | (3R)-7-chloro-3-(4-[4-(4-methyl-1H-imidazol-1-yl)phenyl]-1H-1,2,3-triazol-1-yl)-1-(2,2,2-trifluoroethyl)-1,3,4,5-tetrahydro-2H-1-benzazepin-2-one | Calc'd 501.1, found 501.1 |

TABLE IV-continued

| EX. | Structure | Name | [M + H]⁺ |
|---|---|---|---|
| 450 | 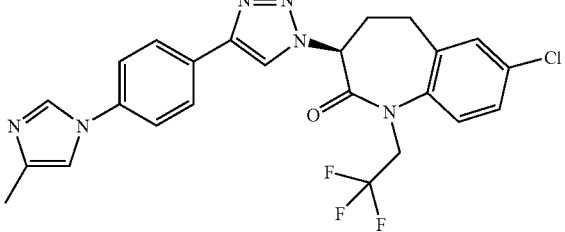 | (3S)-7-chloro-3-{4-[4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 501.1, found 501.1 |
| 451 | 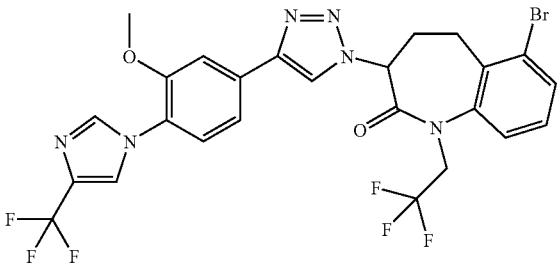 | 6-bromo-3-(4-{3-methoxy-4-[4-(trifluoromethyl)-1H-imidazol-1-yl]phenyl}-1H-1,2,3-triazol-1-yl)-1-(2,2,2-trifluoroethyl)-1,3,4,5-tetrahydro-2H-1-benzazepin-2-one | Calc'd 629.1, found 631.0 |
| 452 | 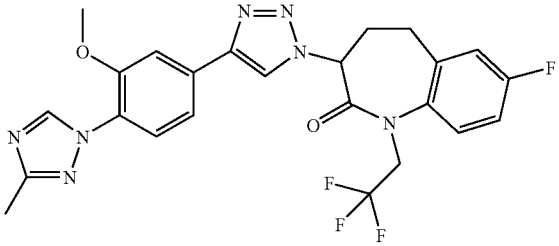 | 7-fluoro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 516.2, found 516.2 |
| 453 | 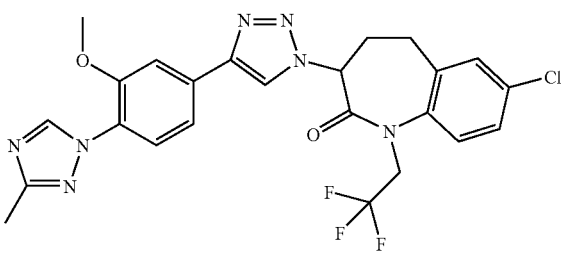 | 7-chloro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 532.1, found 532.1 |
| 454 | 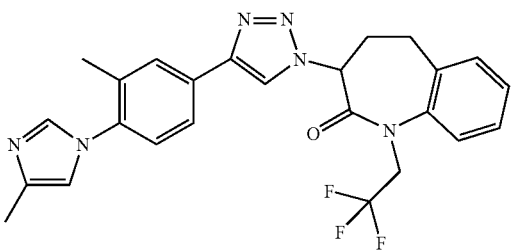 | 3-{4-[3-methyl-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 481.2, found 481.1 |

TABLE IV-continued

| EX. | Structure | Name | [M + H]+ |
|---|---|---|---|
| 455 | 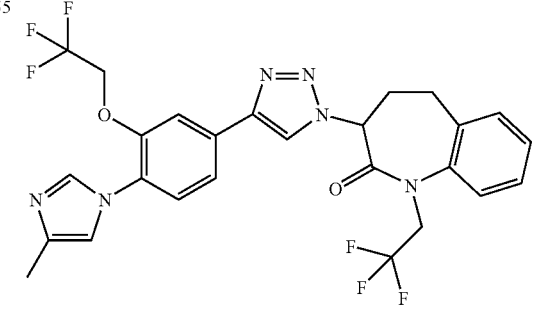 | 3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 565.2, found 565.1 |
| 456 | 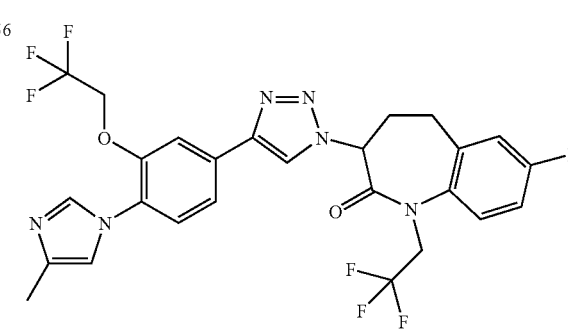 | 7-fluoro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 583.2, found 583.1 |
| 457 | 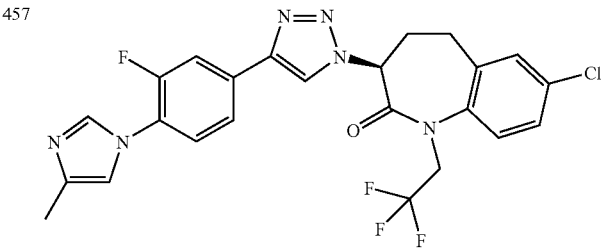 | (3S)-7-chloro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 519.1, found 519.1 |
| 458 | 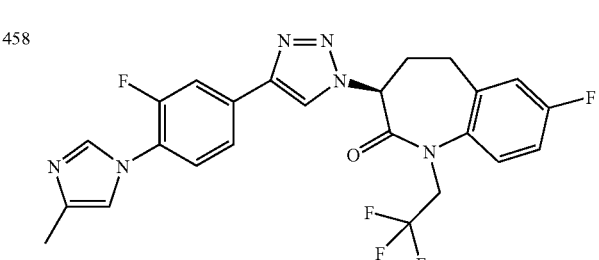 | (3S)-7-fluoro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 503.2, found 503.2 |
| 459 | 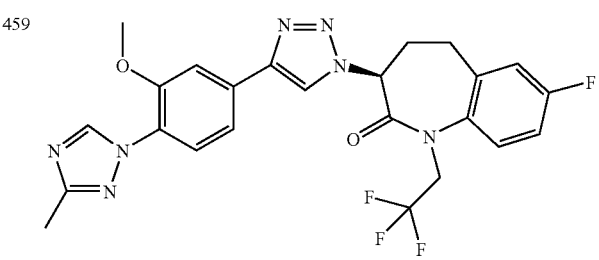 | (3S)-7-fluoro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 516.2, found 515.9 |

TABLE IV-continued

| EX. | Structure | Name | [M + H]+ |
|---|---|---|---|
| 460 | 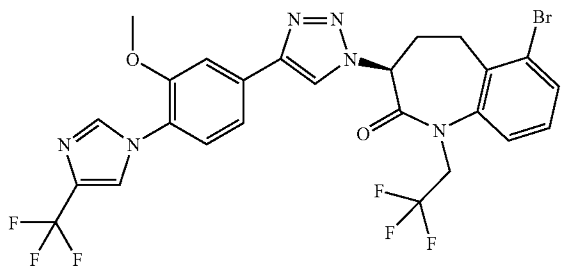 | (3S)-6-bromo-3-(4-{3-methoxy-4-[4-(trifluoromethyl)-1H-imidazol-1-yl]phenyl}-1H-1,2,3-triazol-1-yl)-1-(2,2,2-trifluoroethyl)-1,3,4,5-tetrahydro-2H-1-benzazepin-2-one | Calc'd 629.1, found 631.0 |
| 461 | 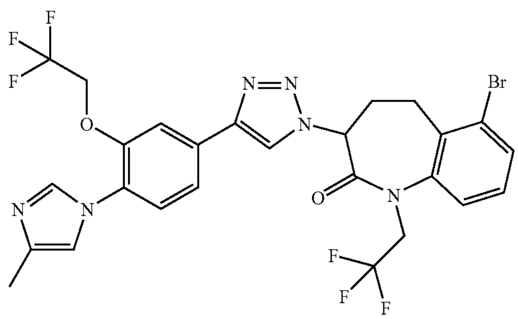 | 6-bromo-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 643.1, found 642.7 |
| 462 | 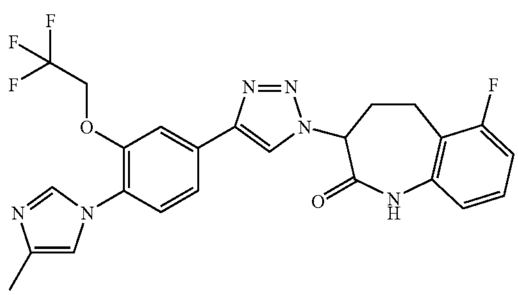 | 6-fluoro-3-{4-[4-(4-methyl-1H-imidazol-1-yl)-3-(2,2,2-trifluoroethoxy)phenyl]-1H-1,2,3-triazol-1-yl}-1,3,4,5-tetrahydro-2H-1-benzazepin-2-one | Calc'd 501.2, found 500.9 |
| 463 | 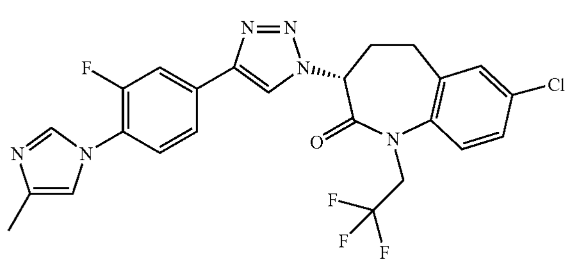 | (3R)-7-chloro-3-{4-[3-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 519.1, found 519.1 |
| 464 | 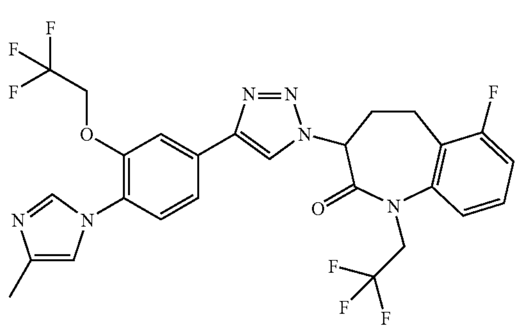 | 6-fluoro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 583.2, found 582.8 |

TABLE IV-continued

| EX. | Structure | Name | [M + H]⁺ |
|---|---|---|---|
| 465 | 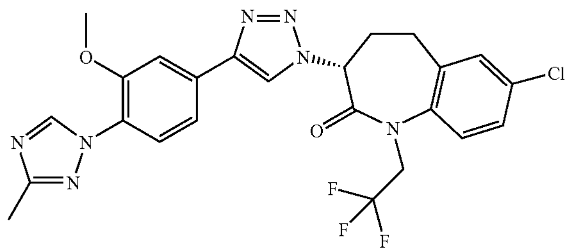 | (3R)-7-chloro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 532.1, found 531.8 |
| 466 | 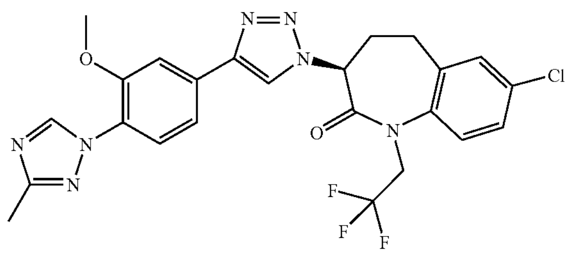 | (3S)-7-chloro-3-{4-[3-methoxy-4-(3-methyl-1H-1,2,4-triazol-1-yl)phenyl]-1H-1,2,3-triazol-1-yl}-1-(2,2,2-trifluoroethyl)-1,3,4,5-tetrahydro-2H-1-benzazepin-2-one | Calc'd 532.1, found 531.8 |
| 467 | 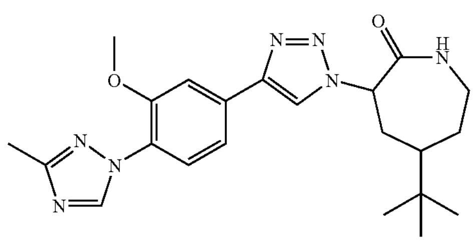 | 5-tert-butyl-3-{4-[3-methoxy-4-(3-methyl-1H-1,2,4-triazol-1-yl)phenyl]-1H-1,2,3-triazol-1-yl}azepan-2-one | Calc'd 424.2, found 424.0 |
| 468 | 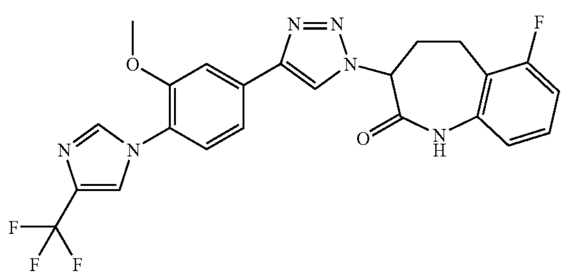 | 6-fluoro-3-(4-{3-methoxy-4-[4-(trifluoromethyl)-1H-imidazol-1-yl]phenyl}-1H-1,2,3-triazol-1-yl)-1,3,4,5-tetrahydro-2H-1-benzazepin-2-one | Calc'd 487.2, found 486.9 |
| 469 | 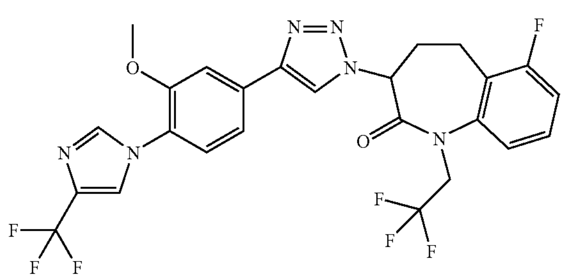 | 6-fluoro-3-(4-{3-methoxy-4-[4-(trifluoromethyl)-1H-imidazol-1-yl]phenyl}-1H-1,2,3-triazol-1-yl)-1-(2,2,2-trifluoroethyl)-1,3,4,5-tetrahydro-2H-1-benzazepin-2-one | Calc'd 569.2, found 568.8 |
| 470 | 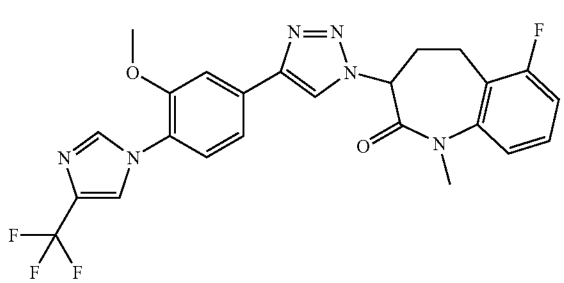 | 6-fluoro-3-(4-{3-methoxy-4-[4-(trifluoromethyl)-1H-imidazol-1-yl]phenyl}-1H-1,2,3-triazol-1-yl)-1-methyl-1,3,4,5-tetrahydro-2H-1-benzazepin-2-one | Calc'd 501.2, found 500.9 |

TABLE IV-continued

| EX. | Structure | Name | [M + H]+ |
|---|---|---|---|
| 471 | 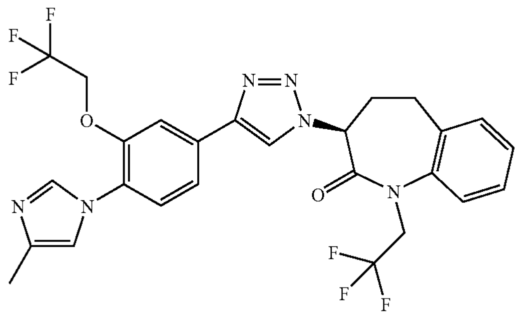 | (3S)-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 565.2, found 565.1 |
| 472 | 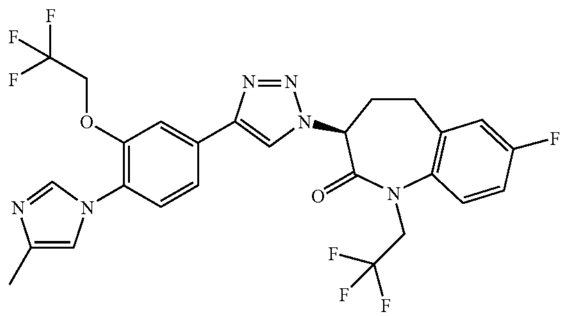 | (3S)-7-fluoro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 583.2, found 583.1 |
| 473 | 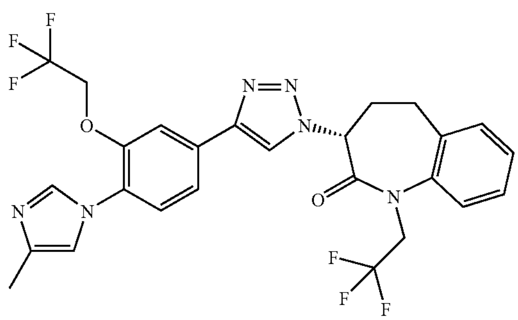 | (3R)-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 565.2, found 565.1 |
| 474 | 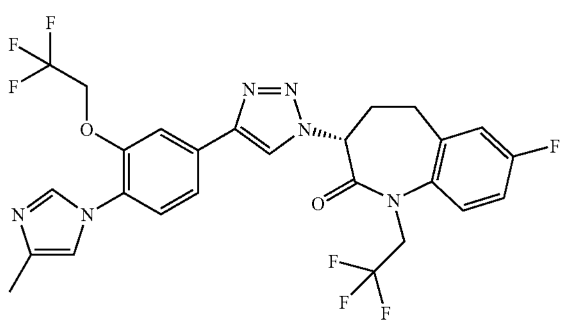 | (3R)-7-fluoro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 583.2, found 583.1 |
| 475 | 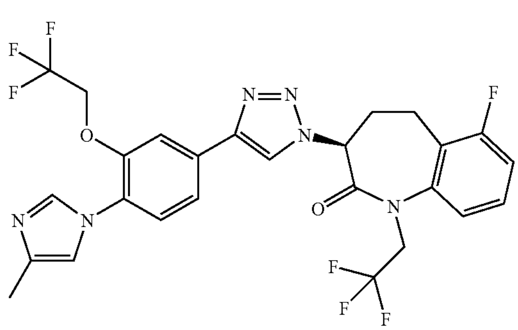 | (3S)-6-fluoro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 583.2, found 582.8 |

TABLE IV-continued

| EX. | Structure | Name | [M + H]+ |
|---|---|---|---|
| 476 | 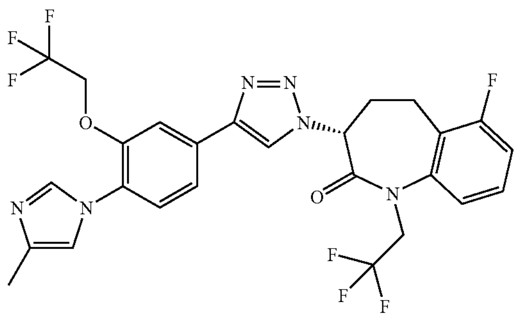 | (3R)-6-fluoro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 583.2, found 582.8 |
| 477 | 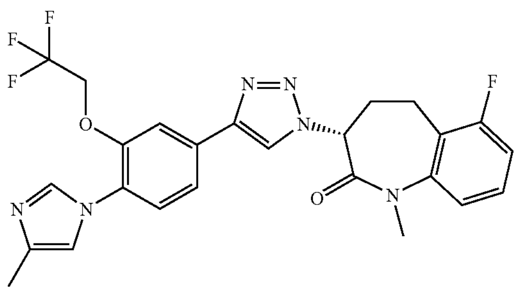 | (3R)-6-fluoro-1-methyl-3-{4-[4-(4-methyl-1H-imidazol-1-yl)-3-(2,2,2-trifluoroethoxy)phenyl]-1H-1,2,3-triazol-1-yl}-1,3,4,5-tetrahydro-2H-1-benzazepin-2-one | Calc'd 515.2, found 515.1 |
| 478 | 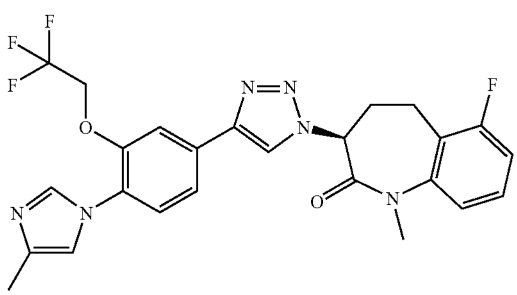 | (3S)-6-fluoro-1-methyl-3-{4-[4-(4-methyl-1H-imidazol-1-yl)-3-(2,2,2-trifluoroethoxy)phenyl]-1H-1,2,3-triazol-1-yl}-1,3,4,5-tetrahydro-2H-1-benzazepin-2-one | Calc'd 515.2, found 515.1 |
| 479 | 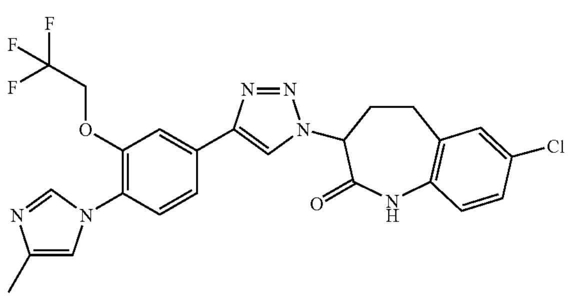 | 7-chloro-3-{4-[4-(4-methyl-1H-imidazol-1-yl)-3-(2,2,2-trifluoroethoxy)phenyl]-1H-1,2,3-triazol-1-yl}-1,3,4,5-tetrahydro-2H-1-benzazepin-2-one | Calc'd 517.1, found 517.1 |
| 480 | 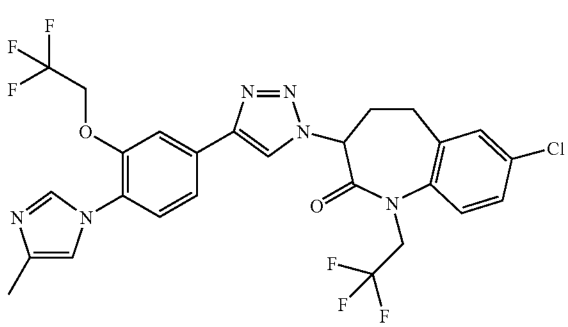 | 7-chloro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 599.1, found 599.1 |

TABLE IV-continued

| EX. | Name | [M + H]⁺ |
|---|---|---|
| 481 | 3-{4-[3-methoxy-4-(3-methyl-1H-1,2,4-triazol-1-yl)phenyl]-1H-1,2,3-triazol-1-yl}-1-(2,2,2-trifluoroethyl)-5-(trifluoromethyl)azepan-2-one | Calc'd 518.2, found 518.1 |
| 482 | 3-{4-[3-methoxy-4-(2-methyl-1H-imidazol-1-yl)phenyl]-1H-1,2,3-triazol-1-yl}-1,3,4,5-tetrahydro-2H-1-benzazepin-2-one | Calc'd 415.2, found 415.2 |
| 483 | (3R,5R)-5-tert-butyl-3-{4-[3-methoxy-4-(3-methyl-1H-1,2,4-triazol-1-yl)phenyl]-1H-1,2,3-triazol-1-yl}-1-(2,2,2-trifluoroethyl)azepan-2-one | Calc'd 506.2, found 506.1 |
| 484 | (3S,5S)-5-tert-butyl-3-{4-[3-methoxy-4-(3-methyl-1H-1,2,4-triazol-1-yl)phenyl]-1H-1,2,3-triazol-1-yl}-1-(2,2,2-trifluoroethyl)azepan-2-one | Calc'd 506.2, found 506.1 |
| 485 | 3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 497.2, found 497.2 |

TABLE IV-continued

| EX. | Name | [M + H]+ |
|---|---|---|
| 486 | (3S)-7-chloro-3-{4-[4-(4-methyl-1H-imidazol-1-yl)-3-(2,2,2-trifluoroethoxy)phenyl]-1H-1,2,3-triazol-1-yl}-1-(2,2,2-trifluoroethyl)-1,3,4,5-tetrahydro-2H-1-benzazepin-2-one | Calc'd 599.1, found 599.1 |
| 487 | 3-{4-[4-(2,4-dimethyl-1H-imidazol-1-yl)-3-methoxyphenyl]-1H-1,2,3-triazol-1-yl}-1,3,4,5-tetrahydro-2H-1-benzazepin-2-one | Calc'd 429.2, found 429.2 |
| 488 | 5-{1-[(3R)-6-fluoro-2-oxo-1-(2,2,2-trifluoroethyl)-2,3,4,5-tetrahydro-1H-1-benzazepin-3-yl]-1H-1,2,3-triazol-4-yl}-2-(4-methyl-1H-imidazol-1-yl)benzonitrile | Calc'd 510.2, found 510.1 |
| 489 | 1-[(3S)-6-fluoro-2-oxo-1-(2,2,2-trifluoroethyl)-2,3,4,5-tetrahydro-1H-1-benzazepin-3-yl]-1H-1,2,3-triazol-4-yl}-2-(4-methyl-1H-imidazol-1-yl)benzonitrile | Calc'd 510.2, found 510.1 |
| 490 | 3-{4-[4-(2,4-dimethyl-1H-imidazol-1-yl)-3-methoxyphenyl]-1H-1,2,3-triazol-1-yl}-1-(2,2,2-trifluoroethyl)-1,3,4,5-tetrahydro-2H-1-benzazepin-2-one | Calc'd 511.2, found 511.2 |
| 491 | 6-fluoro-3-{4-[3-methoxy-4-(2-methyl-1H-imidazol-1-yl)phenyl]-1H-1,2,3-triazol-1-yl}-1,3,4,5-tetrahydro-2H-1-benzazepin-2-one | Calc'd 433.2, found 433.2 |

TABLE IV-continued

| EX. | Structure | Name | [M + H]+ |
|---|---|---|---|
| 492 | 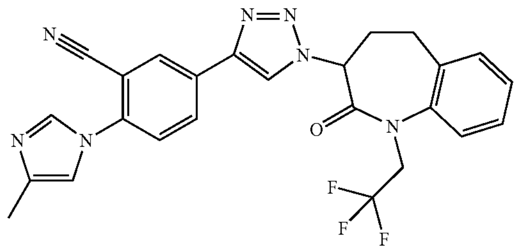 | 2-(4-methyl-1H-imidazol-1-yl)-5-{1-[2-oxo-1-(2,2,2-trifluoroethyl)-2,3,4,5-tetrahydro-1H-1-benzazepin-3-yl]-1H-1,2,3-triazol-4-yl}benzonitrile | Calc'd 492.2, found 492.1 |
| 493 | 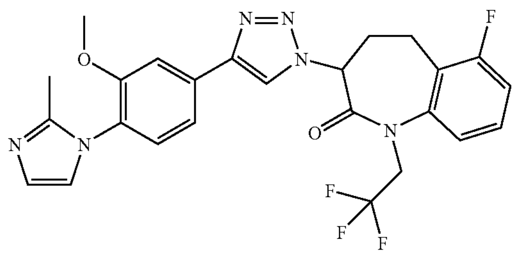 | 6-fluoro-3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 494 | 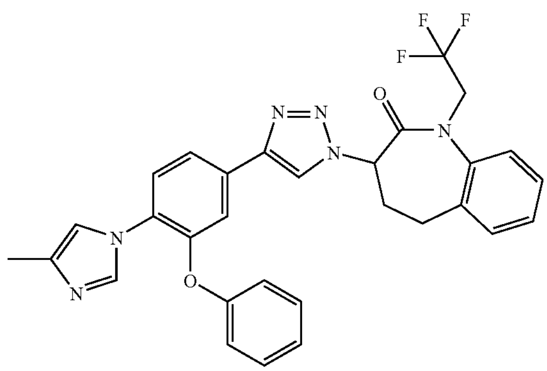 | 3-{4-[4-(4-methyl-1H-imidazol-1-yl)-3-phenoxyphenyl]-1H-1,2,3-triazol-1-yl}-1-(2,2,2-trifluoroethyl)-1,3,4,5-tetrahydro-2H-1-benzazepin-2-one | Calc'd 559.2, found 559.2 |
| 495 | 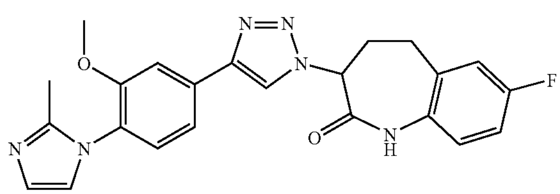 | 7-fluoro-3-{4-[3-methoxy-4-(2-methyl-1H-imidazol-1-yl)phenyl]-1H-1,2,3-triazol-1-yl}-1,3,4,5-tetrahydro-2H-1-benzazepin-2-one | Calc'd 433.2, found 433.1 |
| 496 | 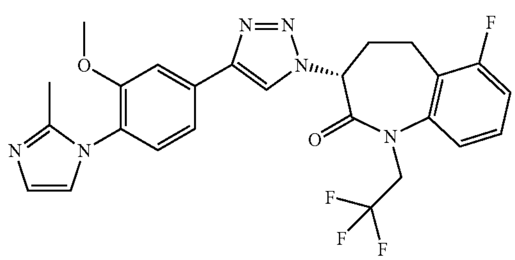 | (3R)-6-fluoro-3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 497 | 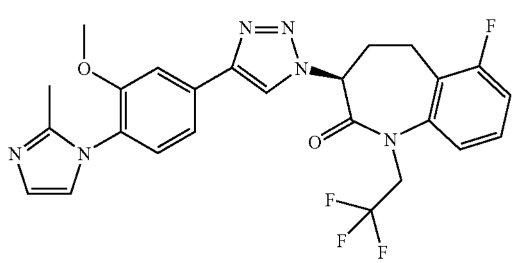 | (3S)-6-fluoro-3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |

TABLE IV-continued

| EX. | Structure | Name | [M + H]+ |
|---|---|---|---|
| 498 | 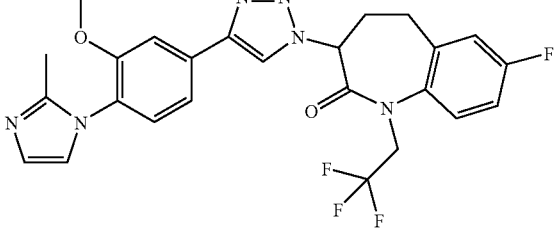 | 7-fluoro-3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 499 | 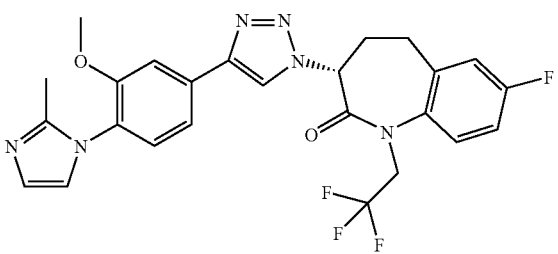 | (3R)-7-fluoro-3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 500 | 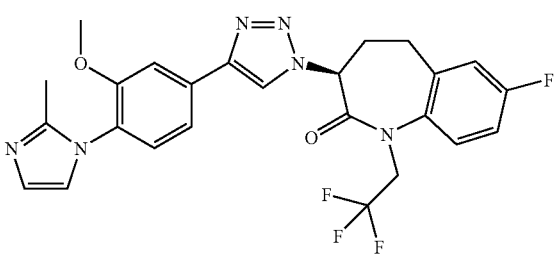 | (3S)-7-fluoro-3-{4-[3-methoxy-4-(2-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 515.2, found 515.1 |
| 501 | 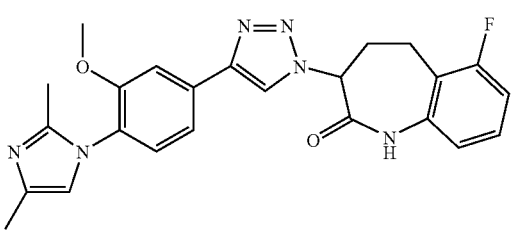 | 3-{4-[4-(2,4-dimethyl-1H-imidazol-1-yl)-3-methoxyphenyl]-1H-1,2,3-triazol-1-yl}-6-fluoro-1,3,4,5-tetrahydro-2H-1-benzazepin-2-one | Calc'd 447.2, found 447.2 |
| 502 | 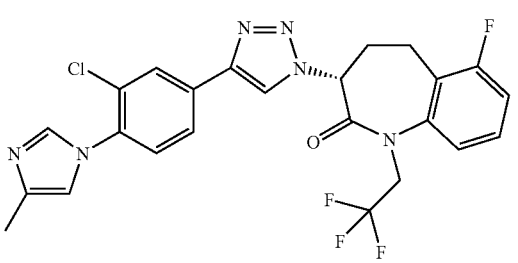 | (3R)-3-{4-[3-chloro-4-(4-methyl-1H-imidazol-1-yl)phenyl]-1H-1,2,3-triazol-1-yl}-6-fluoro-1-(2,2,2-trifluoroethyl)-1,3,4,5-tetrahydro-2H-1-benzazepin-2-one | Calc'd 519.1, found 519.0 |
| 503 | 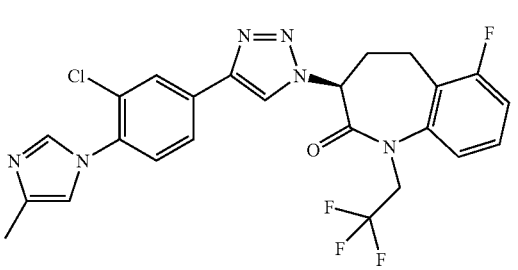 | (3S)-3-{4-[3-chloro-4-(4-methyl-1H-imidazol-1-yl)phenyl]-1H-1,2,3-triazol-1-yl}-6-fluoro-1-(2,2,2-trifluoroethyl)-1,3,4,5-tetrahydro-2H-1-benzazepin-2-one | Calc'd 519.1, found 519.0 |

TABLE IV-continued

| EX. | Structure | Name | [M + H]+ |
|---|---|---|---|
| 504 | 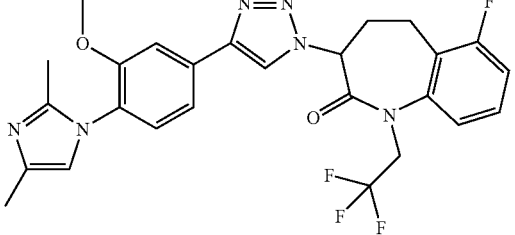 | 3-{4-[4-(2,4-dimethyl-1H-imidazol-1-yl)-3-methoxyphenyl]-1H-1,2,3-triazol-1-yl}-6-fluoro-1-(2,2,2-trifluoroethyl)-1,3,4,5-tetrahydro-2H-1-benzazepin-2-one | Calc'd 529.2, found 529.1 |
| 505 | 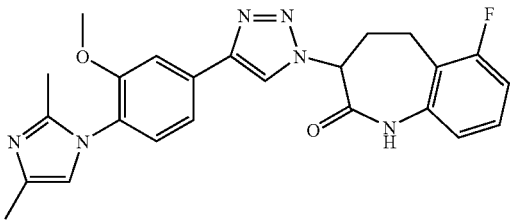 | 7-bromo-3-{4-[4-(2,4-dimethyl-1H-imidazol-1-yl)-3-methoxyphenyl]-1H-1,2,3-triazol-1-yl}-6-fluoro-1,3,4,5-tetrahydro-2H-1-benzazepin-2-one | Calc'd 525.1, found 525.0 |
| 506 | 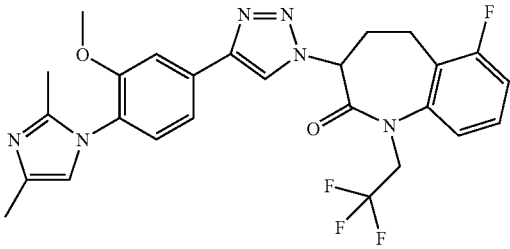 | 7-bromo-3-{4-[4-(2,4-dimethyl-1H-imidazol-1-yl)-3-methoxyphenyl]-1H-1,2,3-triazol-1-yl}-6-fluoro-1-(2,2,2-trifluoroethyl)-1,3,4,5-tetrahydro-2H-1-benzazepin-2-one | Calc'd 607.1, found 607.0 |
| 507 | 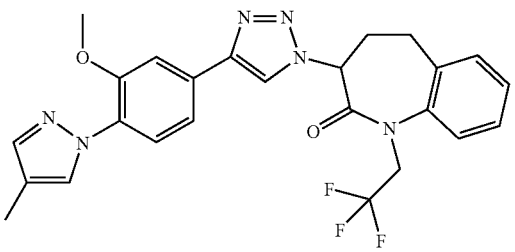 | 3-{4-[3-methoxy-4-(4-methyl-1H-pyrazol-1-yl)phenyl]-1H-1,2,3-triazol-1-yl}-1-(2,2,2-trifluoroethyl)-1,3,4,5-tetrahydro-2H-1-benzazepin-2-one | Calc'd 497.2, found 497.1 |
| 508 | 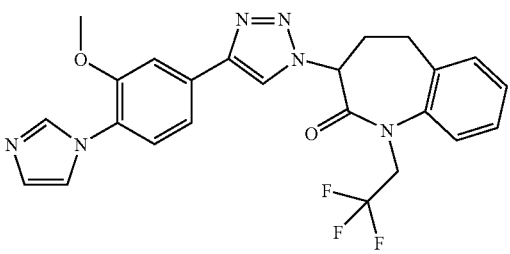 | 3-{4-[4-(1H-imidazol-1-yl)-3-methoxyphenyl]-1H-1,2,3-triazol-1-yl}-1-(2,2,2-trifluoroethyl)-1,3,4,5-tetrahydro-2H-1-benzazepin-2-one | Calc'd 483.2, found 483.1 |
| 509 | 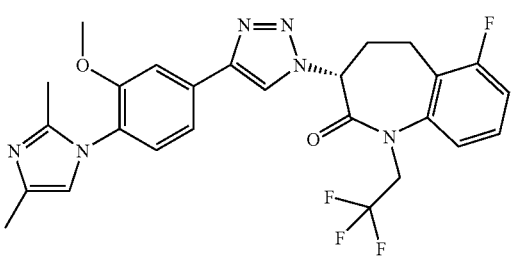 | (3R)-3-{4-[4-(2,4-dimethyl-1H-imidazol-1-yl)-3-methoxyphenyl]-1H-1,2,3-triazol-1-yl}-6-fluoro-1-(2,2,2-trifluoroethyl)-1,3,4,5-tetrahydro-2H-1-benzazepin-2-one | Calc'd 529.2, found 529.1 |

TABLE IV-continued

| EX. | Structure | Name | [M + H]⁺ |
|---|---|---|---|
| 510 | 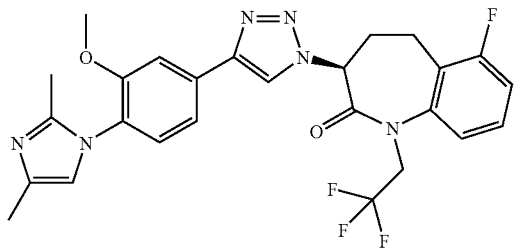 | (3S)-3-{4-[4-(2,4-dimethyl-1H-imidazol-1-yl)-3-methoxyphenyl]-1H-1,2,3-triazol-1-yl}-6-fluoro-1-(2,2,2-trifluoroethyl)-1,3,4,5-tetrahydro-2H-1-benzazepin-2-one | Calc'd 529.2, found 529.1 |
| 511 | 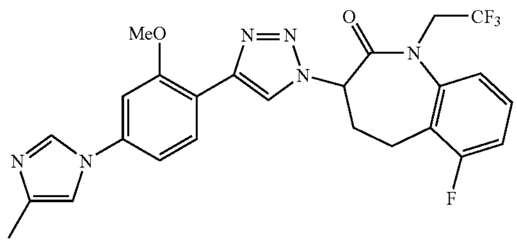 | 6-fluoro-3-{4-[2-methoxy-4-(4-methyl-1H-imidazol-1-yl)phenyl]-1H-1,2,3-triazol-1-yl}-1-(2,2,2-trifluoroethyl)-1,3,4,5-tetrahydro-2H1-1-benzazepin-2-one | Calc'd 515.2, found 515.1 |
| 512 | 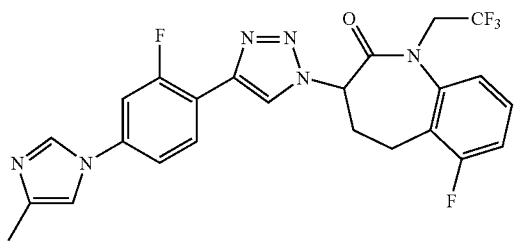 | 6-fluoro-3-{4-[2-fluoro-4-(4-methyl-1H-imidazol-1-yl)phenyl]-1H-1,2,3-triazol-1-yl}-1-(2,2,2-trifluoroethyl)-1,3,4,5-tetrahydro-2H-1-benzazepin-2-one | Calc'd 503.2, found 503.1 |
| 513 | 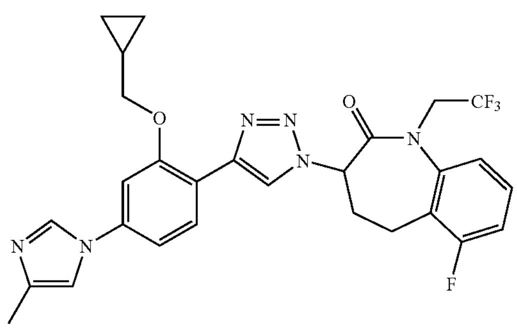 | 3-{4-[2-(cyclopropylmethoxy)-4-(4-methyl-1H-imidazol-1-yl)phenyl]-1H-1,2,3-triazol-1-yl}-6-fluoro-1-(2,2,2-trifluoroethyl)-1,3,4,5-tetrahydro-2H-1-benzazepin-2-one | Calc'd 555.2, found 555.2 |

The invention claimed is:

1. A compound of formula I:

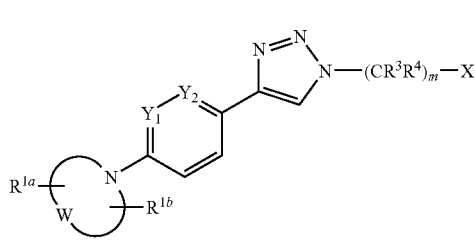

or a pharmaceutically acceptable salt or hydrate thereof; wherein:

W completes an imidazole, triazole or pyrazole ring;

$R^{1a}$ and $R^{1b}$ independently represent H, $C_{1-6}$alkyl, or $CF_3$;

Y1 and Y2 each independently represents N or $CR^2$ provided Y1 and Y2 do not both represent N;

$R^2$ represents H, halogen, CN, $C_{1-6}$alkyl, $C_{1-6}$alkoxy or phenoxy, said alkyl, alkoxy and phenoxy optionally having up to 3 fluorine substituents or a cyclopropyl substituent;

each $R^3$ and each $R^4$ is independently H, $C_{1-6}$alkyl, F, $CO_2R^a$ or phenyl, where $R^a$ is H or $C_{1-4}$alkyl, with the proviso that not more than one $R^3$ or $R^4$ group may represent $CO_2R^a$ or phenyl;

or $R^3$ and $R^4$ attached to the same carbon atom may represent =O or may together complete a carbocycle of 3 to 6 atoms;

m is 0 or an integer in the range 1-6;

or —$(CR^3R^4)_m$— is a linker selected from:

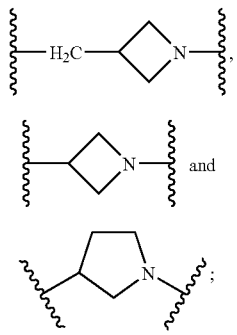

(i)

(ii)

(iii)

X is selected from H, $R^5$, $OR^6$, $OCOR^5$, $SR^5$, $NR^6R^7$, $NR^7COR^5$, $NR^7CO_2R^8$ and $Si(R^8)_3$;

$R^5$ is selected from:

(a) $C_{1-10}$alkyl, phenyl$C_{1-4}$alkyl, diphenylmethyl, $C_{3-10}$cycloalkyl or $C_{3-10}$cycloalkenyl, said $C_{3-10}$cycloalkyl or $C_{3-10}$cycloalkenyl optionally having up to 2 benzene rings fused thereto;

(b) phenyl which optionally forms part of a polycyclic system containing up to 3 additional rings, each of which independently comprises 5, 6 or 7 members and is independently carbocyclic or heterocyclic;

(c) 4-, 5-, 6- or 7-membered heterocyclic which optionally forms part of a polycyclic system containing up to 3 additional rings, each of which independently comprises 5, 6 or 7 members and is independently carbocyclic or heterocyclic;

where the term "polycyclic system" at each occurrence thereof refers to a system of fused rings, or a system of rings linked by covalent bonds, or any combination of fused and covalently-linked rings;

the group represented by $R^5$ optionally bearing up to 5 substituents independently selected from halogen, CN, $NO_2$, OH, oxo, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, phenylsulfonyl, benzoyl, benzyl, naphthylmethyl, pyridylmethyl, $SO_2NR_2$, $CONR_2$, $NR_2$ and $R_2N$—$C_{1-4}$alkyl where each R is independently H or $C_{1-4}$alkyl or the two R groups together with the nitrogen to which they are attached complete a ring selected from azetidine, pyrrolidine, piperidine, piperazine and morpholine, and where the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$;

$R^6$ represents H or has the same definition as $R^5$;

$R^7$ represents H or $C_{1-6}$alkyl which optionally bears a substituent selected from halogen, CN, OH, polyfluoro$C_{1-4}$alkyl, $C_{3-4}$cycloalkyl, $C_{1-4}$alkoxy, polyfluoro $C_{1-4}$alkoxy, $C_{1-4}$alkylcarbonyl and $C_{1-4}$alkoxycarbonyl;

or $R^7$ represents $C_{3-6}$cycloalkyl, benzyl or phenyl, said $C_{3-6}$cycloalkyl, benzyl and phenyl optionally bearing up to 3 substituents selected from halogen, CN, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl;

or $R^6$ and $R^7$ attached to the same nitrogen atom may complete a heterocyclic ring of up to 6 members, optionally forming part of a fused ring system of up to 20 ring atoms, said ring or fused ring system optionally bearing up to 3 substituents selected from halogen, $C_{1-4}$alkyl, polyfluoro$C_{1-4}$alkyl, $C_{3-4}$cycloalkyl, phenyl, OH, $C_{1-4}$alkoxy, polyfluoro$C_{1-4}$alkoxy, $C_{1-4}$alkylcarbonyl, $C_{1-4}$alkoxycarbonyl $C_{1-4}$alkylthio, $C_{1-4}$alkylsulfonyl, $CONR_2$ and $NR_2$ where each $R_2$ is independently H or $C_{1-4}$alkyl or the two $R_2$ groups together with the nitrogen to which they are attached complete a ring selected from azetidine, pyrrolidine, piperidine, piperazine and morpholine; and $R^8$ represents $C_{1-6}$alkyl, $C_{3-6}$cycloalkyl or phenyl;

with the proviso that if m is 0 or —$(CR^3R^4)_m$— is a linker represented by (i), (ii) or (iii) then X represents $R^5$ and $R^5$ is not N-heterocyclyl.

2. A compound according to claim 1 or a pharmaceutically acceptable salt thereof, wherein W, $R^{1a}$ and $R^{1b}$ complete a group selected from: 4-methyl-1H-imidazol-1-yl, 2-methyl-1H-imidazol-1-yl, 2,4-dimethyl-1H-imidazol-1-yl, 4-trifluoromethyl-1H-imidazol-1-yl, 1H-imidazol-1-yl, 3-methyl-1H-1,2,4-triazol-1-yl and 4-methyl-1H-pyrazol-1-yl.

3. A compound according to claim 1 or a pharmaceutically acceptable salt thereof, wherein one of Y1 and Y2 represents CH and the other represents $CR^2$ and $R^2$ represents H, F, Cl, CN, methyl, methoxy, 2,2,2-trifluoroethoxy, cyclopropylmethoxy or phenoxy.

4. A compound according to claim 1 or a pharmaceutically acceptable salt thereof, wherein the linker $(CR^3CR^4)_m$ is selected from a bond, $CH_2$, $CH_2CH_2$, $CH_2CH_2CH_2$, $CF_2$, $CH_2CO$, $CF_2CO$, $CH(CH_3)$, $CH(Ph)CO$, $CHFCO$, (1,1-cyclobutanediyl)CO, $CH(CO_2H)CH_2CH_2$, $CH(CO_2CH_3)$ $CH_2C(CH_3)_2$ and the structures (i), (ii) and (iii):

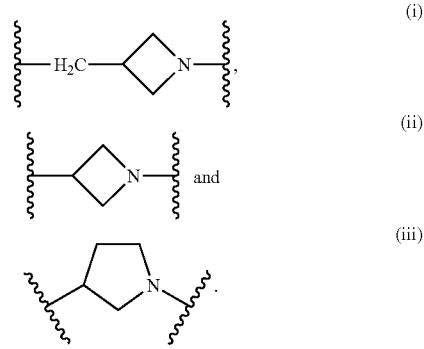

(i)

(ii)

and (iii)

5. A compound according to claim 1 of formula II:

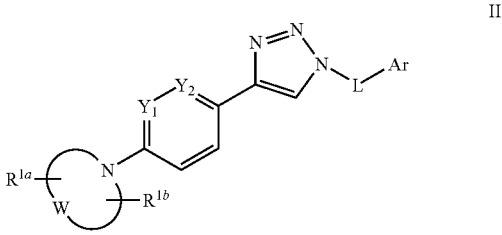

II or a pharmaceutically acceptable salt or hydrate thereof; wherein:

L represents $CR^3R^4$, $CH_2CH_2$ or $CH_2CH_2CH_2$; and

Ar represents an aromatic moiety selected from:
(a) phenyl which is optionally fused to 1, 2 or 3 additional 5- or 6-membered carbocycles;
(b) phenyl which is fused to a 5- or 6-membered heterocycle;
(c) 5- or 6-membered heteroaryl which is optionally fused to 1 or 2 additional 5- or 6-membered carbocyclic or heterocyclic rings; and
(d) a covalently linked bicyclic or tricyclic system represented by the formula Ar1-Ar2-(Ar3)y where Ar1, Ar2 and Ar3 are independently selected from phenyl, 5- or 6-membered heteroaryl and benzofused 5- or 6-membered heteroaryl, and y is 0 or 1;

the moiety Ar bearing 0-4 substituents independently selected from halogen, $NO_2$, CN, OH, $C_{1-4}$alkyl, $CF_3$, cyclopropyl, cyclobutyl, $C_{1-4}$alkoxy, and $OCF_3$.

6. A compound according to claim 1 of formula III:

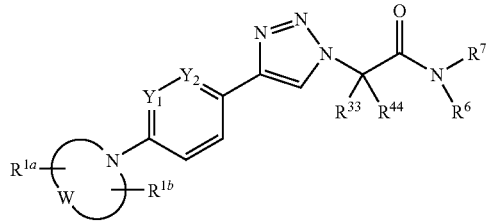

or a pharmaceutically acceptable salt or hydrate thereof; wherein:

$R^{33}$ and $R^{44}$ independently represent H, $C_{1-6}$alkyl, F or phenyl, with the proviso that not more than one of $R^{33}$ and $R^{44}$ may represent phenyl;

or $R^{33}$ and $R^{44}$ together complete a carbocycle of 3 to 6 atoms.

7. A compound according to claim 6 or a pharmaceutically acceptable salt thereof, wherein:

$R^6$ is selected from optionally-substituted $C_{1-10}$alkyl, phenyl$C_{1-4}$alkyl, $C_{3-10}$cycloalkyl, phenyl and 5- or 6-membered heteroaryl, wherein the said phenyl and 5- or 6-membered heteroaryl are optionally fused to a further 5- or 6-membered carbocyclic or heterocyclic ring, and wherein "optionally-substituted" refers to 0-4 substituents independently selected from halogen, CN, $NO_2$, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl, $C_{1-4}$alkoxycarbonyl, $C_{1-4}$alkylthio, $C_{1-4}$alkylsulfonyl, $CONR_2$ and $NR_2$ where each R is independently H or $C_{1-4}$alkyl or the two R groups together with the nitrogen to which they are attached complete a ring selected from azetidine, pyrrolidine, piperidine, piperazine and morpholine;

$R^7$ represents H or $C_{1-6}$alkyl which optionally bears a substituent selected from halogen, CN, OH, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl;

or $R^7$ represents $C_{3-6}$cycloalkyl, benzyl or phenyl, said $C_{3-6}$cycloalkyl, benzyl and phenyl optionally bearing up to 3 substituents selected from halogen, CN, OH, $C_{1-4}$alkyl, polyfluoro$C_{1-4}$alkyl, $C_{3-4}$cycloalkyl, $C_{1-4}$alkoxy, polyfluoro$C_{1-4}$alkoxy, $C_{1-4}$alkylcarbonyl and $C_{1-4}$alkoxycarbonyl;

or $R^6$ and $R^7$ together complete a heterocyclic ring of up to 6 members, optionally forming part of a fused ring system of up to 20 ring atoms, said ring or fused ring system optionally bearing up to 3 substituents selected from halogen, $C_{1-4}$alkyl, polyfluoro$C_{1-4}$alkyl, $C_{3-4}$cycloalkyl, phenyl, $C_{1-4}$alkoxy, polyfluoro$C_{1-4}$alkoxy, $C_{1-4}$alkylcarbonyl, $C_{1-4}$alkoxycarbonyl $C_{1-4}$alkylthio, $C_{1-4}$alkylsulfonyl, $CONR_2$ and $NR_2$ where each $R_2$ is independently H or $C_{1-4}$alkyl.

8. A compound according to claim 1 of formula IV:

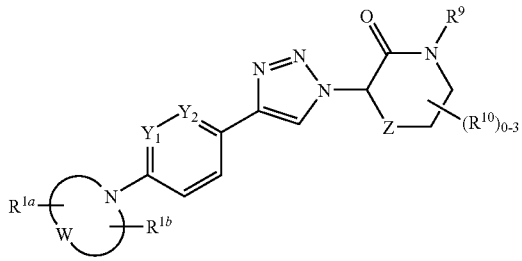

or a pharmaceutically acceptable salt or hydrate thereof; wherein:

Z represents $CH_2$, $CH_2$—$CH_2$, O, S, NH, $CH_2$—O, $CH_2$—S or $CH_2$—NH;

$R^9$ represent H, $C_{1-4}$alkyl, $C_{2-4}$alkenyl, polyfluoro$C_{1-4}$alkyl, $C_{3-6}$cycloalkyl, $C_{3-6}$cycloalkyl$C_{1-4}$alkyl, $C_{1-4}$alkoxy$C_{1-4}$alkyl, amino $C_{1-4}$alkyl, $C_{1-4}$alkylcarbonyl, polyfluoro$C_{1-4}$alkylcarbonyl, $C_{1-4}$alkylsulfonyl, phenyl, phenylsulfonyl, benzoyl, benzyl, naphthylmethyl or pyridylmethyl, where said phenyl and the aromatic portions of said phenylsulfonyl, benzoyl, benzyl, naphthylmethyl and pyridylmethyl optionally bear up to 3 substituents selected from halogen, $C_{1-4}$alkyl, $C_{1-4}$alkoxy and $CF_3$; and each $R^{10}$ independently represents halogen, OH, $C_{1-4}$alkyl, $C_{2-4}$alkenyl, polyfluoro$C_{1-4}$alkyl, $C_{3-6}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each R is independently H or $C_{1-4}$alkyl or the two $R_2$ groups together with the nitrogen to which they are attached complete a ring selected from azetidine, pyrrolidine, piperidine, piperazine and morpholine; or phenyl or benzyl either of which optionally is substituted with halogen, $C_{1-4}$alkyl, $C_{1-4}$alkoxy or $CF_3$;

or two $R^{10}$ groups attached to adjacent ring positions optionally complete a fused benzene, naphthalene, cyclopentane, cyclohexane, pyridine, thiophene or furan ring which optionally bears up to 2 substituents independently selected from halogen, $NO_2$, CN, OH, phenyl, $C_{1-4}$alkyl, $C_{2-4}$alkenyl, polyfluoro$C_{1-4}$alkyl, $C_{3-4}$cycloalkyl, $C_{3-6}$cycloalkyl$C_{1-4}$alkyl, $C_{1-4}$alkoxy, $C_{1-4}$alkoxy$C_{1-4}$alkyl, polyfluoro$C_{1-4}$alkoxy, $C_{1-4}$alkylcarbonyl, polyfluoro$C_{1-4}$alkylcarbonyl, $C_{1-4}$alkoxycarbonyl, $C_{1-4}$alkylthio, $C_{1-4}$alkylsulfonyl, $SO_2NR_2$, $CONR_2$ or $NR_2$ where each $R_2$ is independently H or $C_{1-4}$alkyl;

or two $R^{10}$ groups attached to non-adjacent ring positions optionally complete a $CH_2$ or $CH_2CH_2$ bridge.

9. A compound according to claim 8 of formula IV(a):

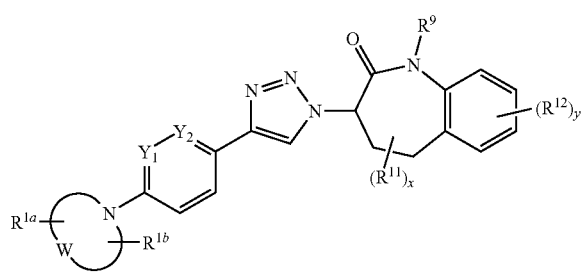

IV(a)

or a pharmaceutically acceptable salt or hydrate thereof; wherein x is 0, 1 or 2;

y is 0, 1 or 2;

$R^{11}$ represents methyl or phenyl with the proviso that x is not 2 when $R^{11}$ is phenyl, and each $R^{12}$ is independently selected from phenyl, $NO_2$, halogen, $C_{1-4}$alkyl, polyfluoro$C_{1-4}$alkyl, $C_{1-4}$alkoxy and polyfluoro$C_{1-4}$alkoxy with the provision that not more than one $R^{12}$ represents phenyl or $NO_2$.

10. A pharmaceutical composition comprising a compound according to claim 1 or a pharmaceutically acceptable salt thereof and a pharmaceutically acceptable carrier.

\* \* \* \* \*